US010301377B2

(12) United States Patent
Graham et al.

(10) Patent No.: US 10,301,377 B2
(45) Date of Patent: May 28, 2019

(54) MIDDLE EAST RESPIRATORY SYNDROME CORONAVIRUS IMMUNOGENS, ANTIBODIES, AND THEIR USE

(71) Applicant: The United States of America, as represented by the Secretary, Department of Health and Human Services, Washington, DC (US)

(72) Inventors: Barney Graham, Rockville, MD (US); Wing-Pui Kong, Germantown, MD (US); Kayvon Modjarrad, Bethesda, MD (US); Lingshu Wang, North Potomac, MD (US); Wei Shi, Rockville, MD (US); Michael Gordon Joyce, Washington, DC (US); Masaru Kanekiyo, Chevy Chase, MD (US); John Mascola, Rockville, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/553,466

(22) PCT Filed: Feb. 24, 2016

(86) PCT No.: PCT/US2016/019395
§ 371 (c)(1),
(2) Date: Aug. 24, 2017

(87) PCT Pub. No.: WO2016/138160
PCT Pub. Date: Sep. 1, 2016

(65) Prior Publication Data
US 2018/0244756 A1 Aug. 30, 2018

Related U.S. Application Data

(60) Provisional application No. 62/120,353, filed on Feb. 24, 2015.

(51) Int. Cl.
*A61K 39/12* (2006.01)
*C07K 16/10* (2006.01)
(Continued)

(52) U.S. Cl.
CPC .............. *C07K 16/10* (2013.01); *A61K 39/12* (2013.01); *A61K 39/215* (2013.01);
(Continued)

(58) Field of Classification Search
None
See application file for complete search history.

(56) References Cited

U.S. PATENT DOCUMENTS

2006/0286124 A1  12/2006  Burt et al.

FOREIGN PATENT DOCUMENTS

| WO | WO 2004/076677 | 9/2004 |
| WO | WO 2005/056585 | 6/2005 |

(Continued)

OTHER PUBLICATIONS

Chen, et al. "A DNA prime-protein boost vaccination strategy targeting turkey coronavirus spike protein fragment containing neutralizing epitope against infectious challenge." *Veterinary Immunology and Immunopathology* 152, No. 3 (2013): 359-369.
(Continued)

*Primary Examiner* — Michelle S Horning
(74) *Attorney, Agent, or Firm* — Klarquist Sparkman, LLP

(57) ABSTRACT

Methods of inducing an immune response in a subject to the Middle East respiratory syndrome coronavirus (MERS-CoV) are provided. In several embodiments, the immune response is a protective immune response that inhibits or prevents MERS-CoV infection in the subject. Recombinant MERS-CoV polypeptides and nucleic acid molecules encoding same are also provided. Additionally, neutralizing antibodies that specifically bind to MERS-CoV S protein and antigen binding fragments thereof are disclosed. The antibodies and antigen binding fragments are useful, for example, in methods of detecting MERS-CoV S protein in a sample or in a subject, as well as methods of preventing and treating a MERS-CoV infection in a subject.

23 Claims, 36 Drawing Sheets

Specification includes a Sequence Listing.

(51) Int. Cl.
*C07K 14/165* (2006.01)
*A61K 39/215* (2006.01)
*C07K 14/005* (2006.01)
*G01N 33/569* (2006.01)
*A61K 39/00* (2006.01)

(52) U.S. Cl.
CPC .......... *C07K 14/005* (2013.01); *C07K 14/165* (2013.01); *G01N 33/56983* (2013.01); *A61K 2039/53* (2013.01); *A61K 2039/545* (2013.01); *A61K 2039/55505* (2013.01); *A61K 2039/55566* (2013.01); *A61K 2039/55572* (2013.01); *A61K 2039/57* (2013.01); *C07K 2317/21* (2013.01); *C07K 2317/24* (2013.01); *C07K 2317/33* (2013.01); *C07K 2317/34* (2013.01); *C07K 2317/52* (2013.01); *C07K 2317/54* (2013.01); *C07K 2317/55* (2013.01); *C07K 2317/56* (2013.01); *C07K 2317/565* (2013.01); *C07K 2317/567* (2013.01); *C07K 2317/622* (2013.01); *C07K 2317/76* (2013.01); *C07K 2317/92* (2013.01); *C12N 2770/20034* (2013.01); *G01N 2333/165* (2013.01)

(56) References Cited

FOREIGN PATENT DOCUMENTS

| WO | WO 2006/068663 | 6/2006 |
| WO | WO 2007/010399 | 1/2007 |
| WO | WO 2010/063685 | 6/2010 |
| WO | WO 2014/045254 | 3/2014 |

OTHER PUBLICATIONS

Coleman, et al. "Purified coronavirus spike protein nanoparticles induce coronavirus neutralizing antibodies in mice." *Vaccine* 32, No. 26 (2014): 3169-3174.

Du, et al. "A conformation-dependent neutralizing monoclonal antibody specifically targeting receptor-binding domain in Middle East raspiratory syndrome coronavirus spike protein." *Journal of Virology* 88, No. 12, (2014): 7045-7053.

Du, et al. A truncated receptor-binding domain of MERS-CoV spike protein 515 potently inhibits MERS-CoV infection and induces strong neutralizing antibody 516 responses: implication for developing therapeutics and vaccines. *PloS One* 8 (2013): e81587.

Jiang, et al. "Potent neutralization of MERS-CoV by human neutralizing monoclonal antibodies to the viral spike glycoprotein." *Science Translational Medicine* 6, No. 234 (2014): 2334ra59-234ra59.

Jiang, et al. "Roadmap to developing a recombinant coronavirus S protein receptor-binding domain vaccine for severe acute respiratory syndrome." *Expert Review of Vaccines* 11, No. 12 (2012): 1405-1413.

Lan, et al. "Tailoring subunit vaccine immunity with adjuvant combinations and delivery routes using the Middle East respiratory coronavirus (MERS-CoV) receptor-binding domain as an antigen." *PLoS One* 9, No. 11 (2014): e112602.

Ma, et al. "Intranasal vaccination with recombinant receptor-binding domain of MERS-CoV spike protein induces much stronger local mucosal immune responses than subcutaneous immunization: Implication for designing novel mucosal MERS vaccines." *Vaccine* 32, No. 18 (2014): 2100-2108.

Meng, et al. "Rapid generation of human-like neutralizing monoclonal antibodies in urgent preparedness for influenza pandemics and virulent infectious diseases." *PloS One* 8, No. 6 (2013): e66276.

Ohnuma, et al. "Inhibition of Middle East respiratory syndrome coronavirus infection by anti-CD26 monoclonal antibody." *Journal of Virology* 87, No. 24 (2013): 13892-13899.

Song, et al. "Middle East respiratory syndrome coronavirus spike protein delivered by modified vaccinia virus Ankara efficiently induces virus-neutralizing antibodies." *Journal of Virology* 87, No. 21 (2013): 11950-11954.

Tang, et al. "Identification of human neutralizing antibodies against MERS-CoV and their role in virus adaptive evolution." *Proceedings of the National Academy of Sciences* 111, No. 19 (2014): E2018-E2026.

Wang, et al. "Evaluation of candidate vaccine approaches for MERS-CoV." *Nature Communications* 6 (2015): 7712.

Woo, et al. "SARS coronavirus spike polypeptide DNA vaccine priming with recombinant spike polypeptide from *Escherichia coli* as booster induces high titer of neutralizing antibody against SARS coronavirus." *Vaccine* 23, No. 42 (2005): 4959-4968.

Ying, et al. "Development of human neutralizing monoclonal antibodies for prevention and therapy of MERS-CoV infections." *Microbes and Infection* 17, No. 2 (2015): 142-148.

Ying, et al. "Exceptionally potent neutralization of Middle East respiratory syndrome coronavirus by human monoclonal antibodies." *Journal of Virology* 88, No. 14 (2014): 7796-7805.

Zhang, et al. "Cuirent advancements and potential strategies in the development of MERS-CoV vaccines." *Expert Review of Vaccines* 13, No. 6 (2014): 761-774.

| Antibody | Antigen | Binding kinetics | | | Neutralization (µg/ml) | |
|---|---|---|---|---|---|---|
| | | $K_{on}$ (1/Ms) | $K_{off}$ (1/s) | $K_D$ (M) | $IC_{50}$ | $IC_{80}$ |
| D12 | RBD | 4.91E+05 | 4.88E-03 | 9.93E-09 | 0.013 | 0.040 |
| | S1 | 1.15E+05 | 7.60E-04 | 6.63E-09 | | |
| F11 | RBD | 6.91E+04 | 7.90E-03 | 1.14E-07 | 0.008 | 0.052 |
| | S1 | 1.12E+05 | 3.91E-04 | 3.49E-09 | | |
| G2 | S1 | 1.11E+05 | 1.88E-04 | 1.69E-09 | 0.013 | 0.350 |
| G4 | S2 | 6.14E+04 | 5.09E-04 | 8.29E-09 | 0.133 | 0.806 |

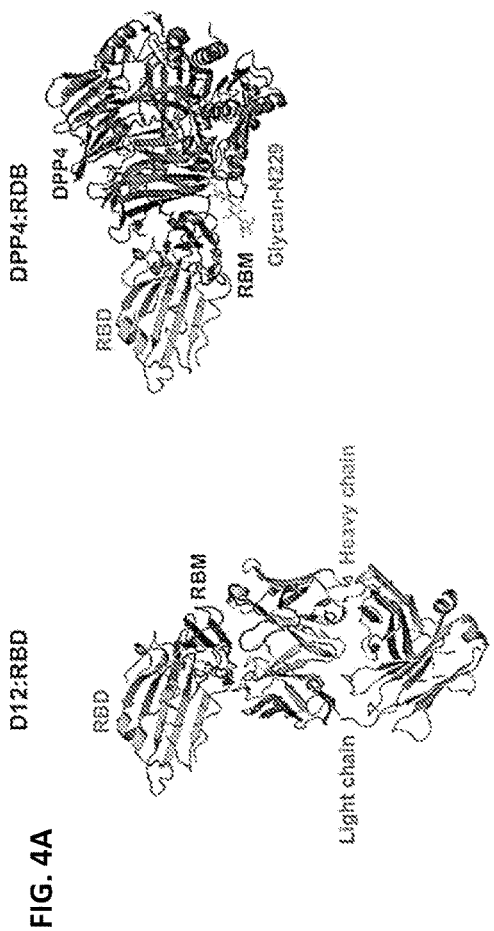
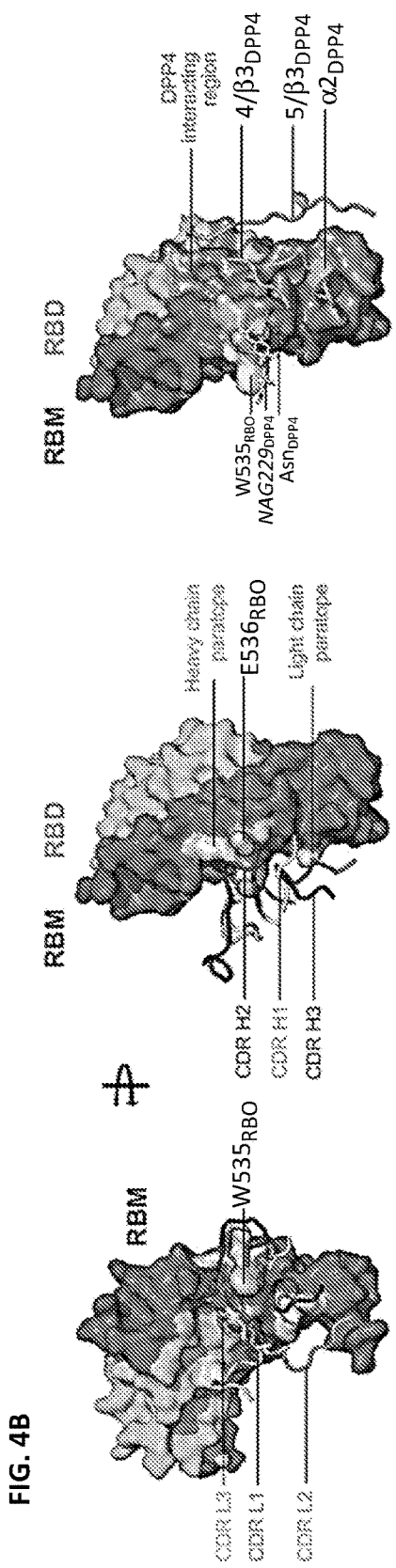
FIG. 4A
FIG. 4B

FIG. 4C
FIG. 4D
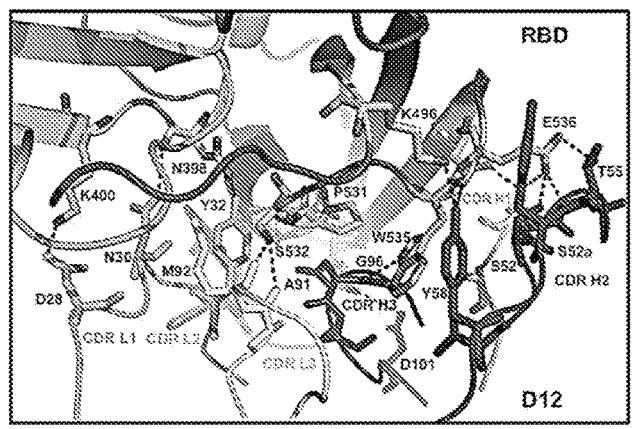
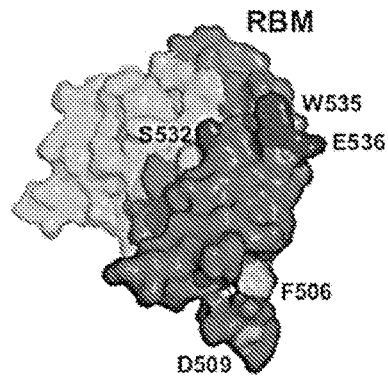
FIG. 4E
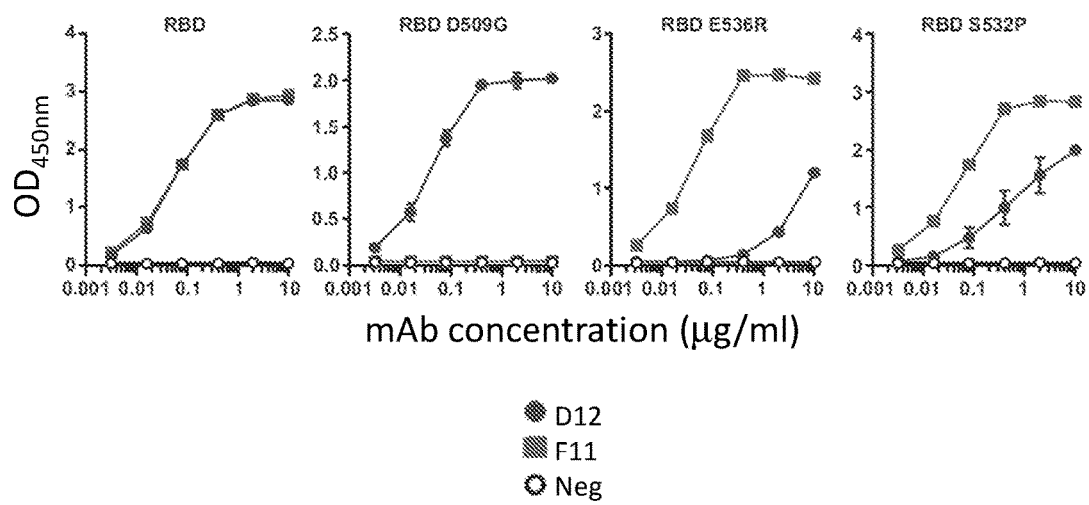
mAb concentration (µg/ml)
● D12
▨ F11
○ Neg

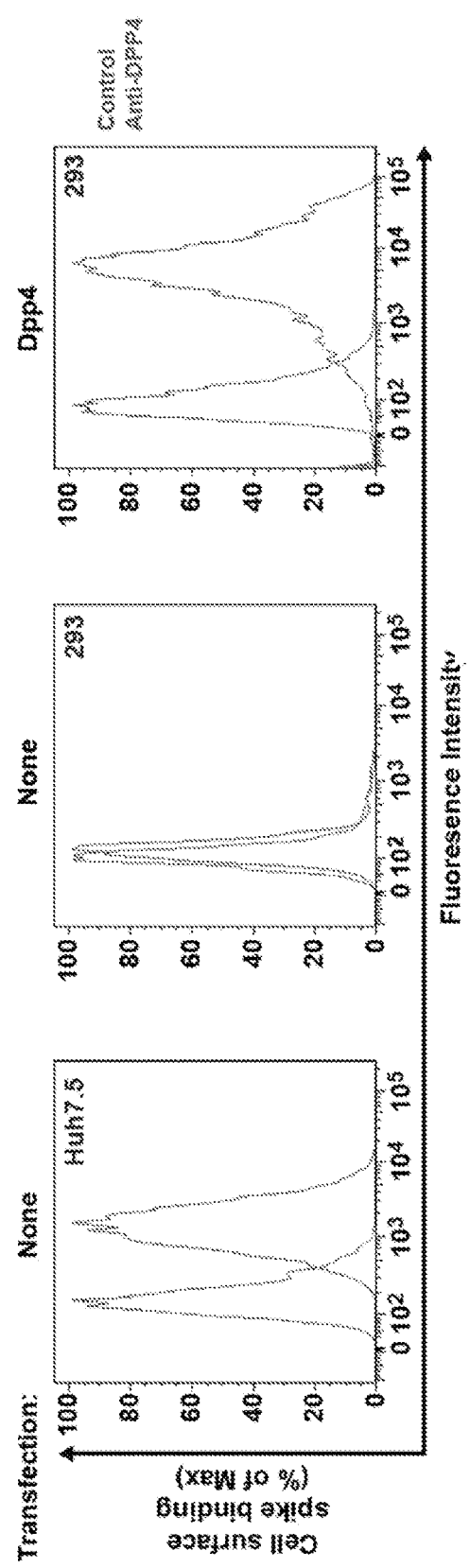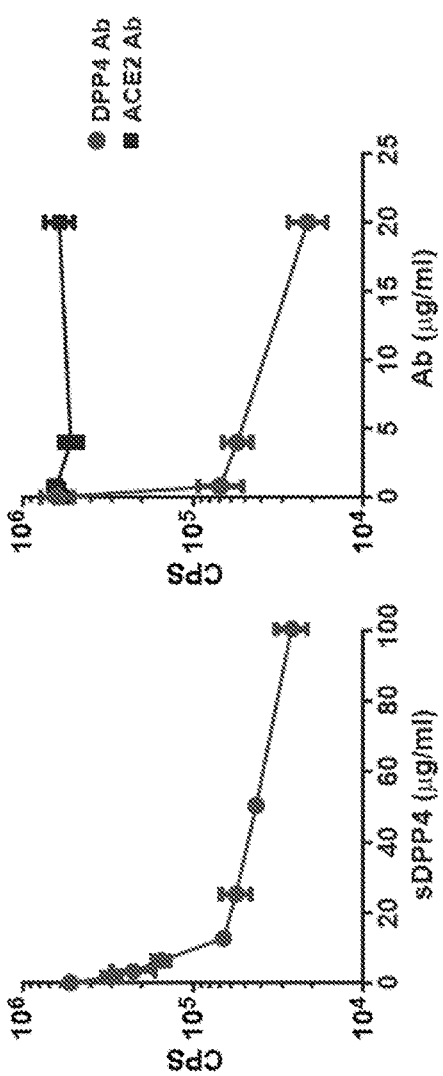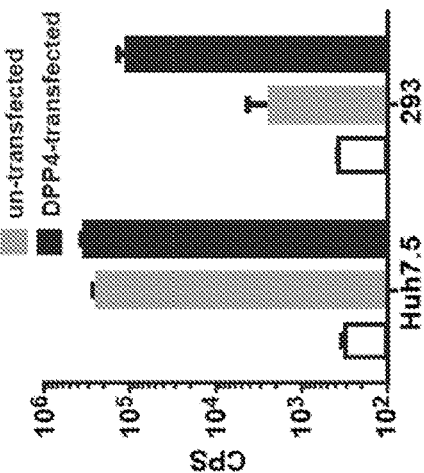
FIG. 6A
FIG. 6B
FIG. 6C
FIG. 6D

FIG. 8

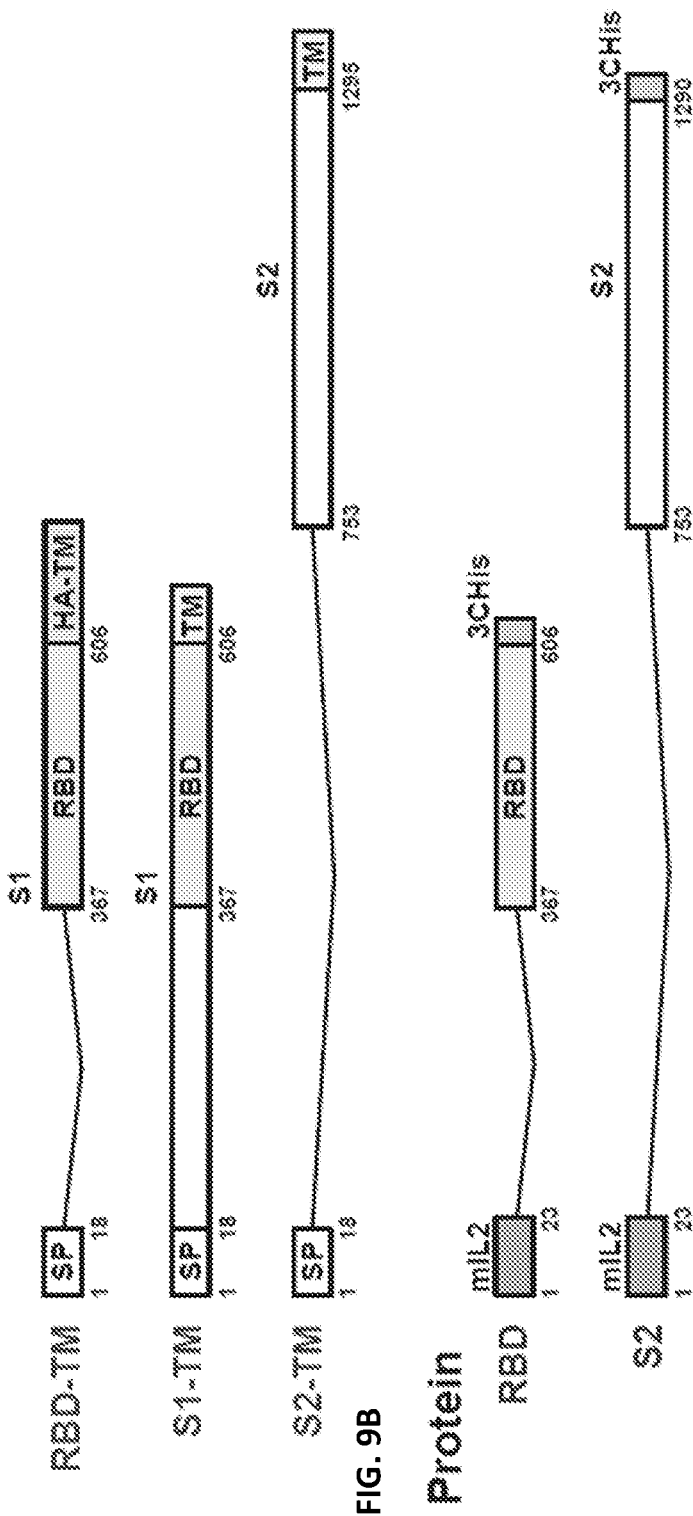

FIG. 11

| | mAb | Neutralization | Binding | | | Western Blot |
|---|---|---|---|---|---|---|
| | | Pseudovirus (England1) | ELISA | | | Denatured S |
| | | | RBDs | S1 | S-ΔTM | |
| RBD specific | A8 | 83.7 | 3.04 | 2.96 | 0.57 | No |
| | C7 | 83.7 | 3.11 | 1.95 | 0.27 | No |
| | C8 | 99.7 | 3.03 | 0.59 | 0.14 | No |
| | C9 | 85.6 | 3.11 | 0.77 | 0.12 | No |
| | C10 | 77.1 | 3.23 | 0.69 | 0.10 | No |
| | C12 | 86.3 | 3.19 | 0.73 | 0.05 | No |
| | D2 | 99.0 | 3.23 | 3.33 | 0.22 | No |
| | D6 | 44.5 | 3.14 | 3.01 | 0.28 | No |
| | D10 | 72.3 | 3.14 | 3.24 | 0.07 | No |
| | D12 | 99.8 | 3.31 | 3.26 | 0.05 | No |
| | E2 | 77.1 | 2.96 | 0.95 | 0.05 | No |
| | F10 | 99.2 | 3.17 | 2.64 | 0.11 | No |
| | F11 | 99.4 | 3.16 | 2.67 | 0.09 | No |
| S1 specific (non-RBD) | A6 | 70.0 | 0.06 | 1.88 | 2.75 | No |
| | A7 | 77.8 | 0.09 | 2.74 | 1.18 | No |
| | B4 | 32.2 | 0.05 | 0.87 | 0.05 | No |
| | B5 | 79.0 | 0.04 | 2.80 | 0.14 | No |
| | B11 | 65.4 | 0.05 | 0.74 | 0.96 | No |
| | B12 | 60.4 | 0.06 | 1.27 | 0.10 | No |
| | C1 | 21.6 | 0.03 | 2.82 | 0.14 | Yes |
| | C2 | 20.0 | 0.04 | 2.94 | 1.16 | Yes |
| | C3 | -1.7 | 0.05 | 2.97 | 0.34 | No |
| | D1 | 23.5 | 0.06 | 3.33 | 0.55 | Yes |
| | D8 | 8.08 | 0.04 | 1.85 | 0.12 | No |
| | F1 | 64.3 | 0.03 | 3.03 | 0.32 | No |
| | F4 | 2.2 | 0.05 | 3.17 | 2.35 | No |
| | F6 | 7.2 | 0.05 | 2.08 | 0.36 | No |
| | G2 | 80.9 | 0.04 | 3.15 | 0.58 | No |
| | G3 | 23.0 | 0.05 | 2.70 | 0.27 | No |
| | H5 | 4.8 | 0.05 | 3.09 | 2.61 | No |
| | H6 | 3.4 | 0.05 | 3.03 | 2.75 | No |
| | H7 | -2.0 | 0.04 | 3.05 | 2.76 | No |
| S2 specific | A3 | 85.3 | 0.25 | 0.05 | 2.33 | Yes |
| | A4 | 1.4 | 0.04 | 0.04 | 2.24 | No |
| | A10 | 85.3 | 0.05 | 0.05 | 2.48 | Yes |
| | A12 | 79.9 | 0.06 | 0.05 | 1.32 | No |
| | B2 | 39.2 | 0.04 | 0.05 | 2.12 | No |
| | C6 | 83.6 | 0.04 | 0.05 | 3.07 | No |
| | D5 | 50.7 | 0.04 | 0.05 | 2.69 | Yes |
| | F7 | 28.5 | 0.06 | 0.10 | 3.12 | Yes |
| | F8 | 59.9 | 0.06 | 0.06 | 3.81 | Yes |
| | F9 | 61.6 | 0.10 | 0.10 | 1.58 | No |
| | G1 | 69.1 | 0.06 | 0.05 | 3.09 | Yes |
| | F3 | 94.3 | 0.05 | 0.05 | 2.45 | No |
| | G4 | 87.5 | 0.05 | 0.06 | 2.80 | No |

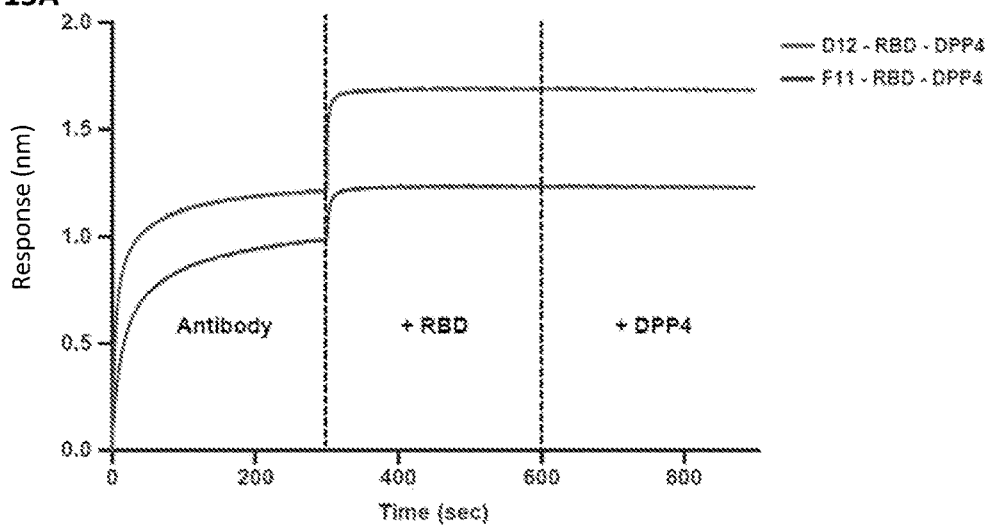
FIG. 15A Neutralizing antibodies block RBD binding to soluble DPP4
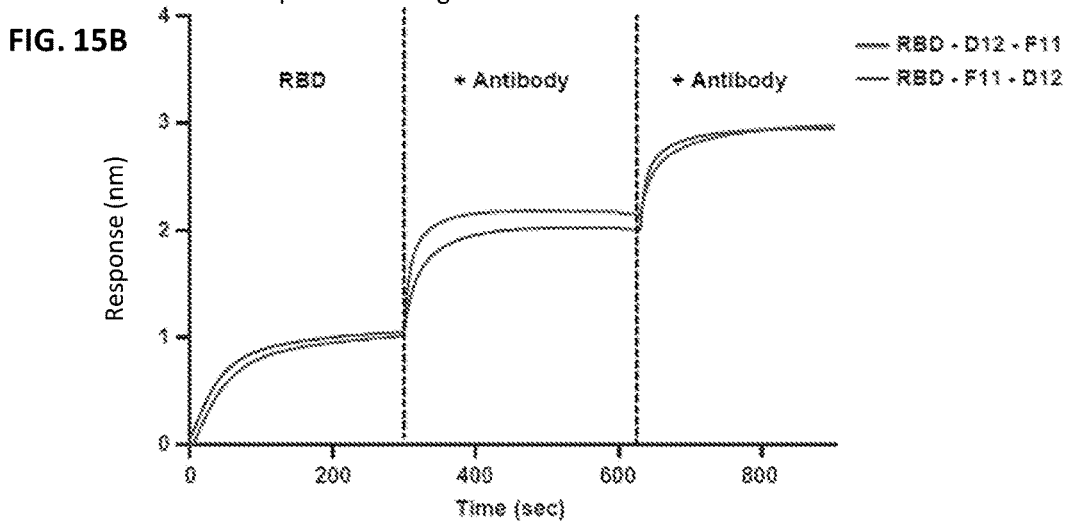
FIG. 15B Multiple neutralizing antibodies are accessible on RBD
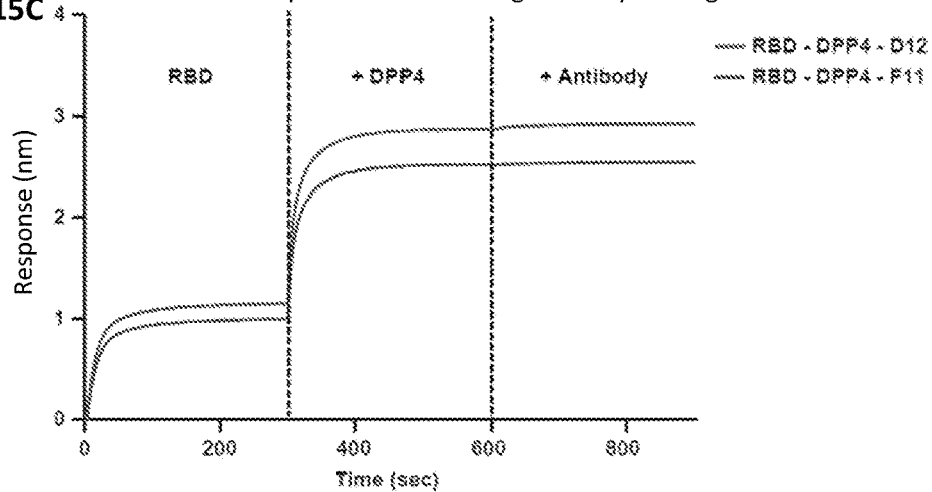
FIG. 15C Soluble DPP4 prevents neutralizing antibody binding

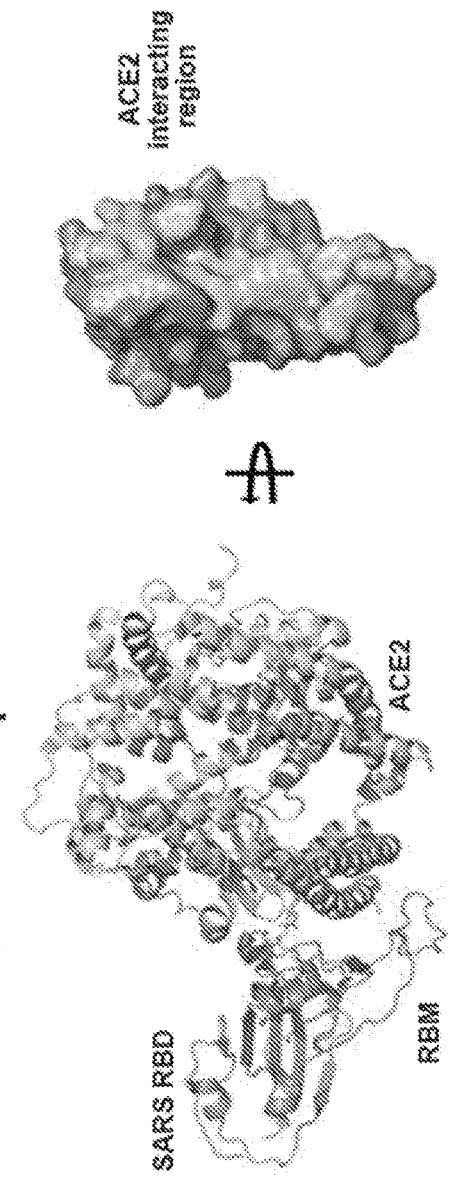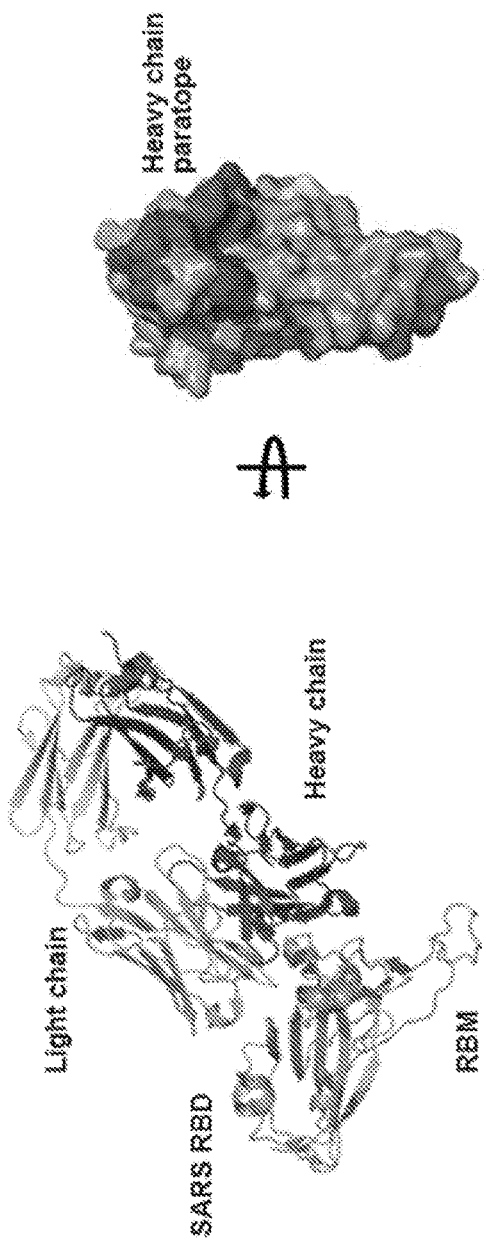
FIG. 16A  SARS RBD and ACE2 receptor
FIG. 16B  SARS RBD and M396 Fab (human FIG. 16C SARS RBD and F26G19 Fab (mouse vaccine induced)

FIG. 16D SARS RBD and 80R Fv (human phage display)

Unvaccinated control

2xDNA-Protein

2x Protein

FIG. 20

Supp. Table 1. Crystallographic data collection and refinement statistics

| | RBD England1 + D12 crystal form 1 | RBD England1 + D12 crystal form 2 | RBD England1 |
|---|---|---|---|
| PDB accession code | XXXX | YYYY | ZZZZ |
| Data collection | | | |
| Growth condition | 0.1 M sodium acetate pH 5.5, 50 mM sodium chloride, 10 % PEG 400, 11 % PEG 8,000 | 0.1 M sodium cacodylate pH 6.5, 80 mM magnesium acetate, 14.5 % PEG 8,000 | 0.1 M Tris-HCl pH 8.5, 10 % MPD, 29 % PEG 1,500 |
| Space group | $P2_12_12_1$ | $P2_12_12_1$ | $P2_12_12_1$ |
| Cell constants | | | |
| $a, b, c$ (Å) | 74.5, 128.8, 170.9 | 76.2, 106.1, 171.1 | 46.7, 109.9, 125.3 |
| $\alpha, \beta, \gamma$ (°) | 90.0, 90.0, 90.0 | 90.0, 90.0, 90.0 | 90.0, 90.0, 90.0 |
| Wavelength (Å) | 1.00 | 1.00 | 1.00 |
| Resolution (Å) | 50.0-2.65 (2.71-2.65) | 50.0-3.25 (3.36-3.25) | 50.0-3.17 (3.31-3.17) |
| $R_{merge}$ | 11.5 | 13.3 | 17.8 |
| No. unique reflections | 75350 (3346) | 40988 (2566) | 10616 (903) |
| $I/\sigma I$ | 9.3 (2.0) | 32.4 (2.0) | 5.7 (2.0) |
| Completeness (%) | 999.2 (99.7) | 85.4 (76.3) | 91.7 (81.3) |
| Refinement | | | |
| Resolution (Å) | 48.70-2.65 (2.72-2.65) | 50.0-3.25 (3.33-3.25) | 43.7-3.17 (3.31-3.17) |
| $R_{work} / R_{free}$ (%) | 18.5/24.8 | 22.5/26.7 | 22.1/25.0 |
| No. atoms | | | |
| Protein | 9710 | 9652 | 3222 |
| Ligand/ion | 762 | - | 167 |
| Water | 734 | 56 | 106 |
| B-factors | | | |
| Protein | 40.0 | 77.0 | 69.25 |
| NAG/ion | 110 | - | 127.2 |
| Water | 46.0 | 82.4 | 44.1 |
| R.m.s. deviations | | | |
| Bond lengths (Å) | 0.010 | 0.006 | 0.010 |
| Bond angles (°) | 1.2 | 1.42 | 1.22 |
| Ramachandran | | | |
| Most favored regions (%) | 95.2 | 95.2 | 95.0 |
| Additional allowed regions (%) | 4.0 | 4.0 | 4.3 |
| Disallowed regions (%) | 0.8 | 0.8 | 0.7 |

Values in parentheses are for the highest-resolution data shell

FIG. 21A

Supp. Table 2a. D12 antibody interactions with MERS England1 RBD

| | D12 antibody | MERS RBD | Distance (Å) |
|---|---|---|---|
| Hydrogen Bonds | | | |
| | H:SER 52[ OG ] | I:GLU 536[ OE1] | 2.5 |
| | H:SER 52a[ OG ] | I:ASP 539[ OD1] | 2.7 |
| | H:GLY 53[ N ] | I:GLU 536[ OE1] | 3.5 |
| | H:THR 55[ N ] | I:GLU 536[ OE1] | 3.6 |
| | H:THR 55[ OG1] | I:GLU 536[ OE2] | 2.7 |
| | H:TYR 58[ OH ] | I:LYS 496[ NZ ] | 3.3 |
| | H:TYR 58[ OH ] | I:TRP 535[ O ] | 3.1 |
| | H:GLY 96[ O ] | I:TRP 535[ NE1] | 3.0 |
| | H:SER 98[ OG ] | I:LYS 543[ NZ ] | 3.8 |
| | H:ASP 101[ OD2] | I:LYS 543[ NZ ] | 3.7 |
| | L:ASP 28[ OD2] | I:LYS 400[ NZ ] | 2.8 |
| | L:ASN 30[ ND2] | I:ASN 398[ O ] | 2.9 |
| | L:TYR 32[ OH ] | I:ASN 398[ ND2] | 2.8 |
| | L:ALA 91[ O ] | I:SER 532[ OG ] | 3.2 |
| | L:LEU 92[ O ] | I:SER 532[ OG ] | 2.4 |
| Salt bridges | | | |
| | H:ASP 101[ OD1] | I:LYS 543[ NZ ] | 3.9 |
| | H:ASP 101[ OD2] | I:LYS 543[ NZ ] | 3.7 |
| | L:ASP 28[ OD1] | I:LYS 400[ NZ ] | 3.9 |
| | L:ASP 28[ OD2] | I:LYS 400[ NZ ] | 2.8 |

FIG. 21B

Buried surface area of D12 antibody in complex with MERS England1 RBD. Residues that form hydrogen bonds and salt bridges are indicated.

D12 antibody

| Residue | Bond type | Accessible Surface Area (Å²) | Buried Surface Area (Å²) |
|---|---|---|---|
| H:SER 31 |  | 74.7 | 28.7 |
| H:TYR 32 |  | 69.7 | 25.0 |
| H:ALA 33 |  | 24.5 | 18.9 |
| H:TRP 47 |  | 88.6 | 3.1 |
| H:THR 50 |  | 24.0 | 22.7 |
| H:SER 52 | H | 27.2 | 27.2 |
| H:SER 52a | H | 41.9 | 27.9 |
| H:GLY 54 | H | 59.3 | 7.9 |
| H:THR 55 | H | 109.9 | 13.3 |
| H:TYR 56 |  | 136.2 | 45.6 |
| H:TYR 58 | H | 117.1 | 68.8 |
| H:ASP 95 |  | 14.4 | 5.7 |
| H:GLY 96 | H | 59.4 | 48.0 |
| H:ASN 97 |  | 152.4 | 86.7 |
| H:SER 98 | H | 60.9 | 6.9 |
| H:ASP 101 | HS | 68.4 | 22.5 |
| L:GLN 27 |  | 103.7 | 11.1 |
| L:ASP 28 | HS | 92.2 | 31.9 |
| L:ASN 30 | H | 87.1 | 65.3 |
| L:TYR 32 | H | 84.5 | 74.4 |
| L:LEU 46 |  | 50.9 | 6.3 |
| L:TYR 49 |  | 94.6 | 68.4 |
| L:TYR 50 |  | 81.1 | 51.7 |
| L:ARG 53 |  | 118.1 | 39.1 |
| L:LEU 54 |  | 66.9 | 12.7 |
| L:ASP 55 |  | 50.4 | 5.3 |
| L:SER 56 |  | 107.2 | 33.0 |
| L:GLY 68 |  | 24.7 | 3.2 |
| L:ALA 91 | H | 49.2 | 10.9 |
| L:LEU 92 | H | 66.2 | 28.2 |
| L:SER 93 |  | 53.0 | 10.5 |
| L:SER 94 |  | 109.4 | 22.1 |
| L:SER 96 |  | 64.1 | 0.9 |

FIG. 21C

MERS England1 RBD

| Residue | Bond type | Accessible Surface Area (Å²) | Buried Surface Area (Å²) |
|---|---|---|---|
| I:THR 392 | | 78.7 | 14.8 |
| I:PRO 394 | | 29.6 | 13.0 |
| I:TYR 397 | | 1.4 | 1.4 |
| I:ASN 398 | H | 42.0 | 37.6 |
| I:PHE 399 | | 4.0 | 2.6 |
| I:LYS 496 | H | 54.2 | 32.7 |

| Residue | Bond type | Accessible Surface Area (Å²) | Buried Surface Area (Å²) |
|---|---|---|---|
| I:TYR 523 | | 86.0 | 0.7 |
| I:PRO 525 | | 59.5 | 1.7 |
| I:VAL 527 | | 53.6 | 42.1 |
| I:SER 528 | | 88.3 | 88.3 |
| I:ILE 529 | | 17.9 | 14.4 |
| I:VAL 530 | | 10.2 | 10.2 |
| I:PRO 531 | | 35.9 | 30.8 |
| I:SER 532 | H | 84.9 | 74.4 |
| I:THR 533 | | 43.0 | 0.6 |
| I:TRP 535 | H | 191.2 | 158.4 |
| I:GLU 536 | H | 113.9 | 87.8 |
| I:ASP 537 | | 84.0 | 5.5 |
| I:ASP 539 | H | 36.7 | 27.6 |
| I:TYR 540 | | 145.3 | 22.3 |
| I:TYR 541 | | 28.4 | 10.9 |
| I:ARG 542 | | 113.4 | 27.4 |
| I:LYS 543 | HS | 121.6 | 117.2 |
| I:GLN 544 | | 123.3 | 36.3 |
| I:LEU 545 | | 30.8 | 2.3 |
| I:SER 546 | | 49.9 | 11.2 |
| I:GLU 549 | | 101.6 | 12.9 |
| I:TRP 553 | | 77.5 | 2.4 |
| I:THR 560 | | 32.3 | 3.6 |

H: Hydrogen bond; S: Salt bridge

|  | Mouse | NHP | Human |
|---|---|---|---|
| RBD-specific | F11<br>D12 | JC57-11<br>JC57-14 | C2<br>C5 |
| S1-specific | G2 | JC57-13<br>FIB_B2<br>FIB_H1 | A2<br>A10 |
| S2-specific | G4 | | |

FIG. 23
NHP mAbs
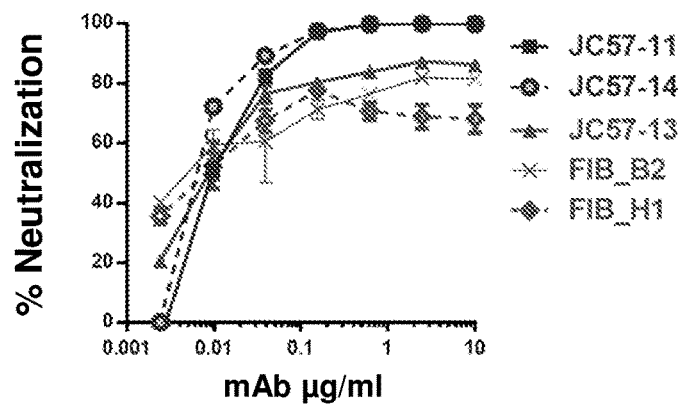
Human mAbs
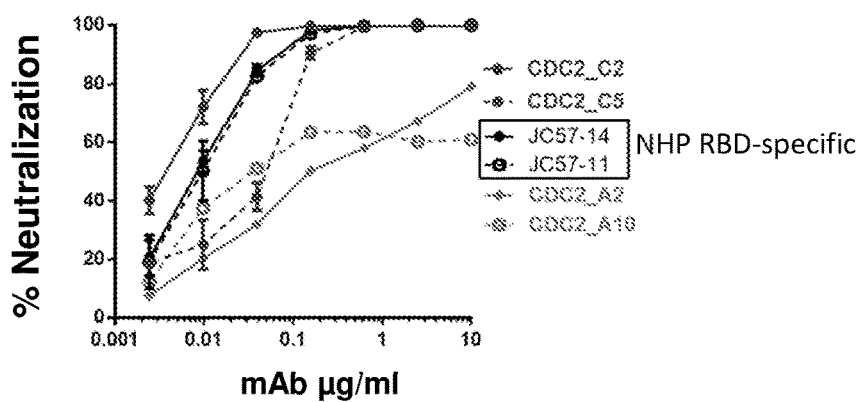
Mouse mAbs
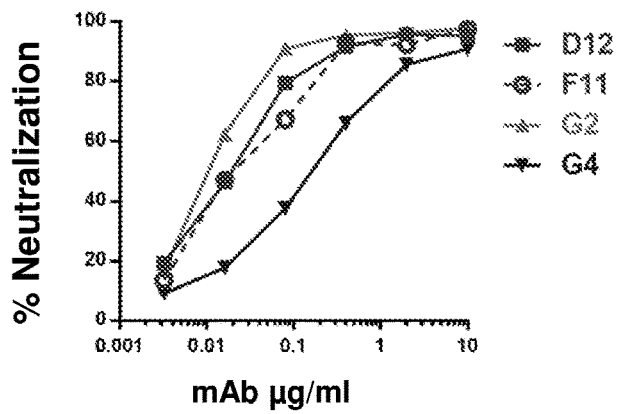

MIDDLE EAST RESPIRATORY SYNDROME CORONAVIRUS IMMUNOGENS, ANTIBODIES, AND THEIR USE

CROSS REFERENCE TO RELATED APPLICATIONS

This is the U.S. National Stage of International Application No. PCT/US2016/019395, filed Feb. 24, 2016, which was published in English under PCT Article 21(2), which in turn claims the benefit of U.S. Provisional Application No. 62/120,353, filed Feb. 24, 2015. The provisional application is incorporated by reference herein in its entirety.

FIELD OF THE DISCLOSURE

This disclosure relates to recombinant Middle East respiratory syndrome coronavirus (MERS-CoV) polypeptides, immunogenic fragments thereof, and monoclonal antibodies specific for same, for treatment and prevention of MERS-CoV infection and disease.

BACKGROUND

MERS-CoV has emerged as a highly fatal cause of severe acute respiratory infection. Thousands of infections and hundreds of deaths have been attributed to the novel beta-coronavirus. As human-to-human transmission of the virus is not sustained, a large zoonotic reservoir may serve as a principal source for transmission events. The high case fatality rate, vaguely defined epidemiology, and absence of prophylactic or therapeutic measures against this novel virus have created an urgent need for an effective vaccine and related therapeutic agents.

SUMMARY

Disclosed herein are new methods for inducing an immune response to MERS-CoV spike (S) protein that are surprisingly effective for inducing neutralizing antibody responses to MERS-CoV in a subject. The methods are useful, for example, for preventing or treating a MERS-CoV infection in the subject.

In several embodiments, the method includes administering a prime-boost vaccination to the subject, comprising administering a nucleic acid molecule encoding a MERS-CoV S protein, and polypeptide comprising or consisting of a S1 subunit of the MERS-CoV S protein (MERS-CoV S1 protein), to the subject to generate the immune response to the MERS-CoV S protein. In a non-limiting example, the prime-boost vaccination can comprise a prime comprising administering the nucleic acid molecule encoding the MERS-CoV S protein to the subject, a first boost, comprising administering a therapeutically effective amount of the nucleic acid molecule encoding the MERS-CoV S protein to the subject, and a second boost comprising administering a therapeutically effective amount of a MERS-CoV S1 protein to the subject. In some embodiments, the MERS-CoV S protein can comprise or consist of the amino acid sequence set forth as SEQ ID NO: 14, and/or the MERS-CoV S1 protein can comprise or consist of the amino acid sequence set forth as SEQ ID NO: 16.

Additionally, novel immunogens including the MERS-CoV S protein or a fragment thereof (such as the receptor binding domain, RBD) are provided. In some embodiments, a polypeptide including the RBD of MERS-CoV S protein linked to a protein nanoparticle is provided, which can be used to generate protein nanoparticles that display the MERS-CoV S protein RBD. Nucleic acid molecules encoding the polypeptides are also provided.

The disclosure also provides isolated monoclonal antibodies and antigen binding fragments that specifically bind to an epitope on MERS-CoV S protein. Also disclosed are compositions including the antibodies and antigen binding fragments, nucleic acids encoding the antibodies and antigen binding fragments, expression vectors comprising the nucleic acids, and isolated host cells that express the nucleic acids. The antibodies and antigen binding fragments can neutralize MERS-CoV infection, and therefore can be used in methods of treating or preventing a MERS-CoV infection in a subject. The methods include administering a therapeutically effective amount of one or more of the antibodies, antigen binding fragments, nucleic acid molecules, vectors, or compositions disclosed herein, to the subject, for example to a subject at risk of or having MERS-CoV infection.

The foregoing and other features and advantages of this disclosure will become more apparent from the following detailed description of several embodiments which proceeds with reference to the accompanying figures.

BRIEF DESCRIPTION OF THE FIGURES

FIGS. 4A-4E illustrate the molecular characterization of MERS-CoV neutralizing mAbs. Vaccine-induced mAb D12 binds directly to the DPP4 interacting region of the MERS-CoV Spike receptor binding domain (RBD) and effect neutralization by directly blocking receptor binding. (A) (left) Comparison of RBD binding to D12 antibody and RBD binding by DPP4. RBD with receptor binding motif (RBM, residues 484-567, magenta) and D12 are shown in cartoon representation. The main interacting regions are contained within CDR H2, CDR H3, and CDR L2. (right) DPP4 is shown in cartoon format with Asparagine 229 and attached N-glycan shown in stick representation. The RBD molecule is oriented identical to (left). (B) Interfaces for antibody:RBD and DPP4:RBD crystal structure complexes. (left) RBD in surface representation is shown with the D12 heavy chain and light chain paratopes, respectively. The CDR loops are shown in ribbon representation. (center) The RBD is rotated to show the full D12 paratope with D12 CDR H2 interacting with the RBD W535 and E536 residues that predominantly interact with the Asparagine 229 associated N-glycan on DPP4. (right) RBD is shown in surface representation with the DPP4 interacting region. Major interacting regions from DPP4 are shown in cartoon representation with asparagine 229 and N-glycan also shown in stick representation in the same way as is shown for the SARS mAbs (FIG. 16). (C) Crystal structure of MERS-CoV England1 RBD and effect of critical RBD mutations on binding. (D) D12 and RBD interface. All CDRs are shown in cartoon format and interacting residues are shown in stick representation with hydrogen bonds depicted by dotted lines. (D, E) RBD residues 506 and 509 that have been observed with various mutations in isolated viruses are highlighted in green. Critical RBD residues identified by structural definition and viral resistance evolution 532, 535 and 536 that reduce or eliminate D12 binding are highlighted. ELISA results show that these mutations can effectively eliminate F11 or D12 binding.

FIGS. 6A-6D illustrate that MERS-CoV pseudovirus utilizes human DPP4 to transduce target cells. (A) DPP4 expression on the cell surface. Huh7.5 cells (left panel), DPP4-untransfected 293 cells (middle panel), and DPP4-transfected 293 cells (right panel) were stained with goat anti-DPP4 antibody and control antibody and analyzed by flow cytometry. (B) Transduction of DPP4-expressing cells by pseudotyped MERS-CoV England1 virus. Huh7.5 and 293 cells without and with DPP4-transfection (in grey and black bars) were transduced by MERS-CoV pseudotyped virus. Relative expression of luciferase activity was measured (CPS). Untransfected and untransduced cells were used as the background control (open bars). (C) Transduction of Huh7.5 cells by MERS-CoV pseudovirus was blocked by soluble human DPP4 (sDPP4). MERS-CoV England1 pseudovirus was incubated with soluble human DPP4 before transduction of Huh7.5 cells. Relative luciferase activity (CPS) is shown. (D) Transduction of Huh7.5 cells by MERS-CoV pseudovirus was blocked by anti-DPP4, but not anti-ACE2 antibody. Huh7.5 cells were incubated with anti-DPP4 or anti-ACE2 polyclonal antibodies and then transduced with MERS-CoV England1 pseudovirus. Relative luciferase activity (CPS) is shown.

FIG. 8 illustrates that MERS-CoV vaccine elicited virus neutralization responses as measured by both pseudotyped and live virus neutralization assays. Eight groups of mice were immunized as indicated in FIG. 1. Neutralizing antibodies from sera five weeks after last vaccine boost were measured by a pseudovirus neutralization assay (black bars) and live virus micro-neutralization assay (open bars) to MERS-CoV JordanN3 respectively.

FIGS. 9A-9C illustrate that MERS-CoV S DNA immunization induced antibody binding to both S1 and S2. (A and B) Schematic representation of MERS-CoV Spike DNA and protein constructs used for cell adsorption assays. (C) Sera from mice immunized with MERS-CoV S DNA, primed with S DNA and boosted with S1 protein plus Ribi adjuvant, or primed and boosted with S1 protein plus Ribi adjuvant were assayed by flow cytometry for their binding to cell surface-expressed MERS-CoV Spike proteins. 293T cells transfected with MERS-CoV S, RBD-HATM, S1-TM and S2-TM were incubated with sera from the three immunization groups (1:200 dilution) and then stained with anti-mouse PE conjugate. S: Spike glycoprotein, RBD: receptor binding domain, HA: hemagglutinin, TM: transmembrane.

FIG. 11 illustrates identification of monoclonal antibodies against the MERS-CoV Spike glycoprotein. Immunized mice in both DNA and protein vaccine groups had their spleens harvested three days after an additional S1 protein. Splenocytes were then fused with Sp2/0 myeloma cells to generate hybridomas that underwent three rounds of screening for binding to the S1, RBD, and S2 domains. The final round of screens generated 45 subclones. Supernatant from the subclones culture were subjected to neutralization and binding tests. Percentage of neutralization against pseudoviruses of Eng1 strain from the subclones was determined and is shown. Supernatants from the subclones were assessed for binding to the RBDs, S1 and S-ΔTM proteins. Western blot analysis was done to assess whether the subclones can recognize denatured S linear epitopes. Based on the ELISA binding data, the mAbs were classified into three groups: RBD specific, S1 specific (non-RBD) and S2 specific as indicated. Four of these mAbs (D12, F11, G2 and G4) were selected for additional characterization based on their antigenic specificity and high neutralization potency.

FIGS. 15A-15C illustrate the assessment of D12 and F11 interactions with MERS-CoV RBD. (A) D12 and F11 directly block RBD binding to DPP4. Mouse monoclonal antibodies D12 and F11 were loaded onto AMC probes for 300 s and association with MERS-CoV RBD was allowed to proceed for 300 s, followed by incubation with soluble DPP4 for 300 s with the responses measured in nm using an Octet Red 384 machine. (B) Multiple neutralizing epitopes are accessible on MERS CoV RBD. MERS CoV RBD was loaded onto anti-penta-His probes for 300 s followed by sequential binding of both D12 and F11 mAbs. (C) Soluble DPP4 prevents binding of RBD to D12 and F11 mAbs. MERS CoV RBD was loaded onto anti-penta-His probes for 300 s followed by sequential binding of DPP4 and either D12 or F11 mAbs. All experiments were carried out at 30° C. in PBS buffer (pH 7.4) supplemented with 1% BSA to minimize non-specific binding. The dotted line indicates the beginning of incubation with the second and third ligand in each of the experiments.

FIGS. 16A-16D show published structures of SARS-CoV neutralizing antibodies that effectively block the receptor interacting region of the virus. (A) SARS receptor binding domain (RBD) with the receptor binding motif (RBM) and the ACE2 receptor are shown in cartoon representation. The ACE2 interacting region is mapped onto the SARS RBD (surface representation, rotated). The RBD region that interacts with the ACE2 glycan is shown. (B-D) SARS RBD and M396 Fab (Prabakaran et al., J Biol Chem 281, 15829, 2006; Zhu et al., PNAS 104, 12123, 2007), F26G19 Fab (Pak et al., J mol biol 388, 815, 2009) and 80R Fv (Hwang et al., J biol chem 281, 34610, 2006) are shown in cartoon representation. The antibody interacting region is mapped onto the RBD.

FIG. 20 is a table showing crystallographic data collection and refinement statistics for the crystal structure of D12 Fab with the MERS-CoV RBD (England1 strain).

FIGS. 21A-21C are a set of tables showing D12 antibody interactions with MERS-CoV S protein RBD (England1 strain) as determined from the crystal structure of D12 Fab with the RBD.

FIG. 23 shows a set of graphs illustrating the neutralization activity of identified NHP antibodies (JC57-11, JC57-14, JC57-13, FIB_B2, and FIB_H1), human antibodies (C2, C5, A2, and A10), and murine antibodies (D12, F11, G2 and G4). Neutralization activity was assayed using a pseudovirus neutralization assay for the MERS-CoV EMC strain as described in the examples.

SEQUENCES

Figure 1A:
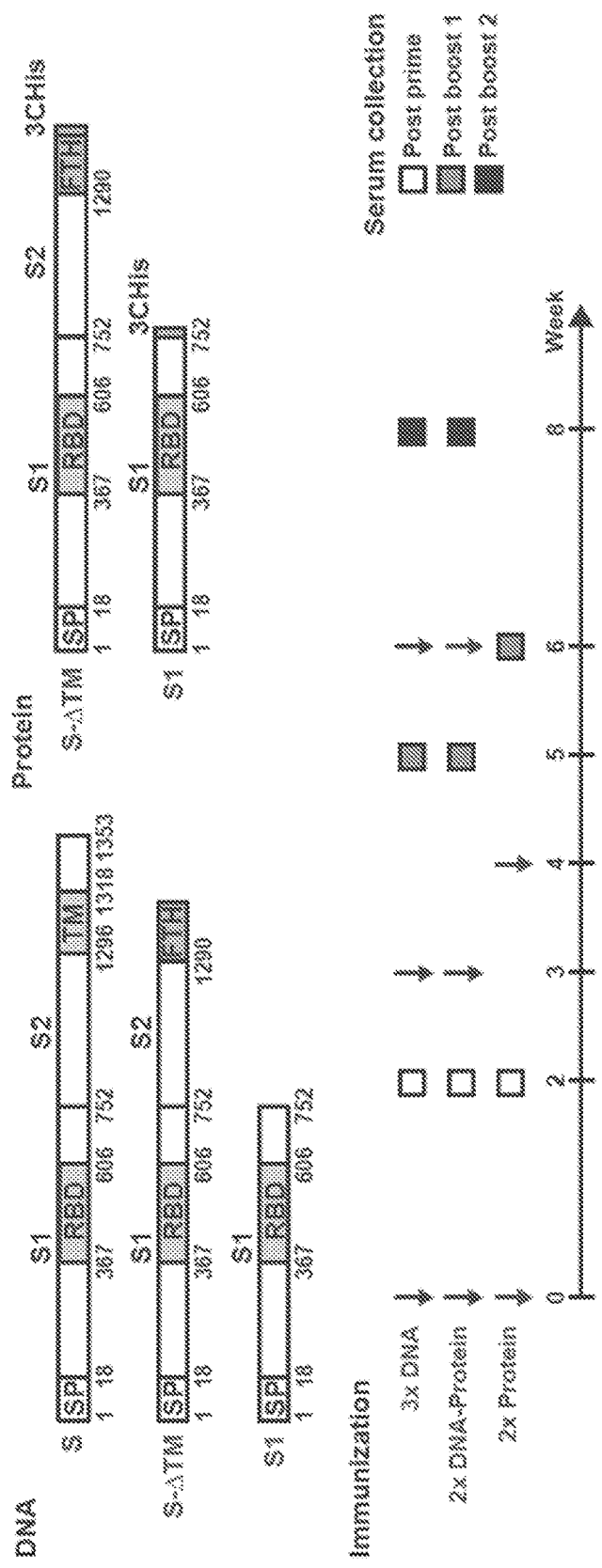
FIGS. 1A-1C illustrate MERS-CoV Spike glycoprotein vaccine design and immunogenicity in mice. Candidate vaccine immunogens were designed around the sole surface glycoprotein of beta-coronaviruses. (A) Schematic representation of MERS-CoV S protein cDNAs and recombinant proteins. Five vaccine constructs were made: three DNA and two protein subunits. DNA constructs consisted of full-length S or truncated versions that either had the transmembrane domain or the entire S2 subunit deleted. The protein constructs contain either a truncated S molecule with the transmembrane domain deleted (S-ΔTM) or the S1 subunit. RBD: receptor binding domain; SP: signal peptide, TM: transmembrane domain; FTH: Foldon (trimerization domain), Thrombin (cleavage site) followed by histidine tag; 3CHis: Human rhinovirus 3C protease cleavage site, followed by 6× histidine tag. (B) Immunogenicity of eight vaccine regimens. Five mice per group were immunized with plasmid DNA only at weeks 0, 3 and 6 (groups 1-3); plasmid DNA at weeks 0 and 3 and protein plus Ribi adjuvant at week 6 (groups 4-6); or protein plus Ribi adjuvant at weeks 0 and 4 (groups 7, 8). Two weeks after each immunization, neutralizing antibody titers were measured against pseudotyped MERS-CoV England1 virus. Open, grey and black bars respectively represent the $IC_{90}$ neutralization titers (GMT with 95% CI) from the post-prime, first post-boost, and second post-boost sera. A non-parametric two-tailed t-test (Mann-Whitney) was used for statistical analysis, and the relevant P values are indicated. (C) MERS-CoV vaccines induced cross-neutralization to eight MERS-CoV strains. The sera from the mice immunized with MERS-CoV S DNA three times, primed with S DNA and boosted with S1 protein plus Ribi adjuvant, or primed and boosted with S1 protein plus Ribi adjuvant were assayed for neutralization to the eight strains of MERS-CoV and SARS-CoV pseudotyped viruses as indicated. $IC_{90}$ titer is shown. Data are presented as the mean of triplicates with standard errors.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~164 kb), which was created on Aug. 23, 2017, and which is incorporated by reference herein. In the accompanying sequence listing:

SEQ ID NO: 1 is an exemplary nucleotide sequence encoding the $V_H$ of the JC57-13 non-human primate (NHP) antibody (VRC 4230).
caggtgcagctgcaggagtcgggcccaggactggtgaagccttcggagac cctgtccctcacctgcgccgtctctggtggctccatcagcagtaactact ggaactggatccgccagtccccagggaaggggctagagtggattgggtat atctatggtggtagtgggagcaccacctacaacccctccctcaagagtcg agtcgccatttcaacagacacgtccaaggaccagttttccctgaagctga gctctgtgaccgccgcggacaccgccgtatattactgtgcgagactgctg cccttagggggggatactgctttgactactggggccagggagtcctggt caccgtctcctca SEQ ID NO: 2 is the amino acid sequence of the $V_H$ of the JC57-13 NHP antibody (VRC 4230).
QVQLQESGPGLVKPSETLSLTCAVSGGSISSNYWNWIRQSPGKGLEWIGY

IYGGSGSTTYNPSLKSRVAISTDTSKDQFSLKLSSVTAADTAVYYCARLL

PLGGGYCFDYWGQGVLVTVSS

SEQ ID NO: 3 is an exemplary nucleotide sequence encoding the $V_L$ of the JC57-13 NHP antibody (VRC 4231).
Gatattgtgatgacccagactccattcaccctgcccgtcacccctggaga ggcggcctccatctcctgcaggtctagtcagagcctcttcgatagtgatt atggaaacacctatttggattggtatctgcagaagccaggccagtctcca cagctcctgatctatatgctttccaacgggcctctggagtccctgatag gttcagtggcagtgggtcaggcactgatttcacactgaaaatcagccggg tggaggctgaggatgttgggttatattactgcatgcaaagtgtagagtat ccattcactttcggccccgggaccaaactggatatcaaa SEQ ID NO: 4 is the amino acid sequence of the $V_L$ of the JC57-13 NHP antibody (VRC 4231).
DIVMTQTPFTLPVTPGEAASISCRSSQSLFDSDYGNTYLDWYLQKPGQSP

QLLIYMLSNRASGVPDRFSGSGSGTDFTLKISRVEAEDVGLYYCMQSVEY

PFTFGPGTKLDIK

SEQ ID NO: 5 is an exemplary nucleotide sequence encoding the $V_H$ of the JC57-11 NHP antibody (VRC 4232).
Gaggtgcagctgctggagtcgggcccaggagtggtgaggccttcggagac cctgtccctctcctgcgctgtctctggtggctccatcagcgatagttacc ggtggagctggatccgccagcccccagggaagggactggagtgggttggc tacatctttgctactggtacgaccaccaactacaaccctccctcaagag tcgagtcaccatttcaaaagacacgtccaagaaccagttctccttgaagc tgagctctgtgaccgccgcggacacggccgtttactactgtgcgagagag ccgttcaaatattgtagtggtggtgtctgctatgcccacaaggacaactc attggatgtctggggccagggagttctggtcaccgtctcctca SEQ ID NO: 6 is the amino acid sequence of the V$_H$ of the JC57-11 NHP antibody (VRC 4232).
EVQLLESGPGVVRPSETLSLSCAVSGGSISDSYRWSWIRQPPGKGLEWVG

YIFATGTTTNYNPSLKSRVTISKDTSKNQFSLKLSSVTAADTAVYYCARE

PFKYCSGGVCYAHKDNSLDVWGQGVLVTVSS

SEQ ID NO: 7 is an exemplary nucleotide sequence encoding the V$_L$ of the JC57-11 NHP antibody (VRC 4233).
Gaaattgtgatgacgcagtctccagccaccctgtctttgtctccagggga aagagccactctctcctgcagggccagtcagagtgttagtagcaacttag cctggtaccagcagaaacctgggcaggctcccaggctcctcatccacagt gcgtccagcagggccactggcatcccagacaggttcagtggcagcgggtc tgggacagagttcagtctcaccatcagcagtctggaggctgaagatgttg gagtttatcactgctatcagcatagcagcgggtacactttcggccccggg accaaactggatatcaaa SEQ ID NO: 8 is the amino acid sequence of the V$_L$ of the JC57-11 NHP antibody (VRC 4233).
EIVMTQSPATLSLSPGERATLSCRASQSVSSNLAWYQQKPGQAPRLLIHS

ASSRATGIPDRFSGSGSGTEFSLTISSLEAEDVGVYHCYQHSSGYTFGPG

TKLDIK

SEQ ID NO: 9 is an exemplary nucleotide sequence encoding the V$_H$ of the JC57-14 NHP antibody (VRC 4234).
Gaggtgcagctgcaggagtcgggcccaggactggtgaagccttcggagac cctgtccctcacctgcgctgtctctggtgactccatcagcagtaactact ggagctggatccgccagcccccagggaagggactggagtggattggacgt ttctctggtagtggtgggagcaccgacttcaaccccctccctcaagagtcg ggtcaccatttcaacagacacgtccaagaaccagttctccctgaacctga ggtctgtgaccgccgcggacacggccgtgtattactgtgcgaaaacctat agcggcacctttgactactggggccagggagtcctggtcaccgtctcctc a SEQ ID NO: 10 is the amino acid sequence of the V$_H$ of the JC57-14 NHP antibody (VRC 4234).
QVQLQESGPGLVKPSETLSLTCAVSGDSISSNYWSWIRQPPGKGLEWIGR

FSGSGGSTDFNPSLKSRVTISTDTSKNQFSLNLRSVTAADTAVYYCAKTY

SGTFDYWGQGVLVTVSS

SEQ ID NO: 11 is an exemplary nucleotide sequence encoding the V$_L$ of the JC57-14 NHP antibody (VRC 4235).
Gacattcagatgacgcagtctccatcctccctgtctgcatctgtaggaga cagagtcaccatcacttgccgggcgagtcaggacattaacaattatttaa gttggtatcagcagaaaccagggaaagcccctaagcccctgatctattat gcatccagtttggaaacaggagtaccttcaaggttcagtggaagtagatc tgggacagattacactctcaccatcagcagtctgcagcttgaagattttg caacatattactgtcaacagtataataattccccgtacagttttggccag gggaccaaagtggagatcaaa SEQ ID NO: 12 is the amino acid sequence of the V$_L$ of the JC57-14 NHP antibody (VRC 4235).
DIQMTQSPSSLSASVGDRVTITCRASQDINNYLSWYQQKPGKAPKPLIYY

ASSLETGVPSRFSGSRSGTDYTLTISSLQLEDFATYYCQQYNNSPYSFGQ

GTKVEIK

SEQ ID NOs: 13 and 14 are nucleic acid and protein sequences of the full-length MERS-CoV S protein, England1 strain.

SEQ ID NOs: 15 and 16 are nucleic acid and protein sequences of the S1 subunit of the MERS-CoV S protein, England1 strain.

SEQ ID NOs: 17 and 18 are nucleic acid and protein sequences of a fragment of the MERS-CoV S protein, England1 strain, including the receptor binding domain (RBD).

SEQ ID NOs: 19 and 20 are nucleic acid and protein sequences of the S-ΔTM fragment of the MERS-CoV S protein, England1 strain.

SEQ ID NO: 21 is the amino acid sequence of a ferritin nanoparticle subunit.

SEQ ID NOs: 22 and 23 are amino acid sequences of MERS-CoV S protein RBD domains linked to a ferritin nanoparticle subunit.

SEQ ID NOs: 24 and 25 are the amino acid sequences of signal peptides.

SEQ ID NOs: 26 and 27 are polynucleotide sequences encoding MERS-CoV S protein RBD domains linked to a ferritin nanoparticle subunit.

SEQ ID NO: 28 is the amino acid sequence of a lumazine synthase nanop article subunit.

SEQ ID NO: 29 is the amino acid sequence of an encapsulin nanoparticle subunit.

SEQ ID NOs: 30 and 31 are amino acid sequences of MERS-CoV S protein RBD domains linked to an encapsulin nanoparticle subunit.

SEQ ID NOs: 32 and 33 are polynucleotide sequences encoding MERS-CoV S protein RBD domains linked to an encapsulin nanoparticle subunit.

SEQ ID NO: 34 is the amino acid sequence of a Sulfur Oxygenase Reductase nanoparticle subunit.

SEQ ID NO: 35 is an exemplary nucleotide sequence encoding the V$_H$ of the C2 human antibody (VRC 4792).
Caggtgcagctggtgcagtctggggctgaggtgaagaagcctggggtcctc ggtgaaggtctcctgcaaggcttctggaggcaccttcagcatctatgcta tcagctgggtgcgacaggcccctggacaagggcttgagtggatgggaggg atcatccctatctttggtacagcaaactacgcacagaagttccagggcag agtcacgattaccgcggacaaatccacgagcacagcctacatggagctga gcagcctgagatctgaggacacggccgtgtattactgtgcgagagagggg ggccaccagggatattgtagtggtggtagctgctacgactttgactactg gggccagggaaccctggtcaccgtctcctca SEQ ID NO: 36 is the amino acid sequence of the V$_H$ of the C2 human antibody (VRC 4792)
QVQLVQSGAEVKKPGSSVKVSCKASGGTFSIYAISWVRQAPGQGLEWMGG

IIPIFGTANYAQKFQGRVTITADKSTSTAYMELSSLRSEDTAVYYCAREG

GHQGYCSGGSCYDFDYWGQGTLVTVSS

SEQ ID NO: 37 is an exemplary nucleotide sequence encoding the V$_L$ of the C2 human antibody (VRC 4793).
gatgttgtgatgactcagtctccactctccctgcccgtcaccctggaga gccggcctccatctcctgcaggtctagtcagagcctcctgcatagtaatg gatacaactatttggattggtacctgcagaagccagggcagtctccacag ctcctgatctatttgggttctaatcgggcctccggggtccctgacaggtt cagtggcagtggatcaggcacagattttacactgaaaatcagcagagtgg aggctgaggatgttggggtttattattgcatgcaagctctacaaactcct gcgttcggcggagggaccaagctggagatcaaa SEQ ID NO: 38 is the amino acid sequence of the V$_L$ of the C2 human antibody (VRC 4793).
DVVMTQSPLSLPVTPGEPASISCRSSQSLLHSNGYNYLDWYLQKPGQSPQ

LLIYLGSNRASGVPDRFSGSGSGTDFTLKISRVEAEDVGVYYCMQALQTP

AFGGGTKLEIK

SEQ ID NO: 39 is an exemplary nucleotide sequence encoding the V$_H$ of the C5 human antibody (VRC 4794).
cagctgcagctgcaggagtcgggcccaggactggtgaagccttcggagac cctgtccctcacctgcactgtctctggtggctccatcagcagtagtagtt actactggggctggatccgccagcccccagggaaggggctggagtggatt gggagtatctattatagtgggagcacctactacaacccgtccctcaagag tcgagtcaccatatccgtagacacgtccaagaaccagttctccctgaagc tgagctctgtgaccgccgcagacacggctgtgtattactgtgcgagcctc ttaaggcccctgatttattgtagtggtggtagctgcaccgactactgggg ccagggaaccctggtcaccgtctcctca SEQ ID NO: 40 is the amino acid sequence of the V$_H$ of the C5 human antibody (VRC 4794).
QLQLQESGPGLVKPSETLSLTCTVSGGSISSSSYYWGWIRQPPGKGLEWI

GSIYYSGSTYYNPSLKSRVTISVDTSKNQFSLKLSSVTAADTAVYYCASL

LRPLIYCSGGSCTDYWGQGTLVTVSS

SEQ ID NO: 41 is an exemplary nucleotide sequence encoding the V$_L$ of the C5 human antibody (VRC 4795).
Cagtctgccctgactcagcctgcctccgtgtctgggtctcctggacagtc gatcaccatctcctgcactggaaccagcagtgacgttggtggttataact atgtctcctggtgccaacagcacccaggcaaagcccccaaactcatgatt tatgaggtcagtaatcggccctcaggggtttctaatcgcttctctggctc caagtctggcaacacggcctccctgaccatctctgggctccaggctgagg acgaggctgattattactgcagctcatatacaagcaacatcactcttgtc ttcggaactgggaccaaggtcaccgtccta SEQ ID NO: 42 is the amino acid sequence of the V$_L$ of the C5 human antibody (VRC 4795).
QSALTQPASVSGSPGQSITISCTGTSSDVGGYNYVSWCQQHPGKAPKLMI

YEVSNRPSGVSNRFSGSKSGNTASLTISGLQAEDEADYYCSSYTSNITLV

FGTGTKVTVL

SEQ ID NO: 43 is an exemplary nucleotide sequence encoding the V$_H$ of the A2 human antibody (VRC 4796).
caggtgcagctggtggagtctggggaggcttggtcaagcctggagggtc cctgagactctcctgtgcagcctctggattcaccttcagtgactactaca tgagctggatccgccaggctccagggaaggggctggagtgggtttcatac attagtagtagtggtagtaccatatactacgcagactctgtgaagggccg attcaccatctccagggacaacgccaagaactcactgtatctgcaaatga acagcctgagagccgaggacacggccgtgtattactgtgcgagagtaggg ttaggcagtggctggtacgactggttcgacccctggggccagggaaccct ggtcaccgtctcctca SEQ ID NO: 44 is the amino acid sequence of the V$_H$ of the A2 human antibody (VRC 4796).
QVQLVESGGGLVKPGGSLRLSCAASGFTFSDYYMSWIRQAPGKGLEWVSY

ISSSGSTIYYADSVKGRFTISRDNAKNSLYLQMNSLRAEDTAVYYCARVG

LGSGWYDWFDPWGQGTLVTVSS

SEQ ID NO: 45 is an exemplary nucleotide sequence encoding the V$_L$ of the A2 human antibody (VRC 4797).
cagtctgccctgactcagccgccctcagtgtctggggcccagggcagag ggtcaccatctcctgcactgggagcagctccaacatcggggcaagttatg atgtacactggtaccagcaccttccaggaacagcccccaaactcctcatc tatggtaacaccaatcggccctcaggggtccctgaccgattctctggctc caagtctggcacctcagcctccctggccatcactgggctccaggctgagg atgaggctgattattactgccagtcctatgacagcagcctgagtggtgtg gtattcagcggagggaccaagctgaccgtcctag SEQ ID NO: 46 is the amino acid sequence of the V$_L$ of the A2 human antibody (VRC 4797).
QSALTQPPSVSGAPGQRVTISCTGSSSNIGASYDVHWYQHLPGTAPKLLI

YGNTNRPSGVPDRFSGSKSGTSASLAITGLQAEDEADYYCQSYDSSLSGV

VFSGGTKLTVL

SEQ ID NO: 47 is an exemplary nucleotide sequence encoding the V$_H$ of the A10 human antibody (VRC 4798).
caggtgcagctggtgcagtctggggctgaggtgaagaagcctggggtcctc ggtgaaggtctcctgcaaggcttctggaggcaccttcagcacctatgctc tcagctgggtgcgacaggcccctggacaagggcttgagtggatgggaggg atcatccctatctttggtacagcaaactacgcacagaagttccagggcag agtcacgattaccgcggacgaatccacgagcacggcctacatggagttga acagcctgagatctgaggacacggccgtgtattactgtgcgagaggaagc cggagcagctcttccgctgaatacttccagcactggggccagggcaccct ggtcaccgtctcctca SEQ ID NO: 48 is the amino acid sequence of the V$_H$ of the A10 human antibody (VRC 4798).
QVQLVQSGAEVKKPGSSVKVSCKASGGTFSTYALSWVRQAPGQGLEWMGG

IIPIFGTANYAQKFQGRVTITADESTSTAYMELNSLRSEDTAVYYCARGS

RSSSSAEYFQHWGQGTLVTVSS

SEQ ID NO: 49 is an exemplary nucleotide sequence encoding the $V_L$ of the A10 human antibody (VRC 4799).
cagtctgccctgactcagcctcgctcagtgtccgggtctcctggacagtc agtcaccatctcctgcactggaaccagcagtgatgttggtggttataact atgtctcctggtaccaacagcacccaggcaaagcccccaaactcatgatt tatgatgtcagtaagcggccctcaggggtccctgatcgcttctctggctc caagtctggcaacacggcctccctgaccatctctgggctccaggctgagg atgaggctgattattactgctgctcatatgcaggcagctacactttagaa gtggtattcggcggagggaccaagctgaccgtcctag SEQ ID NO: 50 is the amino acid sequence of the $V_L$ of the A10 human antibody (VRC 4799).
QSALTQPRSVSGSPGQSVTISCTGTSSDVGGYNYVSWYQQHPGKAPKLMI
YDVSKRPSGVPDRFSGSKSGNTASLTISGLQAEDEADYYCCSYAGSYTLE
VVFGGGTKLTVL SEQ ID NO: 51 is an exemplary nucleotide sequence encoding the $V_H$ of the FIB_B2 NHP antibody (VRC 5069).
caggtgcagctgcaggagtcgggcccaggactggtgaagccttcggagac cctgtctctcacctgcgctgtttctggtggctccatcagcagcaactact ggtactggatccgccagtcccagtgaaggggctggagtggattgggtat atctatggtggtagtggggcaccgaatacaaccctccctcaagagtcg agtcaccatttcaacagacacgtccaagaaccagttttttcctgaagctga gctctgtgaccgccgcggacaccgccgtatattactgtgcgagatccttt tatagctggaacggggaatcctggggccaaggggtcgtcgtcaccgtctc ctca SEQ ID NO: 52 is the amino acid sequence of the $V_H$ of the FIB_B2 NHP antibody (VRC 5069).
QVQLQESGPGLVKPSETLSLTCAVSGGSISSNYWYWIRQSPVKGLEWIGY
IYGGSGGTEYNPSLKSRVTISTDTSKNQFFLKLSSVTAADTAVYYCARSF
YSWNGESWGQGVVVTVSS SEQ ID NO: 53 is an exemplary nucleotide sequence encoding the $V_L$ of the FIB_B2 NHP antibody (VRC 5070).
gacattcagatgtcccagactccatcctccctgtctgcatctgtaggaga cagagtcaccatcacttgccgggcaagtcagggcattaacgattatttaa attggtatcagcagaaaccggggaaagcccctaagctcctgatctattat ggaaacagtttggcaagtggggtcccatcaaggttcagtggcagtggttc tgggacagatttctctctcaccatcagcagcctgcagcctgaagattttg caacttattactgtcaacagggtgatagtttccctctcactttcggcgga gggaccaaagtggatatcaaa SEQ ID NO: 54 is the amino acid sequence of the $V_L$ of the FIB_B2 NHP antibody (VRC 5070).
DIQMSQTPSSLSASVGDRVTITCRASQGINDYLNWYQQKPGKAPKLLIYY
GNSLASGVPSRFSGSGSGTDFSLTISSLQPEDFATYYCQQGDSFPLTFGG
GTKVDIK SEQ ID NO: 55 is an exemplary nucleotide sequence encoding the $V_H$ of the FIB_H1 NHP antibody (VRC 5071).
gaggtgcagctggtgcagtctggggctgaggtgaagaagcctggggcctc agtgaaggtctcctgcaaagcttctggacacattttcaccagttatgtta tcaactggctgcaagaggcccctggacaagggtttgagtggatgggagga atccaccctggtaatggtggcagagactacgcacagaagttccagggcag agtcacgattaccgcggacatgtccacgagcacagtctacatggagctga gaagtctgagatctgaggacatggccgtgtattactgtgcagcatccagt ggtagttatggtgttagctcattggatgtctggggccggggagttctggt caccgtctcctca SEQ ID NO: 56 is the amino acid sequence of the $V_H$ of the FIB_H1 NHP antibody (VRC 5071).
EVQLVQSGAEVKKPGASVKVSCKASGHIFTSYVINWLQEAPGQGFEWMGG
IHPGNGGRDYAQKFQGRVTITADMSTSTVYMELRSLRSEDMAVYYCAASS
GSYGVSSLDVWGRGVLVTVSS SEQ ID NO: 57 is an exemplary nucleotide sequence encoding the $V_L$ of the FIB_H1 NHP antibody (VRC 5072).
cagtctgccctgactcagccaccctccctgtctgcatccccgggagcatc ggccagactcccctgcaccctgagcagtgacctcagtgttggtagtaaaa acatgtactggtaccagcagaagccagggagcgctcccaggttattcctg tactactactccgactcagacaagcagctgggacctggggtccccaatcg agtctctggctccaaggagacctcaagtaacacagcgttttttgctcatct ctgggctccagcctgaggacgaggccgattattactgtcaggtgtatgac agtagtgctaattgggtattcggcggagggacccggctgacagtacta SEQ ID NO: 58 is the amino acid sequence of the $V_L$ of the FIB_H1 NHP antibody (VRC 5072).
QSALTQPPSLSASPGASARLPCTLSSDLSVGSKNMYWYQQKPGSAPRLFL
YYYSDSDKQLGPGVPNRVSGSKETSSNTAFLLISGLQPEDEADYYCQVYD
SSANWVFGGGTRLTVL SEQ ID NOs: 59-109 are amino acid sequences of heavy and light chain CDRs.

SEQ ID NO: 110 is the amino acid sequence of the $V_L$ of the C2 antibody with a G29S mutation.
DVVMTQSPLSLPVTPGEPASISCRSSQSLLHSNSYNYLDWYLQKPGQSPQ
LLIYLGSNRASGVPDRFSGSGSGTDFTLKISRVEAEDVGVYYCMQALQTP
AFGGGTKLEIK SEQ ID NO: 111 is the amino acid sequence of the $V_L$ of the C2 antibody with a G29A mutation.
DVVMTQSPLSLPVTPGEPASISCRSSQSLLHSNAYNYLDWYLQKPGQSPQ
LLIYLGSNRASGVPDRFSGSGSGTDFTLKISRVEAEDVGVYYCMQALQTP
AFGGGTKLEIK SEQ ID NOs: 112 and 113 are amino acid sequences of light chain CDRs.

SEQ ID NO: 114 is an exemplary nucleotide sequence encoding the $V_H$ of the G2 antibody.
cattcccaggtgcagctgcagcagtctggaggtgagctggtgaagcctgg ggcttcagtgaagctgtcctgcaagacttctggcttcaccttcagcagta gctatataagttggttgaagcaaaagcctggacagagtcttgagtggatt

```
gcatggatttatgctggaactggtggtactgaatataatcagaagttcac aggcaaggcccaagtgactgtagacacatcctccagcacagcctacatgc aattcagcagcctgacaactgaggactctgccatctattactgtcaaga ggaggtagtagcttcgctatggactactggggtcaaggaaccctcagtcac cgtctcctca
```

SEQ ID NO: 115 is the amino acid sequence of the
$V_H$ of the G2 antibody.
QVQLQQSGGELVKPGASVKLSCKTSGFTFSSSYISWLKQKPGQSLEWIAW

IYAGTGGTEYNQKFTGKAQVTVDTSSSTAYMQFSSLTTEDSAIYYCARGG

SSFAMDYWGQGTSVTVSS

SEQ ID NO: 116 is an exemplary nucleotide sequence
encoding the $V_L$ of the G2 antibody.
```
caacttgtgctgacccaatctccagcttctttggctgtgtctctaggca gagggccaccatctcctgcagagccagcgaaagtgttgataattatggca ttagttttatgaactggttccaacagaaaccaggacagccacccaaactc ctcatccatactgcatccaaccaaggatccggggtccctgccaggtttag tggcagtgggtctgggacagacttcagcctcaacatccatcctgtggagg acgatgatactgcaatgtatttctgtcagcaaagtgaggaggttcctctc acgttcggtgctgggaccaagctggaaatcaaa
```

SEQ ID NO: 117 is the amino acid sequence of the
$V_L$ of the G2 antibody.
QLVLTQSPASLAVSLGQRATISCRASESVDNYGISFMNWFQQKPGQPPKL

LIHTASNQGSGVPARFSGSGSGTDFSLNIHPVEDDDTAMYFCQQSEEVPL

TFGAGTKLELK

SEQ ID NO: 118 is an exemplary nucleotide sequence
encoding the $V_H$ of the G4 antibody.
```
caggtccagctgcagcagtctgggcctgagctggtgaggcctggggtctc agtgaagatttcctgcaaggggttccggctacacattcactgattatgcta tacactgggtgaagcagagtcatgcaaagagtctagagtggattgggtt tttagtacttactatggtaatacaaactacaaccagaagtttaagggcag ggccacaatgactgtagacaaatcctccagcacagcctatatggaacttg ccagattgacatctgaggattctgccatctattactgtcaagaaagtcc tactatgttgactacgttgatgctatggactactggggtcaaggaacctc agtcaccgtctcctca
```

SEQ ID NO: 119 is the amino acid sequence of the
$V_H$ of the G4 antibody.
QVQLQQSGPELVRPGVSVKISCKGSGYTFTDYAIHWVKQSHAKSLEWIGV

FSTYYGNTNYNQKFKGRATMTVDKSSSTAYMELARLTSEDSAIYYCARKS

YYVDYVDAMDYWGQGTSVTVSS

SEQ ID NO: 120 is an exemplary nucleotide sequence
encoding the $V_L$ of the G4 antibody.
```
gacattgtgctgacccaatctccagcttctttggctgtgtctctaggca gagggccaccatctcctgcagagccagcgaaagtgttgataattatggca ttagttttatgaactggttccaacagaaaccaggacagccacccaaactc ctcatctctgctacatccaaccaaggatccggggtccctgccaggtttat tggcagtgggtctgggacagacttcagcctcaacatccatcctgtggagg aggatgatactgcaatgtatttctgtcagcaaagtaaggaggttcctcgg acgttcggtggaggcaccaagctggaaatcaaac
```

SEQ ID NO: 121 is the amino acid sequence of the
$V_L$ of the G4 antibody.
DIVLTQSPASLAVSLGQRATISCRASESVDNYGISFMNWFQQKPGQPPKL

LISATSNQGSGVPARFIGSGSGTDFSLNIHPVEEDDTAMYFCQQSKEVPR

TFGGGTKLEIK

SEQ ID NO: 122 is an exemplary nucleotide sequence
encoding the $V_H$ of the D12 antibody.
```
gaggtgaagctggtggagtctgggggaggcttagtgaagcctggagggtc cctgaaactctcctgtgcagcctctggattcactttcagtagctatgcca tgtcttgggttcgccagactccggagaagaggctggagtgggtcgcaacc attagtagtggtggtacttacacctactatccagacagtgtgaaggggcg attcaccatctccagagacaatgccgagaacaccctgtacctgcaaatga gcagtctgaggtctgaggacacggccatgtattactgtgtaagagatggt aattctatggactactggggtcaaggaacctcagtcaccgtctcctcagc
```

SEQ ID NO: 123 is the amino acid sequence of the
$V_H$ of the D12 antibody.
EVKLVESGGGLVKPGGSLKLSCAASGFTFSSYAMSWVRQTPEKRLEWVAT

ISSGGTYTYYPDSVKGRFTISRDNAENTLYLQMSSLRSEDTAMYYCVRDG

NSMDYWGQGTSVTVSS

SEQ ID NO: 124 is an exemplary nucleotide sequence
encoding the $V_L$ of the D12 antibody.
```
gatatccagatgacacagactacatcctccctgtctgcctctctgggaga cagagtcaccatcatttgcagggcaagtcaggacattaacaattatttaa actggtatcaacagaaaccagatggaactgttaaactcctgatctactac acatcaagattacactcaggagtcccatcaaggttcagtggcagtgggtc tggatcagattattctctcaccattagcaacctggaacaagaagatattg ccacttacttttgccaacaggctaatacgcttcctcccacgttcggtgct gggaccaagctggaactgaga
```

SEQ ID NO: 125 is the amino acid sequence of the
$V_L$ of the D12 antibody.
DIQMTQTTSSLSASLGDRVTIICRASQDINNYLNWYQQKPDGTVKLLIYY

TSRLHSGVPSRFSGSGSGSDYSLTISNLEQEDIATYFCQQANTLPPTFGA

GTKLELR

SEQ ID NO: 126 is an exemplary nucleotide sequence
encoding the $V_H$ of the F11 antibody.
```
cattccgaggtgaagctggaggagtctgggggaggcttagtgaagcctgg agggtccctgaaactctcctgtgcagcctctggattcactttcagtaggt atgccatgtcttgggttcgccagactccggagaagaggctggagtgggtc gcaaccattaataatggtggtagttacagttactatccagacagtgtgaa gggtcgactcaccatctccagagacaatgccaagaacaccctgtacctgc aaatgagcagtctgaggtctgaggacacggccttgtattactgtgcaaga cactatgattacgacggatattactatactatggacttctggggtcaagg aacctcagtcaccgtctcctcagc
```

SEQ ID NO: 127 is the amino acid sequence of the V$_H$ of the F11 antibody.
EVKLEESGGGLVKPGGSLKLSCAASGFTFSRYAMSWVRQTPEKRLEWVAT

INNGGSYSYYPDSVKGRLTISRDNAKNTLYLQMSSLRSEDTALYYCARHY

DYDGYYYTMDFWGQGTSVTVSS

SEQ ID NO: 128 is an exemplary nucleotide sequence encoding the V$_L$ of the F11 antibody.
gatgttttgatgacccaaattccactctccctgcctgtcagtcttggaga tcaagcctccatttcttgcagatctagtcagagcattgtacatagtaatg gaaacacctatttagaatggtacctgcagaaaccaggccagtctccaaag cccctgatctacaaagtttccaaccgaatttctggggtcccagacaggtt cagtggcagtggatcagggacagatttcacactcaagatcagcagagtgg aggctgaggatctgggagtttattactgctttcaaggttcacatgttccg tacacgttcggaggggggaccaacctggaaataaaacg SEQ ID NO: 129 is the amino acid sequence of the V$_L$ of the F11 antibody.
DVLMTQIPLSLPVSLGDQASISCRSSQSIVHSNGNTYLEWYLQKPGQSPK

PLIYKVSNRISGVPDRFSGSGSGTDFTLKISRVEAEDLGVYYCFQGSHVP

YTFGGGTNLEIKR

SEQ ID NOs: 130-152 are amino acid sequences of heavy and light chain CDRs.

SEQ ID NO: 153 is an exemplary nucleotide sequence encoding a chimeric V$_H$ including the G2 heavy chain variable domain and a human IgG1 constant domain (VRC 5068).
atgggatggtcatgtatcatccttttctagtagcaactgcaaccggtgt acattcccaggtgcagctgcagcagtctggaggtgagctggtgaagcctg gggcttcagtgaagctgtcctgcaagacttctggcttcaccttcagcagt agctatataagttggttgaagcaaaagcctggacagagtcttgagtggat tgcatggatttatgctggaactggtggtactgaatataatcagaagttca caggcaaggcccaagtgactgtagacacatcctccagcacagcctacatg caattcagcagcctgacaactgaggactctgccatctattactgtgcaag aggaggtagtagcttcgctatggactactggggtcaaggaacctcagtca ccgtctcctcagcgtcgaccacgccccatcggtcttcccctggcaccc tcctccaagagcacctctgggggcacagcggcctgggctgcctggtcaa ggactacttccccgaacccgtgacggtgtcgtggaactcaggcgccctga ccagcggcgtgcacaccttcccggctgtcctacagtcctcaggactctac tccctcagcagcgtggtgaccgtgccctccagcagcttgggcacccagac ctacatctgcaacgtgaatcacaagcccagcaacaccaaggtggacaaga aagttgagcccaaatcttgtgacaaaactcacacatgcccaccgtgccca gcacctgaactcctggggggaccgtcagtcttcctcttccccccaaaacc caaggacaccctcatgatctcccggacccctgaggtcacatgcgtggtgg tggacgtgagccacgaagaccctgaggtcaagttcaactggtacgtggac ggcgtggaggtgcataatgccaagacaaagccgcgggaggagcagtacaa cagcacgtaccgtgtggtcagcgtcctcaccgtcctgcaccaggactggc tgaatggcaaggagtacaagtgcaaggtctccaacaaagccctcccagcc cccatcgagaaaaccatctccaaagccaaagggcagccccgagaaccaca ggtgtacaccctgcccccatcccgggatgagctgaccaagaaccaggtca gcctgacctgcctggtcaaaggcttctatcccagcgacatcgccgtggag tgggagagcaatgggcagccggagaacaactacaagaccacgcctcccgt gctggactccgacggctccttcttcctctacagcaagctcaccgtggaca agagcaggtggcagcaggggaacgtcttctcatgctccgtgatgcatgag gctctgcacaaccactacacgcagaagagcctctccctgtctccgggtaa atga SEQ ID NO: 154 is a chimeric V$_H$ including the G2 heavy chain variable domain and a human IgG1 constant domain (VRC 5068).
MGWSCIILFLVATATGVHSQVQLQQSGGELVKPGASVKLSCKTSGFTFSS

SYISWLKQKPGQSLEWIAWIYAGTGGTEYNQKFTGKAQVTVDTSSSTAYM

QFSSLTTEDSAIYYCARGGSSFAMDYWGQGTSVTVSSASTTPPSVFPLAP

SSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHE

ALHNHYTQKSLSLSPGK

DETAILED DESCRIPTION

MERS-CoV has emerged as a highly fatal cause of severe acute respiratory infection. The high case fatality rate, vaguely defined epidemiology, and absence of prophylactic or therapeutic measures against this novel virus have created an urgent need for an effective vaccine, should the outbreak expand to pandemic proportions.

Past efforts to develop coronavirus vaccines have used whole-inactivated virus, live-attenuated virus, recombinant protein subunit, or genetic approaches (Graham et al., *Nature reviews. Microbiology* 11, 836, 2013). This disclosure provides an immunization strategy based on the MERS-CoV Spike glycoprotein (S). In one non-limiting embodiment, a prime-boost immunization strategy including a full-length S DNA prime and S1 subunit protein boost was identified to elicit high titers of neutralizing antibodies against several different MERS-CoV strains. Immunization with DNA expressing full-length S followed by S1 subunit protein yielded potent neutralizing mAbs in both mice and NHPs. Compared to protein alone, S DNA prime/S1 protein boost immunization yielded a more functionally diverse repertoire of neutralizing antibodies and also generated a Th1-biased immune response.

Vaccine-elicited murine monoclonal antibodies were also identified and shown to neutralize virus by targeting the receptor binding domain (RBD), multiple non-RBD portions of S1, or S2.

I. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Adjuvant: A vehicle used to enhance antigenicity. Adjuvants include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL and toll-like receptor (TLR) agonists, such as TLR-9 agonists. The person of ordinary skill in the art is familiar with adjuvants (see, e.g., Singh (ed.) Vaccine Adjuvants and Delivery Systems. Wiley-Interscience, 2007). Adjuvants can be used in combination with the disclosed MERS-CoV immunogens.

Administration: The introduction of a composition into a subject by a chosen route. Administration can be local or systemic. For example, if the chosen route is intravenous, the composition (such as a composition including a disclosed immunogen or antibody) is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Agent: Any substance or any combination of substances that is useful for achieving an end or result; for example, a substance or combination of substances useful for inhibiting MERS-CoV infection in a subject. Agents include proteins, nucleic acid molecules, compounds, small molecules, organic compounds, inorganic compounds, or other molecules of interest. An agent can include a therapeutic agent (such as an anti-retroviral agent), a diagnostic agent or a pharmaceutical agent. In some embodiments, the agent is a protein agent (such as a recombinant MERS-CoV polypeptide or immunogenic fragment thereof, or MERS-CoV-specific antibody), or an anti-viral agent. The skilled artisan will understand that particular agents may be useful to achieve more than one result.

Amino acid substitution: The replacement of one amino acid in a polypeptide with a different amino acid or with no amino acid (i.e., a deletion). In some examples, an amino acid in a polypeptide is substituted with an amino acid from a homologous polypeptide, for example, and amino acid in a recombinant MERS-CoV polypeptide can be substituted with the corresponding amino acid from a different MERS-CoV strain.

Antibody: A polypeptide that specifically binds and recognizes an analyte (antigen) such as MERS-CoV S protein or an antigenic fragment thereof. The term "antibody" is used herein in the broadest sense and encompasses various antibody structures, including but not limited to monoclonal antibodies, polyclonal antibodies, multispecific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B-lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, *Antibodies, A Laboratory Manual*, $2^{nd}$ ed. Cold Spring Harbor Publications, New York (2013).)

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6.sup.th ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., *Nature*, 363:446-448, 1993; Sheriff et al., *Nat. Struct. Biol.*, 3:733-736, 1996). References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab.

Light and heavy chain variable regions contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273, 927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the variable domain of the heavy chain of the antibody in which it is found, whereas a $V_L$ CDR1 is the CDR1 from the variable domain of the light chain of the antibody in which it is found. Light chain CDRs are sometimes referred to as LCDR1, LCDR2, and LCDR3. Heavy chain CDRs are sometimes referred to as HCDR1, HCDR2, and HCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988; Ahmad et al., *Clin. Dev. Immunol.*, 2012, doi:10.1155/2012/980250; Marbry, *IDrugs*, 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used.

In a dsFv the heavy and light chain variable chains have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, Ill.); Kuby, J., *Immunology*, $3^{rd}$ Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manuel.* 1$^{st}$ Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous antigens, such as the disclosed MERS-CoV antigens. Examples of antigens include, but are not limited to, polypeptides, peptides, lipids, polysaccharides, combinations thereof (such as glycopeptides) and nucleic acids containing antigenic determinants, such as those recognized by an immune cell. In some examples, antigens include peptides derived from a pathogen of interest, such as MERS-CoV. An antigen can include one or more epitopes.

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian (such as human) cells. Codon optimization does not alter the amino acid sequence of the encoded protein.

Conditions sufficient to form an immune complex: Conditions which allow an antibody or antigen binding fragment thereof to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, *Antibodies, A Laboratory Manual*, 2$^{nd}$ ed. Cold Spring Harbor Publications, New York (2013) for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Conjugate: A complex of two molecules linked together, for example, linked together by a covalent bond. In some embodiment, an antibody is linked to an effector molecule or detectable marker; for example, an antibody that specifically binds to MERS-CoV covalently linked to an effector molecule or detectable marker. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative variants: "Conservative" amino acid substitutions are those substitutions that do not substantially affect or decrease a function of a protein, such as the ability of the protein to induce an immune response when administered to a subject. For example, in some embodiments, a recombinant MERS-CoV S protein or S1 fragment can include up to 1, 2, 3, 4, 5, 6, 7, 8, 9, or up to 10 conservative substitutions compared to a corresponding native MERS-CoV protein sequence and induce an immune response to MERS-CoV S protein in a subject. The term conservative variation also includes the use of a substituted amino acid in place of an unsubstituted parent amino acid.

Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of protein, e.g., a MERS-CoV S protein, such as the ability to induce an immune response when administered to a subject. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as a peptide, that contacts another polypeptide. Contacting can also include contacting a cell for example by placing a polypeptide in direct physical association with a cell.

Control: A reference standard. In some embodiments, the control is a negative control sample obtained from a healthy patient. In other embodiments, the control is a positive control sample obtained from a patient diagnosed with MERS-CoV infection. In still other embodiments, the control is a historical control or standard reference value or range of values (such as a previously tested control sample, such as a group of MERS-CoV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Degenerate variant: In the context of the present disclosure, a "degenerate variant" refers to a polynucleotide encoding a polypeptide (such as a MERS-CoV S protein or immunogenic fragment thereof) that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013).

Detecting: To identify the existence, presence, or fact of something. General methods of detecting are known to the skilled artisan and may be supplemented with the protocols and reagents disclosed herein. For example, included herein are methods of detecting the level of a protein in a sample or a subject.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Dipeptidyl peptidase 4 (DPP4): A 240 kDa homodimeric, type II membrane glycoprotein that serves as the cellular receptor for MERS-CoV. DPP4 is distributed in most mammalian tissues, and highly expressed in kidney, liver and endothelium. DPP4 includes a short cytoplasmic domain, a transmembrane domain and a relatively large extracellular (ectodomain) sequence of about 740 amino acids. The RBD of MERS-CoV S protein binds to the extracellular domain of DPP4 before fusion with target cell membrane. An exemplary human DPP4 amino acid sequence is provided in GenBank as deposit No. NP_001926.2, which is incorporated by reference herein in its entirety.

Epitope: An antigenic determinant. These are particular chemical groups or peptide sequences on a molecule that are antigenic, such that they elicit a specific immune response, for example, an epitope is the region of an antigen to which B and/or T cells respond. An antibody can bind to a particular antigenic epitope, such as an epitope on MERS-CoV S protein.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Heterologous: Originating from a different genetic source. A nucleic acid molecule that is heterologous to a cell originated from a genetic source other than the cell in which it is expressed. In one specific, non-limiting example, a heterologous nucleic acid molecule encoding a recombinant MERS-CoV polypeptide or specific antibody is expressed in a cell, such as a mammalian cell. Methods for introducing a heterologous nucleic acid molecule in a cell or organism are well known in the art, for example transformation with a nucleic acid, including electroporation, lipofection, particle gun acceleration, and homologous recombination.

Ferritin: A protein that stores iron and releases it in a controlled fashion. The protein is produced by almost all living organisms. Ferritin polypeptides assemble into a globular protein complex of 24 protein subunits, each of the 24 subunits includes a single ferritin polypeptide. In some examples, ferritin is used to form a nanoparticle presenting antigens on its surface, for example, an MERS-CoV antigen.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

IgA: A polypeptide belonging to the class of antibodies that are substantially encoded by a recognized immunoglobulin alpha gene. In humans, this class or isotype comprises $IgA_1$ and $IgA_2$. IgA antibodies can exist as monomers, polymers (referred to as pIgA) of predominantly dimeric form, and secretory IgA. The constant chain of wild-type IgA contains an 18-amino-acid extension at its C-terminus called the tail piece (tp). Polymeric IgA is secreted by plasma cells with a 15-kDa peptide called the J chain linking two monomers of IgA through the conserved cysteine residue in the tail piece.

IgG: A polypeptide belonging to the class or isotype of antibodies that are substantially encoded by a recognized immunoglobulin gamma gene. In humans, this class comprises $IgG_1$, $IgG_2$, $IgG_3$, and $IgG_4$. In mice, this class comprises $IgG_1$, $IgG_{2a}$, $IgG_{2b}$, $IgG_3$.

Immune complex: The binding of antibody or antigen binding fragment (such as a scFv) to a soluble antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. "Enhancing an immune response" refers to co-administration of an adjuvant and an immunogenic agent, wherein the adjuvant increases the desired immune response to the immunogenic agent compared to administration of the immunogenic agent to the subject in the absence of the adjuvant.

Immunogen: A protein or a portion thereof that is capable of inducing an immune response in a mammal, such as a mammal infected or at risk of infection with a pathogen. Administration of an immunogen or nucleic acid encoding the immunogen can lead to protective immunity and/or proactive immunity against a pathogen of interest. In some examples, an immunogen is a recombinant MERS-CoV S protein as disclosed herein.

Immunogenic composition: A composition comprising an immunogenic polypeptide, or a nucleic acid molecule or vector encoding an immunogenic polypeptide that induces a measurable CTL response against the immunogenic polypeptide, or induces a measurable B cell response (such as production of antibodies) against the immunogenic polypeptide. In one example, an "immunogenic composition" is a composition that includes a disclosed MERS-CoV S protein or immunogenic fragment thereof, that induces a measurable CTL response against MERS-CoV S protein, or induces a measurable B cell response (such as production of antibodies) against a MERS-CoV S protein. It further refers to isolated nucleic acids encoding an antigen, such as a nucleic acid that can be used to express the antigen (and thus be used to elicit an immune response against this peptide).

For in vitro use, an immunogenic composition may comprise or consist of the isolated protein or nucleic acid molecule encoding the protein. For in vivo use, the immunogenic composition will typically include the protein or nucleic acid molecule in a pharmaceutically acceptable carrier and may also include other agents, such as an adjuvant. Any particular protein, such as a MERS-CoV S protein or a nucleic acid encoding the protein, can be readily tested for its ability to induce a CTL or B cell response by art-recognized assays. Immunogenic compositions can include adjuvants, which are well known to one of skill in the art.

Isolated: An "isolated" biological component (such as a protein, for example a disclosed immunogen or nucleic acid encoding such an antigen) has been substantially separated or purified away from other biological components, such as other biological components in which the component naturally occurs, such as other chromosomal and extrachromosomal DNA, RNA, and proteins. Proteins, peptides and nucleic acids that have been "isolated" include proteins purified by standard purification methods. The term also embraces proteins or peptides prepared by recombinant expression in a host cell as well as chemically synthesized proteins, peptides and nucleic acid molecules. Isolated does not require absolute purity, and can include protein, peptide, or nucleic acid molecules that are at least 50% isolated, such as at least 75%, 80%, 90%, 95%, 98%, 99%, or even 99.9% isolated.

$K_D$: The dissociation constant for a given interaction, such as a polypeptide ligand interaction or an antibody antigen interaction. For example, for the bimolecular interaction of an antibody or antigen binding fragment and an immunogen (such as MERS-CoV S protein) it is the concentration of the individual components of the bimolecular interaction divided by the concentration of the complex.

Linker: A bi-functional molecule that can be used to link two molecules into one contiguous molecule, for example, to link a carrier molecule to a immunogenic polypeptide. Non-limiting examples of peptide linkers include glycine-serine linkers, such as a (GGGGS, SEQ ID NO: 155)$_x$ linker.

The terms "conjugating," "joining," "bonding," or "linking" can refer to making two molecules into one contiguous molecule; for example, linking two polypeptides into one contiguous polypeptide, or covalently attaching a carrier molecule or other molecule to an immunogenic polypeptide, such as an MERS-CoV S protein as disclosed herein. The linkage can be either by chemical or recombinant means. "Chemical means" refers to a reaction, for example, between the immunogenic polypeptide moiety and the carrier molecule such that there is a covalent bond formed between the two molecules to form one molecule.

Middle East respiratory syndrome coronavirus (MERS-CoV): A positive-sense, single stranded RNA virus of the genus Betacoronavirus that has emerged as a highly fatal cause of severe acute respiratory infection. The viral genome is capped, polyadenylated, and covered with nucleocapsid proteins. The MERS-CoV virion includes a viral envelope with large spike glycoproteins. The MERS-CoV genome, like most coronaviruses, has a common genome organization with the replicase gene included in the 5'-two thirds of the genome, and structural genes included in the 3'-third of the genome. The MERS-CoV genome encodes the canonical set of structural protein genes in the order 5'-spike (S)-envelope (E)-membrane (M) and nucleocapsid (N)-3'. MERS-CoV genomes are currently classified as Clade A or Clade B MERS-CoV. Examples of Clade A and Clade B viruses include the JordanN3/2012 (GenBank ID: KC776174) and England_Qatar/2012 (GenBank ID: KC667074) strains, respectively.

Methods of identifying a subject with a MERS-CoV infection are known in the art and include (see, e.g., Sampathkumar P, *Mayo Clin Proc.* 2014 August; 89(8):1153-8).

MERS-CoV Spike (5) protein: A class I fusion glycoprotein, the MERS-CoV S protein is initially synthesized as a precursor protein of approximately 1350 amino acids in size. Individual precursor S polypeptides form a homotrimer and undergo glycosylation within the Golgi apparatus as well as processing to remove the signal peptide, and cleavage by a cellular protease between approximately position 752/753 to generate separate S1 and S2 polypeptide chains, which remain associated as S1/S2 protomers within the homotrimer. The S1 subunit is distal to the virus membrane and contains the receptor-binding domain (RBD) that mediates virus attachment to its host receptor, dipeptidyl peptidase-4 (DPP4), and includes approximately residues 367-606 of the S protein. The S2 subunit contains a transmembrane domain and two heptad-repeat sequences typical of fusion glycoproteins.

The numbering used in the disclosed MERS-CoV S proteins and fragments thereof is relative to the S protein of the England1 strain of MERS-CoV, the sequence of which is provided as SEQ ID NO: 14, and deposited in GenBank as No. AFY13307.1, which is incorporated by reference herein in its entirety.

Neutralizing antibody: An antibody which reduces the infectious titer of an infectious agent by binding to a specific antigen on the infectious agent. In some examples the infectious agent is a virus. In some examples, an antibody that is specific for MERS-CoV S protein neutralizes the infectious titer of MERS-CoV. A "broadly neutralizing antibody" is an antibody that binds to and inhibits the function of related antigens, such as antigens that share at least 85%, 90%, 95%, 96%, 97%, 98% or 99% identity antigenic surface of antigen. With regard to an antigen from a pathogen, such as a virus, the antibody can bind to and inhibit the function of an antigen from more than one class and/or subclass of the pathogen. For example, with regard to MERS-CoV, the antibody can bind to and inhibit the function of an antigen, such as MERS-CoV S protein from more than one strain of MERS-CoV. In one embodiment, broadly neutralizing antibodies to MERS-CoV S protein are distinct from other antibodies to MERS-CoV S protein in that they neutralize a high percentage of the many types of MERS-CoV in circulation.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A first sequence is an "antisense" with respect to a second sequence if a polynucleotide whose sequence is the first sequence specifically hybridizes with a polynucleotide whose sequence is the second sequence.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired anti-MERS-CoV immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues. A protein can include multiple polypeptide chains; for example, mature MERS-CoV S protein includes S1 and S2 polypeptide chains.

Amino acids in a peptide, polypeptide or protein generally are chemically bound together via amide linkages (CONH). Additionally, amino acids may be bound together by other chemical bonds. For example, linkages for amino acids or amino acid analogs can include $CH_2NH$—, —$CH_2S$—, —$CH_2$—$CH_2$—, —CH=CH— (cis and trans), —$COCH_2$—, —CH(OH)$CH_2$—, and —$CHH_2SO$— (These and others can be found in Spatola, in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci pp. 463-468, 1980; Hudson, et al., *Int J Pept Prot Res* 14:177-185, 1979; Spatola et al. *Life Sci* 38:1243-1249, 1986; Harm *J. Chem. Soc Perkin Trans.* 1307-314, 1982; Almquist et al. *J. Med. Chem.* 23:1392-1398, 1980; Jennings-White et al. *Tetrahedron Lett* 23:2533, 1982; Holladay et al. *Tetrahedron. Lett* 24:4401-4404, 1983; and Hruby Life Sci 31:189-199, 1982.

Polypeptide modifications: Polypeptides and peptides, such as the MERS-CoV S proteins disclosed herein can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Prime-boost vaccination: An immunotherapy including administration to a subject of a first immunogenic composition (the primer vaccine) including a selected target antigen or nucleic acid molecule encoding the target antigen, followed by administration of a second immunogenic composition (the booster vaccine) including the target antigen or nucleic acid molecule encoding the target antigen, to induce an immune response to the target antigen in the subject. The booster vaccine is administered to the subject after the primer vaccine; the skilled artisan will understand a suitable time interval between administration of the primer vaccine and the booster vaccine, and examples of such timeframes are disclosed herein. Additional administrations can be included in the prime-boost protocol, for example a second boost. In some embodiments, the primer vaccine, the booster vaccine, or both primer vaccine and the booster vaccine additionally include an adjuvant. In one non-limiting example, the primer vaccine is a DNA-based vaccine (or other vaccine based on gene delivery), and the booster vaccine is a protein-based vaccine (such as a protein subunit or protein nanoparticle).

Protein nanoparticle: A multi-subunit, protein-based polyhedron shaped structure. The subunits are each composed of proteins or polypeptides (for example a glycosylated polypeptide), and, optionally of single or multiple features of the following: nucleic acids, prosthetic groups, organic and inorganic compounds. Non-limiting examples of protein nanoparticles include ferritin nanoparticles (see, e.g., Zhang, Y. *Int. J. Mol. Sci.,* 12:5406-5421, 2011, incorporated by reference herein), encapsulin nanoparticles (see, e.g., Sutter et al., Nature Struct. and Mol. Biol., 15:939-947, 2008, incorporated by reference herein), Sulfur Oxygenase Reductase (SOR) nanoparticles (see, e.g., Urich et al., Science, 311:996-1000, 2006, incorporated by reference herein), lumazine synthase nanoparticles (see, e.g., Zhang et al., *J. Mol. Biol.,* 306: 1099-1114, 2001) or pyruvate dehydrogenase nanoparticles (see, e.g., Izard et al., PNAS 96: 1240-1245, 1999, incorporated by reference herein). Ferritin, encapsulin, SOR, lumazine synthase, and pyruvate dehydrogenase are monomeric proteins that self-assemble into a globular protein complexes that in some cases consists of 24, 60, 24, 60, and 60 protein subunits, respectively. In some examples, ferritin, encapsulin, SOR, lumazine synthase, or pyruvate dehydrogenase monomers are linked to a MERS-CoV S protein (or fragment thereof) and self-assemble into a protein nanoparticle presenting the MERS-CoV S protein on its surface, which can be administered to a subject to stimulate an immune response to the antigen.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

As used herein, reference to "at least 80% identity" refers to "at least 80%, at least 85%, at least 90%, at least 91%, at least 92%, at least 93%, at least 94%, at least 95%, at least 96%, at least 97%, at least 98%, at least 99%, or even 100% identity" to a specified reference sequence.

Signal Peptide: A short amino acid sequence (e.g., approximately 10-35 amino acids in length) that directs newly synthesized secretory or membrane proteins to and through membranes (for example, the endoplasmic reticulum membrane). Signal peptides are typically located at the N-terminus of a polypeptide and are removed by signal peptidases. Signal peptide sequences typically contain three common structural features: an N-terminal polar basic region (n-region), a hydrophobic core, and a hydrophilic c-region). Exemplary signal peptide sequences are set forth as residues 1-18 of SEQ ID NO: 14 (MERS-CoV S protein England1 strain).

Specifically bind: When referring to the formation of an antibody:antigen protein complex, or a protein:protein complex, refers to a binding reaction which determines the presence of a target protein, peptide, or polysaccharide (for example a glycoprotein), in the presence of a heterogeneous population of proteins and other biologics. Thus, under designated conditions, an particular antibody or protein binds preferentially to a particular target protein, peptide or polysaccharide (such as an antigen present on the surface of a pathogen, for example MERS-CoV S protein) and does not bind in a significant amount to other proteins or polysaccharides present in the sample or subject. Specific binding can be determined by methods known in the art. A first protein or antibody "specifically binds to a target protein when the interaction has a $K_D$ of less than about $10^{-6}$ Molar, such as less than about $10^{-7}$ Molar, $10^{-8}$ Molar, $10^{-9}$, or even less than about $10^{-10}$ Molar.

A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, $2^{nd}$ ed., Cold Spring Harbor Publications, New York (2013), for a description of immunoassay formats and conditions that can be used to determine specific immunoreactivity.

Subject: Living multi-cellular vertebrate organisms, a category that includes human and non-human mammals. In an example, a subject is a human. In a particular example, the subject is a human or a camel, or a bat. In an additional example, a subject is selected that is in need of inhibiting of an MERS-CoV infection. For example, the subject is either uninfected and at risk of MERS-CoV infection or is infected and in need of treatment.

Therapeutically effective amount: The amount of agent, such as a disclosed immunogen or antibody, that is sufficient to prevent, treat (including prophylaxis), reduce and/or ameliorate the symptoms and/or underlying causes of a disorder or disease, for example to prevent, inhibit, and/or treat MERS-CoV infection. In some embodiments, a therapeutically effective amount is sufficient to reduce or eliminate a symptom of a disease, such as MERS-CoV infection. For instance, this can be the amount necessary to inhibit or prevent viral replication or to measurably alter outward symptoms of the viral infection. In general, this amount will be sufficient to measurably inhibit virus replication or infectivity.

In one example, a desired response is to inhibit or reduce or prevent MERS-CoV infection. The MERS-CoV infected cells do not need to be completely eliminated or reduced or prevented for the composition to be effective. For example, administration of a therapeutically effective amount of the agent can decrease the number of MERS-CoV infected cells (or prevent the infection of cells) by a desired amount, for example by at least 10%, at least 20%, at least 50%, at least 60%, at least 70%, at least 80%, at least 90%, at least 95%, at least 98%, or even at least 100% (elimination or prevention of detectable MERS-CoV infected cells), as compared to the number of MERS-CoV infected cells in the absence of the composition.

It is understood that to obtain a protective immune response against a pathogen can require multiple administrations of a disclosed immunogen. Thus, a therapeutically effective amount encompasses a fractional dose that contributes in combination with previous or subsequent administrations to attaining a desired immune response. For example, a therapeutically effective amount of an immunogen can be administered in a single dose, or in several doses, for example daily, during a course of treatment (such as a prime-boost vaccination treatment).

The therapeutically effective amount of a disclosed immunogen or antibody can depend on the subject being treated, the severity and type of the condition being treated, and the manner of administration. A unit dosage form of the immunogen or antibody can be packaged in a therapeutic amount, or in multiples of the therapeutic amount, for example, in a vial (e.g., with a pierceable lid) or syringe having sterile components.

Transmembrane domain: An amino acid sequence that inserts into a lipid bilayer, such as the lipid bilayer of a cell or virus or virus-like particle. A transmembrane domain can be used to anchor an antigen to a membrane. In some examples a transmembrane domain is a MERS-CoV S protein transmembrane domain. Exemplary MERS-CoV S protein transmembrane domains are familiar to the person of ordinary skill in the art, and provided herein, for example as residues 1296-1318 of SEQ ID NO: 14.

Treating or preventing a disease: Inhibiting the full development of a disease or condition, for example, in a subject who is at risk for a disease such as MERS-CoV infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

The term "reduces" is a relative term, such that an agent reduces a response or condition if the response or condition is quantitatively diminished following administration of the agent, or if it is diminished following administration of the agent, as compared to a reference agent. Similarly, the term "prevents" does not necessarily mean that an agent completely eliminates the response or condition, so long as at least one characteristic of the response or condition is eliminated. Thus, an immunogenic composition that reduces or prevents an infection or a response, can, but does not necessarily completely, eliminate such an infection or response, so long as the infection or response is measurably diminished, for example, by at least about 50%, such as by at least about 70%, or about 80%, or even by about 90% of (that is to 10% or less than) the infection or response in the absence of the agent, or in comparison to a reference agent.

Under conditions sufficient for: A phrase that is used to describe any environment that permits a desired activity.

Vaccine: A pharmaceutical composition that induces a prophylactic or therapeutic immune response in a subject. In some cases, the immune response is a protective immune response. Typically, a vaccine induces an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In one specific, non-limiting example, a vaccine induces an immune response that reduces the severity of the symptoms associated with MERS-CoV infection and/or decreases the viral load compared to a control. In another non-limiting example, a vaccine induces an immune response that reduces and/or prevents MERS-CoV infection compared to a control.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. A replication deficient viral vector is a vector that requires complementation of one or more regions of the viral genome required for replication due to a deficiency in at least one replication-essential gene function. For example, such that the viral vector does not replicate in typical host cells, especially those in a human patient that could be infected by the viral vector in the course of a therapeutic method.

Virus-like particle (VLP): A non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. Further, VLPs can be isolated by known techniques, e.g., density gradient centrifugation and identified by characteristic density banding. See, for example, Baker et al. (1991) *Biophys. J.* 60:1445-1456; and Hagensee et al. (1994) *J. Virol.* 68:4503-4505; Vincente, *J Invertebr Pathol.*, 2011; Schneider-Ohrum and Ross, *Curr. Top. Microbiol. Immunol.*, 354: 53073, 2012).

II. Neutralizing Monoclonal Antibodies and Their Use

Isolated monoclonal antibodies and antigen binding fragments thereof that specifically bind an epitope on MERS-CoV S protein are provided. The antibodies and antigen binding fragments can be humanized. In several embodiments, the antibodies and antigen binding fragments can be used to inhibit or treat MERS-CoV infection. Also disclosed herein are compositions including the antibodies and antigen binding fragments and a pharmaceutically acceptable carrier. Nucleic acids encoding the antibodies or antigen binding fragments, expression vectors including these nucleic acids, and isolated host cells that express the nucleic acids are also provided.

The antibodies, antigen binding fragments, nucleic acid molecules, host cells, and compositions can be used for research, diagnostic and therapeutic purposes. For example, the monoclonal antibodies and antigen binding fragments can be used to diagnose or treat a subject with a MERS-CoV infection. Additionally, the antibodies can be used to determine MERS-CoV titer in a subject. The antibodies disclosed herein also can be used to study the biology of MERS-CoV.

A. Antibodies and Antigen Binding Fragments

Isolated monoclonal antibodies and antigen binding fragments that specifically bind an epitope on MERS-CoV S protein are provided. The antibodies and antigen binding fragments can neutralize MERS-CoV infection.

In some embodiments, the antibodies and antigen binding fragments include a variable heavy ($V_H$) and a variable light ($V_L$) chain and specifically bind to MERS-CoV S protein and neutralize MERS-CoV infection. In several embodiments, the antibodies and antigen binding fragments include a heavy chain comprising a heavy chain complementarity determining region (HCDR)1, a HCDR2 and an HCDR3, and a light chain comprising a light chain complementarity determining region (LCDR) 1, a LCDR2, and a LCDR3 and specifically bind to MERS-CoV S protein and optionally also neutralize MERS-CoV infection. In several embodiments, the antibody or antigen binding fragment includes heavy and light chain variable regions including the HCDR1, HCDR2, and HCDR3, and LCDR1, LCDR2, and LCDR3, respectively, of one of the JC57-13, JC57-14, JC57-11, C2, C5, A2, A10, FIB_B2, FIB_H1, G2, G4, D12, or F11 antibodies, and specifically binds to MERS-CoV S protein and optionally also neutralizes MERS-CoV infection.

The discussion of monoclonal antibodies below refers to isolated monoclonal antibodies that include heavy and/or light chain variable domains (or antigen binding fragments thereof) including a CDR1, CDR2, and/or CDR3 with reference to the IMGT numbering scheme (unless the context indicates otherwise). The person of ordinary skill in the art will understand that various CDR numbering schemes (such as the Kabat, Chothia or IMGT numbering schemes) can be used to determine CDR positions. The amino acid sequence and the CDR positions of the heavy and light chain of the JC57-13, JC57-14, JC57-11, C2, C5, A2, A10, FIB_B2, FIB_H1, G2, G4, D12, and F11 monoclonal antibodies according to the IMGT numbering schemes are shown in Table 1 (IMGT).

TABLE 1

IMGT CDR sequences of MERS-CoV S protein specific antibodies

JC57-13 $V_H$

| $V_H$ | SEQ ID NO: 2 residues | A.A. Sequence | CDR SEQ ID NO |
|---|---|---|---|
| HCDR1 | 26-33 | GGSISSNY | 59 |
| HCDR2 | 51-58 | IYGGSGST | 60 |
| HCDR3 | 97-110 | ARLLPLGGGYCFDY | 61 |

JC57-13 $V_L$

| $V_L$ | SEQ ID NO: 4 residues | A.A. Sequence | CDR SEQ ID NO |
|---|---|---|---|
| LCDR1 | 27-38 | QSLFDSDYGNTY | 62 |
| LCDR2 | 56-58 | MLS | 63 |
| LCDR3 | 95-103 | MQSVEYPFT | 64 |

JC57-11 $V_H$

| $V_H$ | SEQ ID NO: 6 residues | A.A. Sequence | CDR SEQ ID NO |
|---|---|---|---|
| HCDR1 | 27-34 | GSISDSYR | 65 |
| HCDR2 | 52-59 | IFATGTTT | 66 |
| HCDR3 | 98-120 | AREPFKYCSGGVCYAHKDNSLDV | 67 |

JC57-11 $V_L$

| $V_L$ | SEQ ID NO: 8 residues | A.A. Sequence | CDR SEQ ID NO |
|---|---|---|---|
| LCDR1 | 27-32 | QSVSSN | 68 |
| LCDR2 | 50-52 | SAS | 69 |
| LCDR3 | 89-96 | YQHSSGYT | 70 |

JC57-14 $V_H$

| $V_H$ | SEQ ID NO: 10 residues | A.A. Sequence | CDR SEQ ID NO |
|---|---|---|---|
| HCDR1 | 26-33 | GDSISSNY | 71 |
| HCDR2 | 51-58 | FSGSGGST | 72 |
| HCDR3 | 97-106 | AKTYSGTFDY | 73 |

JC57-14 $V_L$

| $V_L$ | SEQ ID NO: 12 residues | A.A. Sequence | CDR SEQ ID NO |
|---|---|---|---|
| LCDR1 | 27-32 | QDINNY | 74 |
| LCDR2 | 50-52 | YAS | 75 |
| LCDR3 | 89-97 | QQYNNSPYS | 76 |

TABLE 1-continued

IMGT CDR sequences of MERS-CoV S protein specific antibodies

C2 $V_H$

| $V_H$ | SEQ ID NO: 36 Residues | A.A. Sequence | CDR SEQ ID NO |
|---|---|---|---|
| HCDR1 | 26-33 | GGTFSIYA | 77 |
| HCDR2 | 51-58 | IIPIFGTA | 78 |
| HCDR3 | 97-116 | AREGGHQGYCSGGSCYDFDY | 79 |

C2 $V_L$

| $V_L$ | SEQ ID NO: 38 Residues | A.A. Sequence | CDR SEQ ID NO |
|---|---|---|---|
| LCDR1 | 27-37 | QSLLHSNGYNY | 80 |
| LCDR2 | 55-57 | LGS | 81 |
| LCDR3 | 94-101 | MQALQTPA | 82 |

C2 LCDR1 NG-NS $V_L$

| $V_L$ | SEQ ID NO: 110 Residues | A.A. Sequence | CDR SEQ ID NO |
|---|---|---|---|
| LCDR1 | 27-37 | QSLLHSNSYNY | 112 |
| LCDR2 | 55-57 | LGS | 81 |
| LCDR3 | 94-101 | MQALQTPA | 82 |

C2 LCDR1 NG-NA $V_L$

| $V_L$ | SEQ ID NO: 111 Residues | A.A. Sequence | CDR SEQ ID NO |
|---|---|---|---|
| LCDR1 | 27-37 | QSLLHSNAYNY | 113 |
| LCDR2 | 55-57 | LGS | 81 |
| LCDR3 | 94-101 | MQALQTPA | 82 |

C5 $V_H$

| $V_H$ | SEQ ID NO: 40 Residues | A.A. Sequence | CDR SEQ ID NO |
|---|---|---|---|
| HCDR1 | 26-35 | GGSISSSSYY | 83 |
| HCDR2 | 53-59 | IYYSGST | 84 |
| HCDR3 | 98-115 | ASLLRPLIYCSGGSCTDY | 85 |

C5 $V_L$

| $V_L$ | SEQ ID NO: 42 Residues | A.A. Sequence | CDR SEQ ID NO |
|---|---|---|---|
| LCDR1 | 26-34 | SSDVGGYNY | 86 |
| LCDR2 | 52-54 | EVS | 87 |
| LCDR3 | 91-100 | SSYTSNITLV | 88 |

A2 $V_H$

| $V_H$ | SEQ ID NO: 44 Residues | A.A. Sequence | CDR SEQ ID NO |
|---|---|---|---|
| HCDR1 | 26-33 | GFTFSDYY | 89 |
| HCDR2 | 51-58 | ISSSGSTI | 90 |
| HCDR3 | 97-111 | ARVGLGSGWYDWFDP | 91 |

A2 $V_L$

| $V_L$ | SEQ ID NO: 46 Residues | A.A. Sequence | CDR SEQ ID NO |
|---|---|---|---|
| LCDR1 | 26-34 | SSNIGASYD | 92 |
| LCDR2 | 52-54 | GNT | 93 |
| LCDR3 | 91-101 | QSYDSSLSGVV | 94 |

A10 $V_H$

| $V_H$ | SEQ ID NO: 48 Residues | A.A. Sequence | CDR SEQ ID NO |
|---|---|---|---|
| HCDR1 | 26-33 | GGTFSTYA | 95 |
| HCDR2 | 51-58 | IIPIFGTA | 78 |
| HCDR3 | 97-111 | ARGSRSSSSAEYFQH | 96 |

A10 $V_L$

| $V_L$ | SEQ ID NO: 50 Residues | A.A. Sequence | CDR SEQ ID NO |
|---|---|---|---|
| LCDR1 | 26-34 | SSDVGGYNY | 86 |
| LCDR2 | 52-54 | DVS | 97 |
| LCDR3 | 92-102 | SYAGSYTLEVV | 98 |

FIB_B2 $V_H$

| $V_H$ | SEQ ID NO: 52 Residues | A.A. Sequence | CDR SEQ ID NO |
|---|---|---|---|
| HCDR1 | 26-33 | GGSISSNY | 59 |
| HCDR2 | 51-55 | IYGGSGGT | 99 |
| HCDR3 | 97-107 | ARSFYSWNGES | 100 |

FIB_B2 $V_L$

| $V_L$ | SEQ ID NO: 54 Residues | A.A. Sequence | CDR SEQ ID NO |
|---|---|---|---|
| LCDR1 | 27-32 | QGINDY | 101 |
| LCDR2 | 50-52 | YGN | 102 |
| LCDR3 | 89-97 | QQGDSFPLT | 103 |

TABLE 1-continued

IMGT CDR sequences of MERS-CoV S protein specific antibodies

FIB_H1 V$_H$

| V$_H$ | SEQ ID NO: 56 Residues | A.A. Sequence | CDR SEQ ID NO |
|---|---|---|---|
| HCDR1 | 26-33 | GHIFTSYV | 104 |
| HCDR2 | 51-58 | IHPGNGGR | 105 |
| HCDR3 | 97-110 | AASSGSYGVSSLDV | 106 |

FIB_H1 V$_L$

| V$_L$ | SEQ ID NO: 58 Residues | A.A. Sequence | CDR SEQ ID NO |
|---|---|---|---|
| LCDR1 | 26-34 | SDLSVGSKN | 107 |
| LCDR2 | 52-58 | YYSDSDK | 108 |
| LCDR3 | 97-106 | QVYDSSANWV | 109 |

G2 V$_H$

| V$_H$ | SEQ ID NO: 115 Residues | A.A. Sequence | CDR SEQ ID NO |
|---|---|---|---|
| HCDR1 | 26-33 | GFTFSSSY | 130 |
| HCDR2 | 51-58 | IYAGTGGT | 131 |
| HCDR3 | 97-107 | ARGGSSFAMDY | 132 |

G2 V$_L$

| V$_L$ | SEQ ID NO: 117 Residues | A.A. Sequence | CDR SEQ ID NO |
|---|---|---|---|
| LCDR1 | 26-36 | ESVDNYGISF | 133 |
| LCDR2 | 54-56 | TAS | 134 |
| LCDR3 | 93-97 | QQSEE | 135 |

G4 V$_H$

| V$_H$ | SEQ ID NO: 119 Residues | A.A. Sequence | CDR SEQ ID NO |
|---|---|---|---|
| HCDR1 | 26-33 | GYTFTDYA | 136 |
| HCDR2 | 51-58 | FSTYYGNT | 137 |
| HCDR3 | 97-111 | ARKSYYVDYVDAMDY | 138 |

G4 V$_L$

| V$_L$ | SEQ ID NO: 121 Residues | A.A. Sequence | CDR SEQ ID NO |
|---|---|---|---|
| LCDR1 | 26-36 | ESVDNYGISF | 139 |
| LCDR2 | 54-56 | ATS | 140 |
| LCDR3 | 93-101 | QQSKEVPRT | 141 |

D12 V$_H$

| V$_H$ | SEQ ID NO: 123 Residues | A.A. Sequence | CDR SEQ ID NO |
|---|---|---|---|
| HCDR1 | 26-33 | GFTFSSYA | 142 |
| HCDR2 | 51-58 | ISSGGTYT | 143 |
| HCDR3 | 97-105 | VRDGNSMDY | 144 |

D12 V$_L$

| V$_L$ | SEQ ID NO: 125 Residues | A.A. Sequence | CDR SEQ ID NO |
|---|---|---|---|
| LCDR1 | 26-32 | QDINNY | 74 |
| LCDR2 | 50-52 | YTS | 145 |
| LCDR3 | 89-97 | QQANTLPPT | 146 |

F11 V$_H$

| V$_H$ | SEQ ID NO: 127 Residues | A.A. Sequence | CDR SEQ ID NO |
|---|---|---|---|
| HCDR1 | 26-33 | GFTFSRYA | 147 |
| HCDR2 | 51-58 | INNGGSYS | 148 |
| HCDR3 | 97-111 | ARHYDYDGYYYTMDF | 149 |

F11 V$_L$

| V$_L$ | SEQ ID NO: 129 Residues | A.A. Sequence | CDR SEQ ID NO |
|---|---|---|---|
| LCDR1 | 26-37 | QSIVHSNGNTY | 150 |
| LCDR2 | 55-57 | KVS | 151 |
| LCDR3 | 94-102 | FQGSHVPYT | 152 |

JC57-13

In some embodiments, the antibody or antigen binding fragment can be based on or derived from the JC57-13 antibody, and can specifically bind to MERS-CoV S protein and neutralize MERS-CoV infection. For example, the antibody or antigen binding fragment can comprise a V$_H$ and a V$_L$ comprising the HCDR1, the HCDR2, and the HCDR3, and the LCDR1, the LCDR2, and the LCDR3, respectively (for example, according to IMGT or kabat), of the JC57-13 antibody, and can specifically bind to MERS-CoV S protein and neutralize MERS-CoV infection.

In some embodiments, the antibody or antigen binding fragment can comprise a V$_H$ comprising the HCDR1, the HCDR2, and the HCDR3 of the JC57-13 V$_H$ as set forth in Table 1, and can specifically bind to MERS-CoV S protein and neutralize MERS-CoV infection. In some embodiments, the antibody or antigen binding fragment can comprise a V$_L$ comprising the LCDR1, the LCDR2, and the LCDR3 of the JC57-13 V$_L$ as set forth in Table 1, and can specifically bind to MERS-CoV S protein and neutralize MERS-CoV infection. In some embodiments, the antibody or antigen binding fragment can comprise a V$_H$ and a V$_L$ comprising the HCDR1, the HCDR2, the HCDR3, the LCDR1, the LCDR2, and the LCDR3 of the JC57-13 $V_H$ and $V_L$ as set forth in Table 1, and can specifically bind to MERS-CoV S protein and neutralize MERS-CoV infection.

In some embodiments, the antibody or antigen binding fragment includes at least one CDR (such as an HCDR3) with a sequence that has at least 95% (such as at least 96%, at least 97%, at least 98%, at least 99%, or even 100%) sequence identity to any one of the heavy or light chain CDRs of the JC57-13 $V_H$ or $V_L$ as shown in Table 1, and can specifically bind to MERS-CoV S protein and neutralize MERS-CoV infection. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-58, and 97-110, respectively, of SEQ ID NO: 2, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-38, 56-58, and 95-103, respectively, of SEQ ID NO: 4, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-58, and 97-110, respectively, of SEQ ID NO: 2, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-38, 56-58, and 95-103, respectively, of SEQ ID NO: 2, and can specifically bind to MERS-CoV S protein and neutralize MERS-CoV infection.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 2, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 4, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 2 and 4, respectively, and can specifically bind to MERS-CoV S protein and neutralize MERS-CoV infection.

In additional embodiments, the antibody or antigen binding fragment includes a $V_H$ comprising the amino acid sequence set forth as one of SEQ ID NO: 2, and can specifically bind to MERS-CoV S protein and neutralize MERS-CoV infection. In more embodiments, the antibody or antigen binding fragment includes a $V_L$ comprising the amino acid sequence set forth as SEQ ID NO: 4, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 2 and 4, respectively, and can specifically bind to MERS-CoV S protein and neutralize MERS-CoV infection.

JC57-11

In some embodiments, the antibody or antigen binding fragment can be based on or derived from the JC57-11 antibody. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT), of the JC57-11 antibody, and can specifically bind to MERS-CoV S protein and neutralize MERS-CoV infection.

In some embodiments, the antibody or antigen binding fragment can comprise a $V_H$ comprising the HCDR1, the HCDR2, and the HCDR3 of the JC57-11 $V_H$ as set forth in Table 1, and can specifically bind to MERS-CoV S protein and neutralize MERS-CoV infection. In some embodiments, the antibody or antigen binding fragment can comprise a $V_L$ comprising the LCDR1, the LCDR2, and the LCDR3 of the JC57-11 $V_L$ as set forth in Table 1, and can specifically bind to MERS-CoV S protein and neutralize MERS-CoV infection. In some embodiments, the antibody or antigen binding fragment can comprise a $V_H$ and a $V_L$ comprising the HCDR1, the HCDR2, the HCDR3, the LCDR1, the LCDR2, and the LCDR3 of the JC57-11 $V_H$ and $V_L$ as set forth in Table 1, and can specifically bind to MERS-CoV S protein and neutralize MERS-CoV infection.

In some embodiments, the antibody or antigen binding fragment includes at least one CDR (such as an HCDR3) with a sequence that has at least 95% (such as at least 96%, at least 97%, at least 98%, at least 99%, or even 100%) sequence identity to any one of the heavy or light chain CDRs of the JC57-11 $V_H$ or $V_L$ as shown in Table 1, and can specifically bind to MERS-CoV S protein and neutralize MERS-CoV infection. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 27-38, 52-59, and 98-120, respectively, of SEQ ID NO: 6, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-32, 50-52, and 89-96, respectively, of SEQ ID NO: 8, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 27-38, 52-59, and 98-120, respectively, of SEQ ID NO: 6, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-32, 50-52, and 89-96, respectively, of SEQ ID NO: 8, and can specifically bind to MERS-CoV S protein and neutralize MERS-CoV infection.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 6, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 8, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 6 and 8, respectively, and can specifically bind to MERS-CoV S protein and neutralize MERS-CoV infection.

In additional embodiments, the antibody or antigen binding fragment includes a $V_H$ comprising the amino acid sequence set forth as one of SEQ ID NO: 6, and can specifically bind to MERS-CoV S protein and neutralize MERS-CoV infection. In more embodiments, the antibody or antigen binding fragment includes a $V_L$ comprising the amino acid sequence set forth as SEQ ID NO: 8, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 6 and 8, respectively, and can specifically bind to MERS-CoV S protein and neutralize MERS-CoV infection.

JC57-14

In some embodiments, the antibody or antigen binding fragment can be based on or derived from the JC57-14 antibody. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT), of the JC57-14 antibody, and can specifically bind to MERS-CoV S protein and neutralize MERS-CoV infection.

In some embodiments, the antibody or antigen binding fragment can comprise a $V_H$ comprising the HCDR1, the HCDR2, and the HCDR3 of the JC57-14 $V_H$ as set forth in Table 1, and can specifically bind to MERS-CoV S protein and neutralize MERS-CoV infection. In some embodiments, the antibody or antigen binding fragment can comprise a $V_L$ comprising the LCDR1, the LCDR2, and the LCDR3 of the JC57-14 $V_L$ as set forth in Table 1, and can specifically bind to MERS-CoV S protein and neutralize MERS-CoV infection. In some embodiments, the antibody or antigen binding fragment can comprise a $V_H$ and a $V_L$ comprising the HCDR1, the HCDR2, the HCDR3, the LCDR1, the LCDR2, and the LCDR3 of the JC57-14 $V_H$ and $V_L$ as set forth in Table 1, and can specifically bind to MERS-CoV S protein and neutralize MERS-CoV infection.

In some embodiments, the antibody or antigen binding fragment includes at least one CDR (such as an HCDR3) with a sequence that has at least 95% (such as at least 96%, at least 97%, at least 98%, at least 99%, or even 100%) sequence identity to any one of the heavy or light chain CDRs of the JC57-14 $V_H$ or $V_L$ as shown in Table 1, and can specifically bind to MERS-CoV S protein and neutralize MERS-CoV infection. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-58, and 97-106, respectively, of SEQ ID NO: 10, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-32, 50-52, and 89-97, respectively, of SEQ ID NO: 12, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-58, and 97-106, respectively, of SEQ ID NO: 10, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-32, 50-52, and 89-97, respectively, of SEQ ID NO: 12, and can specifically bind to MERS-CoV S protein and neutralize MERS-CoV infection.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 10, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 12, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 10 and 12, respectively, and can specifically bind to MERS-CoV S protein and neutralize MERS-CoV infection.

In additional embodiments, the antibody or antigen binding fragment includes a $V_H$ comprising the amino acid sequence set forth as one of SEQ ID NO: 10, and can specifically bind to MERS-CoV S protein and neutralize MERS-CoV infection. In more embodiments, the antibody or antigen binding fragment includes a $V_L$ comprising the amino acid sequence set forth as SEQ ID NO: 12, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 10 and 12, respectively, and can specifically bind to MERS-CoV S protein and neutralize MERS-CoV infection.

C2

In some embodiments, the antibody or antigen binding fragment can be based on or derived from the C2 antibody. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT), of the C2 antibody, and can specifically bind to MERS-CoV S protein and neutralize MERS-CoV infection.

In some embodiments, the antibody or antigen binding fragment can comprise a $V_H$ comprising the HCDR1, the HCDR2, and the HCDR3 of the C2 $V_H$ as set forth in Table 1, and can specifically bind to MERS-CoV S protein and neutralize MERS-CoV infection. In some embodiments, the antibody or antigen binding fragment can comprise a $V_L$ comprising the LCDR1, the LCDR2, and the LCDR3 of the C2 $V_L$ as set forth in Table 1, and can specifically bind to MERS-CoV S protein and neutralize MERS-CoV infection. In some embodiments, the antibody or antigen binding fragment can comprise a $V_H$ and a $V_L$ comprising the HCDR1, the HCDR2, the HCDR3, the LCDR1, the LCDR2, and the LCDR3 of the C2 $V_H$ and $V_L$ as set forth in Table 1, and can specifically bind to MERS-CoV S protein and neutralize MERS-CoV infection.

In some embodiments, an antibody or antigen binding fragment based on or derived from the C2 antibody can comprise a $V_L$ comprising a glycine to serine substitution or glycine to alanine substitution at kabat position 29. For example, in some embodiments, the antibody or antigen binding fragment can comprise a $V_H$ comprising the HCDR1, the HCDR2, and the HCDR3 of the C2 $V_H$ as set forth in Table 1, and a $V_L$ comprising the LCDR1, the LCDR2, and the LCDR3 of the C2 LCDR1 NG-NS $V_L$ as set forth in Table 1, and can specifically bind to MERS-CoV S protein and neutralize MERS-CoV infection. In some embodiments, the antibody or antigen binding fragment can comprise a $V_H$ comprising the HCDR1, the HCDR2, and the HCDR3 of the C2 $V_H$ as set forth in Table 1, and a $V_L$ comprising the LCDR1, the LCDR2, and the LCDR3 of the C2 LCDR1 NG-NA $V_L$ as set forth in Table 1, and can specifically bind to MERS-CoV S protein and neutralize MERS-CoV infection.

In some embodiments, the antibody or antigen binding fragment includes at least one CDR (such as an HCDR3) with a sequence that has at least 95% (such as at least 96%, at least 97%, at least 98%, at least 99%, or even 100%) sequence identity to any one of the heavy or light chain CDRs of the C2 $V_H$ or $V_L$ as shown in Table 1, and can specifically bind to MERS-CoV S protein and neutralize MERS-CoV infection. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-58, and 97-116, respectively, of SEQ ID NO: 36, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-37, 55-57, and 94-101, respectively, of SEQ ID NO: 38, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-37, 55-57, and 94-101, respectively, of SEQ ID NO: 110, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-37, 55-57, and 94-101, respectively, of SEQ ID NO: 111, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-58, and 97-116, respectively, of SEQ ID NO: 36, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-37, 55-57, and 94-101, respectively, of SEQ ID NO: 38, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-58, and 97-116, respectively, of SEQ ID NO: 36, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-37, 55-57, and 94-101, respectively, of SEQ ID NO: 113, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-58, and 97-116, respectively, of SEQ ID NO: 36, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-37, 55-57, and 94-101, respectively, of SEQ ID NO: 114, and can specifically bind to MERS-CoV S protein and neutralize MERS-CoV infection.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 36, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 38, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 110, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 111, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 36 and 38, respectively, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NO: 36 and 110, respectively, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NO: 36 and 111, respectively, and can specifically bind to MERS-CoV S protein and neutralize MERS-CoV infection.

In additional embodiments, the antibody or antigen binding fragment includes a $V_H$ comprising the amino acid sequence set forth as one of SEQ ID NO: 36, and can specifically bind to MERS-CoV S protein and neutralize MERS-CoV infection. In more embodiments, the antibody or antigen binding fragment includes a $V_L$ comprising the amino acid sequence set forth as SEQ ID NO: 38, and can specifically bind to MERS-CoV S protein and neutralize MERS-CoV infection. In more embodiments, the antibody or antigen binding fragment includes a $V_L$ comprising the amino acid sequence set forth as SEQ ID NO: 113, and can specifically bind to MERS-CoV S protein and neutralize MERS-CoV infection. In more embodiments, the antibody or antigen binding fragment includes a $V_L$ comprising the amino acid sequence set forth as SEQ ID NO: 114, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 36 and 38, respectively, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 36 and 110, respectively, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 36 and 111, respectively, and can specifically bind to MERS-CoV S protein and neutralize MERS-CoV infection.

C5

In some embodiments, the antibody or antigen binding fragment can be based on or derived from the C5 antibody. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT), of the C5 antibody, and can specifically bind to MERS-CoV S protein and neutralize MERS-CoV infection.

In some embodiments, the antibody or antigen binding fragment can comprise a $V_H$ comprising the HCDR1, HCDR2, and the HCDR3 of the C5 $V_H$ as set forth in Table 1, and can specifically bind to MERS-CoV S protein and neutralize MERS-CoV infection. In some embodiments, the antibody or antigen binding fragment can comprise a $V_L$ comprising the LCDR1, the LCDR2, and the LCDR3 of the C5 $V_L$ as set forth in Table 1, and can specifically bind to MERS-CoV S protein and neutralize MERS-CoV infection. In some embodiments, the antibody or antigen binding fragment can comprise a $V_H$ and a $V_L$ comprising the HCDR1, the HCDR2, the HCDR3, the LCDR1, the LCDR2, and the LCDR3 of the C5 $V_H$ and $V_L$ as set forth in Table 1, and can specifically bind to MERS-CoV S protein and neutralize MERS-CoV infection.

In some embodiments, the antibody or antigen binding fragment includes at least one CDR (such as an HCDR3) with a sequence that has at least 95% (such as at least 96%, at least 97%, at least 98%, at least 99%, or even 100%) sequence identity to any one of the heavy or light chain CDRs of the C5 $V_H$ or $V_L$ as shown in Table 1, and can specifically bind to MERS-CoV S protein and neutralize MERS-CoV infection. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-35, 53-59, and 98-115, respectively, of SEQ ID NO: 40, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 26-34, 52-54, and 91-100, respectively, of SEQ ID NO: 42, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-35, 53-59, and 98-115, respectively, of SEQ ID NO: 40, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 26-34, 52-54, and 91-100, respectively, of SEQ ID NO: 42, and can specifically bind to MERS-CoV S protein and neutralize MERS-CoV infection.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 40, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 42, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 40 and 42, respectively, and can specifically bind to MERS-CoV S protein and neutralize MERS-CoV infection.

In additional embodiments, the antibody or antigen binding fragment includes a $V_H$ comprising the amino acid sequence set forth as one of SEQ ID NO: 40, and can specifically bind to MERS-CoV S protein and neutralize MERS-CoV infection. In more embodiments, the antibody or antigen binding fragment includes a $V_L$ comprising the amino acid sequence set forth as SEQ ID NO: 42, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 40 and 42, respectively, and can specifically bind to MERS-CoV S protein and neutralize MERS-CoV infection.

A2

In some embodiments, the antibody or antigen binding fragment can be based on or derived from the A2 antibody. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT), of the A2 antibody, and can specifically bind to MERS-CoV S protein and neutralize MERS-CoV infection.

In some embodiments, the antibody or antigen binding fragment can comprise a $V_H$ comprising the HCDR1, the HCDR2, and the HCDR3 of the A2 $V_H$ as set forth in Table 1, and can specifically bind to MERS-CoV S protein and neutralize MERS-CoV infection. In some embodiments, the antibody or antigen binding fragment can comprise a $V_L$ comprising the LCDR1, the LCDR2, and the LCDR3 of the A2 $V_L$ as set forth in Table 1, and can specifically bind to MERS-CoV S protein and neutralize MERS-CoV infection. In some embodiments, the antibody or antigen binding fragment can comprise a $V_H$ and a $V_L$ comprising the HCDR1, the HCDR2, the HCDR3, the LCDR1, the LCDR2, and the LCDR3 of the A2 $V_H$ and $V_L$ as set forth in Table 1, and can specifically bind to MERS-CoV S protein and neutralize MERS-CoV infection.

In some embodiments, the antibody or antigen binding fragment includes at least one CDR (such as an HCDR3) with a sequence that has at least 95% (such as at least 96%, at least 97%, at least 98%, at least 99%, or even 100%) sequence identity to any one of the heavy or light chain CDRs of the A2 $V_H$ or $V_L$ as shown in Table 1, and can specifically bind to MERS-CoV S protein and neutralize MERS-CoV infection. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-58, and 97-111, respectively, of SEQ ID NO: 44, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 26-34, 52-54, and 91-101, respectively, of SEQ ID NO: 46, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-58, and 97-111, respectively, of SEQ ID NO: 44, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 26-34, 52-54, and 91-101, respectively, of SEQ ID NO: 46, and can specifically bind to MERS-CoV S protein and neutralize MERS-CoV infection.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 44, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 46, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NO: 44 and 46, respectively, and can specifically bind to MERS-CoV S protein and neutralize MERS-CoV infection.

In additional embodiments, the antibody or antigen binding fragment includes a $V_H$ comprising the amino acid sequence set forth as one of SEQ ID NO: 44, and can specifically bind to MERS-CoV S protein and neutralize MERS-CoV infection. In more embodiments, the antibody or antigen binding fragment includes a $V_L$ comprising the amino acid sequence set forth as SEQ ID NO: 46, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 44 and 46, respectively, and can specifically bind to MERS-CoV S protein and neutralize MERS-CoV infection.

A10

In some embodiments, the antibody or antigen binding fragment can be based on or derived from the A10 antibody. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT), of the A10 antibody, and can specifically bind to MERS-CoV S protein and neutralize MERS-CoV infection.

In some embodiments, the antibody or antigen binding fragment can comprise a $V_H$ comprising the HCDR1, the HCDR2, and the HCDR3 of the A10 $V_H$ as set forth in Table 1, and can specifically bind to MERS-CoV S protein and neutralize MERS-CoV infection. In some embodiments, the antibody or antigen binding fragment can comprise a $V_L$ comprising the LCDR1, the LCDR2, and the LCDR3 of the A10 $V_L$ as set forth in Table 1, and can specifically bind to MERS-CoV S protein and neutralize MERS-CoV infection. In some embodiments, the antibody or antigen binding fragment can comprise a $V_H$ and a $V_L$ comprising the HCDR1, the HCDR2, the HCDR3, the LCDR1, the LCDR2, and the LCDR3 of the A10 $V_H$ and $V_L$ as set forth in Table 1, and can specifically bind to MERS-CoV S protein and neutralize MERS-CoV infection.

In some embodiments, the antibody or antigen binding fragment includes at least one CDR (such as an HCDR3) with a sequence that has at least 95% (such as at least 96%, at least 97%, at least 98%, at least 99%, or even 100%) sequence identity to any one of the heavy or light chain CDRs of the A10 $V_H$ or $V_L$ as shown in Table 1, and can specifically bind to MERS-CoV S protein and neutralize MERS-CoV infection. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-58, and 97-111, respectively, of SEQ ID NO: 48, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 26-34, 52-54, and 92-102, respectively, of SEQ ID NO: 50, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-58, and 97-111, respectively, of SEQ ID NO: 48, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 26-34, 52-54, and 92-102, respectively, of SEQ ID NO: 50, and can specifically bind to MERS-CoV S protein and neutralize MERS-CoV infection.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 48, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 50, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 48 and 50, respectively, and can specifically bind to MERS-CoV S protein and neutralize MERS-CoV infection.

In additional embodiments, the antibody or antigen binding fragment includes a $V_H$ comprising the amino acid sequence set forth as one of SEQ ID NO: 48, and can specifically bind to MERS-CoV S protein and neutralize MERS-CoV infection. In more embodiments, the antibody or antigen binding fragment includes a $V_L$ comprising the amino acid sequence set forth as SEQ ID NO: 50, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 48 and 50, respectively, and can specifically bind to MERS-CoV S protein and neutralize MERS-CoV infection.

FIB_B2

In some embodiments, the antibody or antigen binding fragment can be based on or derived from the FIB_B2 antibody. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT), of the FIB_B2 antibody, and can specifically bind to MERS-CoV S protein and neutralize MERS-CoV infection.

In some embodiments, the antibody or antigen binding fragment can comprise a $V_H$ comprising the HCDR1, the HCDR2, and the HCDR3 of the FIB_B2 $V_H$ as set forth in Table 1, and can specifically bind to MERS-CoV S protein and neutralize MERS-CoV infection. In some embodiments, the antibody or antigen binding fragment can comprise a $V_L$ comprising the LCDR1, the LCDR2, and the LCDR3 of the FIB_B2 $V_L$ as set forth in Table 1, and can specifically bind to MERS-CoV S protein and neutralize MERS-CoV infection. In some embodiments, the antibody or antigen binding fragment can comprise a $V_H$ and a $V_L$ comprising the HCDR1, the HCDR2, the HCDR3, the LCDR1, the LCDR2, and the LCDR3 of the FIB_B2 $V_H$ and $V_L$ as set forth in Table 1, and can specifically bind to MERS-CoV S protein and neutralize MERS-CoV infection.

In some embodiments, the antibody or antigen binding fragment includes at least one CDR (such as an HCDR3) with a sequence that has at least 95% (such as at least 96%, at least 97%, at least 98%, at least 99%, or even 100%) sequence identity to any one of the heavy or light chain CDRs of the FIB_B2 $V_H$ or $V_L$ as shown in Table 1, and can specifically bind to MERS-CoV S protein and neutralize MERS-CoV infection. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-55, and 97-107, respectively, of SEQ ID NO: 52, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-32, 50-52, and 89-97, respectively, of SEQ ID NO: 54, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-55, and 97-107, respectively, of SEQ ID NO: 52, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-32, 50-52, and 89-97, respectively, of SEQ ID NO: 54, and can specifically bind to MERS-CoV S protein and neutralize MERS-CoV infection.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 52, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 54, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NO: 52 and 54, respectively, and can specifically bind to MERS-CoV S protein and neutralize MERS-CoV infection.

In additional embodiments, the antibody or antigen binding fragment includes a $V_H$ comprising the amino acid sequence set forth as one of SEQ ID NO: 52, and can specifically bind to MERS-CoV S protein and neutralize MERS-CoV infection. In more embodiments, the antibody or antigen binding fragment includes a $V_L$ comprising the amino acid sequence set forth as SEQ ID NO: 54, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 52 and 54, respectively, and can specifically bind to MERS-CoV S protein and neutralize MERS-CoV infection.

FIB_H1

In some embodiments, the antibody or antigen binding fragment can be based on or derived from the FIB_H1 antibody. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT), of the FIB_H1 antibody, and can specifically bind to MERS-CoV S protein and neutralize MERS-CoV infection.

In some embodiments, the antibody or antigen binding fragment can comprise a $V_H$ comprising the HCDR1, the HCDR2, and the HCDR3, of the FIB_H1 $V_H$ as set forth in Table 1, and can specifically bind to MERS-CoV S protein and neutralize MERS-CoV infection. In some embodiments, the antibody or antigen binding fragment can comprise a $V_L$ comprising the LCDR1, the LCDR2, and the LCDR3 of the FIB_H1 $V_L$ as set forth in Table 1, and can specifically bind to MERS-CoV S protein and neutralize MERS-CoV infection. In some embodiments, the antibody or antigen binding fragment can comprise a $V_H$ and a $V_L$ comprising the HCDR1, the HCDR2, the HCDR3, the LCDR1, the LCDR2, and the LCDR3 of the FIB_H1 $V_H$ and $V_L$ as set forth in Table 1, and can specifically bind to MERS-CoV S protein and neutralize MERS-CoV infection.

In some embodiments, the antibody or antigen binding fragment includes at least one CDR (such as an HCDR3) with a sequence that has at least 95% (such as at least 96%, at least 97%, at least 98%, at least 99%, or even 100%) sequence identity to any one of the heavy or light chain CDRs of the FIB_H1 $V_H$ or $V_L$ as shown in Table 1, and can specifically bind to MERS-CoV S protein and neutralize MERS-CoV infection. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-55, and 97-107, respectively, of SEQ ID NO: 56, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-32, 50-52, and 89-97, respectively, of SEQ ID NO: 58, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-55, and 97-107, respectively, of SEQ ID NO: 56, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 27-32, 50-52, and 89-97, respectively, of SEQ ID NO: 58, and can specifically bind to MERS-CoV S protein and neutralize MERS-CoV infection.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 56, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 58, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NO: 56 and 58, respectively.

In additional embodiments, the antibody or antigen binding fragment includes a $V_H$ comprising the amino acid sequence set forth as one of SEQ ID NO: 56, and can specifically bind to MERS-CoV S protein and neutralize MERS-CoV infection. In more embodiments, the antibody or antigen binding fragment includes a $V_L$ comprising the amino acid sequence set forth as SEQ ID NO: 58, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 56 and 58, respectively, and can specifically bind to MERS-CoV S protein and neutralize MERS-CoV infection.

G2

In some embodiments, the antibody or antigen binding fragment can be based on or derived from the G2 antibody. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT), of the G2 antibody, and can specifically bind to MERS-CoV S protein and neutralize MERS-CoV infection.

In some embodiments, the antibody or antigen binding fragment can comprise a $V_H$ comprising the HCDR1, the HCDR2, and the HCDR3, of the G2 $V_H$ as set forth in Table 1, and can specifically bind to MERS-CoV S protein and neutralize MERS-CoV infection. In some embodiments, the antibody or antigen binding fragment can comprise a $V_L$ comprising the LCDR1, the LCDR2, and the LCDR3 of the G2 $V_L$ as set forth in Table 1, and can specifically bind to MERS-CoV S protein and neutralize MERS-CoV infection. In some embodiments, the antibody or antigen binding fragment can comprise a $V_H$ and a $V_L$ comprising the HCDR1, the HCDR2, the HCDR3, the LCDR1, the LCDR2, and the LCDR3 of the G2 $V_H$ and $V_L$ as set forth in Table 1, and can specifically bind to MERS-CoV S protein and neutralize MERS-CoV infection.

In some embodiments, the antibody or antigen binding fragment includes at least one CDR (such as an HCDR3) with a sequence that has at least 90% (such as at least 95%, at least 96%, at least 97%, at least 98%, at least 99%, or even 100%) sequence identity to any one of the heavy or light chain CDRs of the G2 $V_H$ or $V_L$ as shown in Table 1, and can specifically bind to MERS-CoV S protein and neutralize MERS-CoV infection. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, at least 99%, or even 100%) identical to amino acids 26-33, 51-58, and 97-107, respectively, of SEQ ID NO: 115, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, at least 99%, or even 100%) identical to amino acids amino acids 26-36, 54-56, and 93-97, respectively, of SEQ ID NO: 117, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, at least 99%, or even 100%) identical to amino acids 26-33, 51-58, and 97-107, respectively, of SEQ ID NO: 115, and a $V_L$ comprising a LCDR1, a LCDR2, and a LCDR3 comprising amino acid sequences at least 90% (such as at least 95%, at least 96%, at least 97%, at least 98%, at least 99%, or even 100%) identical to amino acids amino acids 26-36, 54-56, and 93-97, respectively, of SEQ ID NO: 117, and can specifically bind to MERS-CoV S protein and neutralize MERS-CoV infection.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 115, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 117, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NO: 115 and 117, respectively.

In additional embodiments, the antibody or antigen binding fragment includes a $V_H$ comprising the amino acid sequence set forth as one of SEQ ID NO: 115, and can specifically bind to MERS-CoV S protein and neutralize MERS-CoV infection. In more embodiments, the antibody or antigen binding fragment includes a $V_L$ comprising the amino acid sequence set forth as SEQ ID NO: 117, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 115 and 117, respectively, and can specifically bind to MERS-CoV S protein and neutralize MERS-CoV infection.

In some embodiments, a human chimeric antibody including the $V_H$ of the murine G2 antibody and a human IgG1 constant domain can generated by linking the G2 $V_H$ (SEQ ID NO: 115) to the human IgG1 constant domain. The DNA and protein sequences of the chimeric heavy chain are provided as SEQ ID NOs: 153 and 154. The chimeric $V_H$ includes a KG-TP substitution at the beginning of the constant domain to enhance compatibility of the human heavy chain and the mouse light chain. The G2 mouse-human chimeric mAb (G2-huIgG KG/TP) neutralizes 11 MERS-CoV strains with comparable $IC_{50}$, but slightly lower $IC_{80}$ and $IC_{90}$ to G2, as assayed using a pseudovirus neutralization assay (see the Table 5).

G4

In some embodiments, the antibody or antigen binding fragment can be based on or derived from the G4 antibody. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT), of the G4 antibody, and can specifically bind to MERS-CoV S protein and neutralize MERS-CoV infection.

In some embodiments, the antibody or antigen binding fragment can comprise a $V_H$ comprising the HCDR1, the HCDR2, and the HCDR3 of the G4 $V_H$ as set forth in Table 1, and can specifically bind to MERS-CoV S protein and neutralize MERS-CoV infection. In some embodiments, the antibody or antigen binding fragment can comprise a $V_L$ comprising the LCDR1, the LCDR2, and the LCDR3 of the G4 $V_L$ as set forth in Table 1, and can specifically bind to MERS-CoV S protein and neutralize MERS-CoV infection. In some embodiments, the antibody or antigen binding fragment can comprise a $V_H$ and a $V_L$ comprising the HCDR1, the HCDR2, the HCDR3, the LCDR1, the LCDR2, and the LCDR3 of the G4 $V_H$ and $V_L$ as set forth in Table 1, and can specifically bind to MERS-CoV S protein and neutralize MERS-CoV infection.

In some embodiments, the antibody or antigen binding fragment includes at least one CDR (such as an HCDR3) with a sequence that has at least 90% (such as at least 95%, at least 96%, at least 97%, at least 98%, at least 99%, or even 100%) sequence identity to any one of the heavy or light chain CDRs of the G4 $V_H$ or $V_L$ as shown in Table 1, and can specifically bind to MERS-CoV S protein and neutralize MERS-CoV infection. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, at least 99%, or even 100%) identical to amino acids 26-33, 51-58, and 97-111, respectively, of SEQ ID NO: 119, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, at least 99%, or even 100%) identical to amino acids amino acids 26-36, 54-56, and 93-101, respectively, of SEQ ID NO: 121, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, at least 99%, or even 100%) identical to amino acids 26-33, 51-58, and 97-111, respectively, of SEQ ID NO: 119, and a $V_L$ comprising a LCDR1, a LCDR2, and a LCDR3 comprising amino acid sequences at least 90% (such as at least 95%, at least 96%, at least 97%, at least 98%, at least 99%, or even 100%) identical to amino acids amino acids 26-36, 54-56, and 93-101, respectively, of SEQ ID NO: 121, and can specifically bind to MERS-CoV S protein and neutralize MERS-CoV infection.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 119, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 121, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NO: 119 and 121, respectively.

In additional embodiments, the antibody or antigen binding fragment includes a $V_H$ comprising the amino acid sequence set forth as one of SEQ ID NO: 119, and can specifically bind to MERS-CoV S protein and neutralize MERS-CoV infection. In more embodiments, the antibody or antigen binding fragment includes a $V_L$ comprising the amino acid sequence set forth as SEQ ID NO: 121, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 119 and 121, respectively, and can specifically bind to MERS-CoV S protein and neutralize MERS-CoV infection.

D12

In some embodiments, the antibody or antigen binding fragment can be based on or derived from the D12 antibody. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT), of the D12 antibody, and can specifically bind to MERS-CoV S protein and neutralize MERS-CoV infection.

In some embodiments, the antibody or antigen binding fragment can comprise a $V_H$ comprising the HCDR1, the HCDR2, and the HCDR3, of the D12 $V_H$ as set forth in Table 1, and can specifically bind to MERS-CoV S protein and neutralize MERS-CoV infection. In some embodiments, the antibody or antigen binding fragment can comprise a $V_L$ comprising the LCDR1, the LCDR2, and the LCDR3 of the D12 $V_L$ as set forth in Table 1, and can specifically bind to MERS-CoV S protein and neutralize MERS-CoV infection. In some embodiments, the antibody or antigen binding fragment can comprise a $V_H$ and a $V_L$ comprising the HCDR1, the HCDR2, the HCDR3, the LCDR1, the LCDR2, and the LCDR3 of the D12 $V_H$ and $V_L$ as set forth in Table 1, and can specifically bind to MERS-CoV S protein and neutralize MERS-CoV infection.

In some embodiments, the antibody or antigen binding fragment includes at least one CDR (such as an HCDR3) with a sequence that has at least 90% (such as at least 95%, at least 96%, at least 97%, at least 98%, at least 99%, or even 100%) sequence identity to any one of the heavy or light chain CDRs of the D12 $V_H$ or $V_L$ as shown in Table 1, and can specifically bind to MERS-CoV S protein and neutralize MERS-CoV infection. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, at least 99%, or even 100%) identical to amino acids 26-33, 51-58, and 97-105, respectively, of SEQ ID NO: 123, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, at least 99%, or even 100%) identical to amino acids amino acids 26-32, 50-52, and 89-97, respectively, of SEQ ID NO: 125, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, at least 99%, or even 100%) identical to amino acids 26-33, 51-58, and 97-105, respectively, of SEQ ID NO: 123, and a $V_L$ comprising a LCDR1, a LCDR2, and a LCDR3 comprising amino acid sequences at least 90% (such as at least 95%, at least 96%, at least 97%, at least 98%, at least 99%, or even 100%) identical to amino acids amino acids 26-32, 50-52, and 89-97, respectively, of SEQ ID NO: 125, and can specifically bind to MERS-CoV S protein and neutralize MERS-CoV infection.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 123, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 125, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NO: 123 and 125, respectively.

In additional embodiments, the antibody or antigen binding fragment includes a $V_H$ comprising the amino acid sequence set forth as one of SEQ ID NO: 123, and can specifically bind to MERS-CoV S protein and neutralize MERS-CoV infection. In more embodiments, the antibody or antigen binding fragment includes a $V_L$ comprising the amino acid sequence set forth as SEQ ID NO: 125, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 123 and 125, respectively, and can specifically bind to MERS-CoV S protein and neutralize MERS-CoV infection.

F11

In some embodiments, the antibody or antigen binding fragment can be based on or derived from the F11 antibody. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT), of the F11 antibody, and can specifically bind to MERS-CoV S protein and neutralize MERS-CoV infection.

In some embodiments, the antibody or antigen binding fragment can comprise a $V_H$ comprising the HCDR1, the HCDR2, and the HCDR3, of the F11 $V_H$ as set forth in Table 1, and can specifically bind to MERS-CoV S protein and neutralize MERS-CoV infection. In some embodiments, the antibody or antigen binding fragment can comprise a $V_L$ comprising the LCDR1, the LCDR2, and the LCDR3 of the F11 $V_L$ as set forth in Table 1, and can specifically bind to MERS-CoV S protein and neutralize MERS-CoV infection. In some embodiments, the antibody or antigen binding fragment can comprise a $V_H$ and a $V_L$ comprising the HCDR1, the HCDR2, the HCDR3, the LCDR1, the LCDR2, and the LCDR3 of the F11 $V_H$ and $V_L$ as set forth in Table 1, and can specifically bind to MERS-CoV S protein and neutralize MERS-CoV infection.

In some embodiments, the antibody or antigen binding fragment includes at least one CDR (such as an HCDR3) with a sequence that has at least 90% (such as at least 95%, at least 96%, at least 97%, at least 98%, at least 99%, or even 100%) sequence identity to any one of the heavy or light chain CDRs of the F11 $V_H$ or $V_L$ as shown in Table 1, and can specifically bind to MERS-CoV S protein and neutralize MERS-CoV infection. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, at least 99%, or even 100%) identical to amino acids 26-33, 51-58, and 97-111, respectively, of SEQ ID NO: 127, and can specifically bind to MERS-CoV S protein and neutralize MERS-CoV infection. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, at least 99%, or even 100%) identical to amino acids amino acids 26-37, 55-57, and 94-102, respectively, of SEQ ID NO: 129, and can specifically bind to MERS-CoV S protein and neutralize MERS-CoV infection. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, at least 99%, or even 100%) identical to amino acids 26-33, 51-58, and 97-111, respectively, of SEQ ID NO: 127, and a $V_L$ comprising a LCDR1, a LCDR2, and a LCDR3 comprising amino acid sequences at least 90% (such as at least 95%, at least 96%, at least 97%, at least 98%, at least 99%, or even 100%) identical to amino acids amino acids 26-37, 55-57, and 94-102, respectively, of SEQ ID NO: 129, and can specifically bind to MERS-CoV S protein and neutralize MERS-CoV infection.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 127, and can specifically bind to MERS-CoV S protein and neutralize MERS-CoV infection. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 129, and can specifically bind to MERS-CoV S protein and neutralize MERS-CoV infection. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NO: 127 and 129, respectively.

In additional embodiments, the antibody or antigen binding fragment includes a $V_H$ comprising the amino acid sequence set forth as one of SEQ ID NO: 127, and can specifically bind to MERS-CoV S protein and neutralize MERS-CoV infection. In more embodiments, the antibody or antigen binding fragment includes a $V_L$ comprising the amino acid sequence set forth as SEQ ID NO: 129, and can specifically bind to MERS-CoV S protein and neutralize MERS-CoV infection. In some embodiments, the antibody or antigen binding fragment includes a $V_H$ and a $V_L$ comprising the amino acid sequences set forth as SEQ ID NOs: 127 and 129, respectively, and can specifically bind to MERS-CoV S protein and neutralize MERS-CoV infection.

1. Additional Description of Antibodies and Antigen Binding Fragments

The antibody or antigen binding fragment can be a human antibody or fragment thereof. Chimeric antibodies are also provided. The antibody or antigen binding fragment can include any suitable framework region, such as (but not limited to) a human framework region. Human framework regions, and mutations that can be made in a human antibody framework regions, are known in the art (see, for example, in U.S. Pat. No. 5,585,089, which is incorporated herein by reference). The framework regions of the JC57-13, JC57-14, and JC57-11 antibodies can be swapped for human framework regions to generate a fully human antibody. Alternatively, a heterologous framework region, such as, but not limited to a mouse framework region, can be included in the heavy or light chain of the antibodies. (See, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.)

The antibody can be of any isotype. The antibody can be, for example, an IgM or an IgG antibody, such as $IgG_1$, $IgG_2$, $IgG_3$, or $IgG_4$. The class of an antibody that specifically binds MERS-CoV S protein can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. A nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds MERS-CoV S protein, that was originally IgM may be class switched to an IgG. Class switching can be used to convert one IgG subclass to another, such as from $IgG_1$ to $IgG_2$, $IgG_3$, or $IgG_4$.

In some examples, the disclosed antibodies are oligomers of antibodies, such as dimers, trimers, tetramers, pentamers, hexamers, septamers, octomers and so on.

(a) Binding Affinity

In several embodiments, the antibody or antigen binding fragment can specifically bind MERS-CoV S protein with an affinity (e.g., measured by $K_d$) of less than $1.0 \times 10^{-8}$ M (such as less than $5.0 \times 10^{-8}$ M, less than $1.0 \times 10^{-9}$ M, less than $5.0 \times 10^{-9}$ M, less than $1.0 \times 10^{-10}$ M, less than $5.0 \times 10^{-10}$ M, or less than $1.0 \times 10^{-11}$ M. $K_d$ can be measured, for example, by a radiolabeled antigen binding assay (RIA) performed with the Fab version of an antibody of interest and its antigen using known methods. In one assay, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

In another assay, $K_d$ can be measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE®, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 l/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 l/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds 106 M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

(b) Neutralization

In some embodiments, the antibody or antigen binding fragment can also be distinguished by neutralization breadth. In some embodiments, the antibody or antigen binding fragment can neutralize at least 70% (such as at least 75%, at least 80%, at least 85%, or least 90%,) of the MERS-CoV isolates listed Table 4, for example, with an IC$_{50}$ value of less than 50 µg/ml. The person of ordinary skill in the art if familiar with methods of measuring neutralization breadth and potency. Additionally, exemplary methods for assaying the neutralization breadth and potency of an immune response to a vaccination regimen are provided herein in the Examples section.

(c) Multispecific Antibodies

In some embodiments, the antibody or antigen binding fragment is included on a multispecific antibody, such as a bi-specific antibody. Such multispecific antibodies can be produced by known methods, such as crosslinking two or more antibodies, antigen binding fragments (such as scFvs) of the same type or of different types. Exemplary methods of making multispecific antibodies include those described in PCT Pub. No. WO2013/163427, which is incorporated by reference herein in its entirety. Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

Various types of multi-specific antibodies are known. Bispecific single chain antibodies can be encoded by a single nucleic acid molecule. Examples of bispecific single chain antibodies, as well as methods of constructing such antibodies are known in the art (see, e.g., U.S. Pat. Nos. 8,076,459, 8,017,748, 8,007,796, 7,919,089, 7,820,166, 7,635,472, 7,575,923, 7,435,549, 7,332,168, 7,323,440, 7,235,641, 7,229,760, 7,112,324, 6,723,538, incorporated by reference herein). Additional examples of bispecific single chain antibodies can be found in PCT application No. WO 99/54440; Mack, *J. Immunol.*, 158:3965-3970, 1997; Mack, *PNAS*, 92:7021-7025, 1995; Kufer, *Cancer Immunol. Immunother.*, 45:193-197, 1997; Loffler, *Blood*, 95:2098-2103, 2000; and Bruhl, *J. Immunol.*, 166:2420-2426, 2001. Production of bispecific Fab-scFv ("bibody") molecules are described, for example, in Schoonjans et al. (J. Immunol. 165:7050-57, 2000) and Willems et al. (J Chromatogr B Analyt Technol Biomed Life Sci. 786:161-76, 2003). For bibodies, a scFv molecule can be fused to one of the VL-CL (L) or VH-CH1 chains, e.g., to produce a bibody one scFv is fused to the C-term of a Fab chain.

(d) Fragments

Antigen binding fragments are encompassed by the present disclosure, such as Fab, F(ab')$_2$, and Fv which include a heavy chain and light chain variable region and specifically bind MERS-CoV S protein. These antibody fragments retain the ability to selectively bind with the antigen and are "antigen-binding" fragments. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule. A scFv is a fusion protein in which a light chain variable region of an immunoglobulin and a heavy chain variable region of an immunoglobulin are bound by a linker (see, e.g., Ahmad et al., Clin. Dev. Immunol., 2012, doi:10.1155/2012/980250; Marbry, IDrugs, 13:543-549, 2010). The intramolecular orientation of the $V_H$-domain and the $V_L$-domain in a scFv, is not decisive for the provided antibodies (e.g., for the provided multispecific antibodies). Thus, scFvs with both possible arrangements ($V_H$-domain-linker domain-$V_L$-domain; $V_L$-domain-linker domain-$V_H$-domain) may be used.

(6) A dimer of a single chain antibody (scFV$_2$), defined as a dimer of a scFV. This has also been termed a "minianti-body."

Methods of making these fragments are known in the art (see for example, Harlow and Lane, *Antibodies: A Laboratory Manual*, 2$^{nd}$, Cold Spring Harbor Laboratory, New York, 2013).

Antigen binding fragments can be prepared by proteolytic hydrolysis of the antibody or by expression in a host cell (such as an *E. coli* cell) of DNA encoding the fragment. Antigen binding fragments can also be obtained by pepsin or papain digestion of whole antibodies by conventional methods. For example, antigen binding fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Antigen binding single $V_H$ domains, called domain antibodies (dAb), have also been identified from a library of murine $V_H$ genes amplified from genomic DNA of immunized mice (Ward et al. *Nature* 341:544-546, 1989). Human single immunoglobulin variable domain polypeptides capable of binding antigen with high affinity have also been described (see, for example, PCT Publication Nos. WO 2005/035572 and WO 2003/002609). The CDRs disclosed herein can also be included in a dAb.

In some embodiments, one or more of the heavy and/or light chain complementarity determining regions (CDRs) from a disclosed antibody (such as the JC57-13, JC57-11, JC57-14, FIB_B2, FIB_H1, G2, G4, D12, F11, C2, C5, A2, or A10 antibody) is expressed on the surface of another protein, such as a scaffold protein. The expression of domains of antibodies on the surface of a scaffolding protein are known in the art (see e.g. Liu et al., *J. Virology* 85(17): 8467-8476, 2011). Such expression creates a chimeric protein that retains the binding for MERS-CoV S protein. In some specific embodiments, one or more of the heavy chain CDRs is grafted onto a scaffold protein, such as one or more of heavy chain CDR1, CDR2, and/or CDR3. One or more CDRs can also be included in a diabody or another type of single chain antibody molecule.

In an additional embodiment, the antibody fragment is a camelid antibody, and includes a heavy chain variable domain, but not a light chain variable domain, of a disclosed antibody. Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced. The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for MERS-CoV S protein. In several embodiment, the camelid antibody or nanobody is obtained by grafting the CDRs sequences of the heavy or light chain of the disclosed MERS-CoV S protein specific antibodies into nanobody or single domain antibody framework sequences, as described for example in PCT/EP93/02214.

(e) Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the CDRs and the framework regions. Amino acid substitutions may be introduced into an antibody of interest and the products screened for a desired activity, e.g., retained/improved antigen binding, decreased immunogenicity, or improved ADCC or CDC.

The variants typically retain amino acid residues necessary for correct folding and stabilizing between the $V_H$ and the $V_L$ regions, and will retain the charge characteristics of the residues in order to preserve the low pI and low toxicity of the molecules. Amino acid substitutions can be made in the $V_H$ and the $V_L$ regions to increase yield. Conservative amino acid substitution tables providing functionally similar amino acids are well known to one of ordinary skill in the art.

In some embodiments, the $V_H$ of the antibody includes up to 10 (such as up to 1, up to 2, up to 3, up to 4, up to 5, up to 6, up to 7, up to 8, or up to 9) amino acid substitutions (such as conservative amino acid substitutions), and or the $V_L$ of the antibody includes up to 10 (such as up to 1, up to 2, up to 3, up to 4, up to 5, up to 6, up to 7, up to 8, or up to 9) amino acid substitutions (such as conservative amino acid substitutions), compared to the amino acid sequence of the corresponding $V_H$ and/or $V_L$ of one of the JC57-13, JC57-11, JC57-14, FIB_B2, FIB_H1, G2, G4, D12, F11, C2, C5, A2, or A10 antibodies.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In certain embodiments of the variant VH and VL sequences provided above, each CDR either is unaltered, or contains no more than one, two or three amino acid substitutions.

To increase binding affinity of the antibody, the $V_L$ and $V_H$ segments can be randomly mutated, such as within HCDR3 region or the LCDR3 region, in a process analogous to the in vivo somatic mutation process responsible for affinity maturation of antibodies during a natural immune response. Thus in vitro affinity maturation can be accomplished by amplifying $V_H$ and $V_L$ regions using PCR primers complementary to the HCDR3 or LCDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be tested to determine the binding affinity for MERS-CoV S protein. Methods of in vitro affinity maturation are known (see, e.g., Chowdhury, *Methods Mol. Biol.* 207:179-196 (2008)), and Hoogenboom et al. in *Methods in Molecular Biology* 178:1-37 (O'Brien et al., ed., Human Press, Totowa, N.J., (2001).)

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

In certain embodiments, an antibody or antigen binding fragment is altered to increase or decrease the extent to which the antibody or antigen binding fragment is glycosylated. Addition or deletion of glycosylation sites may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region; however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec 13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In several embodiments, the constant region of the antibody includes one or more amino acid substitutions to optimize in vivo half-life of the antibody. The serum half-life of IgG Abs is regulated by the neonatal Fc receptor (FcRn). Thus, in several embodiments, the antibody includes an amino acid substitution that increases binding to the FcRn. Several such substitutions are known to the person of ordinary skill in the art, such as substitutions at IgG constant regions T250Q and M428L (see, e.g., Hinton et al., *J Immunol.*, 176:346-356, 2006); M428L and N434S (see, e.g., Zalevsky, et al., *Nature Biotechnology*, 28:157-159, 2010); N434A (see, e.g., Petkova et al., *Int. Immunol.*, 18:1759-1769, 2006); T307A, E380A, and N434A (see, e.g., Petkova et al., *Int. Immunol.*, 18:1759-1769, 2006); and M252Y, S254T, and T256E (see, e.g., Dall'Acqua et al., *J. Biol. Chem.*, 281:23514-23524, 2006).

In some embodiments, the constant region of the antibody includes one of more amino acid substitutions to optimize Antibody-dependent cell-mediated cytotoxicity (ADCC). ADCC is mediated primarily through a set of closely related Fcγ receptors. In some embodiments, the antibody includes one or more amino acid substitutions that increase binding to FcγRIIIa. Several such substitutions are known to the person of ordinary skill in the art, such as substitutions at IgG constant regions S239D and I332E (see, e.g., Lazar et al., *Proc. Natl., Acad. Sci. U.S.A.,* 103:4005-4010, 2006); and S239D, A330L, and I332E (see, e.g., Lazar et al., *Proc. Natl., Acad. Sci. U.S.A.,* 103:4005-4010, 2006).

Combinations of the above substitutions are also included, to generate an IgG constant region with increased binding to FcRn and FcγRIIIa. The combinations increase antibody half-life and ADCC. For example, such combination include antibodies with the following amino acid substitution in the Fc region:
(1) S239D/I332E and T250Q/M428L;
(2) S239D/I332E and M428L/N434S;
(3) S239D/I332E and N434A;
(4) S239D/I332E and T307A/E380A/N434A;
(5) S239D/I332E and M252Y/S254T/T256E;
(6) S239D/A330L/I332E and T250Q/M428L;
(7) S239D/A330L/I332E and M428L/N434S;
(8) S239D/A330L/I332E and N434A;
(9) S239D/A330L/I332E and T307A/E380A/N434A; or
(10) S239D/A330L/I332E and M252Y/S254T/T256E.

In some examples, the antibodies, or an antigen binding fragment thereof is modified such that it is directly cytotoxic to infected cells, or uses natural defenses such as complement, antibody dependent cellular cytotoxicity (ADCC), or phagocytosis by macrophages.

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

The antibody or antigen binding fragment can be derivatized or linked to another molecule (such as another peptide or protein). In general, the antibody or antigen binding fragment is derivatized such that the binding to MERS-CoV S protein is not affected adversely by the derivatization or labeling. For example, the antibody or antigen binding fragment can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

B. Conjugates

Monoclonal antibodies and antigen binding fragments that specifically bind to an epitope on MERS-CoV S protein can be conjugated to an agent, such as an effector molecule or detectable marker, using any number of means known to those of skill in the art. Both covalent and noncovalent attachment means may be used. One of skill in the art will appreciate that various effector molecules and detectable markers can be used, including (but not limited to) toxins and radioactive agents such as $^{125}$I, $^{32}$P, $^{14}$C, $^{3}$H and $^{35}$S and other labels, target moieties and ligands, etc. The choice of a particular effector molecule or detectable marker depends on the particular target molecule or cell, and the desired biological effect.

The choice of a particular effector molecule or detectable marker depends on the particular target molecule or cell, and the desired biological effect. Thus, for example, the effector molecule can be a cytotoxin that is used to bring about the death of a particular target cell (such as a MERS-CoV infected cell). In other embodiments, the effector molecule can be a cytokine, such as IL-15; conjugates including the cytokine can be used, e.g., to stimulate immune calls locally.

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on a polypeptide to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15, amino acids long.

In view of the large number of methods that have been reported for attaching a variety of radiodiagnostic compounds, radiotherapeutic compounds, labels (such as enzymes or fluorescent molecules), toxins, and other agents to antibodies one skilled in the art will be able to determine a suitable method for attaching a given agent to an antibody or antigen binding fragment or other polypeptide. For example, the antibody or antigen binding fragment can be conjugated with effector molecules such as small molecular weight drugs such as Monomethyl Auristatin E (MMAE), Monomethyl Auristatin F (MMAF), maytansine, maytansine derivatives, including the derivative of maytansine known as DM1 (also known as mertansine), or other agents to make an antibody drug conjugate (ADC). In several embodiments, conjugates of an antibody or antigen binding fragment and one or more small molecule toxins, such as a calicheamicin, maytansinoids, dolastatins, auristatins, a trichothecene, and CC1065, and the derivatives of these toxins that have toxin activity, are provided.

The antibody or antigen binding fragment can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

The antibody or antigen binding fragment can be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

The antibody or antigen binding fragment can also be conjugated with a radiolabeled amino acid. The radiolabel may be used for both diagnostic and therapeutic purposes. For instance, the radiolabel may be used to detect MERS-CoV S protein and MERS-CoV S protein expressing cells by x-ray, emission spectra, or other diagnostic techniques. Examples of labels for polypeptides include, but are not limited to, the following radioisotopes or radionucleotides: $^3$H, $^{14}$C, $^{15}$N, $^{35}$S, $^{90}$Y, $^{99}$Tc, $^{111}$In, $^{125}$I, $^{131}$I.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The average number of effector molecule or detectable marker moieties per antibody or antigen binding fragment in a conjugate can range, for example, from 1 to 20 moieties per antibody or antigen binding fragment. In certain embodiments, the average number of effector molecule or detectable marker moieties per antibody or antigen binding fragment in a conjugate range from about 1 to about 2, from about 1 to about 3, about 1 to about 8; from about 2 to about 6; from about 3 to about 5; or from about 3 to about 4. The loading (for example, effector molecule/antibody ratio) of an conjugate may be controlled in different ways, for example, by: (i) limiting the molar excess of effector molecule-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number or position of linker-effector molecule attachments.

C. Methods

Methods are disclosed herein for the prevention or treatment of MERS-CoV infection in a subject by administering a therapeutically effective amount of a disclosed MERS-CoV S protein specific antibody or antigen binding fragment, or encoding nucleic acid molecule, to the subject. In some examples, the antibody, antigen binding fragment, or nucleic acid molecule, can be used pre-exposure (for example, to prevent or inhibit MERS-CoV infection). In some examples, the antibody, antigen binding fragment, or nucleic acid molecule, can be used in post-exposure prophylaxis. In some examples, the antibody, antigen binding fragment, or nucleic acid molecule, can be administered to a subject with a MERS-CoV infection, such as a subject being treated with anti-viral therapy. In some examples the antibody, antigen binding fragment, or nucleic acid molecule is modified such that it is directly cytotoxic to infected cells (e.g., by conjugation to a toxin), or uses natural defenses such as complement, antibody dependent cellular cytotoxicity (ADCC), or phagocytosis by macrophages.

MERS-CoV infection does not need to be completely eliminated or prevented for the method to be effective. For example, a method can decrease MERS-CoV infection in the subject by a desired amount, for example by at least 10%, at least 20%, at least 50%, at least 60%, at least 70%, at least 80%, at least 90%, at least 95%, at least 98%, or even at least 100% (elimination of detectable MERS-CoV infected cells), as compared to MERS-CoV infection in the absence of the treatment. In additional embodiments, MERS-CoV replication can be reduced or inhibited by similar methods. MERS-CoV replication does not need to be completely eliminated for the method to be effective. For example, a method can decrease MERS-CoV replication by a desired amount, for example by at least 10%, at least 20%, at least 50%, at least 60%, at least 70%, at least 80%, at least 90%, at least 95%, at least 98%, or even at least 100% (elimination of detectable MERS-CoV), as compared to MERS-CoV replication in the absence of the treatment.

In one embodiment, administration of a disclosed antibody, antigen binding fragment, or conjugate, or nucleic acid molecule, results in a reduction in the establishment of MERS-CoV infection and/or reducing subsequent MERS-CoV disease progression in a subject. A reduction in the establishment of MERS-CoV infection and/or a reduction in subsequent MERS-CoV disease progression encompass any statistically significant reduction in MERS-CoV activity.

For any application, the antibody, antigen binding fragment, or conjugate, or nucleic acid molecule can be combined with anti-viral therapy.

A therapeutically effective amount of a MERS-CoV S protein-specific antibody, antigen binding fragment, or conjugate, or nucleic acid molecule encoding such molecules, will depend upon the severity of the disease and/or infection and the general state of the patient's health. A therapeutically effective amount is that which provides either subjective relief of a symptom(s) or an objectively identifiable improvement as noted by the clinician or other qualified observer. The MERS-CoV S protein-specific antibody, antigen binding fragment, or conjugate, or nucleic acid molecule encoding such molecules, can be administered in conjunction with another therapeutic agent, either simultaneously or sequentially.

Single or multiple administrations of a composition including a disclosed MERS-CoV S protein-specific antibody, antigen binding fragment, or conjugate, or nucleic acid molecule encoding such molecules, can be administered depending on the dosage and frequency as required and tolerated by the patient. Compositions including the MERS-CoV S protein-specific antibody, antigen binding fragment, or conjugate, or nucleic acid molecule encoding such molecules, should provide a sufficient quantity of at least one of the MERS-CoV S protein-specific antibodies, antigen binding fragments, or conjugates, or nucleic acid molecule encoding such molecules to effectively treat the patient. The dosage can be administered once, but may be applied periodically until either a therapeutic result is achieved or until side effects warrant discontinuation of therapy. In one example, a dose of the antibody or antigen binding fragment is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Data obtained from cell culture assays and animal studies can be used to formulate a range of dosage for use in humans. The dosage normally lies within a range of circulating concentrations that include the ED$_{50}$, with little or minimal toxicity. The dosage can vary within this range depending upon the dosage form employed and the route of administration utilized. The therapeutically effective dose can be determined from cell culture assays and animal studies.

In certain embodiments, the antibody or antigen binding fragment that specifically binds MERS-CoV S protein, or conjugate thereof, or a nucleic acid molecule or vector encoding such a molecule, or a composition including such molecules, is administered at a dose in the range of from about 5 or 10 nmol/kg to about 300 nmol/kg, or from about 20 nmol/kg to about 200 nmol/kg, or at a dose of about 5, 10, 15, 20, 25, 30, 35, 40, 45, 50, 55, 60, 65, 70, 75, 80, 85, 90, 95, 100, 110, 120, 125, 130, 140, 150, 160, 170, 175, 180, 190, 200, 210, 220, 230, 240, 250, 260, 270, 280, 290, 300, 350, 400, 450, 500, 750, 1000, 1250, 1500, 1750 or 2000 nmol/kg, or at a dose of about 5, 10, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950 or 1000 µg/kg, or about 1, 1.25, 1.5, 2, 2.5, 3, 3.5, 4, 4.5, 5, 5.5, 6, 6.5, 7, 7.5, 8, 8.5, 9, 9.5 or 10 mg/kg, or other dose deemed appropriate by the treating physician. The doses described herein can be administered according to the dosing frequency/frequency of administration described herein, including without limitation daily, 2 or 3 times per week, weekly, every 2 weeks, every 3 weeks, monthly, etc.

In some embodiments, a disclosed therapeutic agent may be administered intravenously, subcutaneously or by another mode daily or multiple times per week for a period of time, followed by a period of no treatment, then the cycle is repeated. The initial period of treatment (e.g., administration of the therapeutic agent daily or multiple times per week) can be for 1 day, 3 days, 1 week, 2 weeks, 3 weeks, 4 weeks, 5 weeks, 6 weeks, 7 weeks, 8 weeks, 9 weeks, 10 weeks, 11 weeks or 12 weeks, for example. In a related embodiment, the period of no treatment can be for a period of days, weeks, or months, such as 3 days, 1 week, 2 weeks, 3 weeks or 4 weeks, 2 months, 3 months, 4 months, 5 months, 6 months, or more time. In certain embodiments, the dosing regimen of the therapeutic agent is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

Methods are also provided for the detection of the expression of MERS-CoV S protein in vitro or in vivo. In one example, the presence of MERS-CoV S protein can be detected in a biological sample using a disclosed MERS-CoV S protein specific antibody or antigen binding fragment thereof. Detecting the presence of the MERS-CoV S protein in the biological sample indicates that the sample is from a subject with a MERS-CoV infection. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. The method of detection can include contacting a cell or sample, or administering to a subject, an antibody or antigen binding fragment that specifically binds to MERS-CoV S protein, or conjugate there of (e.g. a conjugate including a detectable marker) under conditions sufficient to form an immune complex, and detecting the immune complex (e.g., by detecting a detectable marker conjugated to the antibody or antigen binding fragment.

In several embodiments, a method is provided for detecting MERS-CoV infection in a subject. The disclosure provides a method for detecting MERS-CoV in a biological sample, wherein the method includes contacting a biological sample from a subject with a disclosed antibody or antigen binding fragment under conditions sufficient for formation of an immune complex, and detecting the immune complex, to detect the MERS-CoV S protein in the biological sample. In one example, the detection of MERS-CoV S protein in the sample indicates that the subject has an MERS-CoV infection.

In some embodiments, the disclosed antibodies or antigen binding fragments thereof are used to test vaccines. For example to test if a vaccine composition including MERS-CoV S protein includes an epitope that can be specifically bound by an antibody that neutralizes MERS-CoV infection. Thus provided herein is a method for testing a vaccine, wherein the method includes contacting a sample containing the vaccine, such as a MERS-CoV S protein immunogen, with a disclosed antibody or antigen binding fragment under conditions sufficient for formation of an immune complex, and detecting the immune complex, to detect the vaccine with epitope that can be specifically bound by an antibody that neutralizes MERS-CoV infection in the sample.

In one embodiment, the antibody or antigen binding fragment is directly labeled with a detectable marker. In another embodiment, the antibody that binds MERS-CoV S protein (the first antibody) is unlabeled and a second antibody or other molecule that can bind the antibody that binds the first antibody is utilized for detection. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody, antigen binding fragment or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$.

III. MERS-CoV Immunogens and their Use

A. MERS-CoV S Proteins and Immunogenic Fragments Thereof

Several embodiments concern the MERS-CoV S protein or fragment or variant thereof, or a nucleic acid molecule encoding such proteins. A class I fusion glycoprotein, the MERS-CoV S protein is initially synthesized as a precursor protein of approximately 1350 amino acids in size. Individual precursor S polypeptides form a homotrimer and undergo glycosylation within the Golgi apparatus as well as processing to remove the signal peptide, and cleavage by a cellular protease between approximately position 751/752 to generate separate S1 and S2 polypeptide chains, which remain associated as S1/S2 protomers within the homotrimer, providing a trimer of herterodimers. There is another cleavage event that occurs between 887/888 to expose the N-terminus of S2 and liberate the fusion peptide. The S1 subunit is distal to the virus membrane and contains the receptor-binding domain (RBD) that mediates virus attachment to its host receptor, dipeptidyl peptidase-4 (DPP4), and includes approximately residues 367-606 of the S protein. The S2 subunit contains a transmembrane domain and two heptad-repeat sequences typical of fusion glycoproteins and mediates viral entry via membrane fusion with the host target cell.

The numbering used in the disclosed MERS-CoV S proteins and fragments thereof is relative to the S protein of the England1 strain of MERS-CoV, the sequence of which is provided as SEQ ID NO: 14, and deposited in GenBank as No. AFY13307.1, which is incorporated by reference herein in its entirety. Additional strains of MERS-CoV are known. An exemplary nucleic acid sequence encoding full-length MERS-CoV S protein is provided as SEQ ID NO: 13, below.

```
Full-length MERS-CoV S protein (1-1353) encoding
sequence, England1 strain
                                           (SEQ ID NO: 13)
atgattcactccgtgttcctgctgatgttcctgctgactcctacagagag ctatgtggatgtgggacctgattccgtcaagagcgcctgcatcgaagtgg acattcagcagaccttctttgataagacatggccaagacccatcgacgtg agcaaagccgatggcatcatctaccctcaggggaggacctattccaatat cacaattacttaccagggcctgttcccatatcagggagaccacggcgata tgtacgtgtattctgctggccatgcaacagggaccacacctcagaagctg tttgtggctaactacgccaggacgtcaaacagttcgcaaatggatttgt ggtccgcatcggcgccgctgcaaactctaccggcacagtgatcatttcac ctagcacttccgcaaccatccgaaaaatctacccagccttcatgctggga agctccgtgggcaatttagcgacgggaaaatgggacggttctttaacca caccctggtgctgctgcctgatggatgcggcacactgctgagggctttct actgtatcctggagccacgcagcggaaaccactgccccgcaggaaatagc tacacctcctttgccacatatcatactccagctaccgactgttccgatgg caactacaatcgaaacgcctctctgaatagtttcaaggaatacttcaacc tgcggaattgcacattcatgtacacttataacatcaccgaggacgaaatt ctggagtggttcggaatcactcagaccgcacagggcgtgcacctgttttc tagtcgctacgtcgacctgtatggcgggaacatgttccagtttgccactc tgcccgtgtacgataccatcaagtactattccatcattcctcattcaatc cgcagcattcagtccgatcgaaaggcttgggccgctttctacgtgtataa actgcagccactgaccttcctgctggactttagcgtcgatggctacatcc ggagagccattgactgcgggtttaatgatctgtcccagctgcactgttct tacgaaagtttcgacgtggagtccggcgtgtattctgtctcaagctttga ggccaagccctctgggagtgtggtcgagcaggctgaaggagtggagtgcg atttcagtcctctgctgtcagggaccccccctcaggtgtacaacttcaag cggctggtctttactaactgtaactacaatctgaccaagctgctgtcact
```
-continued
```
gttcagcgtgaatgactttacatgctcccagatcagcccgcagccattg ctagtaactgttactcctctctgatcctggactacttctcatatccactg agtatgaagagcgacctgagcgtgagttcagccggccccatcagccagtt caactataaacagagcttcagcaatcctacatgcctgattctggctactg tgccacataatctgactaccatcactaagcccctgaaatactcctatatt aacaagtgcagccggttcctgtccgacgatagaaccgaagtgccacagct ggtcaacgccaatcagtactctccctgtgtgagtatcgtcccttcaaccg tgtgggaagacggggattactatagaaaacagctgagccccctggaggga ggaggatggctggtggcatccggatctacagtcgccatgactgagcagct gcagatggggttcggaatcacagtgcagtacggcacagacactaactctg tctgtcccaagctggaattcgctaacgatactaagatcgcaagtcagctg ggaaactgcgtggagtactctctgtatggcgtgagtggcagaggggtctt ccagaattgtaccgcagtgggcgtccgacagcagcggtttgtgtacgacg cctatcagaatctggtcggctactatagcgacgatgggaactactattgc ctgagggcctgtgtgagcgtccctgtgtccgtcatctacgataaggaaac caaaacacacgccacactgttcgggtccgtggcttgcgagcatattagct ccacaatgtctcagtacagtagatcaactaggtcaatgctgaagaggcgc gatagcacctatggacctctgcagacaccagtggggtgtgtcctgggact ggtgaactctagtctgtttgtcgaggactgcaagctgccctgggccaga gcctgtgcgccctgcccgacaccccagcaccctgacccccggagcgtg cggagcgtgccggcgagatgcggctggccagcatcgccttcaaccaccc catccaggtggaccagctgaacagcagctacttcaagctgagcatcccca ccaacttcagcttcggcgtgacccaggagtacatccagaccaccatccag aaggtgaccgtggactgcaagcagtacgtgtgcaacggcttccagaagtg cgagcagctgctgcgggagtacggccagttctgcagcaagatcaaccagg ccctgcacggcgccaacctgcggcaggacgacagcgtgcggaacctgttc gccagcgtgaagagcagccagagcagccccatcatccccggcttcggcgg cgacttcaacctgaccctgctggagccgtgagcatcagcaccggcagcc ggagcgcccggagcgccatcgaggacctgctgttcgacaaggtgaccatc gccgaccccggctacatgcagggctacgacgactgcatgcagcagggccc cgccagcgcccgggacctgatctgcgcccagtacgtggccggctacaagg tgctgccccccctgatggacgtgaacatggaggccgcctacaccagcagc ctgctgggcagcatcgccggcgtgggctggaccgccggcctgagcagctt cgccgccatcccttcgcccagagcatcttctaccggctgaacggcgtgg gcatcacccagcaggtgctgagcgagaaccagaagctgatcgccaacaag ttcaaccaggccctgggcgccatgcagaccggcttcaccaccaccaacga ggccttccacaaggtgcaggacgccgtgaacaacaacgcccaggccctga gcaagctggccagcgagctgagcaacaccttcggcgccatcagcgccagc atcggcgacatcatccagcggctggacgtgctggagcaggacgcccagat cgaccggctgatcaacggccggctgaccaccctgaacgccttcgtggccc agcagctggtgcggagcgagagcgccgccctgagcgcccagctggccaag
```

-continued
```
gacaaggtgaacgagtgcgtgaaggcccagagcaagcggagcggcttctg
cggccagggcacccacatcgtgagcttcgtggtgaacgcccccaacggcc
tgtacttcatgcacgtgggctactaccccagcaaccacatcgaggtggtg
agcgcctacggcctgtgcgacgccgccaaccccaccaactgcatcgcccc
cgtgaacggctacttcatcaagaccaacaacacccggatcgtggacgagt
ggagctacaccggcagcagcttctacgcccccgagcccatcaccagcctg
aacaccaagtacgtggcccccaggtgacctaccagaacatcagcaccaa
cctgccccccccctgctgggcaacagcaccggcatcgacttccaggacg
agctggacgagttcttcaagaacgtgagcaccagcatccccaacttcggc
agcctgacccagatcaacaccaccctgctggacctgacctacgagatgct
gagcctgcagcaggtggtgaaggccctgaacgagagctacatcgacctga
aggagctgggcaactacacctactacaacaagtgggcctggtacatctgg
ctgggcttcatcgccggcctggtggccctggccctgtgcgtgttcttcat
cctgtgctgcaccggctgcggcaccaactgcatgggcaagctgaagtgca
accggtgctgcgaccggtacgaggagtacgacctggagccccacaaggtg
cacgtgcactga
```

An exemplary MERS-CoV S protein, England1 strain is provided as SEQ ID NO: 14, below:

```
                                      (SEQ ID NO: 14)
MIHSVFLLMELLTPTESYVDVGPDSVKSACIEVDIQQTFFDKTWPRPIDV

SKADGIIYPQGRTYSNITITYQGLFPYQGDHGDMYVYSAGHATGTTPQKL

FVANYSQDVKQFANGFVVRIGAAANSTGTVIISPSTSATIRKIYPAFMLG

SSVGNFSDGKMGRFFNHTLVLLPDGCGTLLRAFYCILEPRSGNHCPAGNS

YTSFATYHTPATDCSDGNYNRNASLNSFKEYFNLRNCTFMYTYNITEDEI

LEWFGITQTAQGVHLFSSRYVDLYGGNMFQFATLPVYDTIKYYSIIPHSI

RSIQSDRKAWAAFYVYKLQPLTFLLDFSVDGYIRRAIDCGFNDLSQLHCS

YESFDVESGVYSVSSFEAKPSGSVVEQAEGVECDFSPLLSGTPPQVYNFK

RLVFTNCNYNLTKLLSLFSVNDFTCSQISPAAIASNCYSSLILDYFSYPL

SMKSDLSVSSAGPISQFNYKQSFSNPTCLILATVPHNLTTITKPLKYSYI

NKCSRFLSDDRTEVPQLVNANQYSPCVSIVPSTVWEDGDYYRKQLSPLEG

GGWLVASGSTVAMTEQLQMGFGITVQYGTDTNSVCPKLEFANDTKIASQL

GNCVEYSLYGVSGRGVFQNCTAVGVRQQRFVYDAYQNLVGYYSDDGNYYC

LRACVSVPVSVIYDKETKTHATLFGSVACEHISSTMSQYSRSTRSMLKRR

DSTYGPLQTPVGCVLGLVNSSLFVEDCKLPLGQSLCALPDTPSTLTPRSV

RSVPGEMRLASIAFNHPIQVDQLNSSYFKLSIPTNFSFGVTQEYIQTTIQ

KVTVDCKQYVCNGFQKCEQLLREYGQFCSKINQALHGANLRQDDSVRNLF

ASVKSSQSSPIIPGFGGDFNLTLLEPVSISTGSRSARSAIEDLLFDKVTI

ADPGYMQGYDDCMQQGPASARDLICAQYVAGYKVLPPLMDVNMEAAYTSS

LLGSIAGVGWTAGLSSFAAIPFAQSIFYRLNGVGITQQVLSENQKLIANK

FNQALGAMQTGFTTTNEAFHKVQDAVNNNAQALSKLASELSNTFGAISAS

IGDIIQRLDVLEQDAQIDRLINGRLTTLNAFVAQQLVRSESAALSAQLAK

DKVNECVKAQSKRSGFCGQGTHIVSFVVNAPNGLYFMHVGYYPSNHIEVV

SAYGLCDAANPTNCIAPVNGYFIKTNNTRIVDEWSYTGSSFYAPEPITSL

NTKYVAPQVTYQNISTNLPPPLLGNSTGIDFQDELDEFFKNVSTSIPNFG

SLTQINTTLLDLTYEMLSLQQVVKALNESYIDLKELGNYTYYNKWPWYIW

LGFIAGLVALALCVFFILCCTGCGTNCMGKLKCNRCCDRYEEYDLEPHKV

HVH
```

Individual precursor S polypeptides form a homotrimer and undergo glycosylation within the Golgi apparatus as well as processing to remove the signal peptide, and cleavage by a cellular protease between approximately position 751/752 to generate separate S1 and S2 polypeptide chains, which remain associated as S1/S2 protomers within the homotrimer. An exemplary nucleic acid molecule encoding the MERS-CoV S1 protein is provided as SEQ ID NO: 15, below:

MERS-CoV S1 (1-752) encoding sequence, England1 strain:
```
                                      (SEQ ID NO: 15)
atgattcactccgtgttcctgctgatgttcctgctgactcctacagagag ctatgtggatgtgggacctgattccgtcaagagcgcctgcatcgaagtgg acattcagcagaccttctttgataagacatggccaagacccatcgacgtg agcaaagccgatggcatcatctaccctcaggggaggacctattccaatat cacaattacttaccagggcctgttcccatatcagggagaccacggcgata tgtacgtgtattctgctggccatgcaacagggaccacacctcagaagctg tttgtggctaactacagccaggacgtcaaacagttcgcaaatggattttgt ggtccgcatcggcgccgctgcaaactctaccggcacagtgatcatttcac ctagcacttccgcaaccatccgaaaaatctacccagccttcatgctggga agctccgtgggcaattttagcgacgggaaaatgggacggttcttaacca caccctggtgctgctgcctgatggatgcggcacactgctgagggctttct actgtatcctggagccacgcagcggaaaccactgccccgcaggaaatagc tacacctcctttgccacatatcatactccagctaccgactgttccgatgg caactacaatcgaaacgcctctctgaatagtttcaaggaatacttcaacc tgcggaattgcacattcatgtacacttataacatcaccgaggacgaaatt ctggagtggttcggaatcactcagaccgcacagggcgtgcacctgttttc tagtcgctacgtcgacctgtatggcgggaacatgttccagtttgccactc tgccccgtgtacgataccatcaagtactattccatcattcctcattcaatc cgcagcattcagtccgatcgaaaggcttgggccgctttctacgtgtataa actgcagccactgaccttcctgctggactttagcgtcgatggctacatcc ggagagccattgactgcgggtttaatgatctgtcccagctgcactgttct tacgaaagtttcgacgtggagtccggcgtgtattctgtctcaagctttga ggccaagccctctgggagtgtggtcgagcaggctgaaggagtggagtgcg atttcagtcctctgctgtcagggacccccctcaggtgtacaacttcaag cggctggtctttactaactgtaactacaatctgaccaagctgctgtcact gttcagcgtgaatgactttacatgctcccagatcagcccgcagccattg ctagtaactgttactcctctctgatcctggactacttctcatatccactg
```

-continued
```
agtatgaagagcgacctgagcgtgagttcagccggccccatcagccagtt
caactataaacagagcttcagcaatcctacatgcctgattctggctactg
tgccacataatctgactaccatcactaagcccctgaaatactcctatatt
aacaagtgcagccggttcctgtccgacgatagaaccgaagtgccacagct
ggtcaacgccaatcagtactctccctgtgtgagtatcgtcccttcaaccg
tgtgggaagacggggattactatagaaaacagctgagcccctggaggga
ggaggatggctggtggcatccggatctacagtcgccatgactgagcagct
gcagatggggttcggaatcacagtgcagtacggcacagacactaactctg
tctgtcccaagctggaattcgctaacgatactaagatcgcaagtcagctg
ggaaactgcgtggagtactctctgtatggcgtgagtggcagagggggtctt
ccagaattgtaccgcagtgggcgtccgacagcagcggtttgtgtacgacg
cctatcagaatctggtcggctactatagcgacgatgggaactactattgc
ctgagggcctgtgtgagcgtccctgtgtccgtcatctacgataaggaaac
caaaacacacgccacactgttcgggtccgtggcttgcgagcatattagct
ccacaatgtctcagtacagtagatcaactaggtcaatgctgaagaggcgc
gatagcacctatggacctctgcagacaccagtggggtgtgtcctgggact
ggtgaactctagtctgtttgtcgaggactgcaagctgcccctgggccaga
gcctgtgcgccctgcccgacaccccagcaccctgaccccggagcgtg
cggagctga
```

An exemplary MERS-CoV S1 protein sequence, England1 strain, is provided as SEQ ID NO: 16, below

```
                                        (SEQ ID NO: 16)
MIHSVFLLMFLLTPTESYVDVGPDSVKSACIEVDIQQTFFDKTWPRPIDV

SKADGIIYPQGRTYSNITITYQGLFPYQGDHGDMYVYSAGHATGTTPQKL

FVANYSQDVKQFANGFVVRIGAAANSTGTVIISPSTSATIRKIYPAFMLG

SSVGNFSDGKMGRFFNHTLVLLPDGCGTLLRAFYCILEPRSGNHCPAGNS

YTSFATYHTPATDCSDGNYNRNASLNSFKEYFNLRNCTFMYTYNITEDEI

LEWFGITQTAQGVHLFSSRYVDLYGGNMFQFATLPVYDTIKYYSIIPHSI

RSIQSDRKAWAAFYVYKLQPLTFLLDFSVDGYIRRAIDCGFNDLSQLHCS

YESFDVESGVYSVSSFEAKPSGSVVEQAEGVECDFSPLLSGTPPQVYNFK

RLVFTNCNYNLTKLLSLFSVNDFTCSQISPAAIASNCYSSLILDYFSYPL

SMKSDLSVSSAGPISQFNYKQSFSNPTCLILATVPHNLTTITKPLKYSYI

NKCSRFLSDDRTEVPQLVNANQYSPCVSIVPSTVWEDGDYYRKQLSPLEG

GGWLVASGSTVAMTEQLQMGFGITVQYGTDTNSVCPKLEFANDTKIASQL

GNCVEYSLYGVSGRGVFQNCTAVGVRQQRFVYDAYQNLVGYYSDDGNYYC

LRACVSVPVSVIYDKETKTHATLFGSVACEHISSTMSQYSRSTRSMLKRR

DSTYGPLQTPVGCVLGLVNSSLFVEDCKLPLGQSLCALPDTPSTLTPRSV

RS
```

The S1 subunit is distal to the virus membrane and contains the receptor-binding domain (RBD) that mediates virus attachment to its host receptor, dipeptidyl peptidase-4 (DPP4). The RBD includes approximately residues 367-606 of the S protein. An exemplary nucleic acid sequence encoding the MERS-CoV S protein RBD, England1 strain is provided as SEQ ID NO: 17, below.

```
                                        (SEQ ID NO: 17)
gaggccaagccctctgggagtgtggtcgagcaggctgaaggagtggagtg cgatttcagtcctctgctgtcagggacccccctcaggtgtacaacttca agcggctggtctttactaactgtaactacaatctgaccaagctgctgtca ctgttcagcgtgaatgactttacatgctcccagatcagccccgcagccat tgctagtaactgttactcctctctgatcctggactacttctcatatccac tgagtatgaagagcgacctgagcgtgagttcagccggccccatcagccag ttcaactataaacagagcttcagcaatcctacatgcctgattctggctac tgtgccacataatctgactaccatcactaagcccctgaaatactcctata ttaacaagtgcagccggttcctgtccgacgatagaaccgaagtgccacag ctggtcaacgccaatcagtactctccctgtgtgagtatcgtcccttcaac cgtgtgggaagacggggattactatagaaaacagctgagcccctggagg gaggaggatggctggtggcatccggatctacagtcgccatgactgagcag ctgcagatggggttcggaatcacagtgcagtacggcacagacactaactc tgtctgtcccaagctggaattcgctaacgatactaagatcgcaagtcagc tgggaaactgcgtggagtac
```

An exemplary polypeptide sequence of the MERS-CoV S protein RBD is provided as SEQ ID NO: 18, below:

```
                                        (SEQ ID NO: 18)
EAKPSGSVVEQAEGVECDFSPLLSGTPPQVYNFKRLVFTNCNYNLTKLLS

LFSVNDFTCSQISPAAIASNCYSSLILDYFSYPLSMKSDLSVSSAGPISQ

FNYKQSFSNPTCLILATVPHNLTTITKPLKYSYINKCSRFLSDDRTEVPQ

LVNANQYSPCVSIVPSTVWEDGDYYRKQLSPLEGGGWLVASGSTVAMTEQ

LQMGFGITVQYGTDTNSVCPKLEFANDTKIASQLGNCVEY
```

Another fragment of the MERS-CoV S protein is the ΔTM fragment, which includes the extracellular portion of the S protein. An exemplary nucleic acid sequence encoding the MERS-CoV S ΔTM fragment is provided as SEQ ID NO: 19, below.

```
S-ATM (VRC4228) DNA sequence
                                        (SEQ ID NO: 19)
atgattcactccgtgttcctgctgatgttcctgctgactcctacagagag ctatgtggatgtgggacctgattccgtcaagagcgcctgcatcgaagtgg acattcagcagaccttctttgataagacatggccaagacccatcgacgtg agcaaagccgatggcatcatctaccctcaggggaggacctattccaatat cacaattacttaccagggcctgttcccatatcagggagaccacggcgata tgtacgtgtattctgctggccatgcaacagggaccacacctcagaagctg tttgtggctaactacagccaggacgtcaaacagttcgcaaatggatttgt ggtccgcatcggcgccgctgcaaactctaccggcacagtgatcatttcac ctagcacttccgcaaccatccgaaaaatctacccagcctcatgctggga agctccgtgggcaattttagcgacgggaaaatgggacggttcttttaacca
```

```
cacccTggtgctgctgcctgatggatgcggcacactgctgagggctttct
actgtatcctggagccacgcagcgaaaccactgcccgcaggaaatagc
tacacctcctttgccacatatcatactccagctaccgactgttccgatgg
caactacaatcgaaacgcctctctgaatagtttcaaggaatacttcaacc
tgcggaattgcacattcatgtacacttataacatcaccgaggacgaaatt
ctggagtggttcggaatcactcagaccgcacagggcgtgcacctgttttc
tagtcgctacgtcgacctgtatggcgggaacatgttccagtttgccactc
tgcccgtgtacgataccatcaagtactattccatcattcctcattcaatc
cgcagcattcagtccgatcgaaaggcttgggccgctttctacgtgtataa
actgcagccactgaccttcctgctggactttagcgtcgatggctacatcc
ggagagccattgactgcgggtttaatgatctgtcccagctgcactgttct
tacgaaagtttcgacgtggagtccggcgtgtattctgtctcaagctttga
ggccaagccctctgggagtgtggtcgagcaggctgaaggagtggagtgcg
atttcagtcctctgctgtcagggaccccccctcaggtgtacaacttcaag
cggctggtctttactaactgtaactacaatctgaccaagctgctgtcact
gttcagcgtgaatgactttacatgctcccagatcagccccgcagccattg
ctagtaactgttactcctctctgatcctggactacttctcatatccactg
agtatgaagagcgacctgagcgtgagttcagccggccccatcagccagtt
caactataaacagagcttcagcaatcctacatgcctgattctggctactg
tgccacataatctgactaccatcactaagcccctgaaatactcctatatt
aacaagtgcagccggttcctgtccgacgatagaaccgaagtgccacagct
ggtcaacgccaatcagtactctccctgtgtgagtatcgtcccttcaaccg
tgtgggaagacggggattactatagaaaacagctgagccccctggaggga
ggaggatggctggtggcatccggatctacagtcgccatgactgagcagct
gcagatggggtcggaatcacagtgcagtacggcacagacactaactctg
tctgtcccaagctggaattcgctaacgatactaagatcgcaagtcagctg
ggaaactgcgtggagtactctctgtatggcgtgagtggcagaggggtcttt
ccagaattgtaccgcagtgggcgtccgacagcagcggtttgtgtacgacg
cctatcagaatctggtcggctactatagcgacgatgggaactactattgc
ctgagggcctgtgtgagcgtccctgtgtccgtcatctacgataaggaaac
caaaacacacgccacactgttcgggtccgtggcttgcgagcatattagct
ccacaatgtctcagtacagtagatcaactaggtcaatgctgaagaggcgc
gatagcacctatggacctctgcagacaccagtggggtgtgtcctgggact
ggtgaactctagtctgtttgtcgaggactgcaagctgcccctgggccaga
gcctgtgcgccctgcccgacaccccagcaccctgacccccggagcgtg
cggagcgtgcccggcgagatgcggctggccagcatcgccttcaaccaccc
catccaggtggaccagctgaacagcagctacttcaagctgagcatcccca
ccaacttcagcttcggcgtgacccaggagtacatccagaccaccatccag
aaggtgaccgtggactgcaagcgtacgtgtgcaacggcttccagaagtg
cgagcagctgctgcgggagtacggccagttctgcagcaagatcaaccagg
ccctgcacggcgccaacctgcggcaggacgacagcgtgcggaacctgttc
gccagcgtgaagagcagccagagcagccccatcatcccggcttcggcgg
cgacttcaacctgaccctgctggagcccgtgagcatcagcaccggcagcc
ggagcgcccggagcgccatcgaggacctgctgttcgacaaggtgaccatc
gccgaccccggctacatgcagggctacgacgactgcatgcagcagggccc
cgccagcgcccgggacctgatctgcgcccagtacgtggccggctacaagg
tgctgccccccctgatggacgtgaacatggaggccgcctacaccagcagc
ctgctgggcagcatcgccggcgtgggctggaccgccggcctgagcagctt
cgccgccatcccttcgcccagagcatcttctaccggctgaacggcgtgg
gcatcacccagcaggtgctgagcgagaaccagaagctgatcgccaacaag
ttcaaccaggccctgggcgccatgcagaccggcttcaccaccaccaacga
ggccttccacaaggtgcaggacgccgtgaacaacaacgcccaggccctga
gcaagctggccagcgagctgagcaacaccttcggcgccatcagcgccagc
atcggcgacatcatccagcggctggacgtgctggagcaggacgcccagat
cgaccggctgatcaacggccggctgaccaccctgaacgccttcgtggccc
agcagctggtgcggagcgagagcgccgccctgagcgcccagctggccaag
gacaaggtgaacgagtgcgtgaaggcccagagcaagcgggagcggcttctg
cggccagggcacccacatcgtgagcttcgtggtgaacgcccccaacggcc
tgtacttcatgcacgtgggctactacccagcaaccacatcgaggtggtg
agcgcctacgcctgtgcgacgccgccaacccccaccaactgcatcgcccc
cgtgaacggctacttcatcaagaccaacaacacccggatcgtggacgagt
ggagctacaccggcagcagcttctacgccccgagccatcaccagcctg
aacaccaagtacgtggcccccaggtgacctaccagaacatcagcaccaa
cctgccccccccctgctgggcaacagcaccggcatcgacttccaggacg
agctggacgagttcttcaagaacgtgagcaccagcatcccaacttcggc
agcctgacccagatcaacaccaccctgctggacctgacctacgagatgct
gagcctgcagcaggtggtgaaggccctgaacgagagctacatcgacctga
aggagctgggcaactacacc
```

An exemplary polypeptide sequence of the MERS-CoV S ΔTM fragment is provided as SEQ ID NO: 20, below.

```
S-ATM (VRC4228) amino acid sequence
                                        (SEQ ID NO: 20)
MIHSVFLLMELLTPTESYVDVGPDSVKSACIEVDIQQTFFDKTWPRPIDV
SKADGIIYPQGRTYSNITITYQGLFPYQGDHGDMYVYSAGHATGTTPQKL
FVANYSQDVKQFANGFVVRIGAAANSTGTVIISPSTSATIRKIYPAFMLG
SSVGNFSDGKMGRFFNHTLVLLPDGCGTLLRAFYCILEPRSGNHCPAGNS
YTSFATYHTPATDCSDGNYNRNASLNSFKEYFNLRNCTFMYTYNITEDEI
LEWFGITQTAQGVHLFSSRYVDLYGGNMFQFATLPVYDTIKYYSIIPHSI
RSIQSDRKAWAAFYVYKLQPLTFLLDFSVDGYIRRAIDCGFNDLSQLHCS
YESFDVESGVYSVSSFEAKPSGSVVEQAEGVECDFSPLLSGTPPQVYNFK
RLVFTNCNYNLTKLLSLFSVNDFTCSQISPAAIASNCYSSLILDYFSYPL
SMKSDLSVSSAGPISQFNYKQSFSNPTCLILATVPHNLTTITKPLKYSYI
```

-continued
```
NKCSRFLSDDRTEVPQLVNANQYSPCVSIVPSTVWEDGDYYRKQLSPLEG

GGWLVASGSTVAMTEQLQMGFGITVQYGTDTNSVCPKLEFANDTKIASQL

GNCVEYSLYGVSGRGVFQNCTAVGVRQQRFVYDAYQNLVGYYSDDGNYYC

LRACVSVPVSVIYDKETKTHATLFGSVACEHISSTMSQYSRSTRSMLKRR

DSTYGPLQTPVGCVLGLVNSSLFVEDCKLPLGQSLCALPDTPSTLTPRSV

RSVPGEMRLASIAFNHPIQVDQLNSSYFKLSIPTNFSFGVTQEYIQTTIQ

KVTVDCKQYVCNGFQKCEQLLREYGQFCSKINQALHGANLRQDDSVRNLF

ASVKSSQSSPIIPGFGGDFNLTLLEPVSISTGSRSARSAIEDLLFDKVTI

ADPGYMQGYDDCMQQGPASARDLICAQYVAGYKVLPPLMDVNMEAAYTSS

LLGSIAGVGWTAGLSSFAAIPFAQSIFYRLNGVGITQQVLSENQKLIANK

FNQALGAMQTGFTTTNEAFHKVQDAVNNNAQALSKLASELSNTFGAISAS

IGDIIQRLDVLEQDAQIDRLINGRLTTLNAFVAQQLVRSESAALSAQLAK

DKVNECVKAQSKRSGFCGQGTHIVSFVVNAPNGLYFMHVGYYPSNHIEVV

SAYGLCDAANPTNCIAPVNGYFIKTNNTRIVDEWSYTGSSFYAPEPITSL

NTKYVAPQVTYQNISTNLPPPLLGNSTGIDFQDELDEFFKNVSTSIPNFG

SLTQINTTLLDLTYEMLSLQQVVKALNESYIDLKELGNYT
```

The MERS-CoV S protein or fragments thereof can be isolated from native sources or produced using recombinant techniques, or chemically or enzymatically synthesized.

Analogs and variants of the MERS-CoV S protein or fragments thereof may be used in the methods and systems of the present invention. Through the use of recombinant DNA technology, variants of the MERS-CoV S protein or fragments thereof may be prepared by altering the underlying DNA. All such variations or alterations in the structure of the MERS-CoV S protein or fragments thereof resulting in variants are included within the scope of this invention. Such variants include insertions, substitutions, or deletions of one or more amino acid residues, glycosylation variants, unglycosylated The MERS-CoV S protein or fragments thereof, organic and inorganic salts, covalently modified derivatives of the MERS-CoV S protein or fragments thereof, or a precursor thereof. Such variants may maintain one or more of the functional, biological activities of the MERS-CoV S protein or fragment thereof, such as binding to DPP4. The MERS-CoV S protein or a fragment thereof (e.g., a MERS-CoV S1 protein) can be modified, for example, by PEGylation, to increase the half-life of the protein in the recipient, to retard clearance from the pericardial space, and/or to make the protein more stable for delivery to a subject.

In some embodiments, a MERS-CoV S protein or fragment thereof useful within the disclosure is modified to produce peptide mimetics by replacement of one or more naturally occurring side chains of the 20 genetically encoded amino acids (or D-amino acids) with other side chains, for example with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclics. For example, proline analogs can be made in which the ring size of the proline residue is changed from a 5-membered ring to a 4-, 6-, or 7-membered ring. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl. Peptides, as well as peptide analogs and mimetics, can also be covalently bound to one or more of a variety of nonproteinaceous polymers, for example, polyethylene glycol, polypropylene glycol, or polyoxyalkenes, as described in U.S. Pat. Nos. 4,640,835; 4,496,668; 4,301,144; 4,668,417; 4,791,192; and 4,179,337.

In addition to the naturally occurring genetically encoded amino acids, amino acid residues in a MERS-CoV S protein or fragment thereof may be substituted with naturally occurring non-encoded amino acids and synthetic amino acids. Certain commonly encountered amino acids which provide useful substitutions include, but are not limited to, β-alanine and other omega-amino acids, such as 3-aminopropionic acid, 2,3-diaminopropionic acid, 4-aminobutyric acid and the like; α-aminoisobutyric acid; ε-aminohexanoic acid; δ-aminovaleric acid; N-methylglycine or sarcosine; ornithine; citrulline; t-butylalanine; t-butylglycine; N-methylisoleucine; phenylglycine; cyclohexylalanine; norleucine; naphthylalanine; 4-chlorophenylalanine; 2-fluorophenylalanine; 3-fluorophenylalanine; 4-fluorophenylalanine; penicillamine; 1,2,3,4-tetrahydroisoquinoline-3-carboxylic acid; β-2-thienylalanine; methionine sulfoxide; homoarginine; N-acetyl lysine; 2,4-diaminobutyric acid; 2,3-diaminobutyric acid; p-aminophenylalanine; N-methyl valine; homocysteine; homophenylalanine; homoserine; hydroxyproline; homoproline; N-methylated amino acids; and peptoids (N-substituted glycines).

While in certain embodiments, the amino acids of a MERS-CoV S protein or fragment thereof will be substituted with L-amino acids; however, the substitutions are not limited to L-amino acids. Thus, also encompassed by the present disclosure are modified forms of the SAHPs, wherein an L-amino acid is replaced with an identical D-amino acid (e.g., L-Arg→D-Arg) or with a conservatively-substituted D-amino acid (e.g., L-Arg→D-Lys), and vice versa.

Other peptide analogs and mimetics within the scope of the disclosure include glycosylation variants, and covalent or aggregate conjugates with other chemical moieties. Covalent derivatives can be prepared by linkage of functionalities to groups which are found in amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues (e.g., lysine or arginine). Acyl groups are selected from the group of alkyl-moieties including C3 to C18 normal alkyl, thereby forming alkanoyl aroyl species. Also embraced are versions of a native primary amino acid sequence which have other minor modifications, including phosphorylated amino acid residues, for example, phosphotyrosine, phosphoserine, or phosphothreonine, or other moieties, including ribosyl groups or cross-linking reagents.

In another embodiment, an additional functional domain or peptide can be linked to a MERS-CoV S protein or fragment or analog disclosed herein, creating a peptide/peptide analog-additional functional domain/peptide conjugate. The additional functional domain or peptide can be linked to the RLX polypeptide or peptide analog at either the N- and/or C-terminus.

Optionally, a linker can be included between the MERS-CoV S protein or fragment or analog and the additional functional domain or peptide. The linkers contemplated by the present disclosure can be any bifunctional molecule capable of covalently linking two peptides to one another. Thus, suitable linkers are bifunctional molecules in which the functional groups are capable of being covalently attached to the N- and/or C-terminus of a peptide. Functional groups suitable for attachment to the N- or C-terminus of peptides are well known in the art, as are suitable chemistries for effecting such covalent bond formation. The linker may be flexible, rigid or semi-rigid. Suitable linkers include, for example, amino acid residues such as Pro or Gly or peptide segments containing from about 2 to about 5, 10, 15, 20, or even more amino acids, bifunctional organic compounds such as $H_2N(CH_2)_nCOOH$ where n is an integer from 1 to 12, and the like. Examples of such linkers, as well as methods of making such linkers and peptides incorporating such linkers, are well-known in the art (see, e.g., Hunig et al., *Chem. Ber.* 100:3039-3044, 1974 and Basak et al., *Bioconjug. Chem.* 5:301-305, 1994).

Conjugation methods applicable to the present disclosure include, by way of non-limiting example, reductive amination, diazo coupling, thioether bond, disulfide bond, amidation and thiocarbamoyl chemistries. In one embodiment, the amphipathic alpha-helical domains are "activated" prior to conjugation. Activation provides the necessary chemical groups for the conjugation reaction to occur. In one specific, non-limiting example, the activation step includes derivatization with adipic acid dihydrazide. In another specific, non-limiting example, the activation step includes derivatization with the N-hydroxysuccinimide ester of 3-(2-pyridyl dithio)-propionic acid. In yet another specific, non-limiting example, the activation step includes derivatization with succinimidyl 3-(bromoacetamido) propionate. Further, non-limiting examples of derivatizing agents include succinimidylformylbenzoate and succinimidyllevulinate.

Also encompassed by the present disclosure are polypeptides including dimers, trimers, tetramers and even higher order polymers (i.e., "multimers") comprising the same or different MERS-CoV S protein or fragment thereof. In multimers, the MERS-CoV S protein or fragment thereof may be directly attached to one another or separated by one or more linkers. The MERS-CoV S protein or fragment thereof can be connected in a head-to-tail fashion (i.e., N-terminus to C-terminus), a head-to-head fashion, (i.e., N-terminus to N-terminus), a tail-to-tail fashion (i.e., C-terminus to C-terminus), and/or combinations thereof. In one embodiment, the multimers are tandem repeats of two, three, four, and up to about ten MERS-CoV S proteins or fragments thereof, but any number of MERS-CoV S proteins or fragments thereof can be used.

B. Protein Nanoparticles

In some embodiments a protein nanoparticle is provided that includes one or more of the disclosed MERS-CoV S protein or fragment thereof (e.g., a MERS-CoV S protein or S1 protein, or RBD). Non-limiting example of nanoparticles include ferritin nanoparticles, encapsulin nanoparticles, Sulfur Oxygenase Reductase (SOR) nanoparticles, and lumazine synthase nanoparticles, which are comprised of an assembly of monomeric subunits including ferritin proteins, encapsulin proteins, SOR proteins, and lumazine synthase, respectively. Exemplary sequences of recombinant MERS-CoV S protein or fragment thereof linked to a nanoparticle subunit are provided below. To construct protein nanoparticles including a MERS-CoV S protein or immunogenic fragment thereof, the MERS-CoV S protein or fragment can be linked to a subunit of the protein nanoparticle (such as a ferritin protein, an encapsulin protein, a SOR protein, or a lumazine synthase protein). The fusion protein self-assembles into a nanoparticle under appropriate conditions.

In several embodiments, the protein nanoparticle comprises two or more MERS-CoV S proteins or immunogenic fragments thereof, wherein the two or more MERS-CoV S proteins or fragments are from at least two different strains of MERS-CoV.

In some embodiments, a MERS-CoV S protein or immunogenic fragment thereof can be linked to a ferritin subunit to construct a ferritin nanoparticle. Ferritin nanoparticles and their use for immunization purposes (e.g., for immunization against influenza antigens) have been disclosed in the art (see, e.g., Kanekiyo et al., *Nature*, 499:102-106, 2013, incorporated by reference herein in its entirety). Ferritin is a globular protein that is found in all animals, bacteria, and plants, and which acts primarily to control the rate and location of polynuclear $Fe(III)_2O_3$ formation through the transportation of hydrated iron ions and protons to and from a mineralized core. The globular form of the ferritin nanoparticle is made up of monomeric subunits, which are polypeptides having a molecule weight of approximately 17-20 kDa. An example of the amino acid sequence of one such monomeric ferritin subunit is represented by:

(SEQ ID NO: 21)
ESQVRQQFSKDIEKLLNEQVNKEMQSSNLYMSMSSWCYTHSLDGAGLFLF

DHAAEEYEHAKKLIIFLNENNVPVQLTSISAPEHKFEGLTQIFQKAYEHE

QHISESINNIVDHAIKSKDHATFNFLQWYVAEQHEEEVLFKDILDKIELI

GNENHGLYLADQYVKGIAKSRKS

Each monomeric subunit has the topology of a helix bundle which includes a four antiparallel helix motif, with a fifth shorter helix (the c-terminal helix) lying roughly perpendicular to the long axis of the 4 helix bundle. According to convention, the helices are labeled 'A, B, C, D & E' from the N-terminus respectively. The N-terminal sequence lies adjacent to the capsid three-fold axis and extends to the surface, while the E helices pack together at the four-fold axis with the C-terminus extending into the capsid core. The consequence of this packing creates two pores on the capsid surface. It is expected that one or both of these pores represent the point by which the hydrated iron diffuses into and out of the capsid. Following production, these monomeric subunit proteins self-assemble into the globular ferritin protein. Thus, the globular form of ferritin comprises 24 monomeric, subunit proteins, and has a capsid-like structure having 432 symmetry. Methods of constructing ferritin nanoparticles are known to the person of ordinary skill in the art and are further described herein (see, e.g., Zhang, *Int. J. Mol. Sci.*, 12:5406-5421, 2011, which is incorporated herein by reference in its entirety).

In specific examples, the ferritin polypeptide is *E. coli* ferritin, *Helicobacter pylori* ferritin, human light chain ferritin, bullfrog ferritin or a hybrid thereof, such as *E. coli*-human hybrid ferritin, *E. coli*-bullfrog hybrid ferritin, or human-bullfrog hybrid ferritin. Exemplary amino acid sequences of ferritin polypeptides and nucleic acid sequences encoding ferritin polypeptides for use to make a ferritin nanoparticle including a MERS-CoV S protein or immunogenic fragment thereof can be found in GEN-BANK®, for example at accession numbers ZP_03085328, ZP_06990637, EJB64322.1, AAA35832, NP_000137 AAA49532, AAA49525, AAA49524 and AAA49523, which are specifically incorporated by reference herein in their entirety as available Jun. 20, 2014. In some embodiments, a MERS-CoV S protein or fragment thereof can be linked to a ferritin subunit including an amino acid sequence at least 80% (such as at least 85%, at least 90%, at least 95%, or at least 97%) identical to amino acid sequence set forth as SEQ ID NO: 21.

In some embodiments, the RBD domain of MERS-CoV S protein can be linked to a ferritin nanoparticle subunit. For example, the RBD domain can comprise or consist of amino acids 367-601, 367-606, or 381-588 of the MERS-CoV S protein sequence forth as SEQ ID NO: 14, and can be linked to a ferritin nanoparticle subunit. Specific examples of polypeptide sequences of the RBD domain of MERS-CoV S protein linked to a ferritin nanoparticle subunit are provided as the amino acid sequences set forth as SEQ ID NOs: 22 and 23, below. In some embodiments, the RBD domain linked to the protein nanoparticle subunit includes an amino acid sequence at least 80% (such as at least 90%, at least 95%, or 100%) identical to the sequence set forth as one of SEQ ID NOs: 22 or 23.

MERS-CoV S-RBD(367-601)_506F_ferritin
(SEQ ID NO: 22)
EAKPSGSVVEQAEGVECDFSPLLSGTPPQVYNFKRLVFTNCNYNLTKLLS

LFSVNDFTCSQISPAAIASNCYSSLILDYFSYPLSMKSDLSVSSAGPISQ

FNYKQSFSNPTCLILATVPHNLTTITKPLKYSYINKCSRFLSDDRTEVPQ

LVNANQYSPCVSIVPSTVWEDGDYYRKQLSPLEGGGWLVASGSTVAMTEQ

LQMGFGITVQYGTDTNSVCPKLEFANDTKIASQLGSGESQVRQQFSKDIE

KLLNEQVNKEMQSSNLYMSMSSWCYTHSLDGAGLFLFDHAAEEYEHAKKL

IIFLNENNVPVQLTSISAPEHKFEGLTQIFQKAYEHEQHISESINNIVDH

AIKSKDHATFNFLQWYVAEQHEEEVLFKDILDKIELIGNENHGLYLADQY

VKGIAKSRKSGS

MERS-CoV S-RBD(381-588)_506F_ferritin
(SEQ ID NO: 23)
VECDFSPLLSGTPPQVYNFKRLVFTNCNYNLTKLLSLFSVNDFTCSQISP

AAIASNCYSSLILDYFSYPLSMKSDLSVSSAGPISQFNYKQSFSNPTCLI

LATVPHNLTTITKPLKYSYINKCSRFLSDDRTEVPQLVNANQYSPCVSIV

PSTVWEDGDYYRKQLSPLEGGGWLVASGSTVAMTEQLQMGFGITVQYGTD

TNSVCPKLSGESQVRQQFSKDIEKLLNEQVNKEMQSSNLYMSMSSWCYTH

SLDGAGLFLFDHAAEEYEHAKKLIIFLNENNVPVQLTSISAPEHKFEGLT

QIFQKAYEHEQHISESINNIVDHAIKSKDHATFNFLQWYVAEQHEEEVLF

KDILDKIELIGNENHGLYLADQYVKGIAKSRKSGS

For production purposes, the RBD domain linked to the nanoparticle subunit can include a signal peptide that is cleaved during cellular processing. For example, the RBD domain linked to the protein nanoparticle can include a signal peptide at its N-terminus including the amino acid sequence set forth as:

bPRL(LA) signal peptide
(SEQ ID NO: 24)
MDSKGSSQKGSRLLLLLVVSNLLLPQGVLA hCD5 signal peptide
(SEQ ID NO: 25)
MPMGSLQPLATLYLLGMLVASVLA Exemplary nucleic acid molecule sequences encoding the disclosed RBD domains linked to a ferritin nanoparticle sequence are provided as SEQ ID NOs: 26 and 27, below.

(SEQ ID NO: 26)
CMV8xR-bPRL(LA)-MERS-CoV S-RBD(367-601)_506F_ferritin (SEQ ID NO: 27)
CMV8xR-bPRL(LA)-MERS-CoV S-RBD(381-588)_506F_ferritin In additional embodiments, any of the disclosed MERS-CoV S proteins or fragments thereof can be linked to a lumazine synthase subunit to construct a lumazine synthase nanoparticle. The globular form of lumazine synthase nanoparticle is made up of monomeric subunits; an example of the sequence of one such lumazine synthase subunit is provides as the amino acid sequence set forth as:

(SEQ ID NO: 28)
MQIYEGKLTAEGLRFGIVASRFNHALVDRLVEGAIDAIVRHGGREEDITL

VRVPGSWEIPVAAGELARKEDIDAVIAIGVLIRGATPHFDYIASEVSKGL

ADLSLELRKPITFGVITADTLEQAIERAGTKHGNKGWEAALSAIEMANLF

KSLR.

In some embodiments, a disclosed MERS-CoV S protein or immunogenic fragment thereof can be linked to a lumazine synthase subunit including an amino acid sequence at least 80% (such as at least 85%, at least 90%, at least 95%, or at least 97%) identical to amino acid sequence set forth as SEQ ID NO: 28.

In additional embodiments, the MERS-CoV S protein or immunogenic fragment thereof can be linked to an encapsulin nanoparticle subunit to construct an encapsulin nanoparticle. The globular form of the encapsulin nanoparticle is made up of monomeric subunits; an example of the sequence of one such encapsulin subunit is provides as the amino acid sequence set forth as (SEQ ID NO: 29)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKF.

In some embodiments, a MERS-CoV S protein or immunogenic fragment thereof can be linked to an encapsulin subunit including an amino acid sequence at least 80% (such as at least 85%, at least 90%, at least 95%, or at least 97%) identical to amino acid sequence set forth as SEQ ID NO: 29.

Encapsulin proteins are a conserved family of bacterial proteins also known as linocin-like proteins that form large protein assemblies that function as a minimal compartment to package enzymes. The encapsulin assembly is made up of monomeric subunits, which are polypeptides having a molecule weight of approximately 30 kDa. Following production, the monomeric subunits self-assemble into the globular encapsulin assembly including 60, or in some cases, 180 monomeric subunits. Methods of constructing encapsulin nanoparticles are known to the person of ordinary skill in the art, and further described herein (see, for example, Sutter et al., Nature Struct. and Mol. Biol., 15:939-947, 2008, which is incorporated by reference herein in its entirety). In specific examples, the encapsulin polypeptide is bacterial encapsulin, such as *Thermotoga maritime* or *Pyrococcus furiosus* or *Rhodococcus erythropolis* or *Myxococcus xanthus* encapsulin.

In some embodiments, the RBD domain of MERS-CoV S protein can be linked to an encapsulin nanoparticle subunit. For example, the RBD domain can comprise or consist of amino acids 367-601, 367-606, or 381-588 of the MERS-CoV S protein sequence set forth as SEQ ID NO: 14 and can be linked to an encapsulin nanoparticle subunit. Specific examples of polypeptide sequences of the RBD domain of MERS-CoV S protein linked to an encapsulin nanoparticle subunit are provided as the amino acid sequences set forth as SEQ ID NO: 30 and 31, below. In some embodiments, the RBD domain linked to the encapsulin nanoparticle subunit includes an amino acid sequence at least 80% (such as at least 90%, at least 95%, or 100%) identical to the sequence set forth as one of SEQ ID NOs: 30 or 31. For production purposes, the RBD domain linked to the encapsulin nanoparticle subunit can include a signal peptide that is cleaved during cellular processing. For example, the RBD domain linked to the protein nanoparticle can include a signal peptide at its N-terminus including the amino acid sequence set forth as SEQ ID NO: 24 or SEQ ID NO: 25.

```
MERS-CoV S-RBD(367-601)_506F_encapsulin
                                            (SEQ ID NO: 30)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKSGEAKPSGSVVEQAEGVECDFSPLLSGTPPQVYNFK

RLVFTNCNYNLTKLLSLFSVNDFTCSQISPAAIASNCYSSLILDYFSYPL

SMKSDLSVSSAGPISQFNYKQSFSNPTCLILATVPHNLTTITKPLKYSYI

NKCSRFLSDDRTEVPQLVNANQYSPCVSIVPSTVWEDGDYYRKQLSPLEG

GGWLVASGSTVAMTEQLQMGFGITVQYGTDTNSVCPKLEFANDTKIASQL

G

MERS-CoV S-RBD(381-588)_506F_encapsulin
                                            (SEQ ID NO: 31)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKSGVECDFSPLLSGTPPQVYNFKRLVFTNCNYNLTKL

LSLFSVNDFTCSQISPAAIASNCYSSLILDYFSYPLSMKSDLSVSSAGPI

SQFNYKQSFSNPTCLILATVPHNLTTITKPLKYSYINKCSRFLSDDRTEV

PQLVNANQYSPCVSIVPSTVWEDGDYYRKQLSPLEGGGWLVASGSTVAMT

EQLQMGFGITVQYGTDTNSVCPKL
```

Exemplary nucleic acid molecule sequences encoding the disclosed RBD domains linked to an encapsulin nanoparticle subunit are provided as SEQ ID NOs: 32 and 33.

```
                                            (SEQ ID NO: 32)
CMV8xR-hCD5-MERS-CoV S-RBD(367-601)_506F_ encapsulin (SEQ ID NO: 33)
CMV8xR-hCD5-MERS-CoV S-RBD(381-588)_506F_ encapsulin
```

In additional embodiments, a MERS-CoV S protein or immunogenic fragment thereof can be linked to a Sulfur Oxygenase Reductase (SOR) subunit to construct a recombinant SOR nanoparticle. In some embodiments, the SOR subunit can include the amino acid sequence set forth as

```
                                            (SEQ ID NO: 34)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKF.
```

In some embodiments, a MERS-CoV S protein or immunogenic fragment thereof can be linked to a SOR subunit including an amino acid sequence at least 80% (such as at least 85%, at least 90%, at least 95%, or at least 97%) identical to amino acid sequence set forth as SEQ ID NO: 34.

SOR proteins are microbial proteins (for example from the thermoacidophilic archaeon *Acidianus ambivalens* that form 24 subunit protein assemblies. Methods of constructing SOR nanoparticles are known to the person of ordinary skill in the art (see, e.g., Urich et al., Science, 311:996-1000, 2006, which is incorporated by reference herein in its entirety). An example of an amino acid sequence of a SOR protein for use to make SOR nanoparticles is set forth in Urich et al., Science, 311:996-1000, 2006, which is incorporated by reference herein in its entirety.

In some examples, the MERS-CoV S protein or immunogenic fragment thereof can be linked to the N- or C-terminus, or placed within an internal loop of a ferritin, encapsulin, SOR, or lumazine synthase subunit, for example with a linker, such as a Ser-Gly linker. When the constructs have been made in HEK 293 Freestyle cells, the fusion proteins are secreted from the cells and self-assembled into nanoparticles. The nanoparticles can be purified using known techniques, for example by a few different chromatography procedures, e.g. Mono Q (anion exchange) followed by size exclusion (SUPEROSE® 6) chromatography.

Several embodiments include a monomeric subunit of a ferritin, encapsulin, SOR, or lumazine synthase protein, or any portion thereof which is capable of directing self-assembly of monomeric subunits into the globular form of the protein. Amino acid sequences from monomeric subunits of any known ferritin, encapsulin, SOR, or lumazine synthase protein can be used to produce fusion proteins with the MERS-CoV S protein or immunogenic fragment thereof, so long as the monomeric subunit is capable of self-assembling into a nanoparticle displaying the MERS-CoV S protein or immunogenic fragment thereof on its surface.

The fusion proteins need not comprise the full-length sequence of a monomeric subunit polypeptide of a ferritin, encapsulin, SOR, or lumazine synthase protein. Portions, or regions, of the monomeric subunit polypeptide can be utilized so long as the portion comprises amino acid sequences that direct self-assembly of monomeric subunits into the globular form of the protein.

In some embodiments, it may be useful to engineer mutations into the amino acid sequence of the monomeric ferritin, encapsulin, SOR, or lumazine synthase subunits. For example, it may be useful to alter sites such as enzyme recognition sites or glycosylation sites in order to give the fusion protein beneficial properties (e.g., half-life).

It will be understood by those skilled in the art that fusion of any of the MERS-CoV S protein (e.g., in trimeric form) or immunogenic fragment thereof (such as RBD domain) to the ferritin, encapsulin, SOR, or lumazine synthase protein should be done such that the MERS-CoV S protein or immunogenic fragment thereof does not interfere with self-assembly of the monomeric ferritin, encapsulin, SOR, or lumazine synthase subunits into the globular protein, and that the ferritin, encapsulin, SOR, or lumazine synthase subunits do not interfere with the ability of the disc MERS-CoV S protein or immunogenic fragment thereof to elicit an immune response to MERS-CoV. In some embodiments, the ferritin, encapsulin, SOR, or lumazine synthase protein and MERS-CoV S protein or immunogenic fragment thereof can be joined together directly without affecting the activity of either portion. In other embodiments, the ferritin, encapsulin, SOR, or lumazine synthase protein and the MERS-CoV S protein or immunogenic fragment thereof can be joined using a linker (also referred to as a spacer) sequence. The linker sequence is designed to position the ferritin, encapsulin, SOR, or lumazine synthase portion of the fusion protein and the MERS-CoV S protein or immunogenic fragment thereof can be linked to an portion of the fusion protein, with regard to one another, such that the fusion protein maintains the ability to assemble into nanoparticles, and also elicit an immune response to MERS-CoV. In several embodiments, the linker sequences comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine. One example of such a linker sequence is SGG. Amino acids can be added or subtracted as needed. Those skilled in the art are capable of determining appropriate linker sequences for construction of protein nanoparticles.

C. Virus-Like Particles

In some embodiments, a virus-like particle (VLP) is provided that includes a disclosed immunogen (e.g., a MERS-CoV S protein or immunogenic fragment thereof). VLPs lack the viral components that are required for virus replication and thus represent a highly attenuated form of a virus. The VLP can display a polypeptide (e.g., a MERS-CoV S protein or immunogenic fragment thereof) that is capable of eliciting an immune response to MERS-CoV when administered to a subject. Virus like particles and methods of their production are known and familiar to the person of ordinary skill in the art, and viral proteins from several viruses are known to form VLPs, including human papillomavirus, HIV (Kang et al., Biol. Chem. 380: 353-64 (1999)), Semliki-Forest virus (Notka et al., Biol. Chem. 380: 341-52 (1999)), Chikungunya virus (Akahata et al., Nat. Med. 16:334-338 (2010)), human polyomavirus (Goldmann et al., J. Virol. 73: 4465-9 (1999)), rotavirus (Jiang et al., Vaccine 17: 1005-13 (1999)), parvovirus (Casal, Biotechnology and Applied Biochemistry, Vol 29, Part 2, pp 141-150 (1999)), canine parvovirus (Hurtado et al., J. Virol. 70: 5422-9 (1996)), hepatitis E virus (Li et al., J. Virol. 71: 7207-13 (1997)), and Newcastle disease virus. The formation of such VLPs can be detected by any suitable technique. Examples of suitable techniques known in the art for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

D. Viral Vectors

The nucleic acid molecules encoding the disclosed immunogens (e.g., MERS-CoV S protein or fragment thereof) can be included in a viral vector, for example for expression of the antigen in a host cell, or for immunization of a subject as disclosed herein. In some embodiments, the viral vectors are administered to a subject as part of a prime-boost vaccination. In several embodiments, the viral vectors are included in a vaccine, such as a primer vaccine or a booster vaccine for use in a prime-boost vaccination.

In several examples, the viral vector can be replication-competent. For example, the viral vector can have a mutation in the viral genome that does not inhibit viral replication in host cells. The viral vector also can be conditionally replication-competent. In other examples, the viral vector is replication-deficient in host cells.

A number of viral vectors have been constructed, that can be used to express the disclosed antigens, including polyoma, i.e., SV40 (Madzak et al., 1992, *J. Gen. Virol.*, 73:15331536), adenovirus (Berkner, 1992, *Cur. Top. Microbiol. Immunol.*, 158:39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256), vaccinia virus (Mackett et al., 1992, *Biotechnology*, 24:495-499), adeno-associated virus (Muzyczka, 1992, *Curr. Top. Microbiol. Immunol.*, 158:91-123; On et al., 1990, *Gene*, 89:279-282), herpes viruses including HSV and EBV (Margolskee, 1992, *Curr. Top. Microbiol. Immunol.*, 158: 67-90; Johnson et al., 1992, *J. Virol.*, 66:29522965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199), Sindbis viruses (H. Herweijer et al., 1995, *Human Gene Therapy* 6:1161-1167; U.S. Pat. Nos. 5,091,309 and 5,2217,879), alphaviruses (S. Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In several embodiments, the viral vector can include an adenoviral vector that expresses a disclosed recombinant MERS-CoV S protein or fragment thereof. Adenovirus from various origins, subtypes, or mixture of subtypes can be used as the source of the viral genome for the adenoviral vector. Non-human adenovirus (e.g., simian, chimpanzee, gorilla, avian, canine, ovine, or bovine adenoviruses) can be used to generate the adenoviral vector. For example, a simian adenovirus can be used as the source of the viral genome of the adenoviral vector. A simian adenovirus can be of serotype 1, 3, 7, 11, 16, 18, 19, 20, 27, 33, 38, 39, 48, 49, 50, or any other simian adenoviral serotype. A simian adenovirus can be referred to by using any suitable abbreviation known in the art, such as, for example, SV, SAdV, SAV or sAV. A gorilla-derived adenovirus vector that is similar to ChAd3 or human Ad5 and is a subtype C adenovirus can also be used (see, e.g., Johnson et al., Mol Ther. 2014 January; 22(1): 196-205). In some examples, a simian adenoviral vector is a simian adenoviral vector of serotype 3, 7, 11, 16, 18, 19, 20, 27, 33, 38, or 39. In one example, a chimpanzee serotype C Ad3 vector is used (see, e.g., Peruzzi et al., Vaccine, 27:1293-1300, 2009). Human adenovirus can be used as the source of the viral genome for the adenoviral vector. Human adenovirus can be of various subgroups or serotypes. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22, 23, 24, 25, 26, 27, 28, 29, 30, 32, 33, 36-39, and 42-48), subgroup E (e.g., serotype 4), subgroup F (e.g., serotypes 40 and 41), an unclassified serogroup (e.g., serotypes 49 and S1), or any other adenoviral serotype. The person of ordinary skill in the art is familiar with replication competent and deficient adenoviral vectors (including singly and multiply replication deficient adenoviral vectors). Examples of replication-deficient adenoviral vectors, including multiply replication-deficient adenoviral vectors, are disclosed in U.S. Pat. Nos. 5,837,511; 5,851,806; 5,994,106; 6,127,175; 6,482,616; and 7,195,896, and International Patent Application Nos. WO 94/28152, WO 95/02697, WO 95/16772, WO 95/34671, WO 96/22378, WO 97/12986, WO 97/21826, and WO 03/022311.

E. Methods of Inducing an Immune Response

The disclosed immunogens (e.g., MERS-CoV S protein or immunogenic fragment thereof, polynucleotides encoding same, protein nanoparticles, viral-like particles, or vectors) and compositions, can be used in methods of inducing an immune response to MERS-CoV S protein. In several embodiments, a therapeutically effective amount of an immunogenic composition including one or more of the disclosed immunogens, can be administered to a subject in order to generate an immune response to MERS-CoV.

In some embodiments, a subject is selected for treatment that has, or is at risk for developing, an MERS-CoV infection, for example because of exposure or the possibility of exposure to MERS-CoV. Following administration of a therapeutically effective amount of a disclosed immunogen, the subject can be monitored for MERS-CoV infection, symptoms associated with MERS-CoV infection, or both.

Typical subjects intended for treatment with the therapeutics and methods of the present disclosure include humans, as well as non-human primates and other animals (such as camels). To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize MERS-CoV infection. These and other routine methods allow the clinician to select patients in need of therapy using the methods and pharmaceutical compositions of the disclosure. In accordance with these methods and principles, a composition can be administered according to the teachings herein, or other conventional methods known to the person of ordinary skill in the art, as an independent prophylaxis or treatment program, or as a follow-up, adjunct or coordinate treatment regimen to other treatments.

The administration of a disclosed immunogen (e.g., MERS-CoV S protein or immunogenic fragment thereof, polynucleotides encoding same, protein nanoparticles, viral-like particles, or vectors) can be for prophylactic or therapeutic purpose. When provided prophylactically, the disclosed therapeutic agents are provided in advance of any symptom, for example in advance of infection. The prophylactic administration of the disclosed therapeutic agents serves to prevent or ameliorate any subsequent infection. Hence in some embodiments the methods involves selecting a subject at risk for contracting MERS-CoV infection, and administering a therapeutically effective amount of a disclosed immunogen (e.g., MERS-CoV S protein or immunogenic fragment thereof, polynucleotides encoding same, protein nanoparticles, viral-like particles, or vectors) to the subject. The therapeutic agents can thus be provided prior to the anticipated exposure to MERS-CoV so as to attenuate the anticipated severity, duration or extent of an infection and/or associated disease symptoms, after exposure or suspected exposure to the virus, or after the actual initiation of an infection.

When provided therapeutically, the disclosed immunogens are provided at or after the onset of a symptom of disease or infection, for example after development of a symptom of MERS-CoV infection, or after diagnosis of MERS-CoV infection. Treatment of MERS-CoV by inhibiting MERS-CoV replication or infection can include delaying and/or reducing signs or symptoms of MERS-CoV infection in a subject. In some examples, treatment using the methods disclosed herein prolongs the time of survival of the subject.

The immunogenic composition including one or more of the disclosed agents (e.g., MERS-CoV S protein or immunogenic fragment thereof, polynucleotides encoding same, protein nanoparticles, viral-like particles, or vectors) can be used in coordinate vaccination protocols or combinatorial formulations. In certain embodiments, novel combinatorial immunogenic compositions and coordinate immunization protocols employ separate immunogens or formulations, each directed toward eliciting an anti-MERS-CoV immune response, such as an immune response to MERS-CoV S protein. Separate immunogenic compositions that elicit the anti-MERS-CoV immune response can be combined in a polyvalent immunogenic composition administered to a subject in a single immunization step, or they can be administered separately (in monovalent immunogenic compositions) in a coordinate immunization protocol.

In one embodiment, a suitable immunization regimen includes at least two separate inoculations with one or more immunogenic compositions, with a second inoculation being administered more than about two, about three to eight, or about four, weeks following the first inoculation. A third inoculation can be administered several months (such as 2-3 months, or 4, 5, or 6, months) after the second inoculation, and in specific embodiments, more than about five months after the first inoculation, more than about six months to about two years after the first inoculation, or about eight months to about one year after the first inoculation. Periodic inoculations beyond the third are also desirable to enhance the subject's "immune memory." The adequacy of the vaccination parameters chosen, e.g., formulation, dose, regimen and the like, can be determined by taking aliquots of serum from the subject and assaying antibody titers during the course of the immunization program. Alternatively, the T cell populations can be monitored by conventional methods. In addition, the clinical condition of the subject can be monitored for the desired effect, e.g., prevention of MERS-CoV infection or improvement in disease state (e.g., reduction in viral load). If such monitoring indicates that vaccination is sub-optimal, the subject can be boosted with an additional dose of immunogenic composition, and the vaccination parameters can be modified in a fashion expected to potentiate the immune response. Thus, for example, the dose of the disclosed immunogen (e.g., MERS-CoV S protein or immunogenic fragment thereof, polynucleotides encoding same, protein nanoparticles, viral-like particles, or vectors) can be increased or the route of administration can be changed.

It is contemplated that there can be several boosts, and that each boost can be a different disclosed immunogen (e.g., MERS-CoV S protein or immunogenic fragment thereof, polynucleotides encoding same, protein nanoparticles, viral-like particles, or vectors). It is also contemplated in some examples that the boost may be the same immunogen (e.g., MERS-CoV S protein or immunogenic fragment thereof, polynucleotides encoding same, protein nanoparticles, viral-like particles, or vectors) as another boost, or the prime.

The prime and boost can be administered as a single dose or multiple doses, for example two doses, three doses, four doses, five doses, six doses or more can be administered to a subject over days, weeks or months. Multiple boosts can also be given, such one to five (e.g., 1, 2, 3, 4 or 5 boosts), or more. Different dosages can be used in a series of sequential inoculations. For example a relatively large dose in a primary inoculation and then a boost with relatively smaller doses. The immune response against the selected antigenic surface can be generated by one or more inoculations of a subject.

In one example, the method can include administering a prime-boost vaccination to a subject, including administering a therapeutically effective amount of a nucleic acid molecule encoding a MERS-CoV S protein to the subject; and administering a therapeutically effective amount of a MERS-CoV S1 protein to the subject. For example the method can include administration of a prime including the nucleic acid molecule encoding the MERS-CoV S protein and a boost including the MERS-CoV S1 protein. The method can include two or more administrations of the nucleic acid molecule encoding the MERS-CoV S protein or the MERS-CoV S1 protein.

In a non-limiting example, the method includes a prime administration comprising administration of a nucleic acid molecule encoding the MERS-CoV S protein, a first boost administration comprising administration of a nucleic acid molecule encoding the MERS-CoV S protein, and a second boost administration including administration of a MERS-CoV S1 protein, to the subject.

In some embodiments, the prime and/or the first boost can include administration of a nucleic acid molecule encoding a MERS-CoV S protein comprising or consisting of the amino acid sequence set forth as SEQ ID NO: 14, or an amino acid sequence at least 80% (such as at least 85%, at least 90%, at least 95%, at least 98%) identical to SEQ ID NO: 14. In more embodiments, the second boost can include administration of a MERS-CoV S1 protein comprising or consisting of the amino acid sequence set forth as SEQ ID NO: 16, or an amino acid sequence at least 80% (such as at least 85%, at least 90%, at least 95%, at least 98%) identical to SEQ ID NO: 16. In more embodiments, the prime and/or the first boost can include administration of a nucleic acid molecule encoding a MERS-CoV S protein comprising or consisting of the amino acid sequence set forth as SEQ ID NO: 14, or an amino acid sequence at least 80% (such as at least 85%, at least 90%, at least 95%, at least 98%) identical to SEQ ID NO: 14, and the second boost can include administration of a MERS-CoV S1 protein comprising or consisting of the amino acid sequence set forth as SEQ ID NO: 16, or an amino acid sequence at least 80% (such as at least 85%, at least 90%, at least 95%, at least 98%) identical to SEQ ID NO: 16.

Upon administration of a disclosed immunogen (e.g., MERS-CoV S protein or immunogenic fragment thereof, polynucleotides encoding same, protein nanoparticles, viral-like particles, or vectors) of this disclosure, the immune system of the subject typically responds to the immunogenic composition by producing antibodies specific for MERS-CoV S protein. Such a response signifies that an immunologically effective dose was delivered to the subject.

An immunologically effective dosage can be achieved by single or multiple administrations (including, for example, multiple administrations per day), daily, or weekly administrations of the immunogen. For each particular subject, specific dosage regimens can be evaluated and adjusted over time according to the individual need and professional judgment of the person administering or supervising the administration of the immunogenic composition. In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including, for example, a MERS-CoV S protein. The methods of using immunogenic compositions, and the related compositions and methods of the disclosure are also useful in increasing resistance to, preventing, ameliorating, and/or treating infection and disease caused by MERS-CoV in animal hosts, and other, in vitro applications.

In several embodiments, a disclosed immunogen can be administered to the subject simultaneously with the administration of an adjuvant. In other embodiments, the immunogen (e.g., MERS-CoV S protein or immunogenic fragment thereof, polynucleotides encoding same, protein nanoparticles, viral-like particles, or vectors) is administered to the subject after the administration of an adjuvant and within a sufficient amount of time to induce the immune response. Non-limiting examples of adjuvants include aluminum hydroxide or aluminum phosphate, TLR9 agonist (like CpG), TLR7 and/or TLR8 agonists, TLR5 agonist (like flagellin), any TLR4 agonist (any variant of lipid A), TLR3 agonist (variants of double-stranded RNA like polyI:C), any oil-in-water immulsion (many of these use squalene), ISCOMS, or anything containing QS21, anything combined with lipid membranes like virosomes.

For prophylactic and therapeutic purposes, a therapeutically effective amount of a disclosed immunogen (e.g., MERS-CoV S protein or immunogenic fragment thereof, polynucleotides encoding same, protein nanoparticles, viral-like particles, or vectors) can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the therapeutic agents can be provided as repeated doses within a prolonged prophylaxis or treatment regimen that will yield clinically significant results to alleviate one or more symptoms or detectable conditions associated with a targeted disease or condition as set forth herein.

Determination of effective dosages in this context is typically based on animal model studies followed up by human clinical trials and is guided by administration protocols that significantly reduce the occurrence or severity of targeted disease symptoms or conditions in the subject, or that induce a desired response in the subject (such as a neutralizing immune response). Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes.

Dosage can be varied by the attending clinician to maintain a desired concentration at a target site (for example, systemic circulation). Higher or lower concentrations can be selected based on the mode of delivery, for example, transepidermal, rectal, oral, pulmonary, or intranasal delivery versus intravenous or subcutaneous delivery. The actual dosage of disclosed immunogen (e.g., MERS-CoV S protein or immunogenic fragment thereof, polynucleotides encoding same, protein nanoparticles, viral-like particles, or vectors) will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response. As described above in the forgoing listing of terms, a therapeutically effective amount is also one in which any toxic or detrimental side effects of the disclosed immunogen and/or other biologically active agent is outweighed in clinical terms by therapeutically beneficial effects.

A non-limiting range for a therapeutically effective amount of the disclosed polypeptide immunogen (e.g., MERS-CoV S protein or immunogenic fragment thereof, polynucleotides encoding same, protein nanoparticles, viral-like particles, or vectors) within the methods and immunogenic compositions of the disclosure is about 0.0001 mg/kg body weight to about 10 mg/kg body weight, such as about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 4 mg/kg, about 5 mg/kg, or about 10 mg/kg, for example 0.01 mg/kg to about 1 mg/kg body weight, about 0.05 mg/kg to about 5 mg/kg body weight, about 0.2 mg/kg to about 2 mg/kg body weight, or about 1.0 mg/kg to about 10 mg/kg body weight.

In some embodiments, the dosage includes a set amount of a disclosed immunogen (e.g., MERS-CoV S protein or immunogenic fragment thereof, polynucleotides encoding same, protein nanoparticles, viral-like particles, or vectors) such as from about 1-300 µg, for example, a dosage of about 1, 2, 3, 4, 5, 6, 7, 8, 9, 10, 15, 20, 30, 40, 50, 60, 70, 80, 90, 100, 150, 200, 250, or about 300 µg.

The dosage and number of doses will depend on the setting, for example, in an adult or anyone primed by prior MERS-CoV infection or immunization, a single dose may be a sufficient booster. In naïve subjects, in some examples, at least two doses would be given, for example, at least three doses. In some embodiments, an annual boost is given, for example, along with an annual influenza vaccination.

Actual methods for preparing administrable compositions will be known or apparent to those skilled in the art and are described in more detail in such publications as *Remingtons Pharmaceutical Sciences*, 19$^{th}$ Ed., Mack Publishing Company, Easton, Pa., 1995.

Administration of a therapeutically effective amount of a disclosed immunogen (e.g., MERS-CoV S protein or immunogenic fragment thereof, polynucleotides encoding same, protein nanoparticles, viral-like particles, or vectors) induces a sufficient immune response to treat or inhibit or prevent the pathogenic infection, for example, to inhibit the infection and/or reduce the signs and/or symptoms of the infection. Amounts effective for this use will depend upon the severity of the disease, the general state of the subject's health, and the robustness of the subject's immune system.

MERS-CoV infection does not need to be completely eliminated or reduced or prevented for the methods to be effective. For example, treatment with one or more of the disclosed therapeutic agents can reduce or inhibit MERS-CoV infection by a desired amount, for example by at least 10%, at least 20%, at least 50%, at least 60%, at least 70%, at least 80%, at least 90%, at least 95%, at least 98%, or even at least 100% (elimination or prevention of detectable MERS-CoV infected cells), as compared to MERS-CoV infection in the absence of the therapeutic agent. In additional examples, MERS-CoV replication can be reduced or inhibited by the disclosed methods. MERS-CoV replication does not need to be completely eliminated for the method to be effective. For example, treatment with one or more of the disclosed immunogens (e.g., MERS-CoV S protein or immunogenic fragment thereof, polynucleotides encoding same, protein nanoparticles, viral-like particles, or vectors) can reduce MERS-CoV replication by a desired amount, for example by at least 10%, at least 20%, at least 50%, at least 60%, at least 70%, at least 80%, at least 90%, at least 95%, at least 98%, or even at least 100% (elimination or prevention of detectable MERS-CoV replication), as compared to MERS-CoV replication in the absence of the therapeutic agent.

In several embodiments, following immunization of a subject with a disclosed immunogen, serum can be collected from the subject at appropriate time points, frozen, and stored for neutralization testing. Methods to assay for neutralization activity are known to the person of ordinary skill in the art and are further described herein, and include, but are not limited to, plaque reduction neutralization (PRNT) assays, microneutralization assays, flow cytometry based assays, single-cycle infection assays, and pseudovirus neutralization assays (e.g., as described in Example 1).

In some embodiments, administration of a therapeutically effective amount of one or more of the disclosed immunogens to a subject (e.g., by a prime-boost administration of a DNA vector encoding a disclosed immunogen (prime) followed by a MERS-CoV S protein or fragment thereof (such as an S1 protein) or a protein nanoparticle including the MERS-CoV S protein or fragment thereof (boost)) induces a neutralizing immune response in the subject. In several embodiments, the neutralizing immune response can be detected using a pseudovirus neutralization assay against a panel of MERS-CoV pseudoviruses including MERS-CoV S proteins from different MERS-CoV strains, for example, as described in Example 1. In some embodiments, administration of the therapeutically effective amount of disclosed immunogens to a subject by the prime-boost administration of a DNA vector encoding a disclosed immunogen (prime) followed by a MERS-CoV S protein or fragment thereof (such as an S1 protein) or a protein nanoparticle including the MERS-CoV S protein or fragment thereof (boost) induces a neutralizing immune response in the subject, wherein serum from the subject neutralizes, with an $ID_{50} \geq 40$, at least 30% (such as at least 40%, at least 50%, at least 60%, at least 70%, at least 80%, or at least 90%) of pseudoviruses in a panel of pseudoviruses including the MERS-CoV S proteins listed in FIG. 1C.

One approach to administration of nucleic acids is direct immunization with plasmid DNA, such as with a mammalian expression plasmid. As described above, the nucleotide sequence encoding a disclosed recombinant MERS-CoV S protein or fragment thereof can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Immunization with RNA-based technology can also be used with the disclosed embodiments. Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 µg encapsulated in ISCOMS™ have been found to produce Class I mediated CTL responses (Takahashi et al., *Nature* 344:873, 1990).

In another approach to using nucleic acids for immunization, a disclosed MERS-CoV S protein or fragment thereof, can also be expressed by attenuated viral hosts or vectors or bacterial vectors. Recombinant vaccinia virus, adeno-associated virus (AAV), herpes virus, retrovirus, cytomegalovirus, alphavirus (e.g., as described in Lundstrom, Viruses, 7(5):2321-2333, 2015), or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991).

In one embodiment, a nucleic acid encoding a disclosed MERS-CoV S protein or fragment thereof, is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

In certain embodiments, the immunogen can be administered sequentially with other anti-MERS-CoV therapeutic agents, such as before or after the other agent. One of ordinary skill in the art would know that sequential administration can mean immediately following or after an appropriate period of time, such as hours, days, weeks, months, or even years later.

IV. Polynucleotides and Expression

Polynucleotides encoding a disclosed MERS-CoV S protein or immunogenic fragment thereof, or protein nanoparticles (or a subunit thereof), or an antibody, antibody binding fragment, or conjugate that specifically binds MERS-CoV S protein are also provided. These polynucleotides include DNA, cDNA and RNA sequences which encode the disclosed MERS-CoV S protein or immunogenic fragment thereof, or protein nanoparticle (or a subunit thereof), or an antibody, antibody binding fragment, or conjugate that specifically binds MERS-CoV S protein. Nucleic acids encoding these molecules can readily be produced by one of skill in the art, using the amino acid sequences provided herein (such as the CDR and heavy chain and light chain sequences for production of antibodies), sequences available in the art (such as framework sequences), and the genetic code. One of skill in the art can readily use the genetic code to construct a variety of functionally equivalent nucleic acids, such as nucleic acids which differ in sequence but which encode the same antibody sequence, or encode a conjugate or fusion protein including the nucleic acid sequence.

Polynucleotides encoding a disclosed MERS-CoV S protein or immunogenic fragment thereof, or protein nanoparticles (or a subunit thereof), or an antibody, antibody binding fragment, or conjugate that specifically binds MERS-CoV S protein can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Examples of appropriate cloning and sequencing techniques, and instructions sufficient to direct persons of skill through many cloning exercises are known (see, e.g, Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The nucleic acid molecules can be expressed in a recombinantly engineered cell such as bacteria, plant, yeast, insect and mammalian cells. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), 4$^{th}$ Ed., Humana Press). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as GnTI$^{-/-}$ cells (ATCC® No. CRL-3022), or HEK-293F cells.

The expression of nucleic acids encoding the proteins described herein can be achieved by operably linking the DNA or cDNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding a disclosed MERS-CoV S protein or immunogenic fragment thereof, or protein nanoparticles (or a subunit thereof), or an antibody, antibody binding fragment, or conjugate that specifically binds MERS-CoV S protein, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

The antibodies, antigen binding fragments, and conjugates can be expressed as individual $V_H$ and/or $V_L$ chain (linked to an effector molecule or detectable marker as needed), or can be expressed as a fusion protein. Methods of expressing and purifying antibodies and antigen binding fragments are known and further described herein (see, e.g., Al-Rubeai (ed), *Antibody Expression and Production*, Springer Press, 2011). An immunoadhesin can also be expressed. Thus, in some examples, nucleic acids encoding a $V_H$ and $V_L$, and immunoadhesin are provided. The nucleic acid sequences can optionally encode a leader sequence.

To create a scFv the $V_H$- and $V_L$-encoding DNA fragments can be operatively linked to another fragment encoding a flexible linker, e.g., encoding the amino acid sequence (Gly4-Ser)$_3$, such that the $V_H$ and $V_L$ sequences can be expressed as a contiguous single-chain protein, with the $V_L$ and $V_H$ domains joined by the flexible linker (see, e.g., Bird et al., *Science* 242:423-426, 1988; Huston et al., *Proc. Natl. Acad. Sci. USA* 85:5879-5883, 1988; McCafferty et al., *Nature* 348:552-554, 1990; Kontermann and Dubel (Ed), Antibody Engineering, Vols. 1-2, $2^{nd}$ Ed., Springer Press, 2010; Harlow and Lane, *Antibodies: A Laboratory Manual*, $2^{nd}$ Cold Spring Harbor Laboratory, New York, 2013,). Optionally, a cleavage site can be included in a linker, such as a furin cleavage site.

The nucleic acid encoding a $V_H$ and/or the $V_L$ optionally can encode an Fc domain (immunoadhesin). The Fc domain can be an IgA, IgM or IgG Fc domain. The Fc domain can be an optimized Fc domain, as described in U.S. Published Patent Application No. 20100/093979, incorporated herein by reference. In one example, the immunoadhesin is an IgG$_1$ Fc.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to MERS-CoV S protein and another antigen, such as, but not limited to CD3. The encoded $V_H$ and $V_L$ optionally can include a furin cleavage site between the $V_H$ and $V_L$ domains.

Methods for expression of antibodies, antigen binding fragments, and conjugates, and/or refolding to an appropriate active form, from mammalian cells, and bacteria such as *E. coli* have been described and are well-known and are applicable to the antibodies disclosed herein. See, e.g., Harlow and Lane, *Antibodies: A Laboratory Manual, $2^{nd}$*, Cold Spring Harbor Laboratory, New York, 2013, Simpson ed., Basic methods in Protein Purification and Analysis: A laboratory Manual, Cold Harbor Press, 2008, and Ward et al., *Nature* 341:544, 1989.

Also provided is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

In several embodiments, the nucleic acid molecule encodes a precursor of a disclosed MERS-CoV S protein or fragment thereof that can be processed into the MERS-CoV S protein or fragment thereof when expressed in an appropriate cell. For example, the nucleic acid molecule can encode a MERS-CoV S protein or fragment thereof including a N-terminal signal sequence for entry into the cellular secretory system that is proteolytically cleaved in the during processing of the MERS-CoV S protein or fragment in the cell. In some embodiments, the signal peptide includes the amino acid sequence set forth as SEQ ID NOs: 24 or 25.

The polynucleotides encoding a MERS-CoV S protein or fragment thereof, or protein nanoparticle subunit linked to such a S protein or fragment can include a recombinant DNA which is incorporated into a vector into an autonomously replicating plasmid or virus or into the genomic DNA of a prokaryote or eukaryote, or which exists as a separate molecule (such as an mRNA or a cDNA) independent of other sequences. The nucleotides can be ribonucleotides, deoxyribonucleotides, or modified forms of either nucleotide. The term includes single and double forms of DNA. In one non-limiting example, a disclosed immunogen is expressed using the pVRC8400 vector (described in Barouch et al., J. Virol, 79, 8828-8834, 2005, which is incorporated by reference herein).

Once expressed, a disclosed MERS-CoV S protein or immunogenic fragment thereof, or protein nanoparticles (or a subunit thereof), or an antibody, antibody binding fragment, or conjugate that specifically binds MERS-CoV S protein can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The MERS-CoV S protein or immunogenic fragment thereof, or protein nanoparticles (or a subunit thereof), or an antibody, antibody binding fragment, or conjugate that specifically binds MERS-CoV S protein need not be 100% pure. Once purified, partially or to homogeneity as desired, if to be used therapeutically, the polypeptides should be substantially free of endotoxin.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, and especially as described by Buchner et al., supra.

In addition to recombinant methods, the antibodies, antigen binding fragments, and/or conjugates can also be constructed in whole or in part using standard peptide synthesis. Solid phase synthesis of the polypeptides can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art.

V. Compositions and Administration

The disclosed agents can be included in a pharmaceutical composition (including therapeutic and prophylactic formulations), often combined together with one or more pharmaceutically acceptable vehicles and, optionally, other therapeutic ingredients (for example, antibiotics or antiviral drugs). In several embodiments, pharmaceutical compositions including one or more of the disclosed immunogens are immunogenic compositions. The compositions are useful, for example, for example, for the treatment or detection of a MERS-CoV infection or induction of an immune response to MERS-CoV in a subject.

The compositions can be prepared in unit dosage forms for administration to a subject. The amount and timing of administration are at the discretion of the treating physician to achieve the desired purposes. A disclosed MERS-CoV S protein or immunogenic fragment thereof, or protein nanoparticle (or a subunit thereof), or an antibody, antibody binding fragment, or conjugate that specifically binds MERS-CoV S protein, or polynucleotide encoding such molecules can be formulated for systemic or local administration. In one example, the disclosed MERS-CoV S protein or immunogenic fragment thereof, or protein nanoparticle (or a subunit thereof), or an antibody, antibody binding fragment, or conjugate that specifically binds MERS-CoV S protein, or polynucleotide encoding such molecules is formulated for parenteral administration, such as intravenous administration.

A disclosed MERS-CoV S protein or immunogenic fragment thereof, or protein nanoparticle (or a subunit thereof), or an antibody, antibody binding fragment, or conjugate that specifically binds MERS-CoV S protein, or polynucleotide encoding such molecules, or a composition including such molecules, as well as additional agents, can be administered to subjects in various ways, including local and systemic administration, such as, e.g., by injection subcutaneously, intravenously, intra-arterially, intranasally, intraperitoneally, intramuscularly, intradermally, or intrathecally. In an embodiment, a therapeutic agent is administered by a single subcutaneous, intravenous, intra-arterial, intraperitoneal, intramuscular, intradermal or intrathecal injection once a day. The therapeutic agent can also be administered by direct injection at or near the site of disease.

A further method of administration is by osmotic pump (e.g., an Alzet pump) or mini-pump (e.g., an Alzet mini-osmotic pump), which allows for controlled, continuous and/or slow-release delivery of the therapeutic agent or pharmaceutical composition over a pre-determined period. The osmotic pump or mini-pump can be implanted subcutaneously, or near a target site.

The therapeutic agent or compositions thereof can also be administered by other modes. Determination of the most effective mode of administration of the therapeutic agent or compositions thereof is within the skill of the skilled artisan. The therapeutic agent can be administered as pharmaceutical formulations suitable for, e.g., oral (including buccal and sub-lingual), rectal, nasal, topical, pulmonary, vaginal or parenteral administration, or in a form suitable for administration by inhalation or insufflation. Depending on the intended mode of administration, the pharmaceutical formulations can be in the form of solid, semi-solid or liquid dosage forms, such as tablets, suppositories, pills, capsules, powders, liquids, suspensions, emulsions, creams, ointments, lotions, and the like.

In some embodiments, the compositions comprise a disclosed MERS-CoV S protein or immunogenic fragment thereof, or protein nanoparticle (or a subunit thereof), or an antibody, antibody binding fragment, or conjugate that specifically binds MERS-CoV S protein, or polynucleotide encoding such molecules in at least about 70%, 75%, 80%, 85%, 90%, 95%, 96%, 97%, 98% or 99% purity. In certain embodiments, the compositions contain less than about 10%, 5%, 4%, 3%, 2%, 1% or 0.5% of macromolecular contaminants, such as other mammalian (e.g., human) proteins.

In some embodiments, the composition can be provided in unit dosage form for use to induce an immune response in a subject, for example, to prevent, inhibit, or treat MERS-CoV infection in the subject. A unit dosage form contains a suitable single preselected dosage for administration to a subject, or suitable marked or measured multiples of two or more preselected unit dosages, and/or a metering mechanism for administering the unit dose or multiples thereof. In other embodiments, the composition further includes an adjuvant.

A typical composition for intravenous administration of an antibody or antigen binding fragment thereof includes about 0.01 to about 30 mg/kg of antibody or antigen binding fragment or conjugate per subject per day (or the corresponding dose of a conjugate including the antibody or antigen binding fragment). Actual methods for preparing administrable compositions will be known or apparent to those skilled in the art and are described in more detail in such publications as *Remington's Pharmaceutical Science*, 19th ed., Mack Publishing Company, Easton, Pa. (1995). In some embodiments, the composition can be a liquid formulation including one or more antibodies, antigen binding fragments (such as an antibody or antigen binding fragment that specifically binds to MERS-CoV S protein), in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

An antibody solution, or an antigen binding fragment can be added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies and antigen binding fragments can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

In several embodiments, an immunogenic composition (e.g., including a disclosed MERS-CoV S protein or immunogenic fragment thereof, or protein nanoparticle (or a subunit thereof) or polynucleotide encoding such molecules) include an adjuvant. The person of ordinary skill in the art is familiar with adjuvants, for example, those that can be included in an immunogenic composition. It will be appreciated that the choice of adjuvant can be different in these different applications, and the optimal adjuvant and concentration for each situation can be determined empirically by those of skill in the art. Adjuvants, such as aluminum hydroxide (ALHYDROGEL®, available from Brenntag Biosector, Copenhagen, Denmark and AMPHOGEL®, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions.

Preparation of immunogenic compositions, including those for administration to human subjects, is known in the art, and generally described, for example, in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757. Typically, the amount of antigen in each dose of the immunogenic composition is selected as an amount which induces an immune response without significant, adverse side effects.

The amount of the disclosed immunogen (for example, disclosed MERS-CoV S protein or immunogenic fragment thereof, or protein nanoparticle (or a subunit thereof), or viral vector or polynucleotide encoding such molecules, included in the immunogenic composition can vary depending upon the specific antigen employed, the route and protocol of administration, and the target population, for example. For protein therapeutics, typically, each human dose will comprise 1-1000 µg of protein, such as from about 1 µg to about 100 µg, for example, from about 1 µg to about 50 µg, such as about 1 µg, about 2 µg, about 5 µg, about 10 µg, about 15 µg, about 20 µg, about 25 µg, about 30 µg, about 40 µg, or about 50 µg. The amount utilized in an immunogenic composition can be selected based on the subject population (e.g., infant or elderly). An optimal amount for a particular composition can be ascertained by standard studies involving observation of antibody titers and other responses in subjects. It is understood that a therapeutically effective amount of a disclosed immunogen, such as disclosed MERS-CoV S protein or immunogenic fragment thereof, or protein nanoparticle (or a subunit thereof), or viral vector or polynucleotide encoding such molecules can include an amount that is ineffective at eliciting an immune response by administration of a single dose, but that is effective upon administration of multiple dosages or in combination administration of a second immunogen, for example in a prime-boost administration protocol.

To formulate the pharmaceutical compositions, the disclosed MERS-CoV S protein or immunogenic fragment thereof, or protein nanoparticle (or a subunit thereof), viral vector or an antibody, antibody binding fragment, or conjugate that specifically binds MERS-CoV S protein, or polynucleotide encoding such molecules, can be combined with various pharmaceutically acceptable additives, as well as a base or vehicle for dispersion of the conjugate. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, TWEEN® 80), solubility enhancing agents (for example, cyclodextrins and derivatives thereof), stabilizers (for example, serum albumin), and reducing agents (for example, glutathione) can be included.

The compositions for administration can include a solution of the disclosed MERS-CoV S protein or immunogenic fragment thereof, or protein nanoparticle (or a subunit thereof), viral vector or an antibody, antibody binding fragment, or conjugate that specifically binds MERS-CoV S protein, or polynucleotide encoding such molecules dissolved in a pharmaceutically acceptable carrier, such as an aqueous carrier. A variety of aqueous carriers can be used, for example, buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of the disclosed MERS-CoV S protein or immunogenic fragment thereof, or protein nanoparticle (or a subunit thereof), viral vector or an antibody, antibody binding fragment, or conjugate that specifically binds MERS-CoV S protein, or polynucleotide encoding such molecules in these formulations can vary widely, and will be selected primarily based on fluid volumes, viscosities, body weight and the like in accordance with the particular mode of administration selected and the subject's needs.

The disclosed MERS-CoV S protein or immunogenic fragment thereof, or protein nanoparticle (or a subunit thereof), viral vector or an antibody, antibody binding fragment, or conjugate that specifically binds MERS-CoV S protein, or polynucleotide encoding such molecules can be provided in lyophilized form and rehydrated with sterile water before administration, although they are also provided in sterile solutions of known concentration.

Controlled-release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The pharmaceutical compositions of the disclosure typically are sterile and stable under conditions of manufacture, storage and use. Sterile solutions can be prepared by incorporating the conjugate in the required amount in an appropriate solvent with one or a combination of ingredients enumerated herein, as required, followed by filtered sterilization. Generally, dispersions are prepared by incorporating the disclosed antigen and/or other biologically active agent into a sterile vehicle that contains a basic dispersion medium and the required other ingredients from those enumerated herein. In the case of sterile powders, methods of preparation include vacuum drying and freeze-drying which yields a powder of the disclosed antigen plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

EXAMPLES

The following examples are provided to illustrate particular features of certain embodiments, but the scope of the claims should not be limited to those features exemplified.

Example 1

Development of a Middle East Respiratory Syndrome Coronavirus Vaccine

The emergence of the Middle East respiratory syndrome coronavirus as a cause of severe respiratory disease ten years after the SARS-CoV outbreak highlights the need for pre-existing platforms to facilitate rapid vaccine development for beta-coronaviruses. This example illustrates an MERS-CoV immunization strategy based on the MERS-CoV Spike glycoprotein (S), consisting of a full-length S DNA prime and S1 subunit protein boost. The disclosed immunization strategy elicited high titers of neutralizing antibodies against eight different MERS-CoV strains. Vaccine-elicited murine monoclonal antibodies (mAb) were characterized and shown to neutralize virus by targeting the receptor binding domain (RBD), non-RBD portions of S1, or S2. The atomic structure of the D12 mAb in complex with RBD supported escape mutation data that indicated several mechanisms by which antibodies block binding to the MERS-CoV receptor, DPP4. Accordingly, gene-based priming with full-length S and S1 protein subunit boosting induced antibodies with diverse mechanisms of neutralization.

INTRODUCTION

Middle East respiratory syndrome coronavirus (MERS-CoV) has emerged as a highly fatal cause of severe acute respiratory infection. Since April 2012, between 1018 and 1034 cases and 366 to 409 deaths have been attributed to the novel beta coronavirus. As human-to-human transmission of the virus is not sustained, a large zoonotic reservoir may serve as a principal source for transmission events (Assiri et al., *Lancet infectious diseases* 13, 752, 2013; Breban, *Lancet* 382, 694, 2013; Cauchemez et al., *Lancet infectious diseases* 14, 50, 2014; Memish et al., *Emerging infectious diseases* 20, 1012, 2014). The high case fatality rate, vaguely defined epidemiology, and absence of prophylactic or therapeutic measures against this novel virus have created an urgent need for an effective vaccine, should the outbreak expand to pandemic proportions.

Past efforts to develop coronavirus vaccines have used whole-inactivated virus, live-attenuated virus, recombinant protein subunit, or genetic approaches (Graham et al., *Nature reviews. Microbiology* 11, 836, 2013). The primary target for neutralizing antibodies is the Spike (S) glycoprotein, cleaved into two subunits: S1, which is distal to the virus membrane; and S2, which contains both a transmembrane domain and two heptad-repeat sequences typical of class I fusion glycoproteins ((Cavanagh, *J general virology* 64 (Pt 12), 2577, 1983; Buchholz et al., *PNAS* 101, 9804, 2004). The S1 subunit has been the focus of most immunization strategies against MERS-CoV (Coleman et al., *Vaccine* 32, 3169, 2014; Du et al., *PloS one* 8, e81587, 2013; Ma et al., *Vaccine* 32, 2100, 2014), as it contains the receptor-binding domain (RBD) that mediates virus attachment to its host receptor, dipeptidyl peptidase-4 (DPP4) (Mou et al., *J virology* 87, 9379, 2013). Expressing the RBD on multiple vaccine platforms can elicit neutralizing antibodies of high potency (Du et al., *J virology* 88, 7045, 2014; Ohnuma et al., *J virology* 87, 13892, 2013; Ying et al., *J virology* 88, 7796, 2014; Jiang et al., *Science translational medicine* 6, 234ra59, 2014; Briese et al., *mBio* 5, e01146, 2014) that prevent viral attachment across viral strains but will not elicit antibodies that contribute to neutralization by mediating fusion inhibition. An alternative vaccine regimen is disclosed herein, based on full-length S DNA and a truncated S1 subunit glycoprotein, to elicit a broad repertoire of antibodies with diverse mechanisms of viral neutralization.
Results Construction and Characterization of Vaccines Based on Spike Glycoprotein.

Figure 1B:
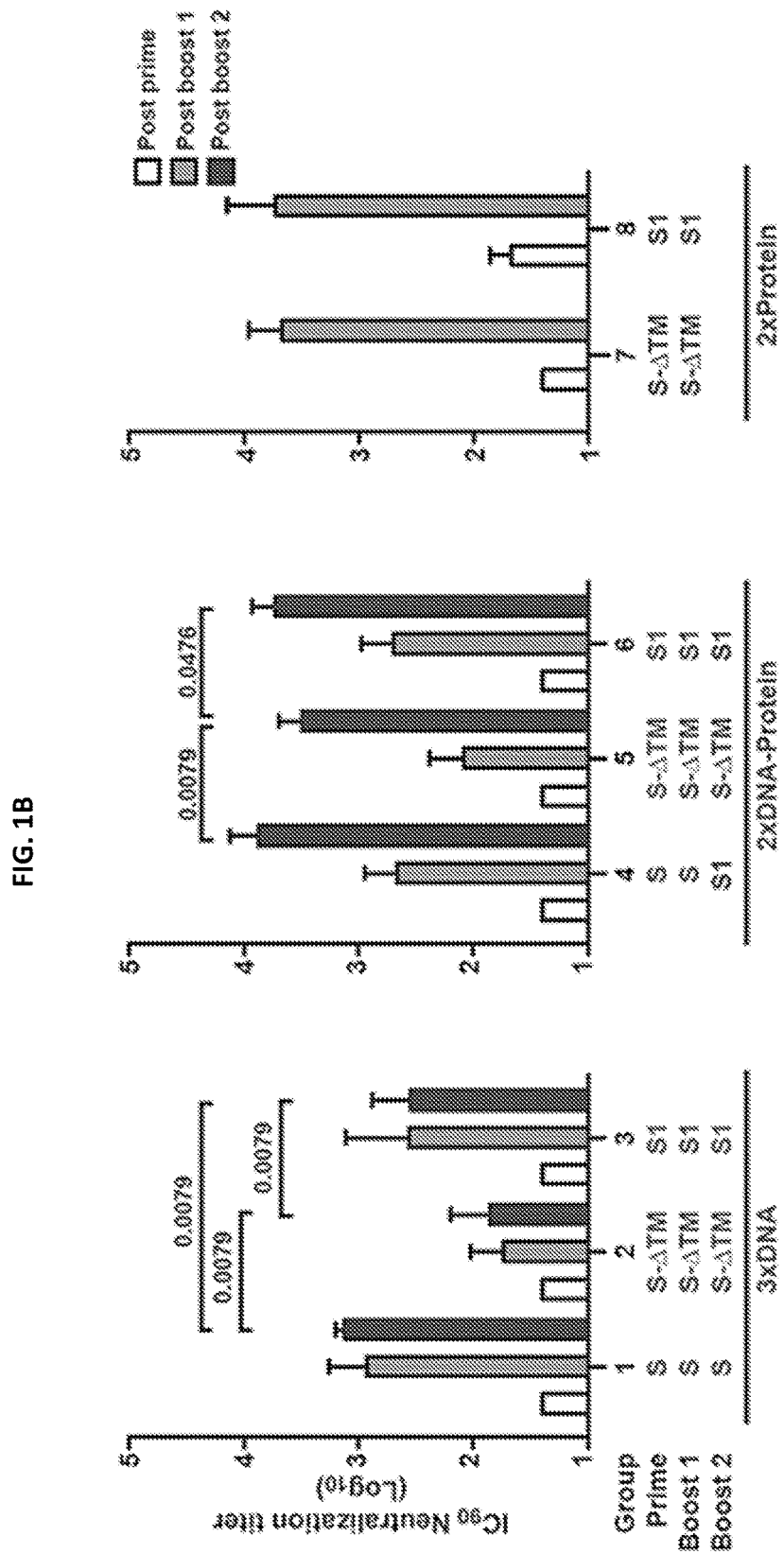

Five vaccine constructs were designed based on sequences from the MERS-CoV S glycoprotein (FIG. 1A). The England1 strain (GenBank ID: AFY13307) was chosen based on the availability of its sequence and its proximity to a consensus among published sequences, particularly within the RBD. Three plasmid vaccines were constructed that encoded: 1) full-length, membrane-anchored S; 2) transmembrane-deleted (ΔTM) S containing the entire ectodomain; and 3) S1 subunit only. All three plasmids were delivered intramuscularly by needle and syringe, followed by electroporation. The two protein subunit vaccines included S-ΔTM and S1 and were delivered intramuscularly by needle and syringe with Ribi adjuvant. These five candidate vaccines were systematically evaluated in mice according to eight immunization regimens (FIG. 1B). To test the immunogenicity of the vaccine candidates against multiple MERS-CoV strains—without the requirement of a biosafety level 3 facility—a pseudotyped reporter virus neutralization assay was developed, similar to that previously developed for SARS-CoV (Martin et al., *Vaccine* 26, 6338, 2008; Yang et al., *Nature* 428, 561, 2004; Naldini et al., *PNAS* 93, 11382, 1996; Yang et al., *PNAS* 102, 797, 2005). It was confirmed that the assay measured viral entry via the MERS-CoV receptor, DPP4, by demonstrating that HEK 293 cells required DPP4 expression on their surface for efficient infection and that soluble DPP4 or anti-DPP4 antibody prevented infection (FIG. 6A-D).

Full-Length S DNA and S1 Protein are the Most Immunogenic Vaccines in Mice.

Figure 1C:
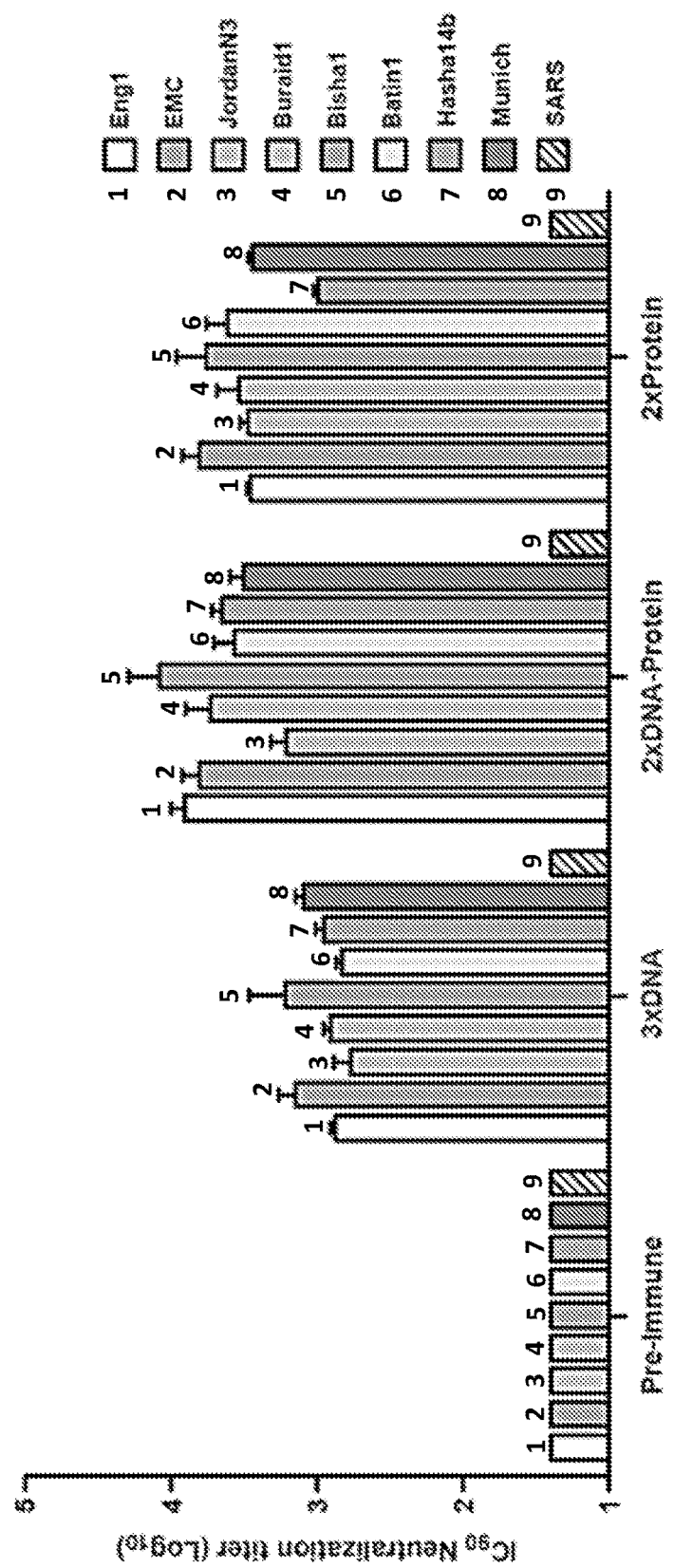
Figure 8:
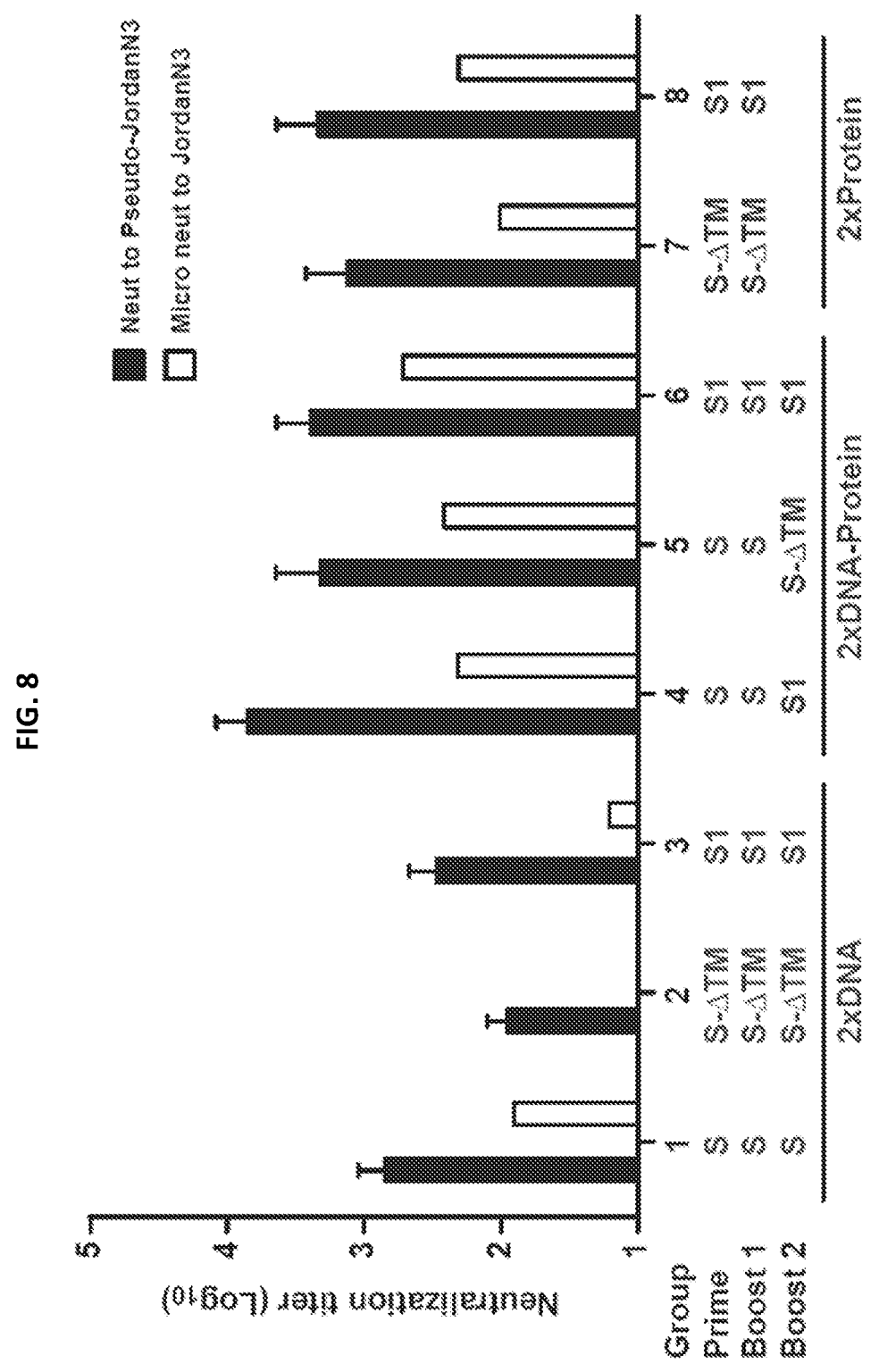

Mice primed either once with S1 protein or twice with S DNA and then boosted once with S1 protein generated the highest neutralizing antibody titers among all groups (FIG. 1B). The full-length S DNA regimen induced a significantly higher antibody response than the truncated S-ΔTM or S1 DNA regimens. Antibody titers tended to be either low or undetectable after the first dose of DNA but boosted ten-fold after immunization with S1 protein. Two doses of S1 protein achieved an $IC_{90}$ near that of the DNA/protein regimen. Three of the eight vaccine regimens—(1) S DNA, (2) S DNA/S1 protein, and (3) S1 protein alone—were carried forward for detailed evaluation. S-ΔTM gave low production yields from transfected HEK 293 cells, and was not evaluated further. Immune sera (5 weeks after final boost) from these three regimens were tested against a panel of eight pseudoviruses and found to generate equally robust neutralizing antibody titers against all strains (FIG. 1C). The sequence homology across strains (FIG. 7) likely accounted for the breadth of neutralization. SARS-CoV pseudovirus was not neutralized by sera from any of the immunized mice. Pseudovirus neutralization results were compared with a live virus microneutralization assay for the JordanN3 strain (GenBank ID: KC776174.1). The pseudovirus neutralization assay was about ten-fold more sensitive to neutralization than the live virus, although the two assays correlated well with one another based on relative magnitude (FIG. 8).

S DNA Prime and S1 Protein Boost Elicit Neutralizing Antibodies Directed at Antigenic Sites on Different Domains of the S Glycoprotein.

Figure 2A:
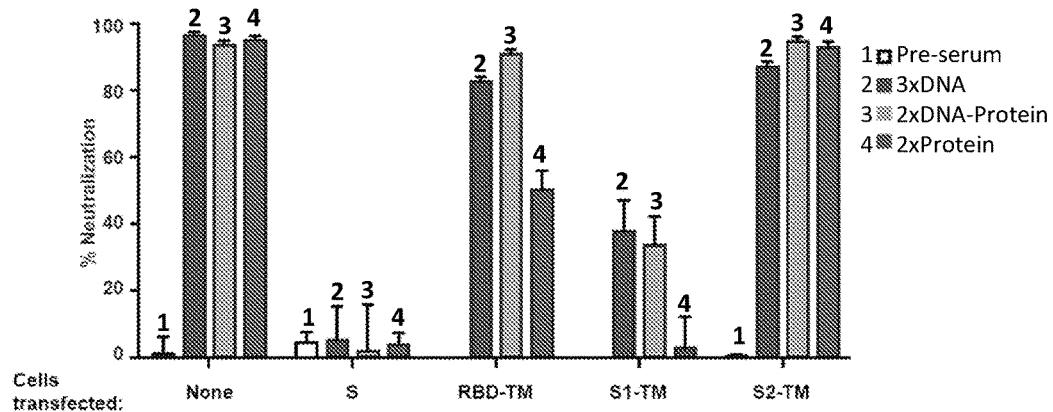
FIGS. 2A and 2B illustrate the antisera targets of neutralization. Immunization with different vaccine regimens elicited neutralizing antibodies that target the Spike (S) glycoprotein within and outside the receptor-binding domain (RBD). (A) Cell adsorption assay. Sera from mice immunized with MERS-CoV S DNA only, S DNA prime and S1 protein plus Ribi adjuvant, or S1 protein plus Ribi adjuvant prime and boost were evaluated for neutralization activity against pseudotyped MERS-CoV (Eng1) after adsorption with 293T cell surface-expressed MERS-CoV Spike proteins: S, RBD, S1, S2. Serum neutralization was tested at a single dilution. Sera adsorbed with untransfected 293T cells served as controls and retained 95% of neutralization activity. Each bar represents the mean of triplicate assays with standard errors. (B) Protein competition neutralization assay. Sera at a single dilution from the immunized mice were also assayed for neutralization of MERS-CoV England1 pseudovirus in the presence of soluble MERS-CoV RBD, S1 and S2 proteins at concentrations of 0.016 to 50 μg/ml.
Figure 9C:
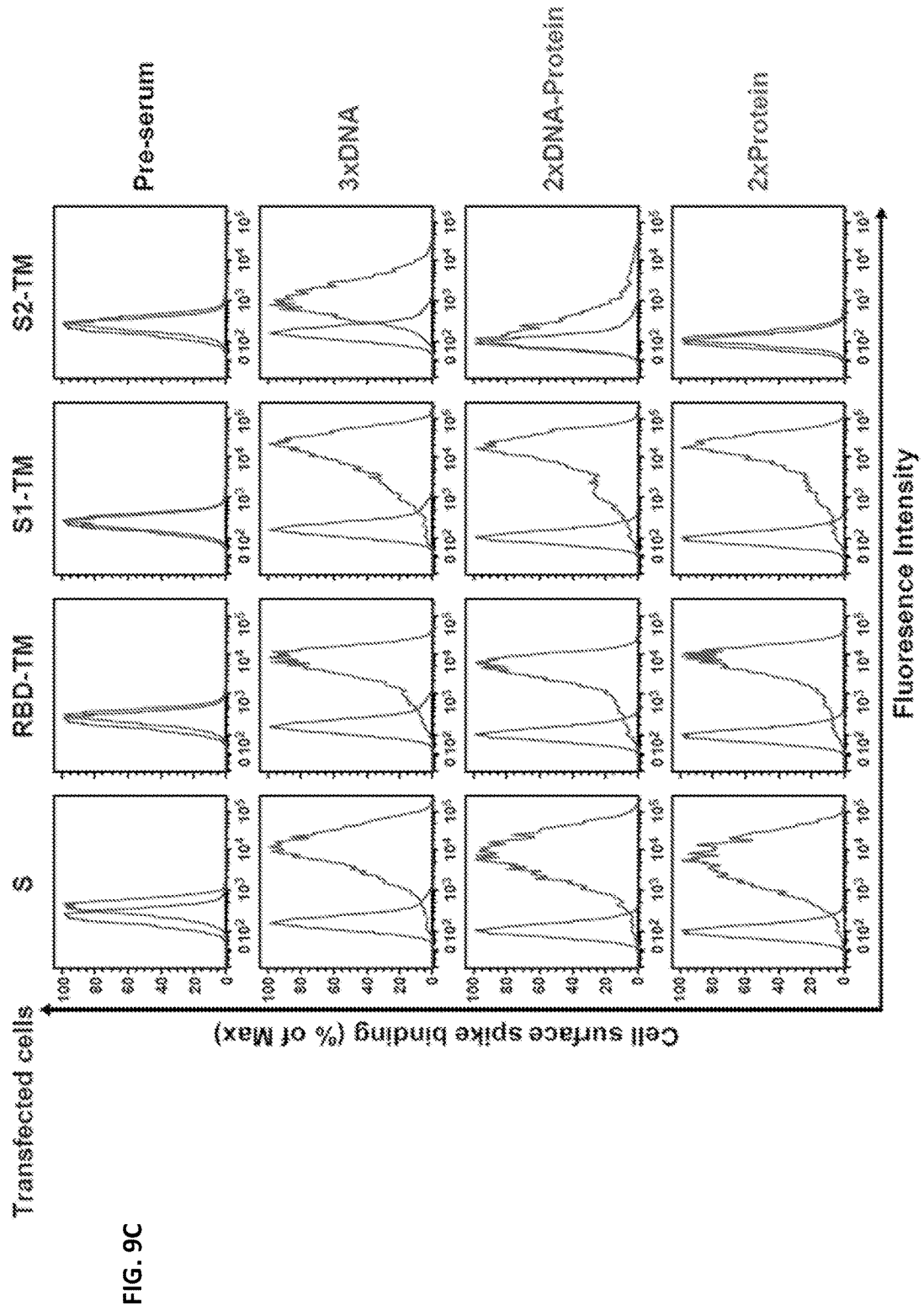
Figure 10A:
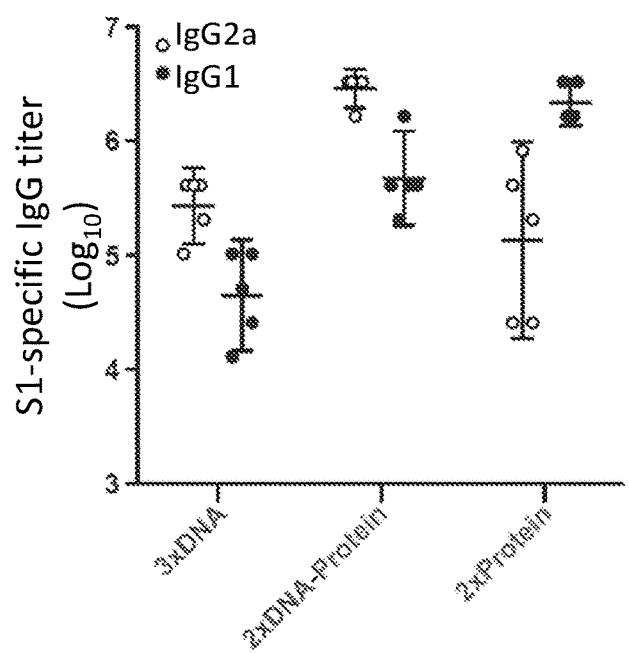
FIGS. 10A and 10B illustrate that MERS-CoV S DNA/S1 protein prime-boost vaccination in mice induced a Th1-biased IgG response compared to a Th2-biased response elicited by a S1 protein prime-boost regimen. (A) Sera from mice immunized with MERS-CoV S DNA, primed with S DNA and boosted with S1 protein plus Ribi adjuvant, or primed and boosted with S1 protein plus Ribi adjuvant were assayed, by ELISA, for their predominance of MERS-CoV S1-specific IgG1 and IgG2a antibody responses. Open and black circles represent IgG2a and IgG1 antibody titers (Geometric mean titer (GMT) with 95% CI), respectively. (B) The GMT ratios of IgG2a to IgG1 in the three groups were calculated from the left panel.
Figure 10B:
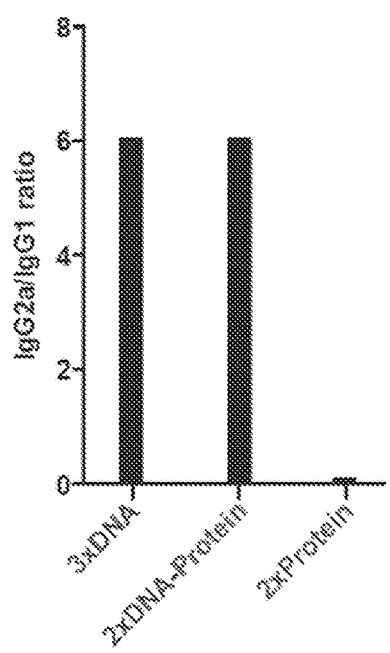

The specificity of neutralizing antibody responses against the different subunits of the MERS-CoV S glycoprotein were analyzed by several methods. First, sera were adsorbed with HEK 293T cells expressing transmembrane-anchored versions of S, S1, S2, and RBD (FIGS. 1A and 9A) and screened for neutralization (FIG. 2A). Sera adsorbed with untransfected cells retained 95% of their original neutralization activity while negative control pre-immune sera showed no capacity for virus neutralization. The full-length S-transfected cells adsorbed virtually all neutralization activity from the immune sera of all three vaccine groups while the RBD expressed by itself on the cell membrane only adsorbed about half of the neutralizing activity, and only in the S1 protein group, suggesting the possibility that the conformation of RBD presented in the full-length S and in the truncated versions may differ. Adsorption with S1 also removed all neutralization activity in the S1 protein group and about 60% of neutralizing capacity in the two DNA-primed groups. In contrast, S2 did not deplete neutralization activity in any of the groups, except slightly in mice vaccinated with DNA alone. It is likely that expression of S2 by itself on cells resulted in rearrangement to the post-fusion conformation, and therefore neutralizing epitopes present on the pre-fusion structure would not have been available for adsorption. Flow cytometric analysis of serum binding to cells that expressed different S subunits gave consistent results (FIG. 9C).

Figure 2B:
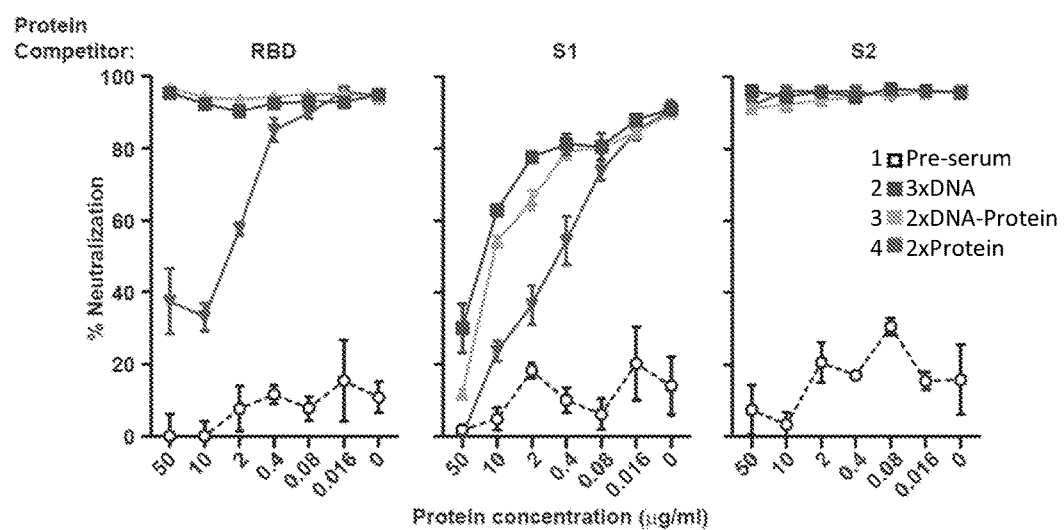

Protein competition neutralization assays also recapitulated the findings of the S-transfected cell adsorption assays (FIG. 2B). Competition with >2 μg/ml soluble RBD (FIG. 9B) reduced immune sera neutralization activity by approximately 50-60% in the S1 protein vaccination group. As seen in the cell adsorption assay, soluble S1 protein removed neutralizing activity of sera from all three vaccine groups, though to a higher degree in the mice immunized only with S1 protein compared to the groups primed with S DNA. Soluble S2 (FIG. 9B) had no impact on serum neutralization capacity and full-length S was not used as a competitor as it could not be expressed in soluble form. Overall, these data indicated that the serum neutralization activity in the protein-only immunization group was directed primarily against the RBD. The S DNA-only or S DNA/S1 protein-induced immune sera were more complex as more than half of the neutralizing activity was directed against S1, but there was residual activity that was not absorbed or competed by S1. It is not conclusively known why S2 did not adsorb or compete with these sera, but it is likely that the conformation of the expressed S2 protein was postfusion as stated above.

DNA and Protein Vaccine Regimens Elicited Antibodies of Different IgG Subclasses.

Figure 5A:
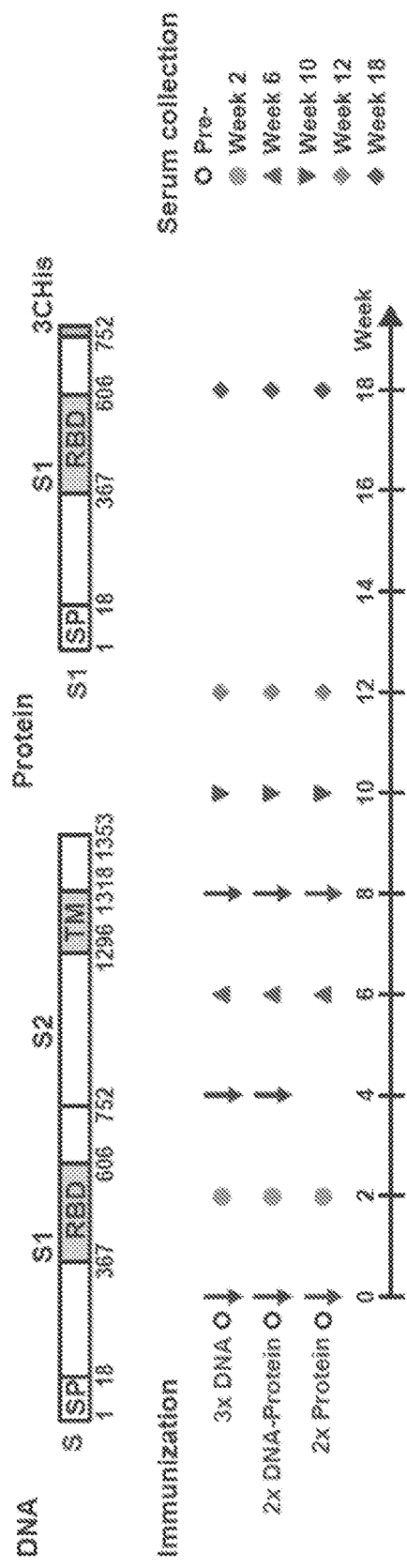
FIGS. 5A-5D illustrate MERS-CoV Spike glycoprotein vaccine design, immunogenicity, and efficacy in non-human primates. Selected candidate vaccine immunogens based on mice studies were evaluated in non-human primates (NHP). (a) Schematic representation of full-length MERS-CoV Spike protein cDNA and recombinant S1 protein. Two vaccine constructs were tested: one DNA and one protein subunit. DNA construct consisted of full-length S that had the transmembrane domain. The protein construct contains a truncated S molecule with the S1 subunit. RBD: receptor binding domain; SP: signal peptide, TM: transmembrane domain; 3CHis: Human rhinovirus 3C protease cleavage site, followed by 6× histidine tag. (b) Immunogenicity of three vaccine regimens. Six NHP per group were immunized intramuscularly with plasmid DNA only, followed by electroporation, at weeks 0, 4 and 8; plasmid DNA and electroporation at weeks 0 and 4; and protein plus aluminum phosphate at week 8 or protein plus aluminum phosphate at weeks 0 and 8. Two weeks after each immunization and at week 12 and week 18, neutralizing antibody titers were measured against pseudotyped MERS-CoV England1 virus. Different symbols indicate sera from 6 NHPs per group that were collected at indicated time points. $IC_{90}$ neutralization titers (GMT with 95% CI) from the sera were determined. Each data point represents the mean of triplicate assays. Assays were repeated once. A non-parametric two-tailed t-test (Mann-Whitney) was used for statistical analysis, and the relevant P values are indicated. (c) MERS-CoV Spike glycoprotein immunogens protect against pulmonary disease in non-human primates (NHPs). Six unimmunized NHPs and 12 NHPs that were immunized with one of two selected candidate vaccine immunogens (1. full-length S DNA prime/S1 subunit protein boost; 2. S1 subunit protein prime/S1 subunit protein boost) were challenged with MERS-CoV 19 weeks after last vaccine boost. Each NHP was intra-tracheally administered $5 \times 10^6$ PFU of the Jordan N3 strain of MERS-CoV (GenBank ID: KC776174.1). The percent abnormal lung volume in all NHPs peaked on day 3 post-challenge; however, the lung infiltrates were significantly more extensive and prolonged in the unvaccinated compared to vaccinated NHPs. A non-parametric two-tailed t-test (Mann-Whitney) was used for statistical analysis. One star (*) represents P values less than 0.05, two stars (**) indicate P values less than 0.01. (d) Abnormal lung segmental images from selected animals on day 6 post challenge are shown. The images correspond to data points circled in black in FIG. 5C. The CT images and abnormal lung segmental images for all 18 animals are shown in FIGS. 18A-18C.
Figure 5B:
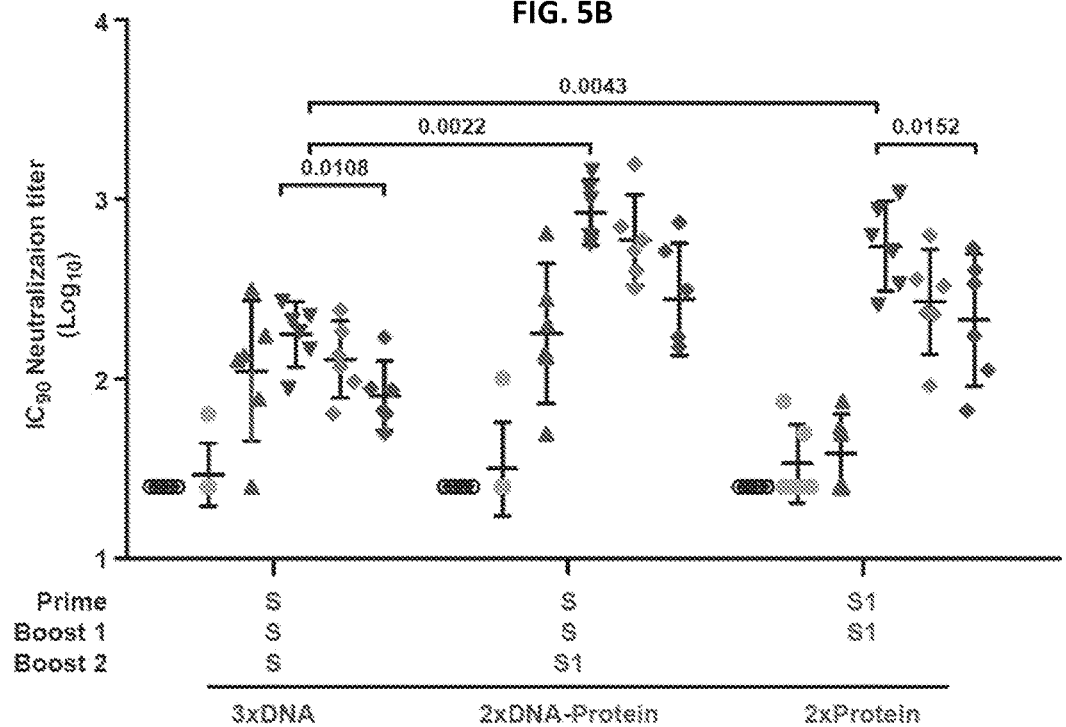

Sera were also analyzed for the quality of the humoral response induced by the different immunization regimens and found to elicit different IgG subclass response patterns (FIGS. 5A and 5B). S DNA immunization induced an IgG2a-dominant response (geometric mean titer (GMT) IgG2a/IgG1 ratio of 6) while S1 protein immunization generated an IgG1-dominant response (GMT IgG2a/IgG1 ratio of 0.06). The IgG subclass response pattern was determined by priming immunization, based on the observation that S DNA prime/S1 protein boost regimen induced a similar pattern and magnitude of IgG2a polarization as the S DNA-only regimen. The IgG2a and IgG1 subclass responses respectively reflect Th1- and Th2-biased immune response patterns in mice (Stevens et al., *Nature* 334, 255, 1988). The IgG2a or Th1-biased response elicited by the DNA-containing regimens is likely due to the induction of IFN-γ producing CD8 T cells that modulate CD4 T cell differentiation (Davis et al., *Human gene therapy* 6, 1447, 1995; Shedlock et al., *J leukocyte biology* 68, 793, 2000).

Surprisingly, monophosphoryl lipid A-based Ribi adjuvant was not sufficient to influence the IgG subclass polarization toward a Th1 phenotype as would be expected (Cargnelutti et al., *The new microbiologica* 36, 145, 2013; Chaitra et al., *Vaccine* 25, 7168, 2007). Thus, compared to priming with a protein, DNA priming generated a T helper response that is generally associated with more effective control of viral infections.

Mouse Monoclonal Antibody Functional Characterization.

Figures 3A, 3B:
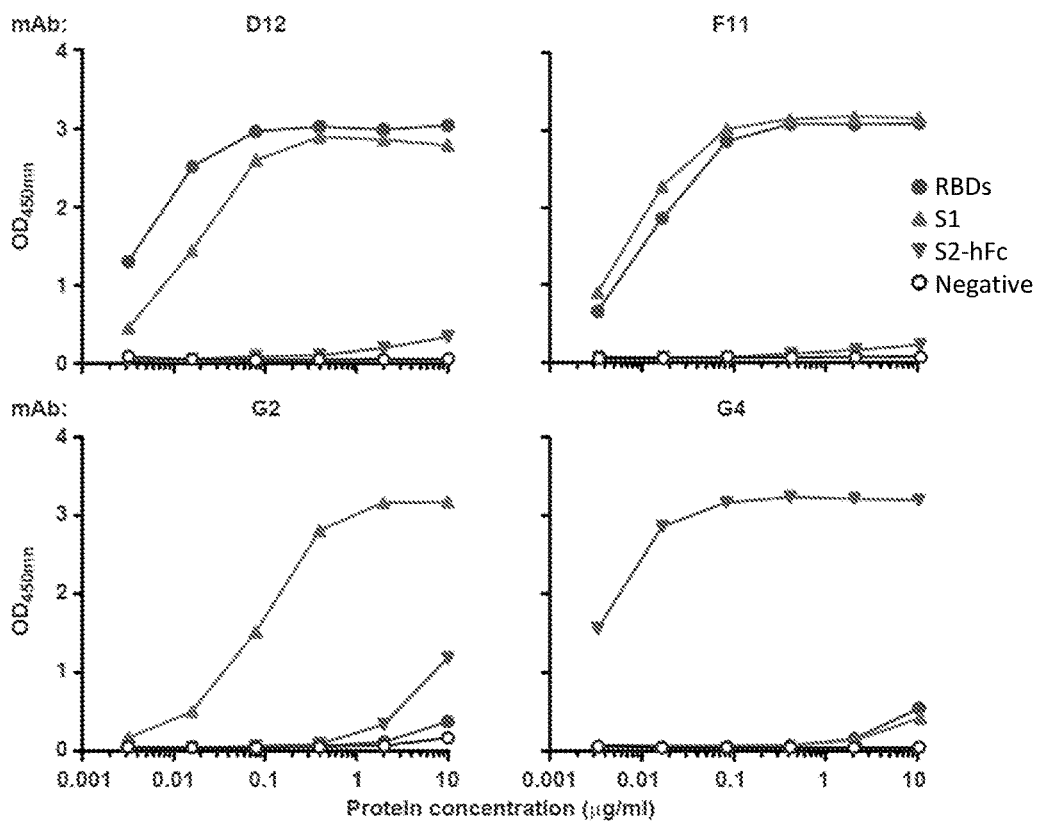
FIGS. 3A and 3B illustrate monoclonal antibody (mAb) binding and neutralization activity. Four mAbs were characterized for their binding specificity and neutralizing activity. (A) Binding specificity. Each of the mAbs was tested, by ELISA, for binding to soluble receptor binding domain (RBD), S1, and S2 conjugated to Fc for stabilization (S2-hFc). (B) Binding affinity and neutralization. Binding affinity and neutralization activity were measured by biolayer interferometry (raw data shown in FIG. 19) and a pseudotyped MERS-CoV (England1) virus neutralization assay, respectively. The mAbs specific for the MERS-CoV RBD—D12 and F11—demonstrated the highest neutralization potency of the four characterized mAbs. G2, which bound S1 outside the RBD, had weaker affinity to S1 than D12 and F11 but near equal neutralization potency. The S2-binding mAb, G4, had a tenfold lower neutralizing potency than the other mAbs.
Figure 12:
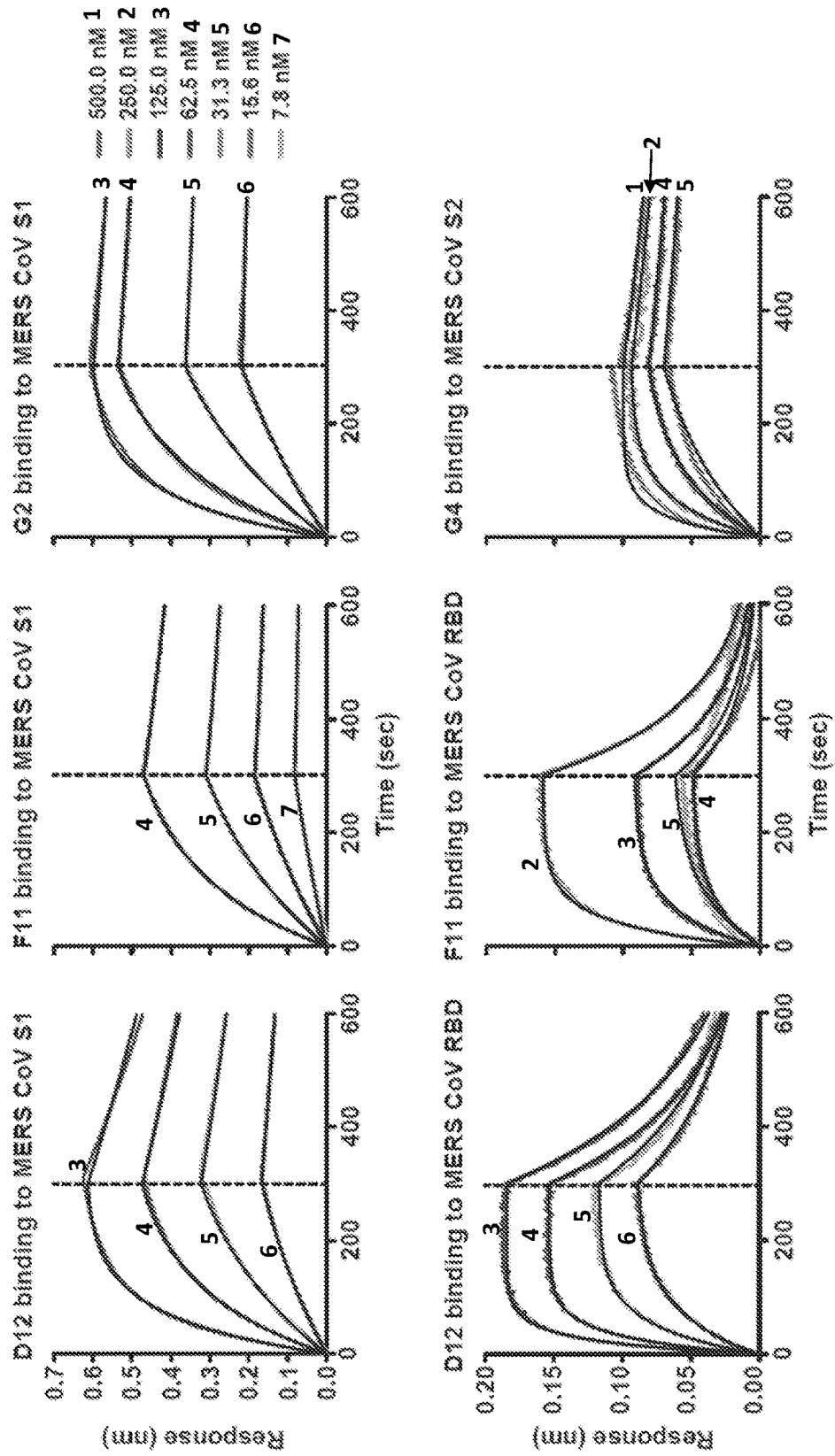
FIG. 12 shows Octet Biosensorgrams of MERS-CoV S1, MERS-CoV RBD, and MERS-CoV S2 molecules binding to vaccine-induced mouse monoclonal IgGs. Mouse monoclonal antibodies were loaded onto AMC probes and association with MERS-CoV antigen was allowed to proceed for 300 s, followed by dissociation for 300 s with the responses measured in nm using an Octet Red 384 machine. The S2 binding to G4 was measured by loading human-Fc-S2 onto AHC probes and measuring association with varying concentrations of G4 Fab. The solid black lines represent the best fit of the kinetic data to a 1:1 binding model. All experiments were carried out at 30° C. in PBS buffer (pH 7.4) supplemented with 1% BSA to minimize non-specific binding. The dotted line indicates the beginning of dissociation and the legend indicates the MERS-CoV antigen and G4 Fab concentrations used.
Figure 13:
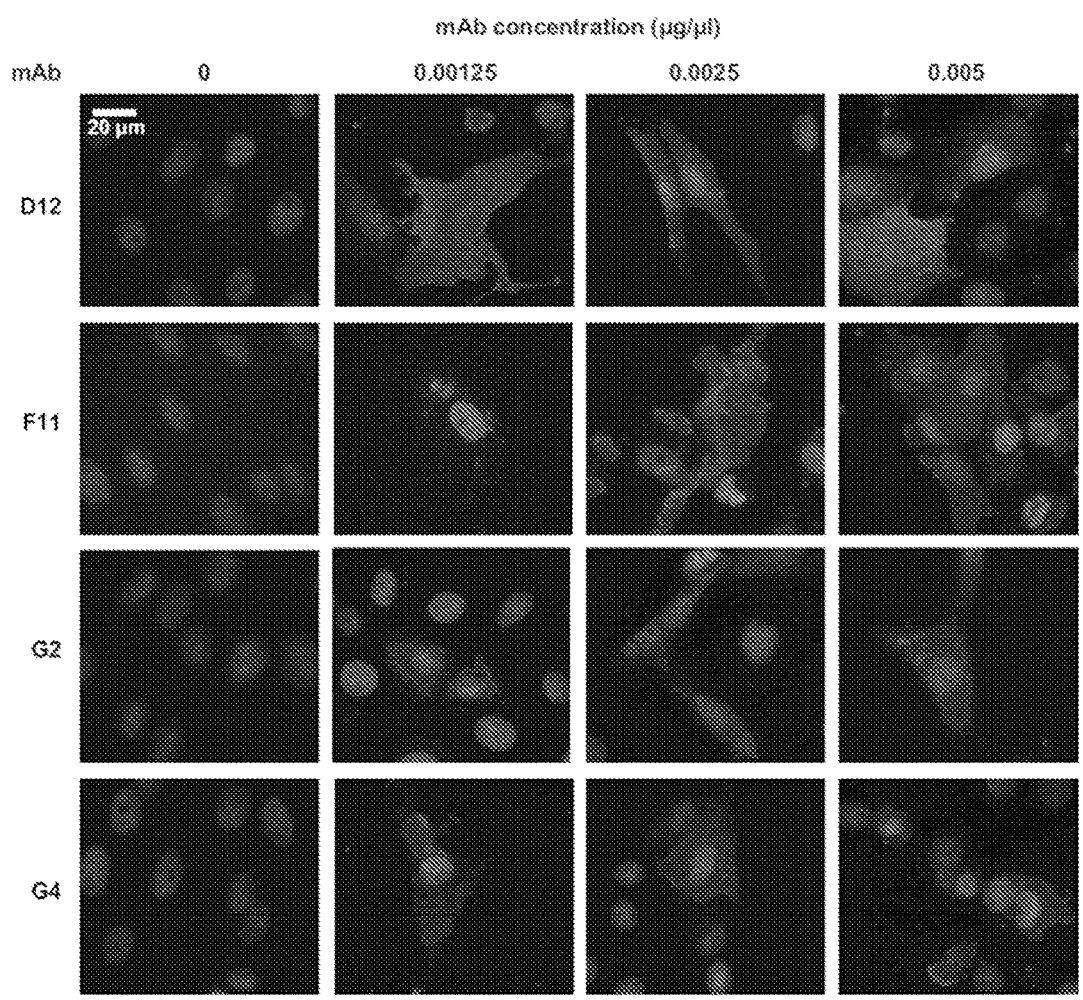
FIG. 13 shows immunofluorescence of monoclonal antibodies (mAb) specific for MERS-CoV infected cells. Red Alexa Fluors 546 signal for isolated mAbs D12, F11, G2 and G4 binding to MERS-CoV (EMC strain)-infected Vero cells was robust for serial mAb dilutions down to 0.00125 µg/µL. Purple regions indicated the nucleus of the Vero cells and 0 µg/ml mAb concentration was used as the control.
Figure 14A:
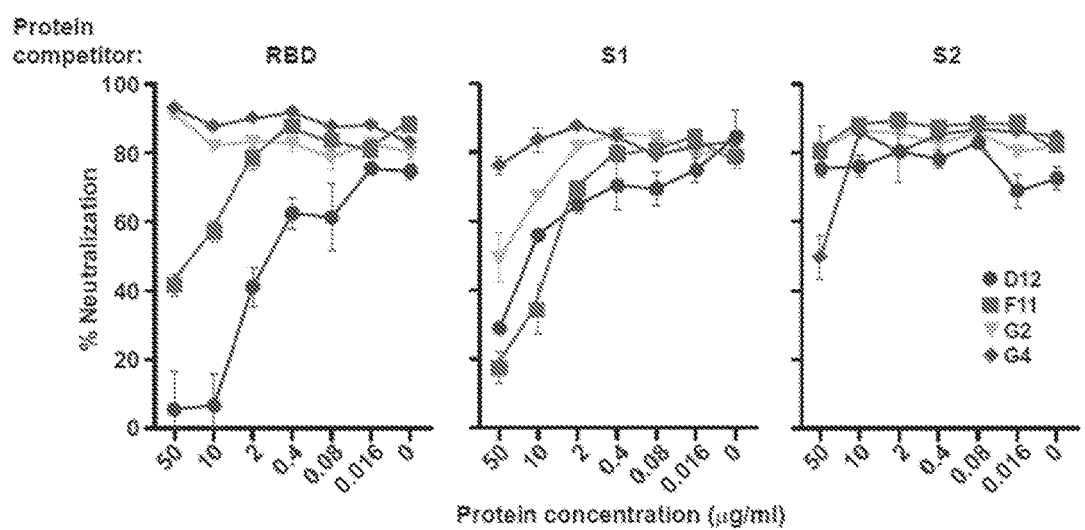
FIGS. 14A-14C show the specificity of the MERS-CoV Spike glycoprotein mAbs. (A) Protein competition neutralization assay. mAbs at a single dilution were assayed for neutralization of MERS-CoV England1 pseudovirus in the presence of soluble MERS-CoV RBD, S1 and S2 proteins at concentrations of 0.016 to 50 µg/ml. (B, C) mAbs were assayed for neutralization to the MERS-CoV or mutant pseudotyped viruses. Data are presented as the mean of triplicates with standard errors. One representative of two repeated experiments is shown.

The humoral response to the S DNA/S1 protein vaccine was further investigated by isolating and characterizing monoclonal antibodies (mAbs) of different specificities. Hybridomas were generated from S DNA-primed and S1 protein-boosted mice and screened for binding to the S1, RBD, and S2 domains. The final round of screens generated 45 subclones (FIG. 11), four of which (D12, F11, G2, G4) were selected for additional characterization based on their binding specificity and neutralization potency (FIGS. 3A-3B and 12). All four mAbs demonstrated, by immunofluorescence, binding to live virus (EMC strain) infected cells (FIG. 13). D12 and H1 bound the S1 subunit within the RBD. mAb G2 was also specific for S1, but it bound outside the RBD. G4 only bound the S2 subunit (FIG. 3A). Although not as potent as the RBD-specific mAbs (FIG. 3B), G2 and G4 were unique as compared to other reported mAbs against MERS-CoV (Du et al., *J virology* 88, 7045, 2014; Ohnuma et al., *J virology* 87, 13892, 2013; Ying et al., *J virology* 88, 7796, 2014; Jiang et al., *Science translational medicine* 6, 234ra59, 2014) in their ability to neutralize virus despite targeting epitopes outside the RBD. Soluble protein competition neutralization results were consistent with those of the binding assays (FIG. 14A). D12 and F11 neutralization were diminished in the presence of RBD and S1, while G2 was competed by S1, and G4 neutralizing activity was only abrogated by high concentrations of S2.

Figure 14B:
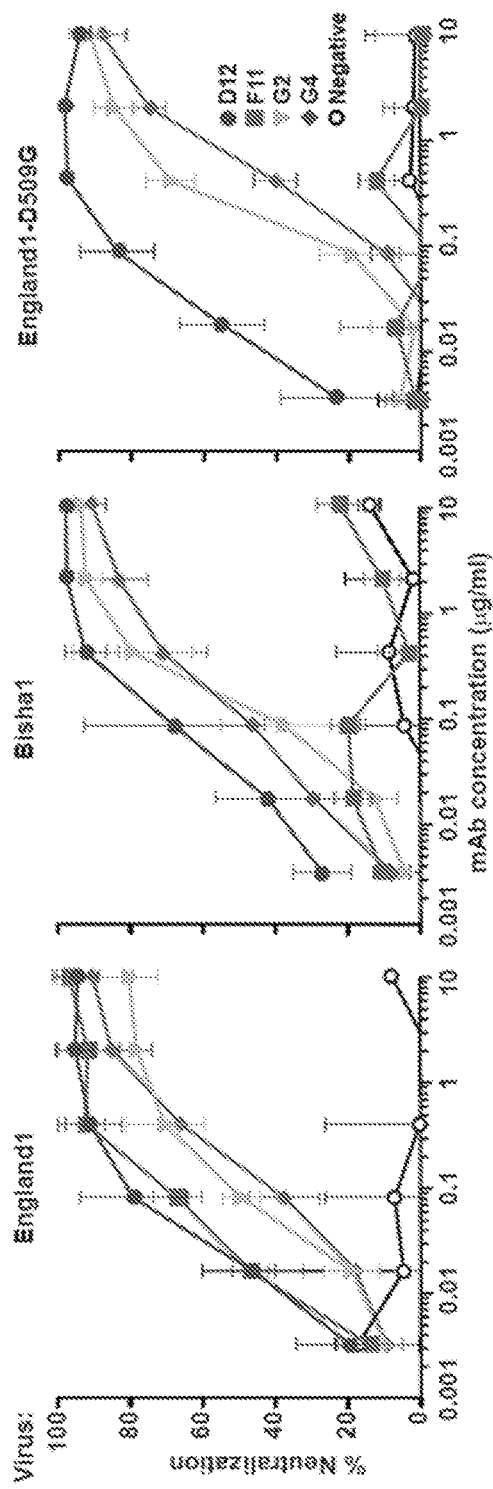

Although the two most potent neutralizing mAbs—D12 and F11—targeted the RBD, their neutralization profiles were different, when mAb neutralization capacity was tested against the panel of eight pseudotyped reporter viruses (FIG. 1C). Notably, F11 was unable to neutralize the Bishal strain (GenBank ID: KF600620.1) of MERS-CoV (FIG. 14B), which differs from other strains by an aspartic acid to glycine substitution at residue 509, rendering it resistant to H1 but susceptible to D12 neutralization. This finding was recapitulated in a pseudotyped virus neutralization assay where H1 neutralization activity against wild-type England1 was ablated with the introduction of a D509G mutation (FIG. 14B). D12, in contrast, neutralized both viruses irrespective of the amino acid change at position 509. In addition, the RBD 509G mutation abrogated F11 binding by ELISA but did not affect D12 binding (FIG. 4E).

Structural and Mutational Analysis of the D12 Antibody in Contact with S RBD.

Figure 7:
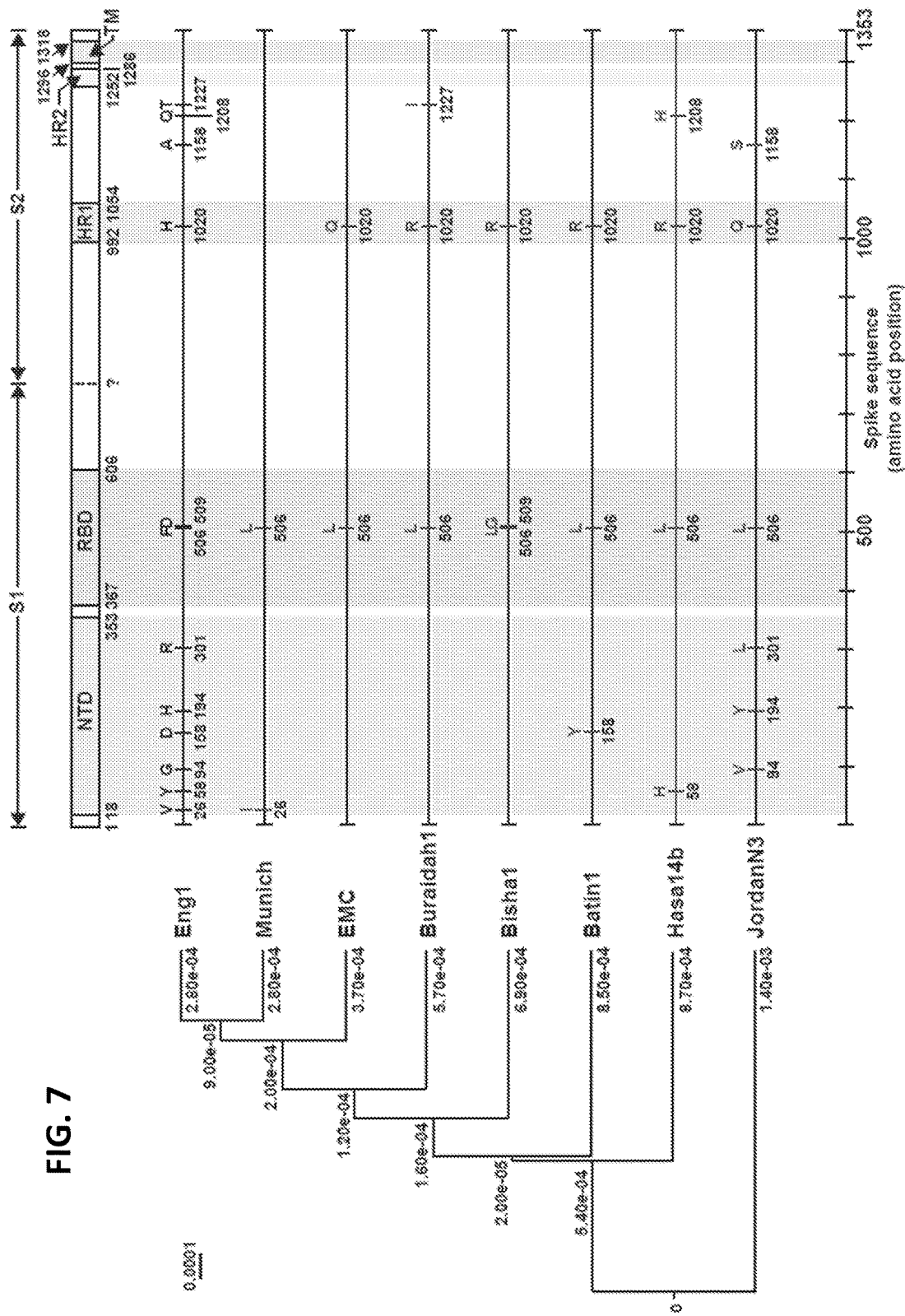
FIG. 7 illustrates a comparison of MERS-CoV Spike (S) glycoprotein sequences across strains used for a pseudotyped virus neutralization assay panel. A schematic representation of MERS-CoV S protein is shown with the N-terminal domain (NTD), receptor binding domain (RBD), heptad repeats 1 and 2 (HR1 and HR2), and transmembrane domain (TM). Eight MERS-CoV S sequences published in GenBank were aligned with the England1 strain. Several amino acid differences are shown with the England1 strain as the referent. Phylogenetic distance between strains is represented by branch length on the phylogenetic tree to the left of the sequences.
Figure 14C:
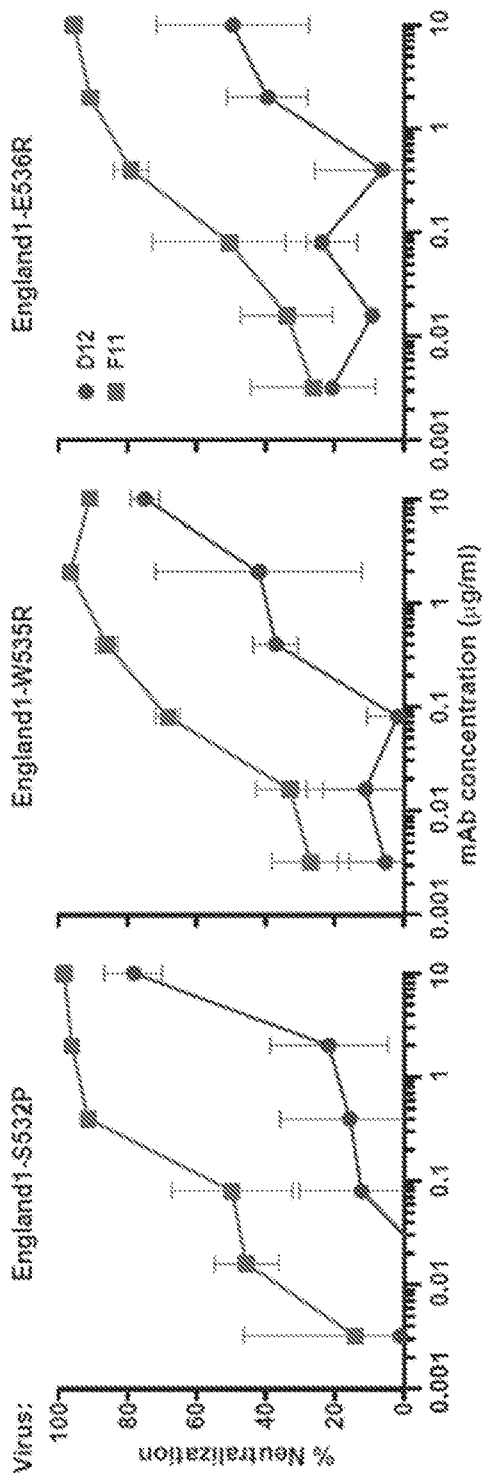

To provide an atomic-level understanding of neutralizing activity, the D12 antibody was crystallized as an antigen-binding fragment (Fab) in complex with the England1 RBD (FIG. 20, FIG. 4A-4B). Additionally, the unbound structure of England 1 RBD was solved (FIG. 4C) and found to be nearly identical to the RBD of the EMC strain (GenBank ID: JX869059.2), either by itself or in complex with DPP4 (Lu et al., *Nature* 500, 227-231, 2013), as it has only one amino acid difference (F506L) in the RBD (FIG. 7). The D12 antibody forms direct contacts with the receptor binding motif (RBM) of the RBD and the heavy chain overlaps with the contact region between MERS RBD and human DPP4 as defined by Lu and colleagues (Lu et al., *Nature* 500, 227-231, 2013). RBD residues W535 and E536, which bind to the conserved glycan on DPP4 are bound by the CDR H2 and CDR H3 within the D12 paratope (FIG. 4C). Mutation of both residues abrogated the ability of D12 to bind (FIG. 4D-4E) and neutralize virus (FIG. 14C). Additional mutational escape analysis demonstrated that another residue within the epitope was critical for D12 neutralization activity. The EMC strain of MERS-CoV escaped neutralization by D12 when the serine at position 532 was mutated to either a proline or tryptophan. The introduction of a proline at position 531 removes two hydrogen bonds to the D12 antibody (FIGS. 4C and 21), while successive prolines at 531 and 532 (proline 532 is native to the RBD) is predicted to alter the side-chain orientation of adjacent residues, likely affecting W535 and E536 interactions with D12. Mutation to a bulky tryptophan side chain likely causes a direct clash with the CDR L3, thus precluding binding of D12 (FIG. 4C-4E). Although it also targets the RBD, F11 neutralizes MERS-CoV by a different mechanism than D12. Site-directed mutagenesis and competition binding studies indicate that F11 makes contact with RBD on the opposing side of D12's binding site, at and around residue 509. Binding studies also show that both D12 and F11 can bind to the RBD at the same time (FIG. 15A-15C), suggesting the potential for additive effects on neutralization. The differing points of contact made by F11 and D12 on the MERS-CoV RBD are analogous to that of other mAbs specific for the SARS-CoV RBD (Prabakaran et al., J Biol Chem 281, 15829, 2006; Zhu et al., *PNAS* 104, 12123, 2007), suggesting convergent mechanisms of neutralization. Furthermore, these data elucidate mechanisms for virus neutralization that involve the disruption of binding between the N-terminal end of the MERS-CoV RBD and its host receptor DPP4.

Full-Length S DNA or S1 Protein Prime and S1 Protein Boost Elicit Potent and Durable Neutralizing Antibody Titers in Non-Human Primates.

Figure 17:
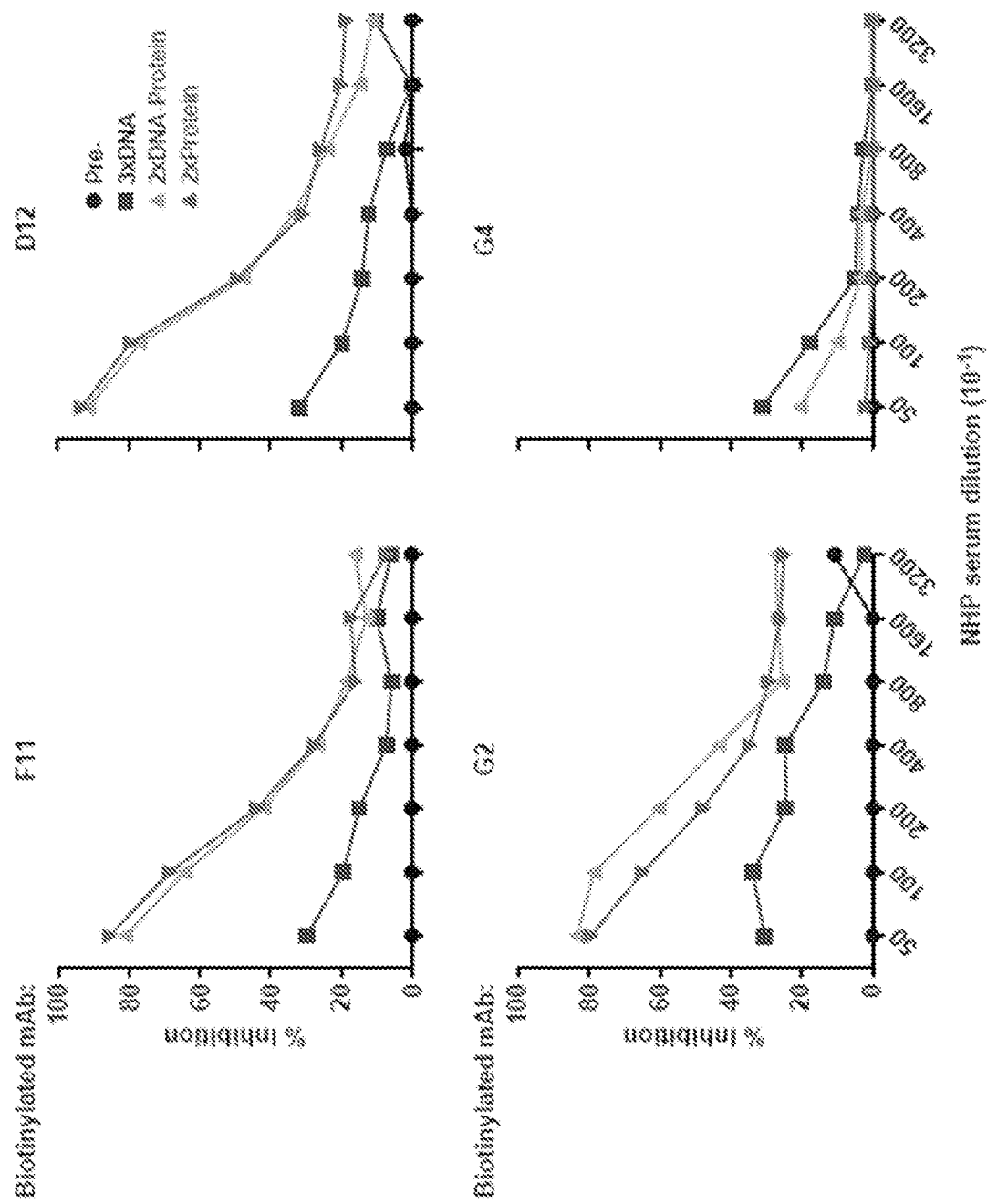
FIG. 17 shows sera from vaccinated non-human primates (NHPs) blocked the binding of murine monoclonal antibodies to MERS-CoV Spike protein. Serial dilutions of mixed NHP sera from three vaccinated groups were tested in competition with biotinylated monoclonal antibodies F11, D12, G2, G4 for binding to MERS-CoV S1 or S-dTM (for mAb G4). Percent inhibition is shown.
Figure 18A:
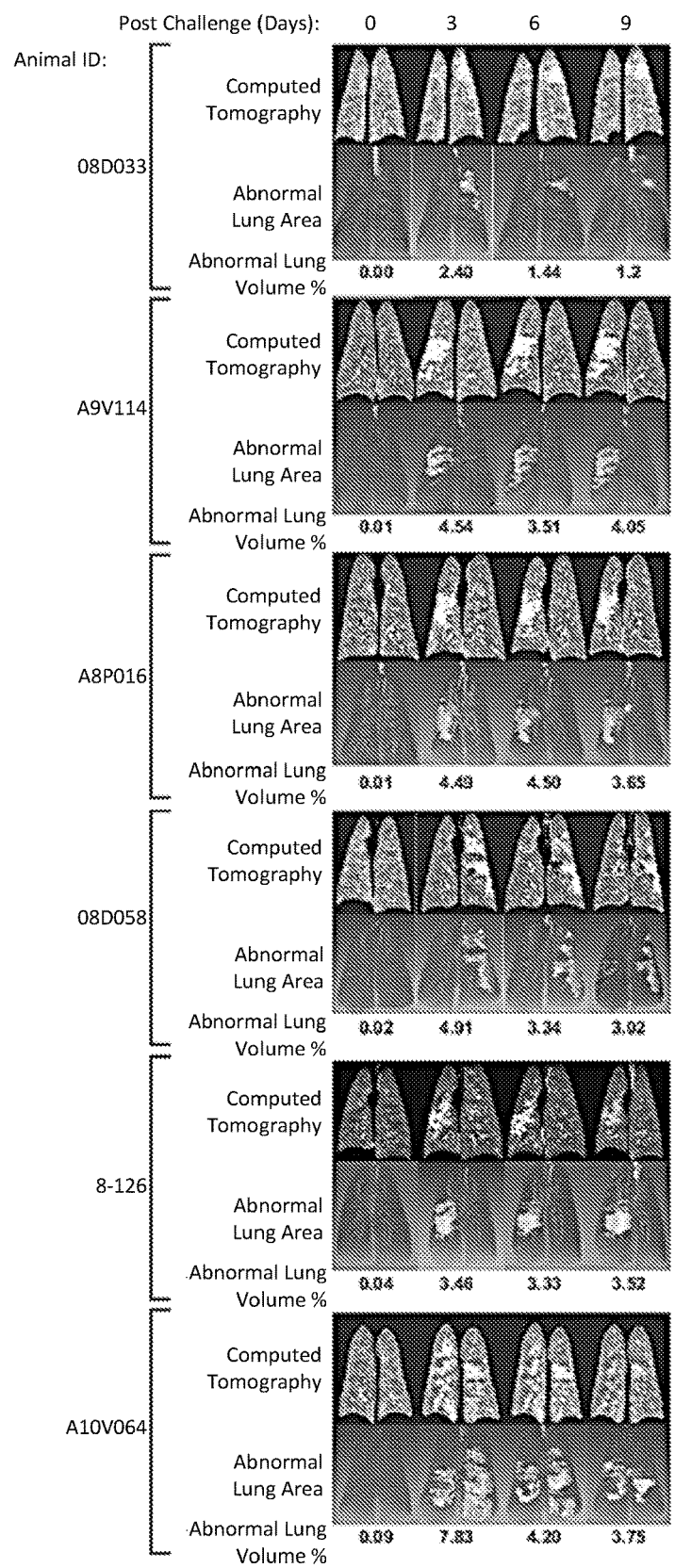
FIGS. 18A-18C show three dimensional computed tomography (CT) visualizations of lungs from non-human primates (NHPs) challenged with MERS-CoV. Unvaccinated NHPs (A) and those vaccinated with S DNA/S1 protein (B) or S1 protein/S1 protein (C) underwent chest CT imaging before virus challenge and days 3, 6, 9, and 14 post-challenge. Two dimensional coronal CT images and three dimensional reconstructions showed larger volumes of percent abnormal lung (infiltrate, consolidation, ground glass opacity) in the unvaccinated compared to vaccinated NHPs.
Figure 18B:
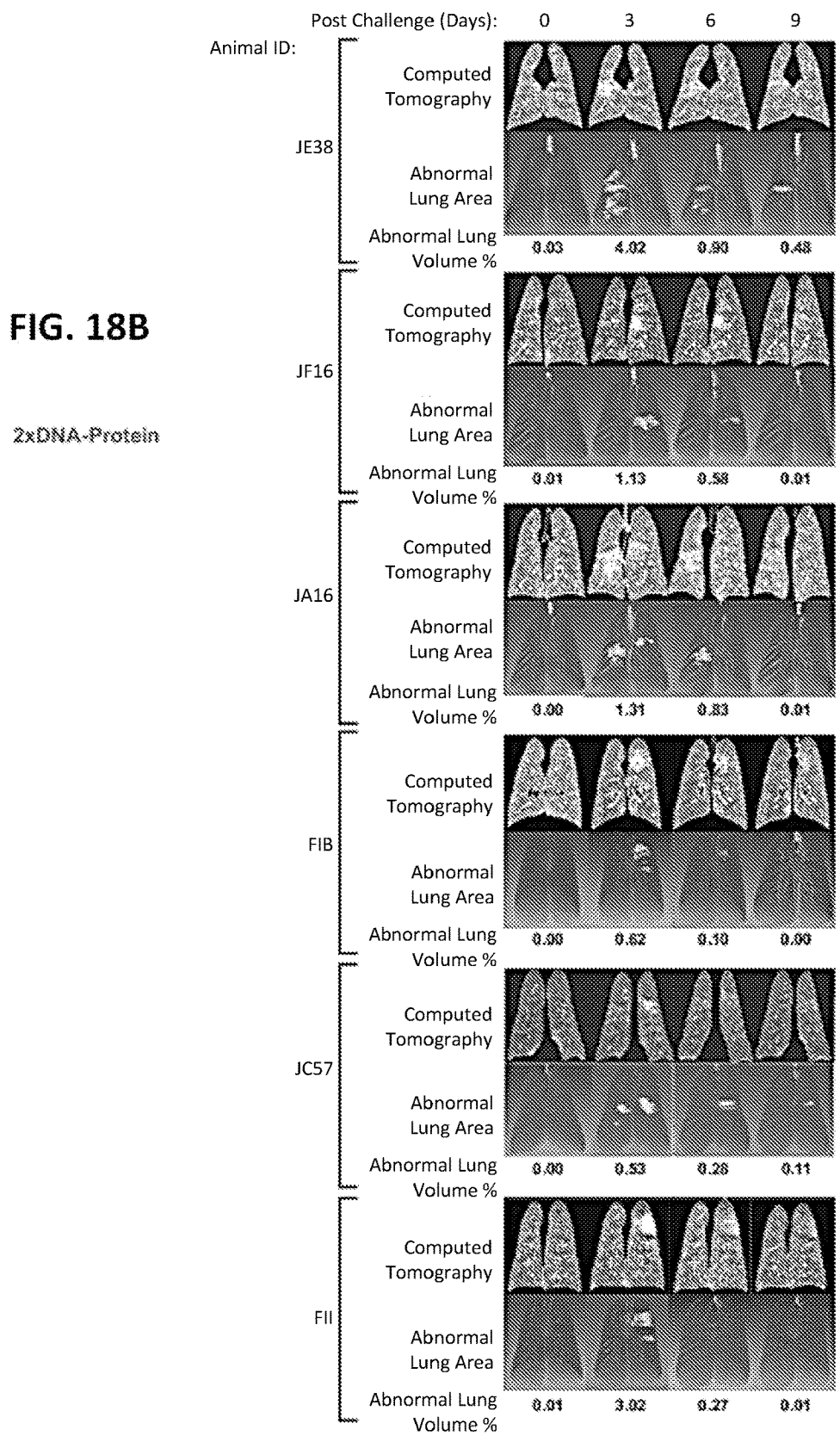
Figure 18C:
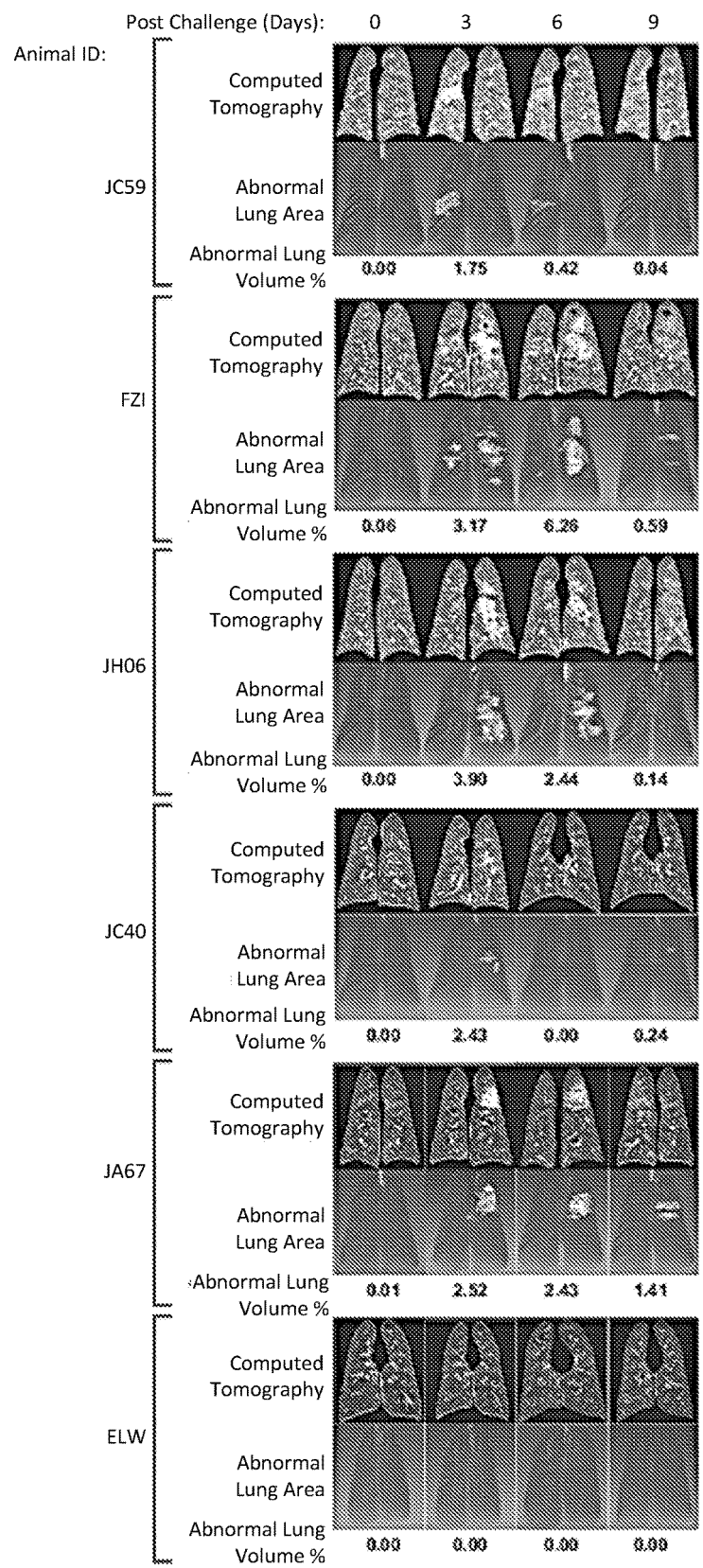

Of the eight vaccine regimens tested in mice, the three most immunogenic were taken forward for evaluation in NHPs (FIG. 5A). Comparable to the mice, NHPs primed with either S1 protein (plus aluminum phosphate adjuvant) or S DNA (followed by electroporation) and boosted with S1 protein (plus aluminum phosphate adjuvant) generated the highest neutralizing antibody titers, as measured by the pseudotyped virus neutralization assay, compared to the S DNA-only group (FIG. 5B). Both groups initially had low antibody titers after priming that increased 10 to 100-fold after boosting. $IC_{90}$ values after the final boost were approximately 1 $\log_{10}$ higher in mice than NHPs, which could be due to the different animal models, vaccine doses or adjuvants used in the two studies. Antibody titers remained high, however, at more than 2.5 $\log_{10}$ at 10-weeks post-boost and persisted at higher levels in the DNA-protein group. A microneutralization assay with the MERS-CoV JordanN3 strain was compared with pseudotyped neutralization assay and demonstrated similar results. Sera from the two groups immunized with S DNA bound all epitopes recognized by the four previously characterized murine antibodies (FIG. 17). Sera from NHPs immunized with S1 protein alone, however, blocked mAbs targeted to the RBD (D12, F11) and non-RBD S1 subunit (G2) but not the S2 subunit (G4).

Full-Length S DNA or S1 Protein Prime and S1 Protein Boost Confer Protection to Non-Human Primates Challenged with MERS-CoV.

Figure 5C:
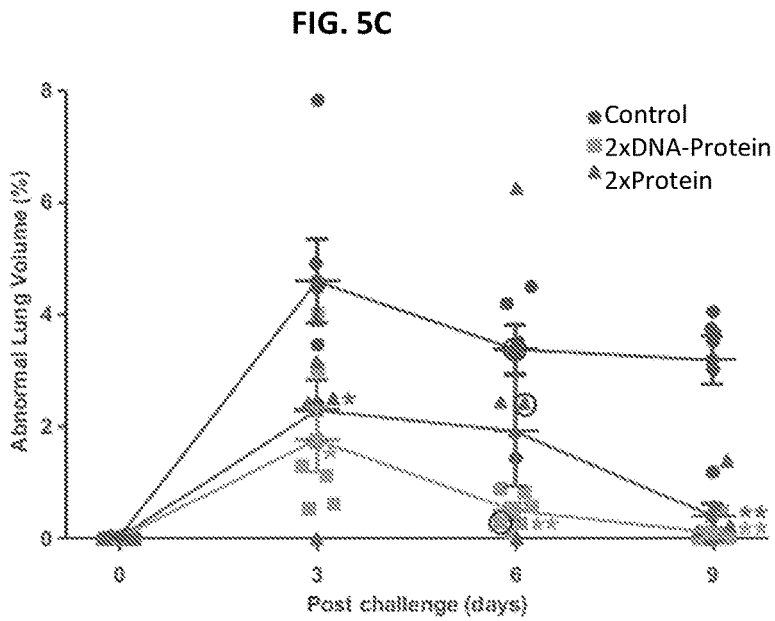
Figure 5D:
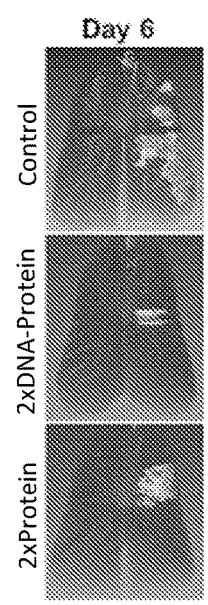
Figure 19A:
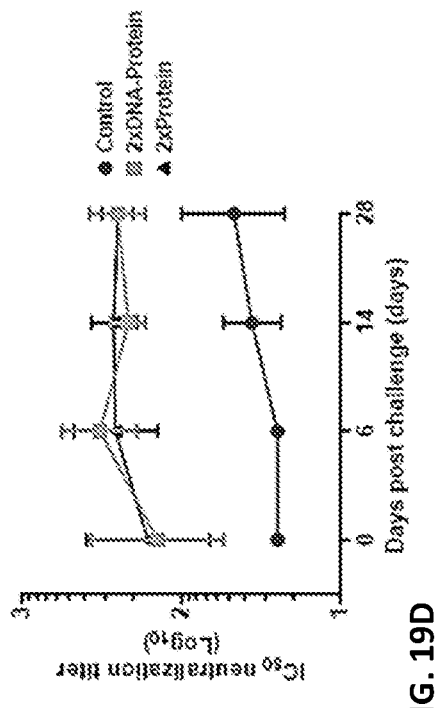
FIGS. 19A-19D illustrate how non-human primate (NHP) anti-MERS-CoV antibody responses increase post-challenge but do not correlate with pulmonary disease. (A) ELISA IgG antibody titers and (B) neutralization titers both rise after challenge with MERS-CoV. There was no significant correlation between neutralization titers of NHP sera at day of challenge (C) or at peak (2 weeks after last boost) (D) and lung disease as measured by percent abnormal lung volume on computed tomography. Graphpad Prism 6 was used to determine the Pearson correlation coefficients and corresponding p values.
Figure 19B:
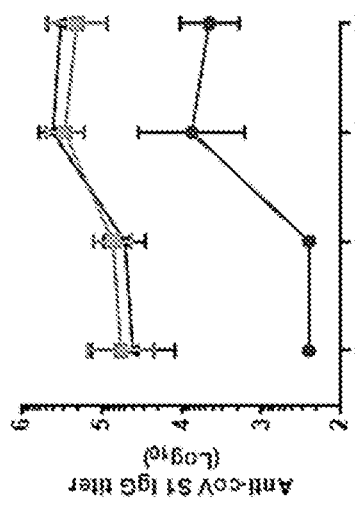
Figure 19C:
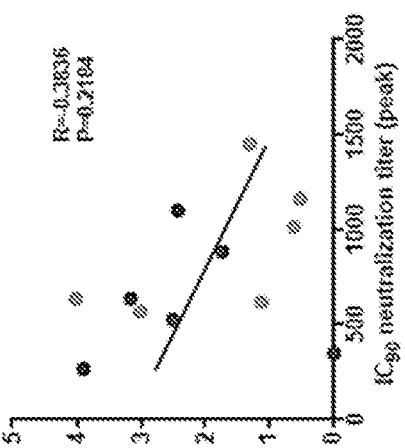
Figure 19D:
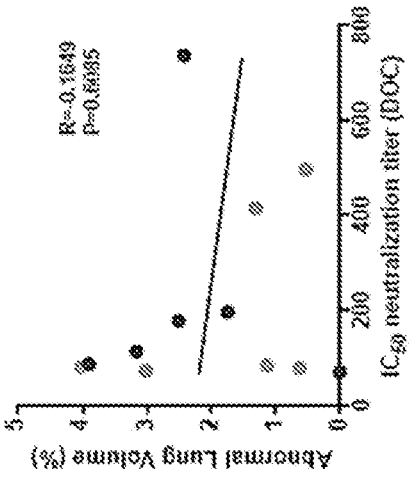

Immunized NHPs were challenged with the JordanN3 strain of MERS-CoV at 19 weeks post-boost and demonstrated earlier and diminished peak lung infiltrates compared to unvaccinated NHPs (FIG. 5C). Immunization with S1/S1 protein or S DNA/S1 protein resulted in a respective four- to six-fold reduction in the peak proportional volume of pulmonary consolidation (FIG. 5C), as demonstrated by high resolution computed tomography (FIG. 5D and FIGS. 18A-18C) and analyzed by a previously described method of lung segmentation (Mansoor et al., *IEEE transactions on medical imaging*, 33, 2293-2310, 2014). NHPs immunized with S DNA/S1 protein experienced a lower peak volume of pulmonary disease than the S1/S1 protein group and cleared the pulmonary infiltrates more rapidly. All three groups exhibited a boost in anti-S1 IgG antibody and virus neutralization titers after challenge. A greater magnitude of rise in titers was observed in the unvaccinated group. Although virus isolates could not be consistently obtained from oral, nasopharyngeal, or tracheal swabs in any of the three challenged groups, anti-S1 IgG and neutralizing antibodies were detected two weeks after challenge in the unvaccinated group and boosted in the vaccinated groups (FIGS. 19A-19B), suggesting viral antigen was produced by infection. No pre- or post-challenge differences between vaccinated and unvaccinated NHPs were observed in clinical symptoms, laboratory values, or histopathology parameters. Additionally, there was no statistically significant correlation between neutralization antibodies either at day of challenge or at peak (two weeks after the last boost) with the percentage of abnormal lung volume (FIGS. 19C-19D).

Discussion

In summary, DNA expression vectors and soluble protein immunogens were developed to elicit cross-reactive neutralizing antibodies against known, circulating strains of MERS-CoV. The induced neutralizing antibodies targeted several regions of the MERS-CoV Spike protein. Immunization with DNA expressing full-length S followed by S1 subunit protein yielded potent neutralizing mAbs in both mice and NHPs. In mice those mAbs were cross-reactive against multiple MERS-CoV strains and directed against the RBD of the S glycoprotein—preventing attachment—and against epitopes outside the RBD in the S1 and S2 subunits. Further, the current immunization strategy is the first to induce MERS-CoV neutralizing antibodies that target multiple epitopes, both within and outside the RBD, which may potentially improve immunogenicity and reduce the likelihood of escape mutations.

Co-crystal structures and analysis of escape mutations provided a mechanistic explanation for neutralization by the RBD-directed neutralizing antibodies. The RBD-specific antibodies we isolated are comparable to others reported in the literature, particularly those isolated from human antibody phage libraries (Tang et al., *PNAS*, 111, E2018-2026, 2014), however D12 and F11 target slightly different epitopes and are approximately a 1000-fold more potent in their neutralization capacities. D12 appears to be highly novel in recognition while F11 does show some epitope overlap with the mAb 3B12 in the T512 loop region but the added sensitivity of 3B12 to mutations at positions 540 and 542 is not seen with F11, thus highlighting the difference in their respective epitopes.

Compared to protein alone, S DNA prime/S1 protein boost immunization yielded a more functionally diverse repertoire of neutralizing antibodies and also generated a Th1-biased immune response. The DNA primed regimen also offered greater and earlier protection in challenged NHPs, suggesting the activation of effector CD8+ T cells. Thus, while a protein-only MERS vaccine may be the simpler approach, there are potential advantages to inclusion of a DNA prime. DNA priming may improve the durability of the immune response (Caulfield et al., *J virology* 76, 10038, 2002) and, through modifications in the boost interval, might improve the magnitude and functional properties of the antibody response as it does for conventional influenza vaccines (Ledgerwood et al., *Lancet infectious diseases* 11, 916, 2011; Ledgerwood et al., *J infectious diseases* 208, 418, 2013); Khurana et al., *J of infectious diseases* 208, 413, 2013)).

The presentation of the S trimer in a native conformation on the surface after DNA immunization may have contributed to the generation of a diverse set of antibodies that could neutralize MERS-CoV by targeting epitopes outside the RBD. In addition to providing a broader array of functional antibody responses, non-RBD antibodies may aid in solving the trimeric S glycoprotein structure by targeting quarternary epitopes and stabilizing the prefusion conformation.

Materials and Methods

Ethics Statement.

Animal experiments were carried out in compliance with all pertinent U.S. National Institutes of Health regulations and policies.

DNA and Protein Vector Constructs.

To evaluate which vaccine candidates and immunization regimens could generate a potent neutralizing antibody response, DNA vaccines of MERS-CoV England1 strain S and two truncated versions, S-ΔTM and S1 were constructed (FIG. 1A). Protein subunit vaccines for S-ΔTM and S1 were also constructed (FIG. 1A). The MERS-CoV S gene (strain England1, GenBank ID: AFY13307) was synthesized according to a previously described method (Yang et al., *J Virol.*, 78, 5642-5650, 2004). Briefly, amino acid sequences were obtained from GenBank™, reverse-translated and codon-optimized for human cell expression. 75-base pair oligonucleotide sets with 25-base pair overlaps were then synthesized and gel purified. Oligonucleotides were assembled into DNA fragments using the Pfu Turbo Hotstart DNA polymerase (Stratagene, La Jolla, Calif.) at a 50° C.-65° C. gradient annealing temperature. DNA fragments were cloned into the pCR-Blunt II-Topo vector (Invitrogen, Carlsbad, Calif.) and sequenced. Fully corrected DNA fragments for each gene were ultimately cloned into the mammalian expression vector VRC8400 (Barouch et al., *J virology* 79, 8828, 2005; Catanzaro et al., *Vaccine* 25, 4085, 2007).

All other truncated versions and domain-swapping mutants were synthesized by PCR, using full length S as the template (FIG. 1A). The PCR fragments were digested with XbaI and BamHI and cloned into the VRC8400. All mutations and fused constructs were confirmed by sequencing. Proteins were expressed in the Expi293 cell line by transfection with expression vectors encoding corresponding genes. The transfected cell culture supernatants were collected and purified through a HisTrap HP column and a Hiload 16/60 Superdex column (GE healthcare, Piscataway N.J.) according to manufacturer's instructions.

In accordance with manufacturer protocols, cDNAs were synthesized encoding S using the QuikChange XL kit (Stratagene, La Jolla, Calif.) and introduced divergent amino acids into the parental S strain (England 1) predicted from the translated sequences of other strains (strain Batin1, GenBank ID KF600628), (strain Bisha1, GenBank ID: KF600620), (strain Buraidah1, GenBank ID: KF600630), (strain EMC, GenBank ID: AFS88936), (strain Hasa14b, GenBank ID: KF600643), (strain JordanN3, GenBank ID: KC776174), (strain Munich, GenBank ID: KF192507). All constructs were confirmed by sequencing.

Cell Lines and Pseudovirus Production.

293, 293T (ATCC) and Huh7.5 cells were cultured in DMEM supplemented with 10% fetal bovine serum, 2 mM glutamine and 1× penicillin/streptomycin in a 37° C. incubator containing 5% $CO_2$. To produce pseudovirus, $15 \times 10^6$ 293 T cells were aliquoted into a 15 cm plate and co-transfected with three plasmids (17.5 µg of packaging plasmid pCMVΔR8.2, 17.5 µg of transducing plasmid pHR' CMV-Luc, and 1 µg of CMV/R-MERS-CoV S plasmid) and calcium phosphate reagent (Invitrogen, Carlsbad Calif.) as described previously (Naldini et al., PNAS 93, 11382, 1996; Yang et al., PNAS 102, 797, 2005). After overnight incubation, media was replaced with fresh 10% FBS-DMEM. 48 hours later, the pseudovirus-containing supernatants were collected, filtered through a 0.45 µm filter, aliquoted, and frozen at −80° C. Pseudovirus was titrated by first plating $1 \times 10^4$ Huh7.5 cells per well in a 96-well white/black Isoplate (PerkinElmer, Waltham, Mass.) and culturing overnight. Media was removed and 2-fold serial dilutions of pseudovirus were added to the cells. After 2 hours of incubation, 100 µl of fresh media was added. Cells were lysed 72 hours later and 50 µl of luciferase substrate (Promega, Madison, Wis.) was added to each well. Luciferase activity was measured according to relative luciferase unit (CPS) by the Microbeta luminescence counter (PerkinElmer, Waltham, Mass.).

Phylogenetic Analysis.

Full-length amino acid sequences of S from MERS-CoV strains England1, Munich, EMC, Buraidah1, Bisha1, Batin1, Hasa14b and Jordan N3 were aligned using MAFFT L-INS-i (version 6.8.6.4, trex.uqam.ca). A phylogenetic tree was generated by the average linkage (UPGMA) method. The phylogenetic tree was drawn on iTOL server (itol.embl.de).

Mouse Immunizations.

Female BALB/cJ mice at age 6-8 weeks (Jackson Laboratory, Bar Harbor, Me.) were immunized according to several different regimens that fall within three categories: (i) 3×S DNA, (ii) 2×S DNA-S1 protein and (iii) 2×S1 protein. Within the first DNA-only category (i) three groups of mice were injected with plasmid DNA encoding either MERS-CoV full-length S (group 1), S with a deleted transmembrane unit (S-ΔTM) (group 2) or S1 (group 3). Injections were given intramuscularly and followed by electroporation with AgilePulse System (Harvard Apparatus, Holliston, Mass.) at weeks 0, 3 and 6. The heterologous regimen DNA-protein groups (ii) were injected twice with plasmid DNA either encoding MERS-CoV full-length S (group 4), S-ΔTM (group 5), or S1 (group 6) at weeks 0 and 3 as described and boosted with either MERS-CoV S-ΔTM (group 5) or S1 (groups 4 and 6) protein plus Ribi adjuvant (Sigma-Aldrich, St. Louis, Mo.) at week 6. The homologous protein groups (iii) were injected twice with MERS-CoV S-ΔTM (group 7) or S1 protein (group 8) plus Ribi adjuvant at weeks 0 and 4.

DNA immunizations were given as bilateral quadriceps muscle injections of 20 µg of plasmid DNA in a total volume of 100 µl of PBS (50 µl each side). Protein immunizations were given as bilateral quadriceps injections of 10 µg of protein in 50 µl PBS mixed with an equal volume of Ribi adjuvant in a total volume of 100 µl (50 µl each side). Two weeks after each injection, sera were collected for measurement of antibody responses.

Non-Human Primate (NHP) Immunizations.

Eighteen (6 female and 12 male) Indian rhesus macaques (Macaca mulatta) weighing 3.2-4.8 kg and with a mean age of 4.4 years were randomly assigned to three groups according to sex and body weight and immunized according to one of three different vaccine regimens: 3×S DNA, 2×S DNA-S1 protein and 2×S1 protein. Sample size was based on convention within the literature. Within the DNA-only group, six NHPs were injected with plasmid DNA encoding MERS-CoV full-length S. Injections were given intramuscularly and followed by electroporation (manufacturer-recommended setting) with AgilePulse System (Harvard Apparatus, Holliston, Mass.) at weeks 0, 4 and 8. Six NHPs in the S DNA-S1 protein group were injected with plasmid DNA encoding MERS-CoV full-length S at weeks 0 and 4 and boosted with MERS-CoV S1 protein and aluminum phosphate adjuvant (Brenntag Biosector, Frederikssund, Denmark) at week 8. Six NHPs in the protein-only group were injected with 100 µg of MERS-CoV S1 protein and aluminum phosphate adjuvant at weeks 0 and 8. DNA immunizations were given as bilateral quadriceps and biceps muscle injections of 1 mg of plasmid DNA in a total volume of 1000 µl of PBS (250 µl each site). Protein immunizations were administered as bilateral quadriceps and biceps injections of 100 µg of protein in 500 µl PBS mixed with an equal volume of aluminum phosphate adjuvant in a total volume of 1000 µl (250 µl each site). Sera were collected for measurement of antibody responses two weeks after each injection and every two-to-four weeks thereafter through week 18.

Non-Human Primate (NHP) Virus Challenge.

Eighteen Indian rhesus macaques—6 unvaccinated, 6 vaccinated with S DNA/S1 protein, 6 vaccinated with S1/S1 protein—were included in a virus challenge experiment with the Jordan N3 strain of MERS-CoV (GenBank ID: KC776174.1) in an approved high containment facility. Due to high intensity of the imaging studies conducted, NHPs were divided into separate challenge cohorts. Prior to challenge, stock virus was diluted to a target concentration of $5\times10^6$ PFU/mL. Approximately 19 weeks following their last vaccine boost, NHPs were inoculated with 1 mL of challenge inoculum by intra-tracheal administration using a laryngoscope and lubricated catheter. Following challenge, virus challenge inoculum was assayed to determine actual delivered dose. Delivered doses were $3.1\times10^6$, $3.6\times10^6$ and $3.4\times10^6$ PFU for Cohorts 1, 2 and 3, respectively. Following virus challenge, all NHPs in each of the three groups were monitored and assessed by clinical, laboratory, and radiologic parameters at days 3, 6, 9, and 14 post-challenge. On day 28 post-challenge all NHPs underwent necropsy.

Non-Human Primate Radiologic Assessment.

Prior to and following virus challenge, NHPs in each of the three groups underwent chest imaging by computed tomography, using the PET/CT Gemini TOF imager (Philips, Andover, Mass.). At the conclusion of data acquisition, images were evaluated and analyzed by two board-certified radiologists. Lung pathology was quantitatively assessed longitudinally using a previously described pulmonary imaging analysis technique (Zhu et al., *PNAS*, 104, 12123-12128, 2007). Briefly, an automated image delineation algorithm was used to determine the lung region of interest (ROI). This procedure was followed by a machine learning algorithm, named "random forest", that assesses the tissue class (i.e., normal or abnormal) of every CT image pixel within the ROI. Once machine the learning algorithm is finalized, the total lung capacity, pathology volume (if present) and their proportion (pathology volume/total lung volume) are calculated as quantitative metrics for describing disease severity. Additionally, we developed a three-dimensional visualization of the lung pathology based on the results of this algorithm. In previous experiments, ground glass opacities (GGO) and consolidations have mostly constituted the abnormal imaging patterns on CT scans. Therefore, the machine-learning algorithm was optimized according to these patterns. Moreover, an additional identification step for airway and vessel recognition was included to minimize false positive findings and increase the efficiency of the computer-aided detection system.

Pseudovirus Neutralization Assay.

Huh7.5 cells (10,000 cells per well) were plated into 96-well white/black Isoplates (PerkinElmer, Waltham, Mass.) the day before infection. Serial dilutions of serum were mixed with different strains of titrated pseudovirus (target CPS of 200,000 in a linear titration range), incubated for 30 minute at room temperature and added to Huh7.5 cells in triplicate. Following 2 hours of incubation, wells were replenished with 100 µl of fresh media. Cells were lysed 72 hours later and 50 µl of luciferase substrate (Promega, Madison, Wis.) was added to each well. Luciferase activity was measured according to relative luciferase unit (CPS) by the Microbeta luminescence counter (PerkinElmer, Waltham, Mass.). $IC_{90}$ neutralization titers were calculated for each individual mouse serum sample.

Microneutralization Assay.

Two-fold dilutions of heat-inactivated, grouped sera were tested in a microneutralization assay for the presence of antibodies that neutralized the infectivity of $100 \times TCID_{50}$ of MERS-CoV JordanN3 strain in Vero cell monolayers, using four wells per dilution in a 96-well plate. Viral cytopathic effect (CPE) was read on days 3 and 4. The dilution of serum that completely prevented CPE in 50% of the wells was calculated by the Reed-Muench formula.

Cell Adsorption and Protein Competition Neutralization Assays.

Mouse sera from mice immunized with 3× full-length S DNA, 2× full-length S DNA+S1 protein, and 2×S1 protein were diluted to concentrations that yielded 90-95% of neutralization activity in Huh7.5 cells (1:400 for 3×DNA and pre-immunization sera, 1:4000 for 2×DNA-protein and 2× protein sera). The diluted sera were then incubated with 293 cells transfected with MERS-CoV S, RBD-HATM, S1-TM, S2-TM for 1 hour at 4° C. on a rocker. After the cells were spun down, supernatants were collected for neutralization assays. To test whether adsorption was complete, residual sera were used to stain against MERS-CoV S, RBD-HATM, S1-TM, S2-TM-transfected 293 cells. Pre-immune sera and untransfected cells were included as negative controls.

The protein competition assay included soluble MERS-CoV S1, RBD and S2 that were diluted and incubated for 1 hour at 37° C. with mouse sera or mAbs diluted to yield a 90-95% neutralization activity. Sera/protein mixtures were then incubated with titrated pseudovirus for 30 minutes at room temperature. The final mixture of protein, serum and pseudovirus was added to 96-well white/black Isoplate (PerkinElmer, Waltham, Mass.) of cells plated the day before. After 2 hours of incubation, 100 μl of fresh media was added to each well. Cells were then lysed 72 hours later and 50 μl of luciferase substrate (Promega, Madison, Wis.) was added to each well. Luciferase activity was measured according to relative luciferase unit (CPS) by the Microbeta luminescence counter (PerkinElmer, Waltham, Mass.).

Cell Surface Binding by FACS.

293 cells were transfected with plasmids expressing MERS-CoV S, RBD-HATM, S1-TM, and S2-TM. 24 hours later, cells were detached with 4 mM EDTA in PBS and stained with Vivid® viability dye (Invitrogen, Carlsbad, Calif.). Cells were then stained with sera (1:200 dilution) from mice immunized with 3× full-length S DNA, with 2× full-length S DNA+S1 protein and 2×S1 protein. Cells were subsequently stained with anti-mouse-PE (Santa Cruz Biotechnology, Santa Cruz, Calif.) and sorted with an LSR (BD Biosciences, San Jose, Calif.). Data were analyzed by FlowJo software (Tree Star, Inc, Ashland, Oreg.).

Competition ELISA.

The detailed methods followed for competition ELISA assays have been published elsewhere (Tomaras et al., *PNAS,* 110, 9019-9024, 2013; Kong et al., *J. Viral.,* 86, 12115-12128, 2012). Briefly, mAbs F11, D12, G2 and G4 were biotinylated with EZ-Link Sulfo-NHS-Biotinylation Kit (Thermo Fisher Scientific, Waltham, Calif.) and titrated on MERS-CoV S1 coated plates. Avidin D HRP conjugate (Vector Laboratories, Burlingame Calif.) and TMB (KPL, Gaithersburg Md.) were used to allow color development. OD450 nm was detected with SpectraMax Plus (Molecular Devices, Sunnyvale Calif.). The concentration of biotin-mAb in the linear range of the titration curve was chosen for competition ELISA. The NHP sera from three vaccinated groups were serially diluted into the biotin-mAb with the designed concentration and added into S1-coated plates. Biotin-mAb alone was used as the binding control. The percent inhibition by the NHP sera was calculated as follows: 100-(NHP sera+biotin-mAb reading)/biotin-mAb reading)×100.

Microscopy.

WHO-Vero cells grown to 60% confluence on 12 millimeter glass coverslips were infected with MERS-CoV (EMC strain) at an MOI of 1 PFU/cell. At 24 hours post-infection, medium was aspirated, and cells were fixed and permeabilized in methanol at −20° C. overnight. Viral studies with MERS-CoV were performed in a BSL-3 laboratory using protocols reviewed and approved by the Institutional Biosafety Committee of Vanderbilt University and the Centers for Disease Control for the safe study and maintenance of MERS-CoV. Cells were rehydrated in PBS for 20 min and blocked in PBS containing 5% bovine serum albumin (BSA). Blocking solution was aspirated, and cells were washed with immunofluorescence (IF) assay wash solution (PBS containing 1% BSA and 0.05% Nonidet P-40) at room temperature. Cells were washed in IF wash solution 3 times for 5 min per wash and incubated in secondary antibodies (Goat α-mouse-AlexaFluors 546 (1:1500), Invitrogen Molecular Probes) for 30 min. Cells were washed 3 times for 5 min per wash, followed by a final wash in PBS, and then rinsed in distilled water. Coverslips were mounted with Aquapolymount (Polysciences) and visualized by immunofluorescence microscopy on a Nikon Eclipse TE-20005 wide field fluorescent microscope. Cells were imaged using a 40× oil-immersion lens through DIC, Cy3, and DAPI filters. Resulting images were merged and assembled using Nikon Elements, ImageJ, and Adobe Photoshop CS2. Infected and mock-infected cells were processed in parallel.

Binding Studies of Vaccine-Induced Mouse Monoclonal Antibodies to MERS-CoV Antigens Using Biolayer Interferometry.

A fortéBio Octet Red384 instrument was used to measure binding kinetics of RBD, S1, and S2 MERS-CoV molecules to the neutralizing antibodies (F11, D12, G2, and G4). All the assays were performed with agitation set to 1,000 rpm in phosphate-buffered saline (PBS) buffer supplemented with 1% bovine serum albumin (BSA) in order to minimize nonspecific interactions. The final volume for all the solutions was 40-50 μl/well. Assays were performed at 30° C. in solid black tilted-bottom 384-well plates (Geiger Bio-One). Mouse antibodies (40-50 μg/ml) in PBS buffer was used to load anti-mouse IgG Fc capture (AMC) probes for 300 s. Typical capture levels were between 1 and 1.5 nm, and variability within a row of eight tips did not exceed 0.1 nm. Biosensor tips were then equilibrated for 180 s in PBS/1% BSA buffer prior to binding assessment of the RBD and S1, MERS-CoV molecules in solution (250 to 7.8 nM) for 300 s; binding was then allowed to dissociate for 300 s. A human-Fc-MERS-CoV S2 chimeric molecule (S2-hFc) was used to load anti-human IgG Fc capture (AHC) probes for 300 s and binding to G4 Fab (X to Y nM) was assessed as described for the other antibodies. Dissociation wells were used only once to prevent contamination. Parallel correction to subtract systematic baseline drift was carried out by subtracting the measurements recorded for a sensor loaded with mouse monoclonal antibodies or hFc-S2 incubated in PBS/1% BSA. Data analysis and curve fitting were carried out using Octet software, version 8.0.

Experimental data were fitted with the binding equations describing a 1:1 interaction. Global analyses of the complete data sets assuming binding was reversible (full dissociation) were carried out using nonlinear least-squares fitting allowing a single set of binding parameters to be obtained simultaneously for all concentrations used in each experiment.

Generation of Hybridomas.

After the third DNA or second protein immunization, immune sera were assessed for S1 binding activity by ELISA and MERS-CoV pseudovirus neutralization capacity. Mice that yielded antisera with good binding activity and high neutralization titers were boosted with an additional 20 µg of S1 delivered intramuscularly. Three days post-boost splenocytes were harvested and fused with Sp2/0 myeloma cells (ATCC, Manassas, Va., USA) using PEG 1450 (50% (w/v), Sigma, St. Louis, Mo., USA) according to the standard methods. Cells were cultured and screened in RPMI complete medium that contained 20% FCS and 1×HAT (100 µM hypoxanthine, 0.4 µM aminopterin, 16 µM thymidine, Sigma). Supernatants from resulting hybridomas were screened for binding, by ELISA, to MERS-CoV S1, RBD, or S-ΔTM as well as for neutralizing activity. Subclones were generated by the limiting dilution methods. After three rounds of screening and subcloning, stable antibody-producing clones were isolated and adapted to hybridoma-serum free medium (Life technologies, Grand Island, N.Y., USA). Supernatants were collected from selected hybridoma clones and purified through a protein A-sepharose column (GE Healthcare, Piscataway, N.J., USA). Generated monoclonal antibodies were isotyped with the Pierce rapid isotyping kit according manufacturer's instructions. The DNA and protein sequences of the G2, G4, D12 and F11 antibodies are provided as SEQ ID NOs: 114-129.

X-Ray Crystallography.

A construct encoding the receptor-binding domain (RBD) of MERS-CoV Eng1 Spike glycoprotein spanning residues 367 to 606 with a c-terminal HRV-3c cleavage site and His6 purification tag was produced in GnTi⁻ cells as previously described for 293 cell expression. Protein was purified by NiNTA affinity chromatography followed by gel filtration using 1×PBS as buffer. Monoclonal antibodies used in crystallization studies were purified using Protein G resin. Fabs were prepared using the Pierce Mouse IgG1 Fab kit following typical protocols. Following purification, RBD England1 was concentrated to ~5 mg/ml for crystallization trials. To prepare RBD England1 Fab complexes for crystallization studies, the RBD molecule was mixed with the Fab in a 1:1.5 molar ratio and allowed to sit for 30 mins at room temperature. The complexes were purified by size exclusion chromatography (Superdex S200; GE Healthcare) and concentrated to ~5-8 mg/ml.

Crystallization screening was carried out using a Mosquito crystallization robot, using the hanging drop vapor diffusion method at 20° C. by mixing 0.1 µl of protein complex with 0.1 µl of reservoir solution. Once initial crystal conditions were observed, further crystallization trials to improve crystal size and shape were carried out by hand using 0.5 µl of protein complex with 0.5 µl of reservoir solution.

Crystals of RBD England1 were obtained using a reservoir solution of 0.1 M Tris-HCl pH 8.5, 10% MPD, 29% PEG 1,500. Crystals were cryogenically cooled in liquid nitrogen using mother liquor containing 20% ethylene glycol as a cryoprotectant. Crystal form 1 of the D12 Fab:RBD England1 complex were obtained using a reservoir solution of 0.1 M sodium acetate pH5.5, 50 mM sodium chloride, 10% PEG 400, 11% PEG 8,000. Crystals were cryo-cooled in liquid nitrogen using mother liquor containing 22% ethylene glycol as a cryoprotectant. Crystal form 2 of D12 Fab:RBD England1 were obtained using a reservoir solution of 0.1 M sodium Cacodylate pH 6.5, 80 mM magnesium acetate, 14.5% PEG 8,000. Crystals were cryo-cooled in liquid nitrogen using mother liquor containing 15% 2R-3R butanediol as a cryoprotectant.

Data for all crystals were collected at a wavelength of 1.00 Å at SER-CAT beamlines ID-22 and BM-22 (Advanced Photon Source, Argonne National Laboratory). All diffraction data were processed with the HKL2000 suite (Otwinowski et al., *Methods Enzymol.* 276, 307, 1997), structures were solved by molecular replacement using PHASER (McCoy et al., *J applied crystallography* 40, 658, 2007), and iterative model building and refinement were performed in COOT (Emsley et al., *Acta crystallographica. Section D, Biological crystallography* 66, 486, 2010) and BUSTER-TNT (Blanc et al., *Acta crystallographica. Section D, Biological crystallography* 60, 2210, 2004), respectively. For the RBD England1 crystals, a molecular replacement solution with two molecules per asymmetric unit was obtained by using the PDB ID 4KR0 (Lu et al., *Nature* 500, 227, 2013) molecule B as a search model. For the two crystal forms of the D12:RBD England1 complex, a molecular replacement solution was obtained using the PDB ID 4KR0 molecule B as a search model for the RBD, PDB ID 1IGM (Fan et al., *J mol biol* 228, 188, 1992) as a search model for the Fab variable domain, and the mouse constant region of the Fab F26G19 PDB ID 3BGF (Pak et al., *J mol biol* 388, 815, 2009) as a search model for the Fab constant domain. In both crystal forms, two RBD-Fab complexes were obtained per asymmetric unit.

During refinement a cross validation (Rfree) test set consisting of 5% of the data was used to assess the model refinement process with structure model validation carried out using MolProbity (Adams et al., *Acta crystallographica. Section D, Biological crystallography* 66, 213, 2010; Chen et al., *Acta crystallographica. Section D, Biological crystallography* 66, 12, 2010). The RBD England1 model was refined to a final Rfactor value of 19.5% and Rfree value of 25% with 99% residues in the favored region of the Ramachandran plot with no outliers. The D12: RBD England1 crystal from 1 gave a structure model with a final Rfactor value of 17.8% and Rfree value of 23.8% with 99% residues in the favored region of the Ramachandran plot with no outliers. The D12: RBD England1 crystal form 2 gave a structure model with a final Rfactor of 22.5% and Rfree value of 26.1% with 99% residues in the favored region of the Ramachandran plot.

MERS-CoV Monoclonal Antibody Escape Mutations.

Cells and viruses. WHO-Vero or Vero81 cells (Vero) were maintained in Dulbecco's modified eagle's medium (Invitrogen) containing 7% FBS, supplemented with penicillin, streptomycin, and amphotericin B. MERS-CoV EMC strain generated from an infectious clone (Scobey et al., *PNAS* 110, 16157, 2013) was propagated and assessed by plaque assay on Vero cells. All incubations of cells and virus were at 37° C. in a 5% $CO_2$ atmosphere. All viral studies were performed in certified BSL3 laboratories and exclusively within biological safety cabinets using protocols for safe study, maintenance, and transfer of that have been reviewed and approved by the Institutional Biosafety Committees of Vanderbilt University.

Plaque Reduction Neutralization Assay.

Starting at a concentration of 10 μg/ml, mAbs were serially diluted 5-fold and mixed with an equal amount of virus a total of six times. Virus-mAb mixtures were incubated at 37° C. for 30 min, then 200 μl of each mixture was used to inoculate Vero cell monolayers in 6-well plates in duplicate. Following 1 h incubation, cells were overlaid with complete media plus 1% agar. Plaques were visualized and counted between 48-52 h post-infection. The amount of infectious virus in the presence of each mAb concentration was calculated and graphed.

Passage for Antibody Escape.

Vero cells were plated in 25-$cm^2$ flasks the day before infection. Immediately prior to infection, media was replaced with 3 ml DMEM containing 3.5% serum. mAb was then added to each flask and cells were infected with MERS-CoV at an MOI of 0.1 PFU/ml. Two days later, mAb was added to new flasks of Vero cells, and 10 μl of the supernatant from the previous infection was added to the new flask. Three separate lineages were carried in parallel. Five passages were completed, with increasing amounts of mAb at each passage. Following the fifth passage, the supernatant was removed, aliquoted and frozen. A small sample of each virus was thawed and titered by plaque assay in the presence and absence of mAb. Ten plaques from each lineage were picked from wells that were titered in the presence of mAb. Each plaque was used to inoculate a 25-$cm^2$ flasks seeded with cells the day before infection. Virus was allowed to replicate for 2 d, then the supernatant was removed, aliquoted and frozen. Cells were lysed using TRIzol reagent (Life Technologies Corp.) according to manufacturer's instructions and the lysates frozen.

Sanger (Dideoxy) Sequence Analysis of the Spike Glycoprotein.

Total cellular RNA was extracted from lysates of mAb-resistant plaque clones using TRIzol reagent. RNA, subjected to RT-PCR with SuperscriptIII (Life Technologies Corp.) and EasyA (Agilent Technologies, Inc.), was set to the following thermal cycling conditions: 50° C.×30 min, 95° C.×5 min, 40 cycles of 95° C.×30 sec, 45° C.×30 sec, 72° C.×1 min and 72° C.×10 min. The MERS-CoV Spike gene was amplified in two amplicons, each about 3 kilobases in length. Each amplicon was sequenced using either 2 or 4 primers, to give complete coverage of the gene. The resulting sequences were assembled and compared with the expected, theoretical sequence for MERS-CoV Spike and differences noted.

Statistical Analysis.

Geometric means (GMT) and 95% confidence intervals (CI) were calculated for all antibody titers. Means and standard errors were calculated for all other data. P values were calculated with a two-tailed, unpaired, nonparametric Mann-Whitney test using Prism software (Version 6.04, GraphPad, La Jolla, Calif.). Statistically significant differences were met a threshold alpha value of 0.05. Statistical variation within each dataset is represented as the standard error in each of the figures. Pearson correlation coefficients and associated p values were calculated using Prism software. Variances were generally similar to justify the use of nonparametric statistical tests.

Example 2

MERS-CoV S Protein Specific Antibodies

The example describes isolation and characterization of MERS-CoV S protein specific antibodies.

Antibody Isolation

Isolation of the G2, G4, D12, and F11 murine antibodies is described above. The DNA and protein sequences of the heavy and light chain variable domains are provided as SEQ ID NOs: 114-129.

The JC57-13, JC57-11, JC57-14, FIB_B2, and FIB_H1 antibodies were isolated from rhesus macaques vaccinated with MERS-CoV 2×DNA-protein (FIG. 5B) using single B cell sorting and IgG heavy and light chain cloning technology as described in detail previously (Wu, et al. Science 2010 DOI: 10.1126/science.1187659). Briefly, MERS-CoV antigen specific B cells were identified by staining with a live/death marker (VIVID) followed by a panel of fluorescently labeled antibodies for CD3, CD4, CD8, CD14, CD20, IgM, IgG and two probes, MERS-CoV RBD and S1 proteins. RBD+ and/or S1+ single B cell was sorted into 96-well PCR plate containing lysis buffer. Reverse transcription (RT) reaction was carried out to produce cDNA followed by 2-round of nested PCR to amplify the IgG heavy and the light chain genes. $2^{nd}$ PCR products were sequenced. PCR products that gave a productive IgH, Igκ or Igλ rearranged sequence were re-amplified from the $1^{st}$ round PCR using custom primers containing unique restriction digest sites and subsequently cloned into the corresponding Igγ1, Igκ or Igλ expression vectors. Monoclonal IgG antibody was expressed by co-transfection of Expi-293 cells with the paired heavy and light plasmids and purified using recombinant protein-A column (GE Healthcare). The protein and nucleic acid sequences of the heavy and light chain variable regions of the JC57-13, JC57-11, JC57-14, FIB_B2, and FIB_H1 antibodies are provided as SEQ ID NOs: 1-12 and S1-58. IMGT CDR sequences are provided in Table 1.

The C2 (CDC_$C_2$), C5 (CDC_$C_5$), A2 (CDC_A2), and A10 (CDC_A10) antibodies were isolated from a human MERS-CoV survivor using single B cell sorting and IgG heavy and light chain cloning technology as described in detail previously (Wu, et al. Science 2010 DOI: 10.1126/science.1187659). Briefly, MERS-CoV antigen specific B cells were identified by staining with a live/death marker (VIVID) followed by a panel of fluorescently labeled antibodies for CD3, CD4, CD8, CD14, CD20, IgG and two probes, MERS-CoV RBD and S1 proteins. RBD+ and/or S1+ single B cell was sorted into 96-well PCR plate containing lysis buffer. Reverse transcription (RT) reaction was carried out to produce cDNA followed by 2-round of nested PCR to amplify the IgG heavy and the light chain genes. $2^{nd}$ PCR products were sequenced. PCR products that gave a productive IgH, Igκ or Igλ rearranged sequence were re-amplified from the $1^{st}$ round PCR using custom primers containing unique restriction digest sites and subsequently cloned into the corresponding Igγ1, Igκ or Igλ expression vectors. Monoclonal IgG antibody was expressed by co-transfection of Expi-293 cells with the paired heavy and light plasmids and purified using recombinant protein-A column (GE Healthcare). The protein and nucleic acid sequences of the heavy and light chain variable regions of the C2, C5, A2, and A10 antibodies are provided as SEQ ID NOs: 35-50. IMGT CDR sequences are provided in Table 1.

Unless indicated otherwise, the heavy and light chain variable regions of the identified antibodies were expressed with human IgG1 constant region (Wu, et al. Science 2010 DOI: 10.1126/science.1187659) for the characterization assays described below.

Antibody Characterization

Figure 22:
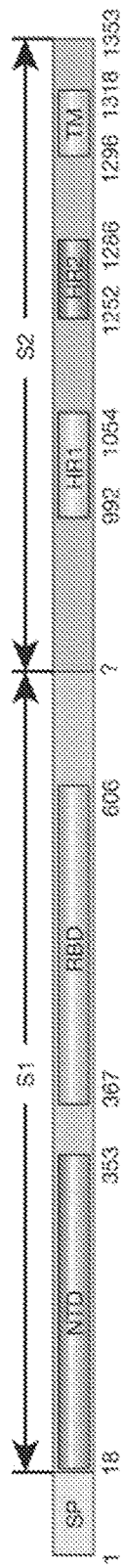
FIG. 22 is a graph and a schematic diagram indicating the structure of MERS-CoV S protein, and the specificity (RBD, S1 (non-RBD), or S2) and source of identified S protein specific antibodies.

Antibody specificity was detected by binding to MERS-CoV RBD, S1, or S2 coated ELISA plates (see FIG. 22). RBD-specific antibodies include F11, D12, JC57-11, JC57-14, C2, and C5. S1-specific antibodies that do not bind to RBD include G2, JC57-13, FIB_B2, and FIB_H1. G4 is an S2 specific antibody.

Antibody neutralization potency was assessed by pseudotyped neutralization assay (FIG. 23) using the MERS-CoV EMC strain. Overall, the RBD-specific mAbs exhibited higher potency than S1 (non-RBD) and S2-specific mAbs. Of the tested antibodies, C2 was the most potent RBD-specific mAb, and G2 was the most potent S1-specific mAb.

Figure 24:
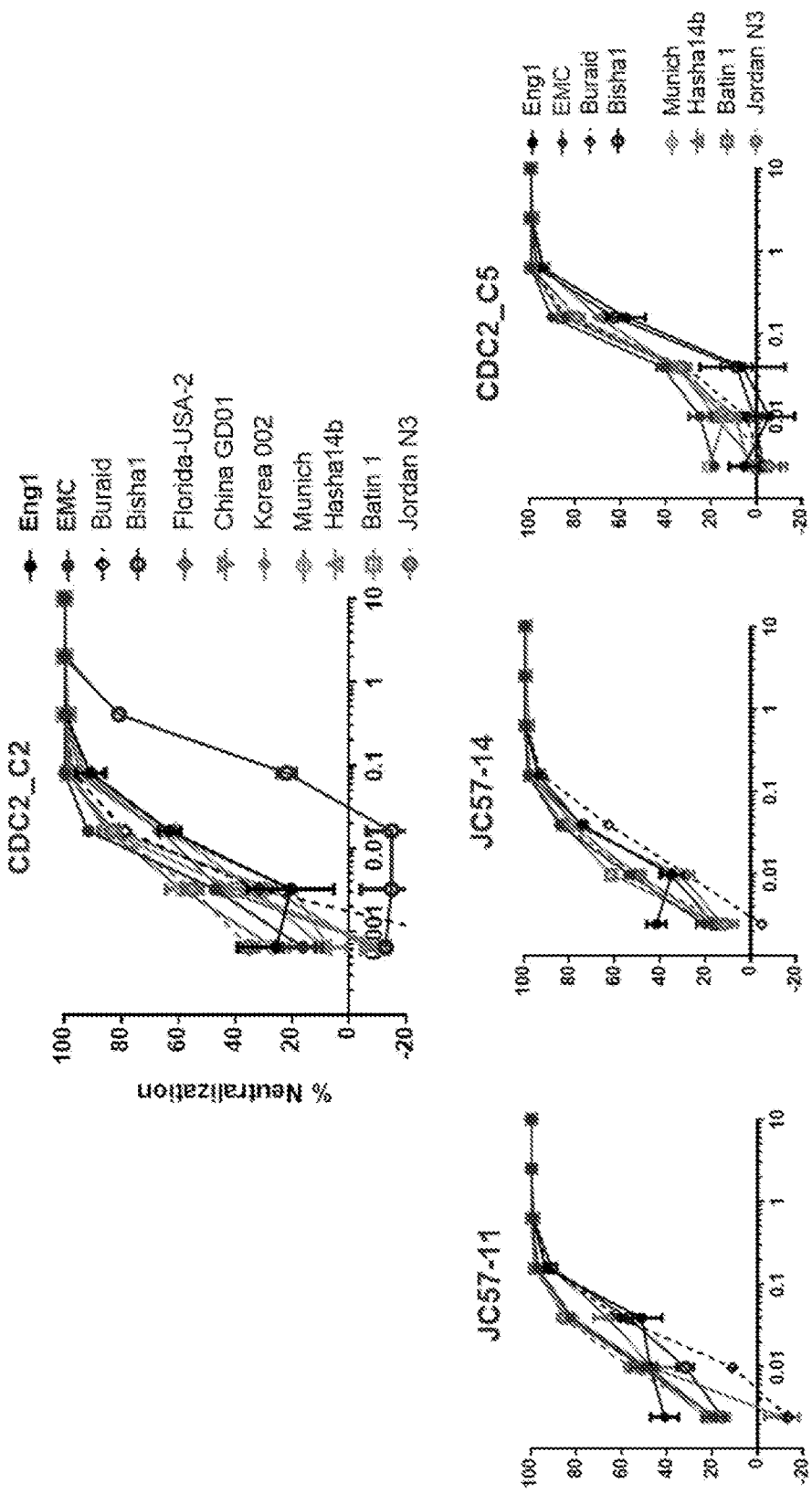
FIG. 24 shows a set of graphs illustrating the neutralization activity of the JC57-11, JC57-14, C2, and C5 antibodies. Neutralization activity was assayed using a pseudovirus neutralization assay for the indicated strains of MRES-CoV.
Figure 25:
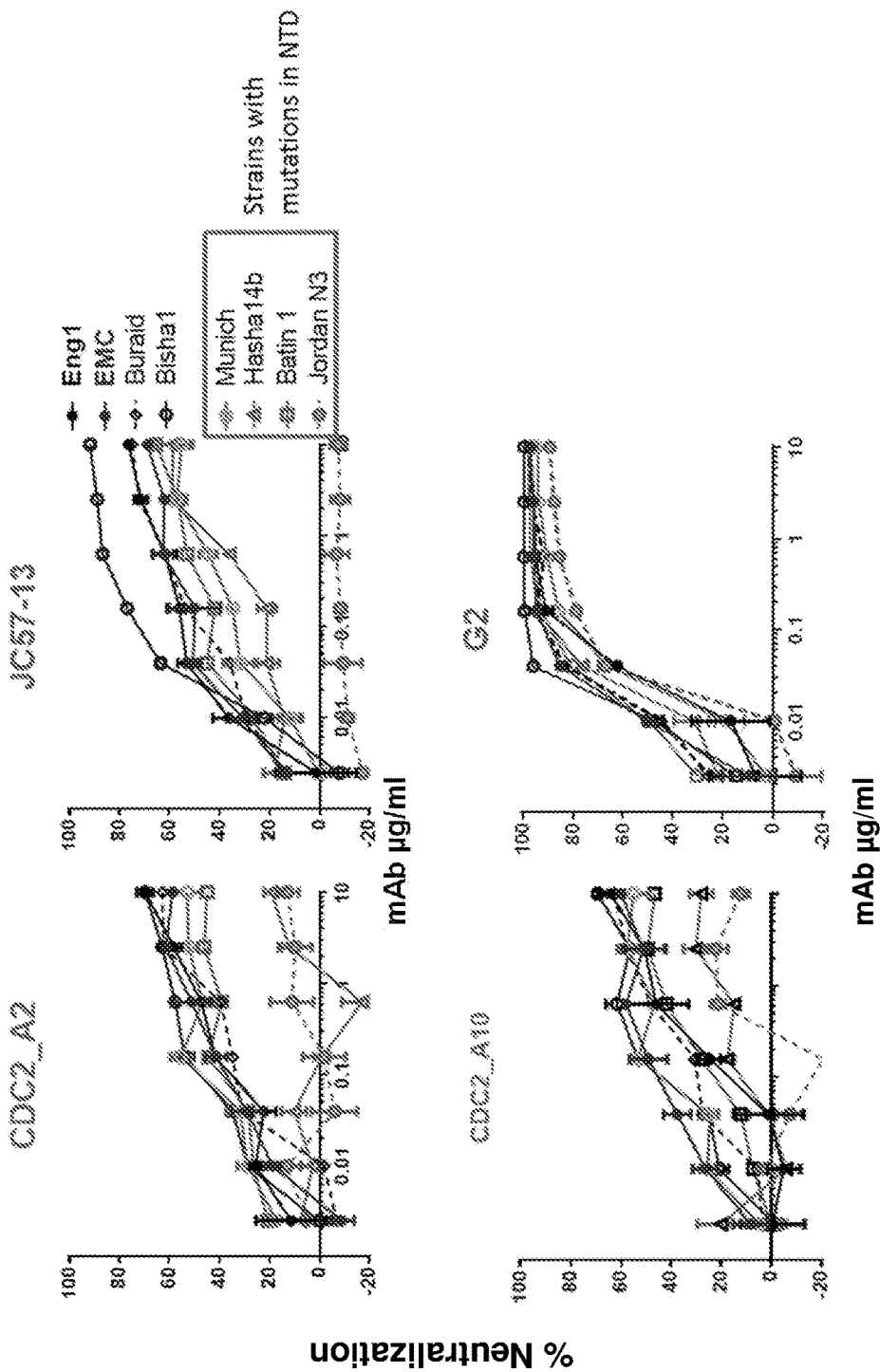
FIG. 25 shows a set of graphs illustrating the neutralization activity of the A2, JC57-13, A10, and G2 antibodies. Neutralization activity was assayed using a pseudovirus neutralization assay for the indicated strains of MRES-CoV.

Antibody neutralization breadth was assessed by pseudotyped neutralization assay. Of the RBD-specific antibodies (FIG. 24), the C2 antibody neutralized 10 MERS-CoV strains with high potency including the most recent strains from Korea and China, but only partially neutralized Bishal (with D509G). The C5, JC57-11, and JC57-14 antibodies cross-neutralized all 8 strains with high potency, but lower than C2. Of the S1 (non-RBD)-specific antibodies (FIG. 25), the G2 antibody neutralized 8 MERS-CoV strains with high potency including strains with mutations in the NTD domain of the MERS-CoV S protein. However, the A2, A10, and JC57-13 antibodies were poor neutralizers of MERS-CoV strains with NTD mutations.

Neutralization assays using the EMC MERS-CoV strain with mutations in the RBD domain were carried out to map the binding site of the RBD-specific antibodies. The EMC S protein was mutated as indicated in the table below, and antibody neutralization was assayed using a pseudovirus neutralization assay as described above. As shown in the table 2, six RBD-specific mAbs can be grouped into three patterns:

1. D12, JC57-14 and C5 are interacting with similar residues, 534, 535, 536 and 539
2. F11 and JC57-11 are different from other mAbs
3. C2 targets a conformation (non-linear) epitope on RBD In the following table, "+" refers to a knock off in neutralization, "+/−" refers to a knock down in neutralization, "E" refers to enhanced neutralization, and an empty cell indicates no change in neutralization.

TABLE 2

|  | L506F | D509G | T512A | S532P | S534A | E535R | E536R | D539R | Y540H | R542G | P547G | N582I |
|---|---|---|---|---|---|---|---|---|---|---|---|---|
| D12 |  |  |  | +/− | +/− | + | + | + |  |  |  |  |
| JC57-14 |  |  |  |  | +/− | + | +/− | +/− |  |  |  |  |
| C5 |  |  |  |  | + | + | + | + |  |  |  |  |
| C2 | +/− | +/− | +/− |  | +/− | +/− | +/− | + | +/− | + |  |  |
| F11 | E | + |  |  | +/− |  | +/− |  | E |  | +/− |  |
| JC57-11 |  |  |  |  |  |  |  | + | +/− | +/− |  |  |

Competition binding assays were performed as described in Example 1 using the identified antibodies to investigate binding patterns. As shown in the Table 3, RBD-specific mAbs and S1 (non-RBD)-specific mAbs do not compete binding to MERS-CoV S1 protein. RBD-specific mAbs can be grouped to 4 patterns: D12, JC57-14, C5; C2; F11; and JC57-11. S1-specific mAbs can be grouped to 2 patterns: G2, JC57-13, and FIB_H1; and A10.

TABLE 3

| Competitor mAb | Biotinylated mAbs | | | | | | | | | | |
|---|---|---|---|---|---|---|---|---|---|---|---|
| (10 µg/ml) | F11 | D12 | JC57-11 | JC57-14 | C2 | C5 | G2 | JC57-13 | FIB_H1 | A2 | A10 |
| F11 | 94.17 | 4.01 | 54.61 | 29.21 | 95.53 | 54.11 | 10.05 | 10.76 | 10.75 | 17.10 | 21.18 |
| D12 | −3.10 | 97.86 | 52.15 | 88.73 | 97.42 | 95.62 | 9.11 | 8.41 | 3.18 | 1.98 | 24.60 |
| JC57-11 | 99.99 | 98.90 | 98.10 | 96.06 | 98.49 | 96.17 | 26.55 | 21.85 | 22.96 | 7.96 | 27.60 |
| JC57-14 | 2.51 | 99.20 | 61.29 | 98.15 | 98.45 | 95.67 | 16.38 | 19.59 | 15.35 | 23.71 | 33.76 |
| C2 | 77.96 | 62.61 | 39.60 | 48.65 | 98.10 | 95.07 | 14.42 | 8.75 | 7.63 | −13.90 | 3.39 |
| C5 | 24.54 | 63.13 | 26.60 | 48.51 | 94.44 | 95.56 | 1.80 | 7.07 | 7.62 | 7.38 | 16.88 |
| G2 | 15.21 | 7.61 | 18.93 | 28.71 | 2.87 | 29.97 | 86.02 | 98.56 | 98.84 | 32.36 | 20.28 |
| JC57-13 | 13.03 | 6.10 | 8.97 | 11.55 | 19.26 | 23.03 | 85.72 | 95.53 | 97.53 | 52.13 | 52.07 |
| FIB_H1 | 18.97 | 8.84 | 7.83 | 16.94 | 20.76 | 22.53 | 82.07 | 96.49 | 95.41 | 8.34 | 46.42 |
| A2 | 9.05 | 2.95 | 7.60 | 9.95 | 7.08 | 39.82 | −1.37 | 6.89 | 9.37 | 1.514 | 3.836 |
| A10 | 11.72 | 5.38 | 5.19 | 5.10 | 1614.55 | 28.80 | 3.74 | 7.72 | 4.02 | 85.70 | 91.29 |

Mutation of C2 to Reduce Deamidation Risk.

An NG motif in the LCDR1 of C2 was mutated to reduce deamidation risk of the C2 antibody. The mutations tested were NG33-34NGS, NG33-34NA, and NG33-34DG. The NG33-34DG mutation decreased neutralization efficiency of the C2 antibody. However, the NG33-34NGS and NG33-34NA mutations did not affect neutralization efficiency (see the Table 4).

TABLE 4

| | | MERS CoV Strain | | | | | | | | | | |
|---|---|---|---|---|---|---|---|---|---|---|---|---|
| mAb | | Eng1 | EMC | JordanN3 | Buraid1 | Bisha1 | Batin | Munich | Hasa14b | China-GD01 | Florida USA-2 | Korea002 |
| C2 | IC50 | 0.0234 | 0.0019 | 0.0017 | 0.0041 | 0.1145 | 0.0037 | 0.0019 | 0.0074 | 0.0035 | 0.0117 | 0.0115 |
|  | IC80 | 0.0569 | 0.0095 | 0.0059 | 0.0161 | 0.3361 | 0.0098 | 0.0071 | 0.0476 | 0.0112 | 0.0375 | 0.0190 |
|  | IC90 | 0.1018 | 0.0162 | 0.0142 | 0.0278 | 0.6116 | 0.0195 | 0.0164 | 0.0770 | 0.0236 | 0.0599 | 0.0217 |
| C2 CDRL1-NS | IC50 | 0.0103 | 0.0035 | 0.0017 | 0.0049 | 0.1503 | 0.0042 | 0.0024 | 0.0073 | 0.0062 | 0.0049 | 0.0098 |
|  | IC80 | 0.0371 | 0.0109 | 0.0122 | 0.0125 | 0.3785 | 0.0111 | 0.0098 | 0.0349 | 0.0152 | 0.0229 | 0.0259 |
|  | IC90 | 0.0665 | 0.0153 | 0.0379 | 0.0249 | 0.6529 | 0.0212 | 0.0225 | 0.0867 | 0.0202 | 0.0624 | 0.0387 |
| C2 CDRL1-NA | IC50 | 0.0470 | 0.0039 | 0.0015 | 0.0015 | 0.3178 | 0.0079 | 0.0018 | 0.0067 | 0.0038 | 0.0083 | 0.0164 |
|  | IC80 | 0.0902 | 0.0105 | 0.0085 | 0.0148 | 0.9897 | 0.0205 | 0.0071 | 0.0356 | 0.0138 | 0.0484 | 0.0464 |
|  | IC90 | 0.1085 | 0.0146 | 0.0282 | 0.0340 | 1.5093 | 0.0268 | 0.0164 | 0.0801 | 0.0216 | 0.1296 | 0.0670 |

A Human Chimeric Antibody Based on the Murine G2 Antibody

A human chimeric antibody including the $V_H$ of the murine G2 antibody and a human IgG1 constant domain was generated by linking the G2 VH to the human IgG1 constant domain. The DNA and protein sequences of the chimeric heavy chain are provided as SEQ ID NOs: 153 and 154. The chimeric $V_H$ includes a KG-TP substitution at the beginning of the constant domain to enhance compatibility of the human heavy chain and the mouse light chain. The G2 mouse-human chimeric mAb (G2-huIgG KG/TP) neutralizes 11 MERS-CoV strains with comparable $IC_{50}$, but slightly lower $IC_{80}$ and $IC_{90}$ to G2, as assayed using a pseudovirus neutralization assay (see the Table 5).

TABLE 5

| | | MERS CoV Strain | | | | | | | | | | |
|---|---|---|---|---|---|---|---|---|---|---|---|---|
| mAb | | Eng1 | EMC | JordanN3 | Buraid1 | Bisha1 | Batin | Munich | Hasa14b | ChinaGD01 | Florida USA-2 | Korea002 |
| Mouse G2 | IC50 | 0.0118 | 0.0126 | 0.0372 | 0.0112 | 0.0119 | 0.0161 | 0.0180 | 0.0247 | 0.0202 | 0.0272 | 0.0144 |
|  | IC80 | 0.0432 | 0.0431 | 0.3636 | 0.0582 | 0.0317 | 0.0904 | 0.1113 | 0.0809 | 0.0592 | 0.0624 | 0.0367 |
|  | IC90 | 0.0950 | 0.1013 | 2.8861 | 0.0903 | 0.0518 | 0.9324 | 0.5930 | 0.1100 | 0.1433 | 0.1059 | 0.0604 |
| hIgG1-G2 KG/TP | IC50 | 0.0140 | 0.0164 | 0.0499 | 0.0029 | 0.0129 | 0.0112 | 0.0457 | 0.1595 | 0.0170 | 0.0268 | 0.0153 |
|  | IC80 |  | 0.0807 |  | 0.0506 | 0.0508 |  |  |  |  | 0.1181 | 0.1025 |
|  | IC90 |  |  |  | 0.1258 | 0.1333 |  |  |  |  |  |  |

It will be apparent that the precise details of the methods or compositions described may be varied or modified without departing from the spirit of the described embodiments. We claim all such modifications and variations that fall within the scope and spirit of the claims below.

We claim:

1. An isolated monoclonal antibody comprising a heavy chain variable region and a light chain variable region, comprising a heavy chain complementarity determining region (HCDR)1, a HCDR2, and a HCDR3, and a light chain complementarity determining region (LCDR)1, a LCDR2, and a LCDR3, of the $V_H$ and $V_L$ set forth as one of:
  (a) SEQ ID NOs: 2 and 4, respectively (JC57-13);
  (b) SEQ ID NOs: 6 and 8, respectively (JC57-11);
  (c) SEQ ID NOs: 10 and 12, respectively (JC57-14);
  (d) SEQ ID NOs: 36 and 38, respectively (C2);
  (e) SEQ ID NOs: 40 and 42, respectively (C5);
  (f) SEQ ID NOs: 44 and 46, respectively (A2);
  (g) SEQ ID NOs: 48 and 50, respectively (A10);
  (h) SEQ ID NOs: 52 and 54, respectively (FIB_B2);
  (i) SEQ ID NOs: 56 and 58, respectively (FIB_H1);
  (j) SEQ ID NOs: 36 and 110, respectively (C2 LCDR1 NG-NS);
  (k) SEQ ID NOs: 36 and 111, respectively (C2 LCDR1 NG-NA);
  (l) SEQ ID NOs: 115 and 117, respectively (G2);
  (m) SEQ ID NOs: 119 and 121, respectively (G4);
  (n) SEQ ID NOs: 123 and 125, respectively (D12); or
  (o) SEQ ID NOs: 127 and 129, respectively (F11); and wherein the monoclonal antibody specifically binds to MERS-CoV S protein.

2. The isolated monoclonal antibody of claim 1, wherein the HCDR1, the HCDR2, the HCDR3, the LCDR1, the LCDR2, and the LCDR3 comprise the amino acids sequences set forth as
- (a) SEQ ID NOs: 59, 60, 61, 62, 63, and 64, respectively (JC57-13);
- (b) SEQ ID NOs: 65, 66, 67, 68, 69, and 70, respectively (JC57-11);
- (c) SEQ ID NOs: 71, 72, 73, 74, 75, and 76, respectively (JC57-14);
- (d) SEQ ID NOs: 77, 78, 79, 80, 81, and 82, respectively (C2);
- (e) SEQ ID NOs: 83, 84, 85, 86, 87, and 88, respectively (C5);
- (f) SEQ ID NOs: 89, 90, 91, 92, 93, and 94, respectively (A2);
- (g) SEQ ID NOs: 95, 78, 96, 86, 97, and 98, respectively (A10);
- (h) SEQ ID NOs: 59, 99, 100, 101, 102, and 103, respectively (FIB_B2);
- (i) SEQ ID NOs: 104, 105, 106, 107, 108, and 109, respectively (FIB_H1);
- (j) SEQ ID NOs: 77, 78, 79, 112, 81, and 82, respectively (C2 LCDR1 NG-NS);
- (k) SEQ ID NOs: 77, 78, 79, 113, 81, and 82, respectively (C2 LCDR1 NG-NA);
- (l) SEQ ID NOs: 130, 131, 132, 133, 134, and 135, respectively (G2);
- (m) SEQ ID NOs: 136, 137, 138, 139, 140, and 141, respectively (G4)
- (n) SEQ ID NOs: 142, 143, 144, 74, 145, and 146, respectively (D12); or
- (o) SEQ ID NOs: 147, 148, 149, 150, 151, and 152, respectively (F11).

3. The isolated monoclonal antibody of claim 1, wherein the $V_H$ and the $V_L$ comprise the amino acid sequences set forth as:
- (a) SEQ ID NOs: 2 and 4, respectively (JC57-13);
- (b) SEQ ID NOs: 6 and 8, respectively (JC57-11);
- (c) SEQ ID NOs: 10 and 12, respectively (JC57-14);
- (d) SEQ ID NOs: 36 and 38, respectively (C2);
- (e) SEQ ID NOs: 40 and 42, respectively (C5);
- (f) SEQ ID NOs: 44 and 46, respectively (A2);
- (g) SEQ ID NOs: 48 and 50, respectively (A10);
- (h) SEQ ID NOs: 52 and 54, respectively (FIB_B2);
- (i) SEQ ID NOs: 56 and 58, respectively (FIB_H1);
- (j) SEQ ID NOs: 36 and 110, respectively (C2 LCDR1 NG-NS);
- (k) SEQ ID NOs: 36 and 111, respectively (C2 LCDR1 NG-NA);
- (l) SEQ ID NOs: 115 and 117, respectively (G2);
- (m) SEQ ID NOs: 119 and 121, respectively (G4);
- (n) SEQ ID NOs: 123 and 125, respectively (D12); or
- (o) SEQ ID NOs: 127 and 129, respectively (F11).

4. The isolated monoclonal antibody of claim 1, comprising a human framework region.

5. The isolated monoclonal antibody of claim 1, wherein the antibody is a humanized antibody comprising a human constant domain.

6. The isolated monoclonal antibody of claim 5, wherein the heavy chain of the antibody comprises the amino acid sequence set forth as SEQ ID NO: 154.

7. The isolated monoclonal antibody of claim 1, wherein the antibody is an IgG.

8. The isolated monoclonal antibody of claim 1, comprising a recombinant constant domain comprising a modification that increases the half-life of the antibody, particularly wherein the modification increases binding to the neonatal Fc receptor.

9. The isolated monoclonal antibody of claim 8, wherein the recombinant constant domain is an $IgG_1$ constant domain comprising M428L and N434S mutations.

10. An antigen binding fragment of the isolated monoclonal antibody of claim 1.

11. The antigen binding fragment of claim 10, wherein the antigen binding fragment is a Fv, Fab, F(ab')$_2$, scFV or a scFV$_2$ fragment.

12. The isolated monoclonal antibody of claim 1, conjugated to an effector molecule or a detectable marker.

13. A pharmaceutical composition for use in treating or preventing a MERS-CoV infection, comprising an effective amount of the antibody of claim 1, or an antigen binding fragment thereof, a nucleic acid molecule encoding the antibody or antigen binding fragment, or a vector comprising the nucleic acid molecule; and
a pharmaceutically acceptable carrier.

14. The pharmaceutical composition of claim 13, wherein the composition is sterile.

15. The pharmaceutical composition of claim 13, wherein the composition is in unit dosage form or a multiple thereof.

16. The pharmaceutical composition of claim 13, comprising:
a first isolated monoclonal antibody comprising a heavy chain variable region and a light chain variable region, comprising a HCDR1, a HCDR2, and a HCDR3, and a LCDR1, a LCDR2, and a LCDR3, of the $V_H$ and $V_L$ set forth as SEQ ID NOs: 36 and 38, respectively (C2), wherein the monoclonal antibody specifically binds to MERS-CoV S protein; and
a second isolated monoclonal antibody comprising a heavy chain variable region and a light chain variable region, comprising a HCDR1, a HCDR2, and a HCDR3, and a LCDR1, a LCDR2, and a LCDR3, of the $V_H$ and $V_L$ set forth as SEQ ID NOs: 115 and 117, respectively (G2), wherein the monoclonal antibody specifically binds to MERS-CoV S protein.

17. The pharmaceutical composition of claim 16, wherein:
the HCDR1, the HCDR2, the HCDR3, the LCDR1, the LCDR2, and the LCDR3 of the first isolated monoclonal antibody comprise the amino acids sequences set forth as SEQ ID NOs: 77, 78, 79, 80, 81, and 82, respectively; and
the HCDR1, the HCDR2, the HCDR3, the LCDR1, the LCDR2, and the LCDR3 of the second isolated monoclonal antibody comprise the amino acids sequences set forth as SEQ ID NOs: 130, 131, 132, 133, 134, and 135, respectively.

18. The pharmaceutical composition of claim 16, wherein:
the $V_H$ and the $V_L$ of the first isolated monoclonal antibody comprise the amino acid sequences set forth as SEQ ID NOs: 36 and 38, respectively (C2); and
the $V_H$ and the $V_L$ of the second isolated monoclonal antibody comprise the amino acid sequences set forth as SEQ ID NOs: 115 and 117, respectively (G2).

19. The pharmaceutical composition of claim 16, wherein:
the heavy chain of the second isolated monoclonal antibody comprises an amino acid sequence set forth as SEQ ID NO: 154.

20. A method of detecting the presence of a MERS-CoV in a biological sample, comprising:
- contacting the biological sample with an effective amount of the antibody of claim 1 or an antigen binding fragment thereof under conditions sufficient to form an immune complex; and
- detecting the presence of the immune complex on the biological sample, wherein the presence of the immune complex on the biological sample indicates the presence of the MERS-CoV in the sample.

21. The method of claim 20, wherein detecting the detecting the presence of the immune complex on the biological sample indicates that the subject has a MERS-CoV infection.

22. A method of treating or inhibiting a MERS-CoV infection in a subject, comprising:
- selecting a subject with or at risk of a MERS-CoV infection; and
- administering to the subject a therapeutically effective amount of the antibody of claim 1 or an antigen binding fragment thereof, or a pharmaceutical composition comprising the antibody of claim 1 or an antigen binding fragment thereof.

23. A kit for detecting MERS-CoV in a sample, detecting MERS-CoV infection in a subject, the kit comprising:
- a container comprising the antibody of claim 1, an antigen binding fragment of the antibody, a nucleic acid molecule encoding the antibody or antigen binding fragment, a vector comprising the nucleic acid molecule, or a pharmaceutical composition comprising the antibody, antigen binding fragment, nucleic acid molecule or vector, and instructions for using the kit.

* * * * *

SEQUENCE LISTING

<160> NUMBER OF SEQ ID NOS: 155

<210> SEQ ID NO 1
<211> LENGTH: 363
<212> TYPE: DNA
<213> ORGANISM: macaca mulatta

<400> SEQUENCE: 1
caggtgcagc tgcaggagtc gggcccagga ctggtgaagc cttcggagac cctgtccctc    60
acctgcgccg tctctggtgg ctccatcagc agtaactact ggaactggat ccgccagtcc   120

```
ccagggaagg ggctagagtg gattgggtat atctatggtg gtagtgggag caccacctac      180
aacccctccc tcaagagtcg agtcgccatt tcaacagaca cgtccaagga ccagttttcc      240
ctgaagctga gctctgtgac cgccgcggac accgccgtat attactgtgc gagactgctg      300
cccttagggg ggggatactg ctttgactac tggggccagg gagtcctggt caccgtctcc      360
tca                                                                    363
```

```
<210> SEQ ID NO 2
<211> LENGTH: 121
<212> TYPE: PRT
<213> ORGANISM: macaca mulatta

<400> SEQUENCE: 2

Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Ser Asn
            20                  25                  30

Tyr Trp Asn Trp Ile Arg Gln Ser Pro Gly Lys Gly Leu Glu Trp Ile
        35                  40                  45

Gly Tyr Ile Tyr Gly Gly Ser Gly Ser Thr Thr Tyr Asn Pro Ser Leu
    50                  55                  60

Lys Ser Arg Val Ala Ile Ser Thr Asp Thr Ser Lys Asp Gln Phe Ser
65                  70                  75                  80

Leu Lys Leu Ser Ser Val Thr Ala Ala Asp Thr Ala Val Tyr Tyr Cys
                85                  90                  95

Ala Arg Leu Leu Pro Leu Gly Gly Gly Tyr Cys Phe Asp Tyr Trp Gly
            100                 105                 110

Gln Gly Val Leu Val Thr Val Ser Ser
        115                 120
```

```
<210> SEQ ID NO 3
<211> LENGTH: 339
<212> TYPE: DNA
<213> ORGANISM: macaca mulatta

<400> SEQUENCE: 3
gatattgtga tgacccagac tccattcacc ctgcccgtca cccctggaga ggcggcctcc       60
atctcctgca ggtctagtca gagcctcttc gatagtgatt atggaaacac ctatttggat      120
tggtatctgc agaagccagg ccagtctcca cagctcctga tctatatgct ttccaaccgg      180
gcctctggag tccctgatag gttcagtggc agtgggtcag gcactgattt cacactgaaa      240
atcagccggg tggaggctga ggatgttggg ttatattact gcatgcaaag tgtagagtat      300
ccattcactt tcggccccgg gaccaaactg gatatcaaa                             339
```

```
<210> SEQ ID NO 4
<211> LENGTH: 113
<212> TYPE: PRT
<213> ORGANISM: macaca mulatta

<400> SEQUENCE: 4

Asp Ile Val Met Thr Gln Thr Pro Phe Thr Leu Pro Val Thr Pro Gly
1               5                   10                  15

Glu Ala Ala Ser Ile Ser Cys Arg Ser Ser Gln Ser Leu Phe Asp Ser
            20                  25                  30

Asp Tyr Gly Asn Thr Tyr Leu Asp Trp Tyr Leu Gln Lys Pro Gly Gln
        35                  40                  45
```

Ser Pro Gln Leu Leu Ile Tyr Met Leu Ser Asn Arg Ala Ser Gly Val
                50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Leu Tyr Tyr Cys Met Gln
                 85                  90                  95

Ser Val Glu Tyr Pro Phe Thr Phe Gly Pro Gly Thr Lys Leu Asp Ile
                100                 105                 110

Lys

<210> SEQ ID NO 5
<211> LENGTH: 393
<212> TYPE: DNA
<213> ORGANISM: macaca mulatta

<400> SEQUENCE: 5
gaggtgcagc tgctggagtc gggcccagga gtggtgaggc cttcggagac cctgtccctc    60
tcctgcgctg tctctggtgg ctccatcagc gatagttacc ggtggagctg gatccgccag   120
cccccaggga agggactgga gtgggttggc tacatctttg ctactggtac gaccaccaac   180
tacaacccct ccctcaagag tcgagtcacc atttcaaaag acacgtccaa gaaccagttc   240
tccttgaagc tgagctctgt gaccgccgcg gacacggccg tttactactg tgcgagagag   300
ccgttcaaat attgtagtgg tggtgtctgc tatgcccaca aggacaactc attggatgtc   360
tggggccagg gagttctggt caccgtctcc tca                                393

<210> SEQ ID NO 6
<211> LENGTH: 131
<212> TYPE: PRT
<213> ORGANISM: macaca mulatta

<400> SEQUENCE: 6

Glu Val Gln Leu Leu Glu Ser Gly Pro Gly Val Val Arg Pro Ser Glu
 1               5                  10                  15

Thr Leu Ser Leu Ser Cys Ala Val Ser Gly Gly Ser Ile Ser Asp Ser
                20                  25                  30

Tyr Arg Trp Ser Trp Ile Arg Gln Pro Pro Gly Lys Gly Leu Glu Trp
                35                  40                  45

Val Gly Tyr Ile Phe Ala Thr Gly Thr Thr Thr Asn Tyr Asn Pro Ser
                50                  55                  60

Leu Lys Ser Arg Val Thr Ile Ser Lys Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Glu Pro Phe Lys Tyr Cys Ser Gly Gly Val Cys Tyr Ala
                100                 105                 110

His Lys Asp Asn Ser Leu Asp Val Trp Gly Gln Gly Val Leu Val Thr
                115                 120                 125

Val Ser Ser
    130

<210> SEQ ID NO 7
<211> LENGTH: 318
<212> TYPE: DNA
<213> ORGANISM: macaca mulatta

<400> SEQUENCE: 7

```
gaaattgtga tgacgcagtc tccagccacc ctgtctttgt ctccagggga aagagccact      60
ctctcctgca gggccagtca gagtgttagt agcaacttag cctggtacca gcagaaacct     120
gggcaggctc ccaggctcct catccacagt gcgtccagca gggccactgg catcccagac     180
aggttcagtg gcagcgggtc tgggacagag ttcagtctca ccatcagcag tctggaggct     240
gaagatgttg gagtttatca ctgctatcag catagcagcg gtacactttt cggccccggg     300
accaaactgg atatcaaa                                                   318

<210> SEQ ID NO 8
<211> LENGTH: 106
<212> TYPE: PRT
<213> ORGANISM: macaca mulatta

<400> SEQUENCE: 8

Glu Ile Val Met Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

His Ser Ala Ser Ser Arg Ala Thr Gly Ile Pro Asp Arg Phe Ser Gly
     50                  55                  60

Ser Gly Ser Gly Thr Glu Phe Ser Leu Thr Ile Ser Ser Leu Glu Ala
 65                  70                  75                  80

Glu Asp Val Gly Val Tyr His Cys Tyr Gln His Ser Ser Gly Tyr Thr
                 85                  90                  95

Phe Gly Pro Gly Thr Lys Leu Asp Ile Lys
            100                 105

<210> SEQ ID NO 9
<211> LENGTH: 351
<212> TYPE: DNA
<213> ORGANISM: macaca mulatta

<400> SEQUENCE: 9
gaggtgcagc tgcaggagtc gggcccagga ctggtgaagc cttcggagac cctgtccctc      60
acctgcgctg tctctggtga ctccatcagc agtaactact ggagctggat ccgccagccc     120
ccagggaagg gactggagtg gattggacgt ttctctggta gtggtgggag caccgacttc     180
aacccctccc tcaagagtcg ggtcaccatt tcaacagaca cgtccaagaa ccagttctcc     240
ctgaacctga ggtctgtgac cgccgcggac acggccgtgt attactgtgc gaaaacctat     300 agcggcaccct ttgactactg gggccaggga gtcctggtca ccgtctcctc a             351

<210> SEQ ID NO 10
<211> LENGTH: 117
<212> TYPE: PRT
<213> ORGANISM: macaca mulatta

<400> SEQUENCE: 10

Gln Val Gln Leu Gln Glu Ser Gly Pro Gly Leu Val Lys Pro Ser Glu
  1               5                  10                  15

Thr Leu Ser Leu Thr Cys Ala Val Ser Gly Asp Ser Ile Ser Ser Asn
             20                  25                  30

Tyr Trp Ser Trp Ile Arg Gln Pro Pro Gly Lys Gly Leu Glu Trp Ile
         35                  40                  45

Gly Arg Phe Ser Gly Ser Gly Gly Ser Thr Asp Phe Asn Pro Ser Leu
```

```
    50                  55                  60

Lys Ser Arg Val Thr Ile Ser Thr Asp Thr Ser Lys Asn Gln Phe Ser
65                  70                  75                  80

Leu Asn Leu Arg Ser Val Thr Ala Ala Asp Thr Ala Val Tyr Tyr Cys
                85                  90                  95

Ala Lys Thr Tyr Ser Gly Thr Phe Asp Tyr Trp Gly Gln Gly Val Leu
            100                 105                 110

Val Thr Val Ser Ser
        115

<210> SEQ ID NO 11
<211> LENGTH: 321
<212> TYPE: DNA
<213> ORGANISM: macaca mulatta

<400> SEQUENCE: 11
gacattcaga tgacgcagtc tccatcctcc ctgtctgcat ctgtaggaga cagagtcacc     60
atcacttgcc gggcgagtca ggacattaac aattatttaa gttggtatca gcagaaacca    120
gggaaagccc ctaagcccct gatctattat gcatccagtt tggaaacagg agtaccttca    180
aggttcagtg gaagtagatc tgggacagat tacactctca ccatcagcag tctgcagctt    240
gaagattttg caacatatta ctgtcaacag tataataatt ccccgtacag ttttggccag    300
gggaccaaag tggagatcaa a                                              321

<210> SEQ ID NO 12
<211> LENGTH: 107
<212> TYPE: PRT
<213> ORGANISM: macaca mulatta

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ser Trp Tyr Gln Gln Lys Pro Gly Lys Ala Pro Lys Pro Leu Ile
        35                  40                  45

Tyr Tyr Ala Ser Ser Leu Glu Thr Gly Val Pro Ser Arg Phe Ser Gly
    50                  55                  60

Ser Arg Ser Gly Thr Asp Tyr Thr Leu Thr Ile Ser Ser Leu Gln Leu
65                  70                  75                  80

Glu Asp Phe Ala Thr Tyr Tyr Cys Gln Gln Tyr Asn Asn Ser Pro Tyr
                85                  90                  95

Ser Phe Gly Gln Gly Thr Lys Val Glu Ile Lys
            100                 105

<210> SEQ ID NO 13
<211> LENGTH: 4062
<212> TYPE: DNA
<213> ORGANISM: Middle East Respiratory Syndrome Coronavirus

<400> SEQUENCE: 13
atgattcact ccgtgttcct gctgatgttc ctgctgactc ctacagagag ctatgtggat     60
gtgggacctg attccgtcaa gagcgcctgc atcgaagtgg acattcagca gaccttcttt    120
gataagacat ggccaagacc catcgacgtg agcaaagccg atggcatcat ctaccctcag    180
gggaggacct attccaatat cacaattact taccagggcc tgttcccata tcagggagac    240
```

-continued

```
cacggcgata tgtacgtgta ttctgctggc catgcaacag ggaccacacc tcagaagctg      300
tttgtggcta actacagcca ggacgtcaaa cagttcgcaa atggatttgt ggtccgcatc      360
ggcgccgctg caaactctac cggcacagtg atcatttcac ctagcacttc cgcaaccatc      420
cgaaaaatct acccagcctt catgctggga agctccgtgg gcaattttag cgacgggaaa      480
atgggacggt tctttaacca caccctggtg ctgctgcctg atggatgcgg cacactgctg      540
agggctttct actgtatcct ggagccacgc agcggaaacc actgcccgc aggaaatagc       600 tacacctcct ttgccacata tcatactcca gctaccgact gttccgatgg caactacaat      660
cgaaacgcct ctctgaatag tttcaaggaa tacttcaacc tgcggaattg cacattcatg      720
tacacttata acatcaccga ggacgaaatt ctggagtggt tcggaatcac tcagaccgca      780
cagggcgtgc acctgttttc tagtcgctac gtcgacctgt atggcgggaa catgttccag      840
tttgccactc tgcccgtgta cgataccatc aagtactatt ccatcattcc tcattcaatc      900
cgcagcattc agtccgatcg aaaggcttgg gccgcttttct acgtgtataa actgcagcca      960
ctgaccttcc tgctggactt tagcgtcgat ggctacatcc ggagagccat tgactgcggg      1020
tttaatgatc tgtcccagct gcactgttct tacgaaagtt tcgacgtgga gtccggcgtg      1080
tattctgtct caagctttga ggccaagccc tctgggagtg tggtcgagca ggctgaagga      1140
gtggagtgcg atttcagtcc tctgctgtca gggaccccc ctcaggtgta caacttcaag       1200
cggctggtct ttactaactg taactacaat ctgaccaagc tgctgtcact gttcagcgtg      1260
aatgacttta catgctccca gatcagcccc gcagccattg ctagtaactg ttactcctct      1320
ctgatcctgg actacttctc atatccactg agtatgaaga cgacctgag cgtgagttca      1380 gccggcccca tcagccagtt caactataaa cagagcttca gcaatcctac atgcctgatt      1440
ctggctactg tgcccacataa tctgactacc atcactaagc cctgaaaata ctcctatatt      1500
aacaagtgca gccggttcct gtccgacgat agaaccgaag tgccacagct ggtcaacgcc      1560
aatcagtact ctccctgtgt gagtatcgtc ccttcaaccg tgtgggaaga cggggattac      1620
tatagaaaac agctgagccc cctggaggga ggaggatggc tggtggcatc cggatctaca      1680
gtcgccatga ctgagcagct gcagatgggg ttcggaatca cagtgcagta cggcacagac      1740
actaactctg tctgtcccaa gctggaattc gctaacgata ctaagatcgc aagtcagctg      1800
ggaaactgcg tggagtactc tctgtatggc gtgagtggca gaggggtctt ccagaattgt      1860
accgcagtgg gcgtccgaca gcagcggttt gtgtacgacg cctatcagaa tctggtcggc      1920
tactatagcg acgatgggaa ctactattgc ctgagggcct gtgtgagcgt ccctgtgtcc      1980
gtcatctacg ataaggaaac caaaacacac gccacactgt tcgggtccgt ggcttgcgag      2040
catattagct ccacaatgtc tcagtacagt agatcaacta ggtcaatgct gaagaggcgc      2100
gatagcacct atggacctct gcagacacca gtggggtgtg tcctgggact ggtgaactct      2160
agtctgtttg tcgaggactg caagctgccc ctgggccaga gctgtgcgc cctgcccgac      2220 acccccagca ccctgacccc ccggagcgtg cggagcgtgc ccgcgagat gcggctggcc      2280 agcatcgcct tcaaccaccc catccaggtg gaccagctga acagcagcta cttcaagctg      2340
agcatcccca ccaacttcag cttcggcgtg acccaggagt acatccagac caccatccag      2400
aaggtgaccg tggactgcaa gcagtacgtg tgcaacggct tccagaagtg cgagcagctg      2460
ctgcgggagt acggccagtt ctgcagcaag atcaaccagg ccctgcacgg cgccaacctg      2520
cggcaggacg acagcgtgcg gaacctgttc gccagcgtga gagcagcca gagcagcccc      2580 atcatccccg gcttcggcgg cgacttcaac ctgaccctgc tggagccgct gagcatcagc      2640
```

-continued

```
accggcagcc ggagcgcccg gagcgccatc gaggacctgc tgttcgacaa ggtgaccatc    2700
gccgaccccg gctacatgca gggctacgac gactgcatgc agcagggccc cgccagcgcc    2760
cgggacctga tctgcgccca gtacgtggcc ggctacaagg tgctgccccc cctgatggac    2820
gtgaacatgg aggccgccta caccagcagc ctgctgggca gcatcgccgg cgtgggctgg    2880
accgccggcc tgagcagctt cgccgccatc cccttcgccc agagcatctt ctaccggctg    2940
aacggcgtgg gcatcaccca gcaggtgctg agcgagaacc agaagctgat cgccaacaag    3000
ttcaaccagg ccctgggcgc catgcagacc ggcttcacca ccaccaacga ggccttccac    3060
aaggtgcagg acgccgtgaa caacaacgcc caggccctga gcaagctggc cagcgagctg    3120
agcaacacct tcggcgccat cagcgccagc atcggcgaca tcatccagcg gctggacgtg    3180
ctggagcagg acgccagat cgaccggctg atcaacggcc ggctgaccac cctgaacgcc    3240
ttcgtggccc agcagctggt gcggagcgag agcgccgccc tgagcgccca gctggccaag    3300
gacaaggtga cgagtgcgt gaaggcccag agcaagcgga gcggcttctg cggccagggc    3360
acccacatcg tgagcttcgt ggtgaacgcc cccaacggcc tgtacttcat gcacgtgggc    3420
tactacccca gcaaccacat cgaggtggtg agcgcctacg gcctgtgcga cgccgccaac    3480
cccaccaact gcatcgcccc cgtgaacggc tacttcatca agaccaacaa caccggatc     3540 gtggacgagt ggagctacac cggcagcagc ttctacgccc ccgagcccat caccagcctg    3600
aacaccaagt acgtggcccc ccaggtgacc taccagaaca tcagcaccaa cctgccccc     3660 cccctgctgg gcaacagcac cggcatcgac ttccaggacg agctggacga gttcttcaag    3720
aacgtgagca ccagcatccc caacttcggc agcctgaccc agatcaacac caccctgctg    3780
gacctgacct acgagatgct gagcctgcag caggtggtga aggccctgaa cgagagctac    3840
atcgacctga aggagctggg caactacacc tactacaaca gtggccctg gtacatctgg    3900 ctgggcttca tcgccggcct ggtggccctg gccctgtgcg tgttcttcat cctgtgctgc    3960
accggctgcg gcaccaactg catgggcaag ctgaagtgca ccggtgctg cgaccggtac    4020 gaggagtacg acctggagcc ccacaaggtg cacgtgcact ga                        4062
```

<210> SEQ ID NO 14
<211> LENGTH: 1353
<212> TYPE: PRT
<213> ORGANISM: Middle East Respiratory Syndrome Coronavirus

<400> SEQUENCE: 14

```
Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
```

```
            115                 120                 125
Thr Val Ile Ile Ser Pro Ser Thr Ala Thr Ile Arg Lys Ile Tyr
            130                 135                 140
Pro Ala Phe Met Leu Gly Ser Ser Val Gly Asn Phe Ser Asp Gly Lys
145                     150                 155                 160
Met Gly Arg Phe Phe Asn His Thr Leu Val Leu Leu Pro Asp Gly Cys
                    165                 170                 175
Gly Thr Leu Leu Arg Ala Phe Tyr Cys Ile Leu Glu Pro Arg Ser Gly
            180                 185                 190
Asn His Cys Pro Ala Gly Asn Ser Tyr Thr Ser Phe Ala Thr Tyr His
            195                 200                 205
Thr Pro Ala Thr Asp Cys Ser Asp Gly Asn Tyr Asn Arg Asn Ala Ser
210                     215                 220
Leu Asn Ser Phe Lys Glu Tyr Phe Asn Leu Arg Asn Cys Thr Phe Met
225                 230                 235                 240
Tyr Thr Tyr Asn Ile Thr Glu Asp Glu Ile Leu Glu Trp Phe Gly Ile
                    245                 250                 255
Thr Gln Thr Ala Gln Gly Val His Leu Phe Ser Ser Arg Tyr Val Asp
            260                 265                 270
Leu Tyr Gly Gly Asn Met Phe Gln Phe Ala Thr Leu Pro Val Tyr Asp
            275                 280                 285
Thr Ile Lys Tyr Tyr Ser Ile Ile Pro His Ser Ile Arg Ser Ile Gln
            290                 295                 300
Ser Asp Arg Lys Ala Trp Ala Ala Phe Tyr Val Tyr Lys Leu Gln Pro
305                     310                 315                 320
Leu Thr Phe Leu Leu Asp Phe Ser Val Asp Gly Tyr Ile Arg Arg Ala
                    325                 330                 335
Ile Asp Cys Gly Phe Asn Asp Leu Ser Gln Leu His Cys Ser Tyr Glu
                    340                 345                 350
Ser Phe Asp Val Glu Ser Gly Val Tyr Ser Val Ser Ser Phe Glu Ala
            355                 360                 365
Lys Pro Ser Gly Ser Val Val Glu Gln Ala Glu Gly Val Glu Cys Asp
            370                 375                 380
Phe Ser Pro Leu Leu Ser Gly Thr Pro Pro Gln Val Tyr Asn Phe Lys
385                     390                 395                 400
Arg Leu Val Phe Thr Asn Cys Asn Tyr Asn Leu Thr Lys Leu Leu Ser
                    405                 410                 415
Leu Phe Ser Val Asn Asp Phe Thr Cys Ser Gln Ile Ser Pro Ala Ala
                    420                 425                 430
Ile Ala Ser Asn Cys Tyr Ser Ser Leu Ile Leu Asp Tyr Phe Ser Tyr
            435                 440                 445
Pro Leu Ser Met Lys Ser Asp Leu Ser Val Ser Ser Ala Gly Pro Ile
            450                 455                 460
Ser Gln Phe Asn Tyr Lys Gln Ser Phe Ser Asn Pro Thr Cys Leu Ile
465                     470                 475                 480
Leu Ala Thr Val Pro His Asn Leu Thr Thr Ile Thr Lys Pro Leu Lys
                    485                 490                 495
Tyr Ser Tyr Ile Asn Lys Cys Ser Arg Phe Leu Ser Asp Asp Arg Thr
                    500                 505                 510
Glu Val Pro Gln Leu Val Asn Ala Asn Gln Tyr Ser Pro Cys Val Ser
            515                 520                 525
Ile Val Pro Ser Thr Val Trp Glu Asp Gly Asp Tyr Tyr Arg Lys Gln
            530                 535                 540
```

```
Leu Ser Pro Leu Glu Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
                580                 585                 590

Asp Thr Lys Ile Ala Ser Gln Leu Gly Asn Cys Val Glu Tyr Ser Leu
                595                 600                 605

Tyr Gly Val Ser Gly Arg Gly Val Phe Gln Asn Cys Thr Ala Val Gly
                610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
                660                 665                 670

Leu Phe Gly Ser Val Ala Cys Glu His Ile Ser Ser Thr Met Ser Gln
                675                 680                 685

Tyr Ser Arg Ser Thr Arg Ser Met Leu Lys Arg Arg Asp Ser Thr Tyr
                690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
                740                 745                 750

Val Pro Gly Glu Met Arg Leu Ala Ser Ile Ala Phe Asn His Pro Ile
                755                 760                 765

Gln Val Asp Gln Leu Asn Ser Ser Tyr Phe Lys Leu Ser Ile Pro Thr
                770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
                820                 825                 830

Gln Ala Leu His Gly Ala Asn Leu Arg Gln Asp Asp Ser Val Arg Asn
                835                 840                 845

Leu Phe Ala Ser Val Lys Ser Ser Gln Ser Ser Pro Ile Ile Pro Gly
                850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
                900                 905                 910

Met Gln Gln Gly Pro Ala Ser Ala Arg Asp Leu Ile Cys Ala Gln Tyr
                915                 920                 925

Val Ala Gly Tyr Lys Val Leu Pro Pro Leu Met Asp Val Asn Met Glu
                930                 935                 940

Ala Ala Tyr Thr Ser Ser Leu Leu Gly Ser Ile Ala Gly Val Gly Trp
945                 950                 955                 960
```

```
Thr Ala Gly Leu Ser Ser Phe Ala Ala Ile Pro Phe Ala Gln Ser Ile
            965                 970                 975

Phe Tyr Arg Leu Asn Gly Val Gly Ile Thr Gln Gln Val Leu Ser Glu
            980                 985                 990

Asn Gln Lys Leu Ile Ala Asn Lys Phe Asn Gln Ala Leu Gly Ala Met
        995                 1000                1005

Gln Thr Gly Phe Thr Thr Thr Asn Glu Ala Phe His Lys Val Gln
    1010                1015                1020

Asp Ala Val Asn Asn Asn Ala Gln Ala Leu Ser Lys Leu Ala Ser
    1025                1030                1035

Glu Leu Ser Asn Thr Phe Gly Ala Ile Ser Ala Ser Ile Gly Asp
    1040                1045                1050

Ile Ile Gln Arg Leu Asp Val Leu Glu Gln Asp Ala Gln Ile Asp
    1055                1060                1065

Arg Leu Ile Asn Gly Arg Leu Thr Thr Leu Asn Ala Phe Val Ala
    1070                1075                1080

Gln Gln Leu Val Arg Ser Glu Ser Ala Ala Leu Ser Ala Gln Leu
    1085                1090                1095

Ala Lys Asp Lys Val Asn Glu Cys Val Lys Ala Gln Ser Lys Arg
    1100                1105                1110

Ser Gly Phe Cys Gly Gln Gly Thr His Ile Val Ser Phe Val Val
    1115                1120                1125

Asn Ala Pro Asn Gly Leu Tyr Phe Met His Val Gly Tyr Tyr Pro
    1130                1135                1140

Ser Asn His Ile Glu Val Val Ser Ala Tyr Gly Leu Cys Asp Ala
    1145                1150                1155

Ala Asn Pro Thr Asn Cys Ile Ala Pro Val Asn Gly Tyr Phe Ile
    1160                1165                1170

Lys Thr Asn Asn Thr Arg Ile Val Asp Glu Trp Ser Tyr Thr Gly
    1175                1180                1185

Ser Ser Phe Tyr Ala Pro Glu Pro Ile Thr Ser Leu Asn Thr Lys
    1190                1195                1200

Tyr Val Ala Pro Gln Val Thr Tyr Gln Asn Ile Ser Thr Asn Leu
    1205                1210                1215

Pro Pro Pro Leu Leu Gly Asn Ser Thr Gly Ile Asp Phe Gln Asp
    1220                1225                1230

Glu Leu Asp Glu Phe Phe Lys Asn Val Ser Thr Ser Ile Pro Asn
    1235                1240                1245

Phe Gly Ser Leu Thr Gln Ile Asn Thr Thr Leu Leu Asp Leu Thr
    1250                1255                1260

Tyr Glu Met Leu Ser Leu Gln Gln Val Val Lys Ala Leu Asn Glu
    1265                1270                1275

Ser Tyr Ile Asp Leu Lys Glu Leu Gly Asn Tyr Thr Tyr Tyr Asn
    1280                1285                1290

Lys Trp Pro Trp Tyr Ile Trp Leu Gly Phe Ile Ala Gly Leu Val
    1295                1300                1305

Ala Leu Ala Leu Cys Val Phe Phe Ile Leu Cys Cys Thr Gly Cys
    1310                1315                1320

Gly Thr Asn Cys Met Gly Lys Leu Lys Cys Asn Arg Cys Cys Asp
    1325                1330                1335

Arg Tyr Glu Glu Tyr Asp Leu Glu Pro His Lys Val His Val His
    1340                1345                1350
```

<210> SEQ ID NO 15
<211> LENGTH: 2259
<212> TYPE: DNA
<213> ORGANISM: Middle East Respiratory Syndrome Coronavirus

<400> SEQUENCE: 15

| | | | | | |
|---|---|---|---|---|---|
| atgattcact | ccgtgttcct | gctgatgttc | ctgctgactc | ctacagagag | ctatgtggat | 60 |
| gtgggacctg | attccgtcaa | gagcgcctgc | atcgaagtgg | acattcagca | gaccttcttt | 120 |
| gataagacat | ggccaagacc | catcgacgtg | agcaaagccg | atggcatcat | ctaccctcag | 180 |
| gggaggacct | attccaatat | cacaattact | taccagggcc | tgttcccata | tcagggagac | 240 |
| cacggcgata | tgtacgtgta | ttctgctggc | catgcaacag | gaccacacc | tcagaagctg | 300 |
| tttgtggcta | actacagcca | ggacgtcaaa | cagttcgcaa | atggatttgt | ggtccgcatc | 360 |
| ggcgccgctg | caaactctac | cggcacagtg | atcatttcac | ctagcacttc | cgcaaccatc | 420 |
| cgaaaaatct | acccagcctt | catgctggga | agctccgtgg | gcaattttag | cgacgggaaa | 480 |
| atgggacggt | tctttaacca | cccctggtg | ctgctgcctg | atggatgcgg | cacactgctg | 540 |
| agggctttct | actgtatcct | ggagccacgc | agcggaaacc | actgcccgc | aggaaatagc | 600 |
| tacacctcct | tgccacata | tcatactcca | gctaccgact | gttccgatgg | caactacaat | 660 |
| cgaaacgcct | ctctgaatag | tttcaaggaa | tacttcaacc | tgcggaattg | cacattcatg | 720 |
| tacacttata | acatcaccga | ggacgaaatt | ctggagtggt | tcggaatcac | tcagaccgca | 780 |
| cagggcgtgc | acctgttttc | tagtcgctac | gtcgacctgt | atggcgggaa | catgttccag | 840 |
| tttgccactc | tgcccgtgta | cgataccatc | aagtactatt | ccatcattcc | tcattcaatc | 900 |
| cgcagcattc | agtccgatcg | aaaggcttgg | gccgctttct | acgtgtataa | actgcagcca | 960 |
| ctgaccttcc | tgctggactt | tagcgtcgat | ggctacatcc | ggagagccat | tgactgcggg | 1020 |
| tttaatgatc | tgtcccagct | gcactgttct | tacgaaagtt | tcgacgtgga | gtccggcgtg | 1080 |
| tattctgtct | caagctttga | ggccaagccc | tctgggagtg | tggtcgagca | ggctgaagga | 1140 |
| gtggagtgcg | atttcagtcc | tctgctgtca | gggaccccc | ctcaggtgta | caacttcaag | 1200 |
| cggctggtct | ttactaactg | taactacaat | ctgaccaagc | tgctgtcact | gttcagcgtg | 1260 |
| aatgacttta | catgctccca | gatcagcccc | gcagccattg | ctagtaactg | ttactcctct | 1320 |
| ctgatcctgg | actacttctc | atatccactg | agtatgaaga | gcgacctgag | cgtgagttca | 1380 |
| gccggcccca | tcagccagtt | caactataaa | cagagcttca | gcaatcctac | atgcctgatt | 1440 |
| ctggctactg | tgccacataa | tctgactacc | atcactaagc | ccctgaaata | ctcctatatt | 1500 |
| aacaagtgca | gccggttcct | gtccgacgat | agaaccgaag | tgccacagct | ggtcaacgcc | 1560 |
| aatcagtact | ctcccctgtgt | gagtatcgtc | ccttcaaccg | tgtgggaaga | cggggattac | 1620 |
| tatagaaaac | agctgagccc | cctggaggga | ggaggatggc | tggtggcatc | cggatctaca | 1680 |
| gtcgccatga | ctgagcagct | gcagatgggg | ttcggaatca | cagtgcagta | cggcacagac | 1740 |
| actaactctg | tctgtcccaa | gctggaattc | gctaacgata | ctaagatcgc | aagtcagctg | 1800 |
| ggaaactgcg | tggagtactc | tctgtatggc | gtgagtggca | gagggtctt | ccagaattgt | 1860 |
| accgcagtgg | gcgtccgaca | gcagcggttt | gtgtacgacg | cctatcagaa | tctggtcggc | 1920 |
| tactatagcg | acgatgggaa | ctactattgc | ctgagggcct | gtgtgagcgt | ccctgtgtcc | 1980 |
| gtcatctacg | ataaggaaac | caaaacacac | gccacactgt | tcgggtccgt | ggcttgcgag | 2040 |
| catattagct | ccacaatgtc | tcagtacagt | agatcaacta | ggtcaatgct | gaagaggcgc | 2100 |
| gatagcacct | atggacctct | gcagacacca | gtggggtgtg | tcctgggact | ggtgaactct | 2160 |

-continued

```
agtctgtttg tcgaggactg caagctgccc ctgggccaga gcctgtgcgc cctgcccgac    2220 accccccagca ccctgacccc ccggagcgtg cggagctga                          2259
```

<210> SEQ ID NO 16
<211> LENGTH: 752
<212> TYPE: PRT
<213> ORGANISM: Middle East Respiratory Syndrome Coronavirus

<400> SEQUENCE: 16

```
Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
```

```
                355                 360                 365
Lys Pro Ser Gly Ser Val Val Glu Gln Ala Glu Gly Val Glu Cys Asp
            370                 375                 380

Phe Ser Pro Leu Leu Ser Gly Thr Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
                435                 440                 445

Pro Leu Ser Met Lys Ser Asp Leu Ser Val Ser Ser Ala Gly Pro Ile
            450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Phe Leu Ser Asp Asp Arg Thr
            500                 505                 510

Glu Val Pro Gln Leu Val Asn Ala Asn Gln Tyr Ser Pro Cys Val Ser
                515                 520                 525

Ile Val Pro Ser Thr Val Trp Glu Asp Gly Asp Tyr Tyr Arg Lys Gln
            530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
            595                 600                 605

Tyr Gly Val Ser Gly Arg Gly Val Phe Gln Asn Cys Thr Ala Val Gly
610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
            645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
            675                 680                 685

Tyr Ser Arg Ser Thr Arg Ser Met Leu Lys Arg Arg Asp Ser Thr Tyr
            690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
            740                 745                 750

<210> SEQ ID NO 17
<211> LENGTH: 720
<212> TYPE: DNA
<213> ORGANISM: Middle East Respiratory Syndrome Coronavirus
```

<400> SEQUENCE: 17

```
gaggccaagc cctctgggag tgtggtcgag caggctgaag gagtggagtg cgatttcagt      60
cctctgctgt cagggacccc ccctcaggtg tacaacttca gcggctggt  ctttactaac     120
tgtaactaca atctgaccaa gctgctgtca ctgttcagcg tgaatgactt acatgctcc      180
cagatcagcc ccgcagccat tgctagtaac tgttactcct ctctgatcct ggactacttc     240
tcatatccac tgagtatgaa gagcgacctg agcgtgagtt cagccggccc catcagccag     300
ttcaactata acagagctt  cagcaatcct acatgcctga ttctggctac tgtgccacat     360
aatctgacta ccatcactaa gcccctgaaa tactcctata ttaacaagtg cagccggttc     420
ctgtccgacg atagaaccga agtgccacag ctggtcaacg ccaatcagta ctctccctgt     480
gtgagtatcg tcccttcaac cgtgtgggaa gacggggatt actatagaaa acagctgagc     540
ccctggagg  gaggaggatg gctggtggca tccggatcta cagtcgccat gactgagcag     600
ctgcagatgg ggttcggaat cacagtgcag tacggcacag acactaactc tgtctgtccc     660
aagctggaat tcgctaacga tactaagatc gcaagtcagc tgggaaactg cgtggagtac     720
```

<210> SEQ ID NO 18
<211> LENGTH: 240
<212> TYPE: PRT
<213> ORGANISM: Middle East Respiratory Syndrome Coronavirus

<400> SEQUENCE: 18

```
Glu Ala Lys Pro Ser Gly Ser Val Val Glu Gln Ala Glu Gly Val Glu
1               5                   10                  15

Cys Asp Phe Ser Pro Leu Leu Ser Gly Thr Pro Pro Gln Val Tyr Asn
            20                  25                  30

Phe Lys Arg Leu Val Phe Thr Asn Cys Asn Tyr Asn Leu Thr Lys Leu
        35                  40                  45

Leu Ser Leu Phe Ser Val Asn Asp Phe Thr Cys Ser Gln Ile Ser Pro
    50                  55                  60

Ala Ala Ile Ala Ser Asn Cys Tyr Ser Ser Leu Ile Leu Asp Tyr Phe
65                  70                  75                  80

Ser Tyr Pro Leu Ser Met Lys Ser Asp Leu Ser Val Ser Ser Ala Gly
                85                  90                  95

Pro Ile Ser Gln Phe Asn Tyr Lys Gln Ser Phe Ser Asn Pro Thr Cys
            100                 105                 110

Leu Ile Leu Ala Thr Val Pro His Asn Leu Thr Thr Ile Thr Lys Pro
        115                 120                 125

Leu Lys Tyr Ser Tyr Ile Asn Lys Cys Ser Arg Phe Leu Ser Asp Asp
    130                 135                 140

Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
                165                 170                 175

Lys Gln Leu Ser Pro Leu Glu Gly Gly Gly Trp Leu Val Ala Ser Gly
            180                 185                 190

Ser Thr Val Ala Met Thr Glu Gln Leu Gln Met Gly Phe Gly Ile Thr
        195                 200                 205

Val Gln Tyr Gly Thr Asp Thr Asn Ser Val Cys Pro Lys Leu Glu Phe
    210                 215                 220

Ala Asn Asp Thr Lys Ile Ala Ser Gln Leu Gly Asn Cys Val Glu Tyr
225                 230                 235                 240
```

<210> SEQ ID NO 19
<211> LENGTH: 3870
<212> TYPE: DNA
<213> ORGANISM: Middle East Respiratory Syndrome Coronavirus

<400> SEQUENCE: 19

| | |
|---|---:|
| atgattcact ccgtgttcct gctgatgttc ctgctgactc ctacagagag ctatgtggat | 60 |
| gtgggacctg attccgtcaa gagcgcctgc atcgaagtgg acattcagca gaccttcttt | 120 |
| gataagacat ggccaagacc catcgacgtg agcaaagccg atggcatcat ctaccctcag | 180 |
| gggaggacct attccaatat cacaattact taccagggcc tgttcccata tcagggagac | 240 |
| cacggcgata tgtacgtgta ttctgctggc catgcaacag ggaccacacc tcagaagctg | 300 |
| tttgtggcta actacagcca ggacgtcaaa cagttcgcaa atggatttgt ggtccgcatc | 360 |
| ggcgccgctg caaactctac cggcacagtg atcatttcac ctagcacttc cgcaaccatc | 420 |
| cgaaaaatct acccagcctt catgctggga agctccgtgg caatttttag cgacgggaaa | 480 |
| atgggacggt tctttaacca caccctggtg ctgctgcctg atggatgcgg cacactgctg | 540 |
| agggcttttct actgtatcct ggagccacgc agcggaaacc actgccccgc aggaaatagc | 600 |
| tacacctcct ttgccacata tcatactcca gctaccgact gttccgatgg caactacaat | 660 |
| cgaaacgcct ctctgaatag tttcaaggaa tacttcaacc tgcggaattg cacattcatg | 720 |
| tacacttata acatcaccga ggacgaaatt ctggagtggt tcggaatcac tcagaccgca | 780 |
| cagggcgtgc acctgttttc tagtcgctac gtcgacctgt atggcgggaa catgttccag | 840 |
| tttgccactc tgcccgtgta cgataccatc aagtactatt ccatcattcc tcattcaatc | 900 |
| cgcagcattc agtccgatcg aaaggcttgg gccgctttct acgtgtataa actgcagcca | 960 |
| ctgaccttcc tgctggactt tagcgtcgat ggctacatcc ggagagccat tgactgcggg | 1020 |
| tttaatgatc tgtcccagct gcactgttct tacgaaagtt tcgacgtgga gtccggcgtg | 1080 |
| tattctgtct caagctttga ggccaagccc tctggagtg tggtcgagca ggctgaagga | 1140 |
| gtggagtgcg atttcagtcc tctgctgtca gggaccccccc ctcaggtgta caacttcaag | 1200 |
| cggctggtct ttactaactg taactacaat ctgaccaagc tgctgtcact gttcagcgtg | 1260 |
| aatgacttta tgctgcccca gatcagcccc gcagccattg ctagtaactg ttactcctct | 1320 |
| ctgatcctgg actacttctc atatcccactg agtatgaaga cgacctgag cgtgagttca | 1380 |
| gccggcccca tcagccagtt caactataaa cagagcttca gcaatcctac atgcctgatt | 1440 |
| ctggctactg tgccacataa tctgactacc atcactaagc cctgaaaata ctcctatatt | 1500 |
| aacaagtgca gccggttcct gtccgacgat agaaccgaag tgccacagct ggtcaacgcc | 1560 |
| aatcagtact ctccctgtgt gagtatcgtc ccttcaaccg tgtgggaaga cggggattac | 1620 |
| tatagaaaac agctgagccc cctggaggga ggaggatggc tggtggcatc cggatctaca | 1680 |
| gtcgccatga ctgagcagct gcagatgggg ttcggaatca cagtgcagta cggcacagac | 1740 |
| actaactctg tctgtcccaa gctggaattc gctaacgata ctaagatcgc aagtcagctg | 1800 |
| ggaaactgcg tggagtactc tctgtatggc gtgagtggca gggggtcttc cagaattgt | 1860 |
| accgcagtgg gcgtccgaca gcagcggttt gtgtacgacg cctatcagaa tctggtcggc | 1920 |
| tactatagcg acgatgggaa ctactattgc ctgagggcct gtgtgagcgt ccctgtgtcc | 1980 |
| gtcatctacg ataaggaaac caaaacacac gccacactgt tcgggtccgt ggcttgcgag | 2040 |
| catattagct ccacaatgtc tcagtacagt agatcaacta ggtcaatgct gaagaggcgc | 2100 |

```
gatagcacct atggacctct gcagacacca gtggggtgtg tcctgggact ggtgaactct    2160
agtctgtttg tcgaggactg caagctgccc ctgggccaga gcctgtgcgc cctgcccgac    2220
acccccagca ccctgacccc cggagcgtg cggagcgtgc ccggcgagat gcggctggcc    2280
agcatcgcct tcaaccaccc catccaggtg gaccagctga acagcagcta cttcaagctg    2340
agcatcccca ccaacttcag cttcggcgtg acccaggagt acatccagac caccatccag    2400
aaggtgaccg tggactgcaa gcagtacgtg tgcaacggct ccagaagtg cgagcagctg    2460 ctgcgggagt acggccagtt ctgcagcaag atcaaccagg ccctgcacgg cgccaacctg    2520
cggcaggacg acagcgtgcg gaacctgttc gccagcgtga agagcagcca gagcagcccc    2580
atcatccccg gcttcggcgg cgacttcaac ctgacccctg ctggagcccgt gagcatcagc    2640 accggcagcc ggagcgcccg gagcgccatc gaggacctgc tgttcgacaa ggtgaccatc    2700
gccgaccccg gctacatgca gggctacgac gactgcatgc agcagggccc cgccagcgcc    2760
cgggacctga tctgcgccca gtacgtggcc ggctacaagg tgctgccccc cctgatggac    2820
gtgaacatgg aggccgccta caccagcagc ctgctgggca gcatcgccgg cgtgggctgg    2880
accgccggcc tgagcagctt cgccgccatc cccttcgccc agagcatctt ctaccggctg    2940
aacggcgtgg gcatcaccca gcaggtgctg agcgagaacc agaagctgat cgccaacaag    3000
ttcaaccagg ccctgggcgc catgcagacc ggcttcacca ccaccaacga ggccttccac    3060
aaggtgcagg acgccgtgaa caacaacgcc caggccctga gcaagctggc cagcgagctg    3120
agcaacacct cggcgccat cagcgccagc atcggcgaca tcatccagcg gctggacgtg    3180
ctggagcagg acgcccagat cgaccggctg atcaacggcc ggctgaccac cctgaacgcc    3240
ttcgtggccc agcagctggt gcggagcgag agcgccgccc tgagcgccca gctggccaag    3300
gacaaggtga cgagtgcgt gaaggcccag agcaagcgga gcggcttctg cggccagggc    3360
acccacatcg tgagcttcgt ggtgaacgcc cccaacggcc tgtacttcat gcacgtgggc    3420
tactacccca gcaaccacat cgaggtggtg agcgcctacg gcctgtgcga cgccgccaac    3480
cccaccaact gcatcgcccc cgtgaacggc tacttcatca agaccaacaa cacccggatc    3540
gtggacgagt ggagctacac cggcagcagc ttctacgccc ccgagcccat caccagcctg    3600
aacaccaagt acgtggcccc ccaggtgacc taccagaaca tcagcaccaa cctgcccccc    3660
cccctgctgg gcaacagcac cggcatcgac ttccaggacg agctggacga gttcttcaag    3720
aacgtgagca ccagcatccc caacttcggc agcctgaccc agatcaacac cacctgctg    3780 gacctgacct acgagatgct gagcctgcag caggtggtga aggccctgaa cgagagctac    3840
atcgacctga aggagctggg caactacacc                                    3870
```

<210> SEQ ID NO 20
<211> LENGTH: 1290
<212> TYPE: PRT
<213> ORGANISM: Middle East Respiratory Syndrome Coronavirus

<400> SEQUENCE: 20

```
Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60
```

```
Ser Asn Ile Thr Ile Thr Tyr Gln Gly Leu Phe Pro Tyr Gln Gly Asp
 65                  70                  75                  80

His Gly Asp Met Tyr Val Tyr Ser Ala Gly His Ala Thr Gly Thr Thr
                 85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Asn Ser Thr Gly
        115                 120                 125

Thr Val Ile Ile Ser Pro Ser Thr Ala Thr Ile Arg Lys Ile Tyr
    130                 135                 140

Pro Ala Phe Met Leu Gly Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480
```

```
Leu Ala Thr Val Pro His Asn Leu Thr Thr Ile Thr Lys Pro Leu Lys
            485                 490                 495

Tyr Ser Tyr Ile Asn Lys Cys Ser Arg Phe Leu Ser Asp Asp Arg Thr
            500                 505                 510

Glu Val Pro Gln Leu Val Asn Ala Asn Gln Tyr Ser Pro Cys Val Ser
            515                 520                 525

Ile Val Pro Ser Thr Val Trp Glu Asp Gly Asp Tyr Tyr Arg Lys Gln
            530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
                580                 585                 590

Asp Thr Lys Ile Ala Ser Gln Leu Gly Asn Cys Val Glu Tyr Ser Leu
            595                 600                 605

Tyr Gly Val Ser Gly Arg Gly Val Phe Gln Asn Cys Thr Ala Val Gly
        610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
                660                 665                 670

Leu Phe Gly Ser Val Ala Cys Glu His Ile Ser Ser Thr Met Ser Gln
            675                 680                 685

Tyr Ser Arg Ser Thr Arg Ser Met Leu Lys Arg Arg Asp Ser Thr Tyr
        690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
                740                 745                 750

Val Pro Gly Glu Met Arg Leu Ala Ser Ile Ala Phe Asn His Pro Ile
            755                 760                 765

Gln Val Asp Gln Leu Asn Ser Ser Tyr Phe Lys Leu Ser Ile Pro Thr
        770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
                820                 825                 830

Gln Ala Leu His Gly Ala Asn Leu Arg Gln Asp Asp Ser Val Arg Asn
            835                 840                 845

Leu Phe Ala Ser Val Lys Ser Ser Gln Ser Ser Pro Ile Ile Pro Gly
        850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
```

```
              900                 905                 910
Met Gln Gln Gly Pro Ala Ser Ala Arg Asp Leu Ile Cys Ala Gln Tyr
        915                 920                 925

Val Ala Gly Tyr Lys Val Leu Pro Pro Leu Met Asp Val Asn Met Glu
        930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
        980                 985                 990

Asn Gln Lys Leu Ile Ala Asn Lys Phe Asn Gln Ala Leu Gly Ala Met
        995                 1000                1005

Gln Thr Gly Phe Thr Thr Thr Asn Glu Ala Phe His Lys Val Gln
        1010                1015                1020

Asp Ala Val Asn Asn Ala Gln Ala Leu Ser Lys Leu Ala Ser
        1025                1030                1035

Glu Leu Ser Asn Thr Phe Gly Ala Ile Ser Ala Ser Ile Gly Asp
        1040                1045                1050

Ile Ile Gln Arg Leu Asp Val Leu Glu Gln Asp Ala Gln Ile Asp
        1055                1060                1065

Arg Leu Ile Asn Gly Arg Leu Thr Thr Leu Asn Ala Phe Val Ala
        1070                1075                1080

Gln Gln Leu Val Arg Ser Glu Ser Ala Ala Leu Ser Ala Gln Leu
        1085                1090                1095

Ala Lys Asp Lys Val Asn Glu Cys Val Lys Ala Gln Ser Lys Arg
        1100                1105                1110

Ser Gly Phe Cys Gly Gln Gly Thr His Ile Val Ser Phe Val Val
        1115                1120                1125

Asn Ala Pro Asn Gly Leu Tyr Phe Met His Val Gly Tyr Tyr Pro
        1130                1135                1140

Ser Asn His Ile Glu Val Val Ser Ala Tyr Gly Leu Cys Asp Ala
        1145                1150                1155

Ala Asn Pro Thr Asn Cys Ile Ala Pro Val Asn Gly Tyr Phe Ile
        1160                1165                1170

Lys Thr Asn Asn Thr Arg Ile Val Asp Glu Trp Ser Tyr Thr Gly
        1175                1180                1185

Ser Ser Phe Tyr Ala Pro Glu Pro Ile Thr Ser Leu Asn Thr Lys
        1190                1195                1200

Tyr Val Ala Pro Gln Val Thr Tyr Gln Asn Ile Ser Thr Asn Leu
        1205                1210                1215

Pro Pro Pro Leu Leu Gly Asn Ser Thr Gly Ile Asp Phe Gln Asp
        1220                1225                1230

Glu Leu Asp Glu Phe Phe Lys Asn Val Ser Thr Ser Ile Pro Asn
        1235                1240                1245

Phe Gly Ser Leu Thr Gln Ile Asn Thr Thr Leu Leu Asp Leu Thr
        1250                1255                1260

Tyr Glu Met Leu Ser Leu Gln Gln Val Val Lys Ala Leu Asn Glu
        1265                1270                1275

Ser Tyr Ile Asp Leu Lys Glu Leu Gly Asn Tyr Thr
        1280                1285                1290
```

<210> SEQ ID NO 21

<211> LENGTH: 173
<212> TYPE: PRT
<213> ORGANISM: Artificial Sequence
<220> FEATURE:
<223> OTHER INFORMATION: ferritin nanoparticle sequence

<400> SEQUENCE: 21

| Glu | Ser | Gln | Val | Arg | Gln | Gln | Phe | Ser | Lys | Asp | Ile | Glu | Lys | Leu | Leu |
|---|---|---|---|---|---|---|---|---|---|---|---|---|---|---|---|
| 1 | | | | 5 | | | | | 10 | | | | | 15 | |

| Asn | Glu | Gln | Val | Asn | Lys | Glu | Met | Gln | Ser | Ser | Asn | Leu | Tyr | Met | Ser |
|---|---|---|---|---|---|---|---|---|---|---|---|---|---|---|---|
| | | | 20 | | | | | 25 | | | | | 30 | | |

| Met | Ser | Ser | Trp | Cys | Tyr | Thr | His | Ser | Leu | Asp | Gly | Ala | Gly | Leu | Phe |
|---|---|---|---|---|---|---|---|---|---|---|---|---|---|---|---|
| | | 35 | | | | | 40 | | | | | 45 | | | |

| Leu | Phe | Asp | His | Ala | Ala | Glu | Glu | Tyr | Glu | His | Ala | Lys | Lys | Leu | Ile |
|---|---|---|---|---|---|---|---|---|---|---|---|---|---|---|---|
| | 50 | | | | | 55 | | | | | 60 | | | | |

| Ile | Phe | Leu | Asn | Glu | Asn | Asn | Val | Pro | Val | Gln | Leu | Thr | Ser | Ile | Ser |
|---|---|---|---|---|---|---|---|---|---|---|---|---|---|---|---|
| 65 | | | | | 70 | | | | | 75 | | | | | 80 |

| Ala | Pro | Glu | His | Lys | Phe | Glu | Gly | Leu | Thr | Gln | Ile | Phe | Gln | Lys | Ala |
|---|---|---|---|---|---|---|---|---|---|---|---|---|---|---|---|
| | | | | 85 | | | | | 90 | | | | | 95 | |

| Tyr | Glu | His | Glu | Gln | His | Ile | Ser | Glu | Ser | Ile | Asn | Asn | Ile | Val | Asp |
|---|---|---|---|---|---|---|---|---|---|---|---|---|---|---|---|
| | | | 100 | | | | | 105 | | | | | 110 | | |

| His | Ala | Ile | Lys | Ser | Lys | Asp | His | Ala | Thr | Phe | Asn | Phe | Leu | Gln | Trp |
|---|---|---|---|---|---|---|---|---|---|---|---|---|---|---|---|
| | | 115 | | | | | 120 | | | | | 125 | | | |

| Tyr | Val | Ala | Glu | Gln | His | Glu | Glu | Val | Leu | Phe | Lys | Asp | Ile | Leu |
|---|---|---|---|---|---|---|---|---|---|---|---|---|---|---|
| | 130 | | | | | 135 | | | | | 140 | | | |

| Asp | Lys | Ile | Glu | Leu | Ile | Gly | Asn | Glu | Asn | His | Gly | Leu | Tyr | Leu | Ala |
|---|---|---|---|---|---|---|---|---|---|---|---|---|---|---|---|
| 145 | | | | | 150 | | | | | 155 | | | | | 160 |

| Asp | Gln | Tyr | Val | Lys | Gly | Ile | Ala | Lys | Ser | Arg | Lys | Ser |
|---|---|---|---|---|---|---|---|---|---|---|---|---|
| | | | | 165 | | | | | 170 | | | |

<210> SEQ ID NO 22
<211> LENGTH: 412
<212> TYPE: PRT
<213> ORGANISM: Artificial Sequence
<220> FEATURE:
<223> OTHER INFORMATION: protein nanoparticle sequence

<400> SEQUENCE: 22

| Glu | Ala | Lys | Pro | Ser | Gly | Ser | Val | Val | Glu | Gln | Ala | Glu | Gly | Val | Glu |
|---|---|---|---|---|---|---|---|---|---|---|---|---|---|---|---|
| 1 | | | | 5 | | | | | 10 | | | | | 15 | |

| Cys | Asp | Phe | Ser | Pro | Leu | Leu | Ser | Gly | Thr | Pro | Pro | Gln | Val | Tyr | Asn |
|---|---|---|---|---|---|---|---|---|---|---|---|---|---|---|---|
| | | | 20 | | | | | 25 | | | | | 30 | | |

| Phe | Lys | Arg | Leu | Val | Phe | Thr | Asn | Cys | Asn | Tyr | Asn | Leu | Thr | Lys | Leu |
|---|---|---|---|---|---|---|---|---|---|---|---|---|---|---|---|
| | | 35 | | | | | 40 | | | | | 45 | | | |

| Leu | Ser | Leu | Phe | Ser | Val | Asn | Asp | Phe | Thr | Cys | Ser | Gln | Ile | Ser | Pro |
|---|---|---|---|---|---|---|---|---|---|---|---|---|---|---|---|
| | 50 | | | | | 55 | | | | | 60 | | | | |

| Ala | Ala | Ile | Ala | Ser | Asn | Cys | Tyr | Ser | Ser | Leu | Ile | Leu | Asp | Tyr | Phe |
|---|---|---|---|---|---|---|---|---|---|---|---|---|---|---|---|
| 65 | | | | | 70 | | | | | 75 | | | | | 80 |

| Ser | Tyr | Pro | Leu | Ser | Met | Lys | Ser | Asp | Leu | Ser | Val | Ser | Ser | Ala | Gly |
|---|---|---|---|---|---|---|---|---|---|---|---|---|---|---|---|
| | | | | 85 | | | | | 90 | | | | | 95 | |

| Pro | Ile | Ser | Gln | Phe | Asn | Tyr | Lys | Gln | Ser | Phe | Ser | Asn | Pro | Thr | Cys |
|---|---|---|---|---|---|---|---|---|---|---|---|---|---|---|---|
| | | | 100 | | | | | 105 | | | | | 110 | | |

| Leu | Ile | Leu | Ala | Thr | Val | Pro | His | Asn | Leu | Thr | Thr | Ile | Thr | Lys | Pro |
|---|---|---|---|---|---|---|---|---|---|---|---|---|---|---|---|
| | | 115 | | | | | 120 | | | | | 125 | | | |

| Leu | Lys | Tyr | Ser | Tyr | Ile | Asn | Lys | Cys | Ser | Arg | Phe | Leu | Ser | Asp | Asp |
|---|---|---|---|---|---|---|---|---|---|---|---|---|---|---|---|
| | 130 | | | | | 135 | | | | | 140 | | | | |

| Arg | Thr | Glu | Val | Pro | Gln | Leu | Val | Asn | Ala | Asn | Gln | Tyr | Ser | Pro | Cys |

```
145                 150                 155                 160
Val Ser Ile Val Pro Ser Thr Val Trp Glu Asp Gly Asp Tyr Tyr Arg
                165                 170                 175

Lys Gln Leu Ser Pro Leu Glu Gly Gly Trp Leu Val Ala Ser Gly
                180                 185                 190

Ser Thr Val Ala Met Thr Glu Gln Leu Gln Met Gly Phe Gly Ile Thr
                195                 200                 205

Val Gln Tyr Gly Thr Asp Thr Asn Ser Val Cys Pro Lys Leu Glu Phe
        210                 215                 220

Ala Asn Asp Thr Lys Ile Ala Ser Gln Leu Gly Ser Gly Glu Ser Gln
225                 230                 235                 240

Val Arg Gln Gln Phe Ser Lys Asp Ile Glu Lys Leu Leu Asn Glu Gln
                245                 250                 255

Val Asn Lys Glu Met Gln Ser Ser Asn Leu Tyr Met Ser Met Ser Ser
                260                 265                 270

Trp Cys Tyr Thr His Ser Leu Asp Gly Ala Gly Leu Phe Leu Phe Asp
                275                 280                 285

His Ala Ala Glu Glu Tyr Glu His Ala Lys Lys Leu Ile Ile Phe Leu
        290                 295                 300

Asn Glu Asn Asn Val Pro Val Gln Leu Thr Ser Ile Ser Ala Pro Glu
305                 310                 315                 320

His Lys Phe Glu Gly Leu Thr Gln Ile Phe Gln Lys Ala Tyr Glu His
                325                 330                 335

Glu Gln His Ile Ser Glu Ser Ile Asn Asn Ile Val Asp His Ala Ile
                340                 345                 350

Lys Ser Lys Asp His Ala Thr Phe Asn Phe Leu Gln Trp Tyr Val Ala
                355                 360                 365

Glu Gln His Glu Glu Val Leu Phe Lys Asp Ile Leu Asp Lys Ile
        370                 375                 380

Glu Leu Ile Gly Asn Glu Asn His Gly Leu Tyr Leu Ala Asp Gln Tyr
385                 390                 395                 400

Val Lys Gly Ile Ala Lys Ser Arg Lys Ser Gly Ser
                405                 410

<210> SEQ ID NO 23
<211> LENGTH: 385
<212> TYPE: PRT
<213> ORGANISM: Artificial Sequence
<220> FEATURE:
<223> OTHER INFORMATION: protein nanoparticle sequence

<400> SEQUENCE: 23

Val Glu Cys Asp Phe Ser Pro Leu Leu Ser Gly Thr Pro Pro Gln Val
1               5                   10                  15

Tyr Asn Phe Lys Arg Leu Val Phe Thr Asn Cys Asn Tyr Asn Leu Thr
                20                  25                  30

Lys Leu Leu Ser Leu Phe Ser Val Asn Asp Phe Thr Cys Ser Gln Ile
            35                  40                  45

Ser Pro Ala Ala Ile Ala Ser Asn Cys Tyr Ser Ser Leu Ile Leu Asp
        50                  55                  60

Tyr Phe Ser Tyr Pro Leu Ser Met Lys Ser Asp Leu Ser Val Ser Ser
65                  70                  75                  80

Ala Gly Pro Ile Ser Gln Phe Asn Tyr Lys Gln Ser Phe Ser Asn Pro
                85                  90                  95

Thr Cys Leu Ile Leu Ala Thr Val Pro His Asn Leu Thr Thr Ile Thr
```

```
            100                 105                 110
Lys Pro Leu Lys Tyr Ser Tyr Ile Asn Lys Cys Ser Arg Phe Leu Ser
            115                 120                 125
Asp Asp Arg Thr Glu Val Pro Gln Leu Val Asn Ala Asn Gln Tyr Ser
            130                 135                 140
Pro Cys Val Ser Ile Val Pro Ser Thr Val Trp Glu Asp Gly Asp Tyr
145                 150                 155                 160
Tyr Arg Lys Gln Leu Ser Pro Leu Glu Gly Gly Trp Leu Val Ala
            165                 170                 175
Ser Gly Ser Thr Val Ala Met Thr Glu Gln Leu Gln Met Gly Phe Gly
            180                 185                 190
Ile Thr Val Gln Tyr Gly Thr Asp Thr Asn Ser Val Cys Pro Lys Leu
            195                 200                 205
Ser Gly Glu Ser Gln Val Arg Gln Gln Phe Ser Lys Asp Ile Glu Lys
            210                 215                 220
Leu Leu Asn Glu Gln Val Asn Lys Glu Met Gln Ser Ser Asn Leu Tyr
225                 230                 235                 240
Met Ser Met Ser Ser Trp Cys Tyr Thr His Ser Leu Asp Gly Ala Gly
            245                 250                 255
Leu Phe Leu Phe Asp His Ala Ala Glu Glu Tyr Glu His Ala Lys Lys
            260                 265                 270
Leu Ile Ile Phe Leu Asn Glu Asn Asn Val Pro Val Gln Leu Thr Ser
            275                 280                 285
Ile Ser Ala Pro Glu His Lys Phe Glu Gly Leu Thr Gln Ile Phe Gln
            290                 295                 300
Lys Ala Tyr Glu His Glu Gln His Ile Ser Glu Ser Ile Asn Asn Ile
305                 310                 315                 320
Val Asp His Ala Ile Lys Ser Lys Asp His Ala Thr Phe Asn Phe Leu
            325                 330                 335
Gln Trp Tyr Val Ala Glu Gln His Glu Glu Val Leu Phe Lys Asp
            340                 345                 350
Ile Leu Asp Lys Ile Glu Leu Ile Gly Asn Glu Asn His Gly Leu Tyr
            355                 360                 365
Leu Ala Asp Gln Tyr Val Lys Gly Ile Ala Lys Ser Arg Lys Ser Gly
            370                 375                 380
Ser
385

<210> SEQ ID NO 24
<211> LENGTH: 30
<212> TYPE: PRT
<213> ORGANISM: Artificial Sequence
<220> FEATURE:
<223> OTHER INFORMATION: Signal sequence

<400> SEQUENCE: 24

Met Asp Ser Lys Gly Ser Ser Gln Lys Gly Ser Arg Leu Leu Leu Leu
1               5                   10                  15
Leu Val Val Ser Asn Leu Leu Leu Pro Gln Gly Val Leu Ala
            20                  25                  30

<210> SEQ ID NO 25
<211> LENGTH: 24
<212> TYPE: PRT
<213> ORGANISM: Artificial Sequence
<220> FEATURE:
<223> OTHER INFORMATION: Signal Sequence
```

<400> SEQUENCE: 25

Met Pro Met Gly Ser Leu Gln Pro Leu Ala Thr Leu Tyr Leu Leu Gly
1               5                   10                  15

Met Leu Val Ala Ser Val Leu Ala
            20

<210> SEQ ID NO 26
<211> LENGTH: 5778
<212> TYPE: DNA
<213> ORGANISM: Artificial Sequence
<220> FEATURE:
<223> OTHER INFORMATION: protein nanoparticle sequence

<400> SEQUENCE: 26

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcagattgg | 240 |
| ctattggcca | ttgcatacgt | tgtatccata | tcataatatg | tacatttata | ttggctcatg | 300 |
| tccaacatta | ccgccatgtt | gacattgatt | attgactagt | tattaatagt | aatcaattac | 360 |
| gggaacttcc | atagcccata | tatggagttc | cgcgttacat | aacttacggg | aatttccaaa | 420 |
| cctggctgac | cgcccaacga | cccccgccca | ttgacgtcaa | taatgacgta | tgttcccata | 480 |
| gtaacgccaa | tagggaactt | ccattgacgt | caatgggtgg | agtatttacg | gtaaactgcc | 540 |
| cacttgggaa | tttccaagtg | tatcatatgc | caagtacgcc | ccctattgac | gtcaatgacg | 600 |
| gtaacttcca | taagcttgca | ttatgcccag | tacatgacct | tatgggaatt | tcctacttgg | 660 |
| cagtacatct | acgtattagt | catcgctatt | accatggtga | tgcggttttg | gcagtacatc | 720 |
| aatgggcgtg | gatagcggtt | tgactcacgg | gaacttccaa | gtctccaccc | cattgacgtc | 780 |
| aatgggagtt | tgttttgact | caccaaaatc | aYacgggaat | tcccaaaatg | tcgtaacaac | 840 |
| tccgccccat | tgacgcaaat | gggcggtagg | cgtgtacggt | gggaggtcta | tataagcaga | 900 |
| gctcgtttag | tgaaccgtca | gatcgcctgg | agacgccatc | cacgctgttt | tgacctccat | 960 |
| agaagacacc | gggaccgatc | cagcctccat | cggctcgcat | ctctccttca | cgcgcccgcc | 1020 |
| gccctacctg | aggccgccat | ccacgccggt | tgagtcgcgt | tctgccgcct | cccgcctgtg | 1080 |
| gtgcctcctg | aactgcgtcc | gccgtctagg | taagtttaaa | gctcaggtcg | agaccgggcc | 1140 |
| tttgtccggc | gctcccttgg | agcctaccta | gactcagccg | gctctccacg | ctttgcctga | 1200 |
| ccctgcttgc | tcaactctag | ttaacggtgg | agggcagtgt | agtctgagca | gtactcgttg | 1260 |
| ctgccgcgcg | cgccaccaga | cataatagct | gacagactaa | cagactgttc | ctttccatgg | 1320 |
| gtcttttctg | cagtcaccgt | cgtcgacacg | tgtgatcaga | tatcgcggcc | gctctagaga | 1380 |
| tatcgccacc | atggacagca | agggcagcag | ccagaagggc | agcagactgc | tgctgctgct | 1440 |
| ggtggtgagc | aacctgctgc | tgcctcaggg | cgtgctagcc | gaggccaagc | cctctgggag | 1500 |
| tgtggtcgag | caggctgaag | gagtggagtg | cgatttcagt | cctctgctgt | cagggacccc | 1560 |
| ccctcaggtg | tacaacttca | agcggctggt | ctttactaac | tgtaactaca | atctgaccaa | 1620 |
| gctgctgtca | ctgttcagcg | tgaatgactt | tacatgctcc | cagatcagcc | ccgcagccat | 1680 |
| tgctagtaac | tgttactcct | ctctgatcct | ggactacttc | tcatatccac | tgagtatgaa | 1740 |
| gagcgacctg | agcgtgagtt | cagccggccc | catcagccag | ttcaactata | aacagagctt | 1800 |

```
cagcaatcct acatgcctga ttctggctac tgtgccacat aatctgacta ccatcactaa    1860 gccctgaaa tactcctata ttaacaagtg cagccggttc ctgtccgacg atagaaccga     1920
agtgccacag ctggtcaacg ccaatcagta ctctccctgt gtgagtatcg tcccttcaac    1980
cgtgtgggaa gacggggatt actatagaaa acagctgagc cccctggagg gaggaggatg    2040
gctggtggca tccggatcta cagtcgccat gactgagcag ctgcagatgg ggttcggaat    2100
cacagtgcag tacggcacag acactaactc tgtctgtccc aagctggaat cgctaacga    2160 tactaagatc gcaagtcagc tgggatccgg agagagccag gtgaggcagc agttcagcaa    2220
ggacatcgag aagctgctga cgagcaggt gaacaaggag atgcagagca gcaacctgta     2280
catgagcatg agcagctggt gctacaccca gcctggac ggcgccggcc tgttcctgtt      2340
cgaccacgcc gccgaggagt acgagcacgc caagaagctg atcatcttcc tgaacgagaa    2400
caacgtgccc gtgcagctga ccagcatcag cgccccgag cacaagttcg agggcctgac    2460
ccagatcttc cagaaggcct acgagcacga gcagcacatc agcgagagca tcaacaacat    2520
cgtggaccac gccatcaaga gcaaggacca cgccaccttc aacttcctgc agtggtacgt    2580
ggccgagcag cacgaggagg aggtgctgtt caaggacatc ctggacaaga tcgagctgat    2640
cggcaacgag aaccacggcc tgtacctggc cgaccagtac gtgaagggca tcgccaagag    2700
caggaagagc ggatcctagc atcatcatca tcattagtct ggaagggcga attgatccag    2760
atctgctgtg ccttctagtt gccagccatc tgttgtttgc ccctcccccg tgccttcctt    2820
gaccctggaa ggtgccactc ccactgtcct ttcctaataa aatgaggaaa ttgcatcgca    2880
ttgtctgagt aggtgtcatt ctattctggg ggtgggtg gggcaggaca gcaaggggga      2940
ggattgggaa gacaatagca ggcatgctgg ggatgcggtg ggctctatgg gtacccaggt    3000
gctgaagaat tgacccggtt cctcctgggc cagaaagaag caggcacatc cccttctctg    3060
tgacacaccc tgtccacgcc cctggttctt agttccagcc ccactcatag gacactcata    3120
gctcaggagg gctccgcctt caatcccacc cgctaaagta cttggagcgg tctctcccctc   3180 cctcatcagc ccaccaaacc aaacctagcc tccaagagtg ggaagaaatt aaagcaagat    3240
aggctattaa gtgcagaggg agagaaaatg cctccaacat gtgaggaagt aatgagagaa    3300
atcatagaat tttaaggcca tgatttaagg ccatcatggc cttaatcttc cgcttcctcg    3360
ctcactgact cgctgcgctc ggtcgttcgg ctgcggcgag cggtatcagc tcactcaaag    3420
gcggtaatac ggttatccac agaatcaggg gataacgcag gaaagaacat gtgagcaaaa    3480
ggccagcaaa aggccaggaa ccgtaaaaag gccgcgttgc tggcgttttt ccataggctc    3540
cgcccccctg acgagcatca caaaaatcga cgctcaagtc agaggtggcg aaacccgaca    3600
ggactataaa gataccaggc gtttccccct ggaagctccc tcgtgcgctc tcctgttccg    3660
accctgccgc ttaccggata cctgtccgcc tttctccctt cgggaagcgt ggcgctttct    3720
catagctcac gctgtaggta tctcagttcg gtgtaggtcg ttcgctccaa gctgggctgt    3780
gtgcacgaac cccccgttca gcccgaccgc tgcgccttat ccggtaacta tcgtcttgag    3840
tccaacccgg taagacacga cttatcgcca ctggcagcag ccactggtaa caggattagc    3900
agagcgaggt atgtaggcgg tgctacagag ttcttgaagt ggtggcctaa ctacggctac    3960
actagaagaa cagtatttgg tatctgcgct ctgctgaagc cagttacctt cggaaaaaga    4020
gttggtagct cttgatccgg caaacaaacc accgctggta gcggtggttt ttttgtttgc    4080
aagcagcaga ttacgcgcag aaaaaaagga tctcaagaag atcctttgat cttttctacg    4140
gggtctgacg ctcagtggaa cgaaaactca cgttaaggga ttttggtcat gagattatca    4200
```

```
aaaaggatct tcacctagat ccttttaaat taaaaatgaa gttttaaatc aatctaaagt    4260
atatatgagt aaacttggtc tgacagttac caatgcttaa tcagtgaggc acctatctca    4320
gcgatctgtc tatttcgttc atccatagtt gcctgactcg ggggggggg gcgctgaggt     4380 ctgcctcgtg aagaaggtgt tgctgactca taccaggcct gaatcgcccc atcatccagc    4440
cagaaagtga gggagccacg gttgatgaga gctttgttgt aggtggacca gttggtgatt    4500
ttgaactttt gctttgccac ggaacggtct gcgttgtcgg aagatgcgt gatctgatcc     4560 ttcaactcag caaaagttcg atttattcaa caaagccgcc gtcccgtcaa gtcagcgtaa    4620
tgctctgcca gtgttacaac caattaacca attctgatta gaaaaactca tcgagcatca    4680
aatgaaactg caatttattc atatcaggat tatcaatacc atattttga aaaagccgtt     4740 tctgtaatga aggagaaaac tcaccgaggc agttccatag gatggcaaga tcctggtatc    4800
ggtctgcgat tccgactcgt ccaacatcaa tacaacctat taatttcccc tcgtcaaaaa    4860
taaggttatc aagtgagaaa tcaccatgag tgacgactga atccggtgag aatggcaaaa    4920
gcttatgcat ttctttccag acttgttcaa caggccagcc attacgctcg tcatcaaaat    4980
cactcgcatc aaccaaaccg ttattcattc gtgattgcgc ctgagcgaga cgaaatacgc    5040
gatcgctgtt aaaaggacaa ttacaaacag gaatcgaatg caaccggcgc aggaacactg    5100
ccagcgcatc aacaatattt tcacctgaat caggatattc ttctaatacc tggaatgctg    5160
ttttcccggg gatcgcagtg gtgagtaacc atgcatcatc aggagtacgg ataaaatgct    5220
tgatggtcgg aagaggcata aattccgtca gccagtttag tctgaccatc tcatctgtaa    5280
catcattggc aacgctacct ttgccatgtt tcagaaacaa ctctggcgca tcgggcttcc    5340
catacaatcg atagattgtc gcacctgatt gcccgacatt atcgcgagcc catttatacc    5400
catataaatc agcatccatg ttggaattta atcgcggcct cgagcaagac gtttcccgtt    5460
gaatatggct cataacaccc cttgtattac tgtttatgta agcagacagt tttattgttc    5520
atgatgatat attttatct tgtgcaatgt aacatcagag attttgagac acaacgtggc     5580 tttcccccc cccccattat tgaagcattt atcagggtta ttgtctcatg agcggataca    5640
tatttgaatg tatttagaaa aataaacaaa taggggttcc gcgcacattt ccccgaaaag    5700
tgccacctga cgtctaagaa accattatta tcatgacatt aacctataaa aataggcgta    5760
tcacgaggcc ctttcgtc                                                  5778
```

<210> SEQ ID NO 27
<211> LENGTH: 5696
<212> TYPE: DNA
<213> ORGANISM: Artificial Sequence
<220> FEATURE:
<223> OTHER INFORMATION: protein nanoparticle sequence

<400> SEQUENCE: 27

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
gggaacttcc atagcccata tatggagttc cgcgttacat aacttacggg aatttccaaa    420
```

```
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgcccatt gacgcaaatg gcggtaggc gtgtacggtg gaggtctat ataagcagag        900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga ccgggcct     1140
ttgtccggcg ctcccttgga gcctacctag actcagccgg ctctccacgc tttgcctgac   1200
cctgcttgct caactctagt aacggtgga gggcagtgta gtctgagcag tactcgttgc    1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tggacagcaa gggcagcagc cagaagggca gcagactgct gctgctgctg   1440
gtggtgagca acctgctgct gcctcagggc gtgctagccg tggagtgcga tttcagtcct   1500
ctgctgtcag ggaccccccc tcaggtgtac aacttcaagc ggctggtctt tactaactgt   1560
aactacaatc tgaccaagct gctgtcactg ttcagcgtga atgactttac atgctcccag   1620
atcagccccg cagccattgc tagtaactgt tactcctctc tgatcctgga ctacttctca   1680
tatccactga gtatgaagag cgacctgagc gtgagttcag ccggccccat cagccagttc   1740
aactataaac agagcttcag caatcctaca tgcctgattc tggctactgt gccacataat   1800
ctgactacca tcactaagcc cctgaaatac tcctatatta caagtgcag ccggttcctg     1860
tccgacgata gaaccgaagt gccacagctg gtcaacgcca atcagtactc tccctgtgtg   1920
agtatcgtcc cttcaaccgt gtgggaagac ggggattact atagaaaaca gctgagcccc   1980
ctggagggag aggatggct ggtggcatcc ggatctacag tcgccatgac tgagcagctg     2040
cagatggggt tcggaatcac agtgcagtac ggcacagaca ctaactctgt ctgtcccaag   2100
ctgtccggag agagccaggt gaggcagcag ttcagcaagg acatcgagaa gctgctgaac   2160
gagcaggtga acaaggagat gcagagcagc aacctgtaca tgagcatgag cagctggtgc   2220
tacacccaca gcctggacgg cgccggcctg ttcctgttcg accacgccgc cgaggagtac   2280
gagcacgcca agaagctgat catcttcctg aacgagaaca cgtgccccgt gcagctgacc   2340
agcatcagcg ccccgagca caagttcgag ggcctgaccc agatcttcca gaaggcctac    2400
gagcacgagc agcacatcag cgagagcatc aacaacatcg tggaccacgc catcaagagc   2460
aaggaccacg ccaccttcaa cttcctgcag tggtacgtgg ccgagcagca cgaggaggag   2520
gtgctgttca aggacatcct ggacaagatc gagctgatcg caacgagaa ccacggcctg    2580
tacctggccg accagtacgt gaagggcatc gccaagagca ggaagagcgg atcctagcat   2640
catcatcatc attagtctgg aagggcgaat tgatccagat ctgctgtgcc ttctagttgc   2700
cagccatctg ttgtttgccc ctcccccgtg ccttccttga ccctggaagg tgccactccc   2760
actgtccttt cctaataaaa tgaggaaatt gcatcgcatt gtctgagtag gtgtcattct   2820
```

```
attctgggggg gtggggtggg gcaggacagc aagggggagg attgggaaga caatagcagg    2880
catgctgggg atgcggtggg ctctatgggt acccaggtgc tgaagaattg acccggttcc    2940
tcctgggcca gaaagaagca ggcacatccc cttctctgtg acacaccctg tccacgcccc    3000
tggttcttag ttccagcccc actcatagga cactcatagc tcaggagggc tccgccttca    3060
atcccacccg ctaaagtact tggagcggtc tctccctccc tcatcagccc accaaaccaa    3120
acctagcctc caagagtggg aagaaattaa agcaagatag gctattaagt gcagagggag    3180
agaaaatgcc tccaacatgt gaggaagtaa tgagagaaat catagaattt taaggccatg    3240
atttaaggcc atcatggcct taatcttccg cttcctcgct cactgactcg ctgcgctcgg    3300
tcgttcggct gcggcgagcg gtatcagctc actcaaaggc ggtaatacgg ttatccacag    3360
aatcagggga taacgcagga agaaacatgt gagcaaaagg ccagcaaaag gccaggaacc    3420
gtaaaaaggc cgcgttgctg gcgttttcc ataggctccg ccccctgac gagcatcaca    3480 aaaatcgacg ctcaagtcag aggtggcgaa acccgacagg actataaaga taccaggcgt    3540
ttccccctgg aagctccctc gtgcgctctc ctgttccgac cctgccgctt accggatacc    3600
tgtccgcctt tctcccttcg ggaagcgtgg cgctttctca tagctcacgc tgtaggtatc    3660
tcagttcggt gtaggtcgtt cgctccaagc tgggctgtgt gcacgaaccc cccgttcagc    3720
ccgaccgctg cgccttatcc ggtaactatc gtcttgagtc caacccggta agacacgact    3780
tatcgccact ggcagcagcc actggtaaca ggattagcag agcgaggtat gtaggcggtg    3840
ctacagagtt cttgaagtgg tggcctaact acggctacac tagaagaaca gtatttggta    3900
tctgcgctct gctgaagcca gttaccttcg gaaaaagagt tggtagctct tgatccggca    3960
aacaaaccac cgctggtagc ggtggttttt tgtttgcaa gcagcagatt acgcgcagaa    4020
aaaaaggatc tcaagaagat cctttgatct tttctacggg gtctgacgct cagtggaacg    4080
aaaactcacg ttaagggatt ttggtcatga gattatcaaa aaggatcttc acctagatcc    4140
ttttaaatta aaaatgaagt tttaaatcaa tctaaagtat atatgagtaa acttggtctg    4200
acagttacca atgcttaatc agtgaggcac ctatctcagc gatctgtcta tttcgttcat    4260
ccatagttgc ctgactcggg gggggggggc gctgaggtct gcctcgtgaa gaaggtgttg    4320
ctgactcata ccaggcctga atcgccccat catccagcca gaaagtgagg gagccacggt    4380
tgatgagagc tttgttgtag gtggaccagt tggtgatttt gaacttttgc tttgccacgg    4440
aacggtctgc gttgtcggga agatgcgtga tctgatcctt caactcagca aaagttcgat    4500
ttattcaaca aagccgccgt cccgtcaagt cagcgtaatg ctctgccagt gttacaacca    4560
attaaccaat tctgattaga aaaactcatc gagcatcaaa tgaaactgca atttattcat    4620
atcaggatta tcaataccat attttgtgaaa agccgtttc tgtaatgaag gagaaaactc    4680
accgaggcag ttccatagga tggcaagatc ctggtatcgg tctgcgattc cgactcgtcc    4740
aacatcaata caacctatta atttcccctc gtcaaaaata aggttatcaa gtgagaaatc    4800
accatgagtg acgactgaat ccggtgagaa tggcaaaagc ttatgcattt ctttccagac    4860
ttgttcaaca ggccagccat tacgctcgtc atcaaaatca ctcgcatcaa ccaaaccgtt    4920
attcattcgt gattgcgcct gagcgagacg aaatacgcga tcgctgttaa aaggacaatt    4980
acaaacagga atcgaatgca accggcgcag gaacactgcc agcgcatcaa caatattttc    5040
acctgaatca ggatattctt ctaataccctg gaatgctgtt ttcccgggga tcgcagtggt    5100
gagtaaccat gcatcatcag gagtacggat aaaatgcttg atggtcggaa gaggcataaa    5160
```

-continued

```
ttccgtcagc cagtttagtc tgaccatctc atctgtaaca tcattggcaa cgctaccttt    5220
gccatgtttc agaaacaact ctggcgcatc gggcttccca tacaatcgat agattgtcgc    5280
acctgattgc ccgacattat cgcgagccca tttataccca tataaatcag catccatgtt    5340
ggaatttaat cgcggcctcg agcaagacgt ttcccgttga atatggctca taacacccct    5400
tgtattactg tttatgtaag cagacagttt tattgttcat gatgatatat ttttatcttg    5460
tgcaatgtaa catcagagat tttgagacac aacgtggctt tcccccccccc cccattattg    5520 aagcatttat cagggttatt gtctcatgag cggatacata tttgaatgta tttagaaaaa    5580
taaacaaata ggggttccgc gcacatttcc ccgaaaagtg ccacctgacg tctaagaaac    5640
cattattatc atgacattaa cctataaaaa taggcgtatc acgaggccct ttcgtc       5696
```

<210> SEQ ID NO 28
<211> LENGTH: 154
<212> TYPE: PRT
<213> ORGANISM: Artificial Sequence
<220> FEATURE:
<223> OTHER INFORMATION: protein nanoparticle sequence

<400> SEQUENCE: 28

```
Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150
```

<210> SEQ ID NO 29
<211> LENGTH: 265
<212> TYPE: PRT
<213> ORGANISM: Artificial Sequence
<220> FEATURE:
<223> OTHER INFORMATION: protein nanoparticle sequence

<400> SEQUENCE: 29

```
Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60
```

```
Val Lys Trp Gly Leu Arg Lys Ser Leu Pro Leu Ile Glu Leu Arg Ala
 65                  70                  75                  80

Thr Phe Thr Leu Asp Leu Trp Glu Leu Asp Asn Leu Glu Arg Gly Lys
                 85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
            115                 120                 125

Lys Gly Leu Leu Ser Phe Glu Glu Arg Lys Ile Glu Cys Gly Ser Thr
130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Ala Gly His Tyr Pro Leu Glu Lys
                180                 185                 190

Arg Val Glu Glu Cys Leu Arg Gly Gly Lys Ile Ile Thr Thr Pro Arg
            195                 200                 205

Ile Glu Asp Ala Leu Val Val Ser Glu Arg Gly Gly Asp Phe Lys Leu
210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265

<210> SEQ ID NO 30
<211> LENGTH: 501
<212> TYPE: PRT
<213> ORGANISM: Artificial Sequence
<220> FEATURE:
<223> OTHER INFORMATION: protein nanoparticle sequence

<400> SEQUENCE: 30

Met Glu Phe Leu Lys Arg Ser Phe Ala Pro Leu Thr Glu Lys Gln Trp
 1               5                  10                  15

Gln Glu Ile Asp Asn Arg Ala Arg Glu Ile Phe Lys Thr Gln Leu Tyr
                20                  25                  30

Gly Arg Lys Phe Val Asp Val Glu Gly Pro Tyr Gly Trp Glu Tyr Ala
             35                  40                  45

Ala His Pro Leu Gly Glu Val Glu Val Leu Ser Asp Glu Asn Glu Val
 50                  55                  60

Val Lys Trp Gly Leu Arg Lys Ser Leu Pro Leu Ile Glu Leu Arg Ala
 65                  70                  75                  80

Thr Phe Thr Leu Asp Leu Trp Glu Leu Asp Asn Leu Glu Arg Gly Lys
                 85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
            115                 120                 125

Lys Gly Leu Leu Ser Phe Glu Glu Arg Lys Ile Glu Cys Gly Ser Thr
130                 135                 140

Pro Lys Asp Leu Leu Glu Ala Ile Val Arg Ala Leu Ser Ile Phe Ser
145                 150                 155                 160
```

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Ser Gly Glu Ala Lys Pro Ser Gly
            260                 265                 270

Ser Val Val Glu Gln Ala Glu Gly Val Glu Cys Asp Phe Ser Pro Leu
        275                 280                 285

Leu Ser Gly Thr Pro Pro Gln Val Tyr Asn Phe Lys Arg Leu Val Phe
    290                 295                 300

Thr Asn Cys Asn Tyr Asn Leu Thr Lys Leu Leu Ser Leu Phe Ser Val
305                 310                 315                 320

Asn Asp Phe Thr Cys Ser Gln Ile Ser Pro Ala Ala Ile Ala Ser Asn
                325                 330                 335

Cys Tyr Ser Ser Leu Ile Leu Asp Tyr Phe Ser Tyr Pro Leu Ser Met
            340                 345                 350

Lys Ser Asp Leu Ser Val Ser Ser Ala Gly Pro Ile Ser Gln Phe Asn
        355                 360                 365

Tyr Lys Gln Ser Phe Ser Asn Pro Thr Cys Leu Ile Leu Ala Thr Val
    370                 375                 380

Pro His Asn Leu Thr Thr Ile Thr Lys Pro Leu Lys Tyr Ser Tyr Ile
385                 390                 395                 400

Asn Lys Cys Ser Arg Phe Leu Ser Asp Asp Arg Thr Glu Val Pro Gln
                405                 410                 415

Leu Val Asn Ala Asn Gln Tyr Ser Pro Cys Val Ser Ile Val Pro Ser
            420                 425                 430

Thr Val Trp Glu Asp Gly Asp Tyr Tyr Arg Lys Gln Leu Ser Pro Leu
        435                 440                 445

Glu Gly Gly Gly Trp Leu Val Ala Ser Gly Ser Thr Val Ala Met Thr
    450                 455                 460

Glu Gln Leu Gln Met Gly Phe Gly Ile Thr Val Gln Tyr Gly Thr Asp
465                 470                 475                 480

Thr Asn Ser Val Cys Pro Lys Leu Glu Phe Ala Asn Asp Thr Lys Ile
                485                 490                 495

Ala Ser Gln Leu Gly
            500

<210> SEQ ID NO 31
<211> LENGTH: 474
<212> TYPE: PRT
<213> ORGANISM: Artificial Sequence
<220> FEATURE:
<223> OTHER INFORMATION: protein nanoparticle sequence

<400> SEQUENCE: 31

Met Glu Phe Leu Lys Arg Ser Phe Ala Pro Leu Thr Glu Lys Gln Trp
1               5                   10                  15

```
Gln Glu Ile Asp Asn Arg Ala Arg Glu Ile Phe Lys Thr Gln Leu Tyr
             20                  25                  30

Gly Arg Lys Phe Val Asp Val Glu Gly Pro Tyr Gly Trp Glu Tyr Ala
         35                  40                  45

Ala His Pro Leu Gly Glu Val Glu Val Leu Ser Asp Glu Asn Glu Val
     50                  55                  60

Val Lys Trp Gly Leu Arg Lys Ser Leu Pro Leu Ile Glu Leu Arg Ala
 65                  70                  75                  80

Thr Phe Thr Leu Asp Leu Trp Glu Leu Asp Asn Leu Glu Arg Gly Lys
                 85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
            115                 120                 125

Lys Gly Leu Leu Ser Phe Glu Glu Arg Lys Ile Glu Cys Gly Ser Thr
130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Ser Gly Val Glu Cys Asp Phe Ser
            260                 265                 270

Pro Leu Leu Ser Gly Thr Pro Pro Gln Val Tyr Asn Phe Lys Arg Leu
        275                 280                 285

Val Phe Thr Asn Cys Asn Tyr Asn Leu Thr Lys Leu Leu Ser Leu Phe
    290                 295                 300

Ser Val Asn Asp Phe Thr Cys Ser Gln Ile Ser Pro Ala Ala Ile Ala
305                 310                 315                 320

Ser Asn Cys Tyr Ser Ser Leu Ile Leu Asp Tyr Phe Ser Tyr Pro Leu
                325                 330                 335

Ser Met Lys Ser Asp Leu Ser Val Ser Ser Ala Gly Pro Ile Ser Gln
            340                 345                 350

Phe Asn Tyr Lys Gln Ser Phe Ser Asn Pro Thr Cys Leu Ile Leu Ala
        355                 360                 365

Thr Val Pro His Asn Leu Thr Thr Ile Thr Lys Pro Leu Lys Tyr Ser
    370                 375                 380

Tyr Ile Asn Lys Cys Ser Arg Phe Leu Ser Asp Asp Arg Thr Glu Val
385                 390                 395                 400

Pro Gln Leu Val Asn Ala Asn Gln Tyr Ser Pro Cys Val Ser Ile Val
                405                 410                 415

Pro Ser Thr Val Trp Glu Asp Gly Asp Tyr Tyr Arg Lys Gln Leu Ser
            420                 425                 430
```

```
Pro Leu Glu Gly Gly Gly Trp Leu Val Ala Ser Ser Thr Val Ala
        435                 440                 445

Met Thr Glu Gln Leu Gln Met Gly Phe Gly Ile Thr Val Gln Tyr Gly
        450                 455                 460

Thr Asp Thr Asn Ser Val Cys Pro Lys Leu
465                 470

<210> SEQ ID NO 32
<211> LENGTH: 6030
<212> TYPE: DNA
<213> ORGANISM: Artificial Sequence
<220> FEATURE:
<223> OTHER INFORMATION: protein nanoparticle sequence

<400> SEQUENCE: 32
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
gggaacttcc atagcccata tatggagttc cgcgttacat aacttacggg aatttccaaa     420
cctggctgac cgcccaacga ccccgccca ttgacgtcaa taatgacgta tgttcccata     480
gtaacgccaa tagggaactt ccattgacgt caatgggtgg agtatttacg gtaaactgcc     540
cacttgggaa ttccaagtg tatcatatgc caagtacgcc ccctattgac gtcaatgacg     600
ggaacttcca taagcttgca ttatgcccag tacatgacct tatgggaatt tcctacttgg     660
cagtacatct acgtattagt catcgctatt accatggtga tgcggttttg gcagtacatc     720
aatgggcgtg gatagcggtt tgactcacgg gaacttccaa gtctccaccc cattgacgtc     780
aatgggagtt tgttttgact caccaaaatc aacgggaatt cccaaaatgt cgtaacaact     840
ccgccccatt gacgcaaatg ggcggtaggc gtgtacggtg ggaggtctat ataagcagag     900
ctcgtttagt gaaccgtcag atcgcctgga cgccatcc acgctgtttt gacctccata     960
gaagacaccg ggaccgatcc agcctccatc ggctcgcatc tctccttcac gcgcccgccg    1020
ccctacctga ggccgccatc cacgccggtt gagtcgcgtt ctgccgcctc ccgcctgtgg    1080
tgcctcctga actgcgtccg ccgtctaggt aagtttaaag ctcaggtcga ccgggcct      1140 ttgtccggcg ctcccttgga gcctacctag actcagccgg ctctccacgc tttgcctgac    1200
cctgcttgct caactctagt aacggtgga gggcagtgta gtctgagcag tactcgttgc     1260
tgccgcgcgc gccaccagac ataatagctg acagactaac agactgttcc tttccatggg    1320
tcttttctgc agtcaccgtc gtcgacacgt gtgatcagat atcgcggccg ctctagacac    1380
catgcccatg gcagcctgc agccctggc caccctgtac ctgctgggca tgctggtggc     1440
tagcgtgctg gccatggagt tcctgaagag gagcttcgcc cctctgaccg agaagcagtg    1500
gcaggagatc gacaacaggg ccagggagat cttcaagacc cagctgtacg gcaggaagtt    1560
cgtggacgtg gagggcccct acggctggga gtacgccgcc cacccctggg cgaggtgga    1620 ggtgctgagc gacgagaacg aggtggtgaa gtggggcctg aggaagagcc tgccctgat    1680 cgagctgagg gccaccttca ccctggacct gtggagctg acaacctgg agaggggcaa     1740 gcccaacgtg gacctgagca gcctggagga gaccgtgagg aaggtggccg agttcgagga    1800
```

```
cgaggtgatc ttcaggggct gcgagaagag cggcgtgaag ggcctgctga gcttcgagga    1860
gaggaagatc gagtgcggca gcaccccaa ggacctgctg gaggccatcg tgagggccct     1920
gagcatcttc agcaaggacg gcatcgaggg ccctacacc ctggtgatca acaccgacag     1980
gtggatcaac ttcctgaagg aggaggccgg ccactacccc ctggagaaga gggtggagga    2040
gtgcctgagg ggcggcaaga tcatcaccac ccccaggatc gaggacgccc tggtggtgag    2100
cgagaggggc ggcgacttca gctgatcct gggccaggac ctgagcatcg ctacgagga     2160
cagggagaag gacgccgtga ggctgttcat caccgagacc ttcaccttcc aggtggtgaa    2220
ccccgaggcc ctgatcctgc tgaagtccgg agaggccaag ccctctggga gtgtggtcga    2280
gcaggctgaa ggagtggagt cgatttcag tcctctgctg tcaggaccc cccctcaggt     2340
gtacaacttc aagcggctgg tctttactaa ctgtaactac aatctgacca agctgctgtc    2400
actgttcagc gtgaatgact ttacatgctc ccagatcagc cccgcagcca ttgctagtaa    2460
ctgttactcc tctctgatcc tggactactt ctcatatcca ctgagtatga agagcgacct    2520
gagcgtgagt tcagccggcc ccatcagcca gttcaactat aaacagagct tcagcaatcc    2580
tacatgcctg attctggcta ctgtgccaca taatctgact accatcacta agcccctgaa    2640
atactcctat attaacaagt gcagccggtt cctgtccgac gatagaaccg aagtgccaca    2700
gctggtcaac gccaatcagt actctccctg tgtgagtatc gtcccttcaa ccgtgtggga    2760
agacggggat tactatagaa acagctgag cccctggag ggaggaggat ggctggtggc      2820
atccggatct acagtcgcca tgactgagca gctgcagatg gggttcggaa tcacagtgca    2880
gtacggcaca gacactaact ctgtctgtcc caagctggaa ttcgctaacg atactaagat    2940
cgcaagtcag ctgggatgat gaggatccca tcatcatcat catcattagt ctggaagggc    3000
gaattgatcc agatctgctg tgccttctag ttgccagcca tctgttgttt gccctcccc    3060
cgtgccttcc ttgaccctgg aaggtgccac tcccactgtc cttcctaat aaaatgagga     3120
aattgcatcg cattgtctga gtaggtgtca ttctattctg gggggtgggg tgggcagga    3180
cagcaagggg gaggattggg aagacaatag caggcatgct ggggatgcgg tgggctctat    3240
gggtacccag gtgctgaaga attgacccgg ttcctcctgg gccagaaaga agcaggcaca    3300
tccccttctc tgtgacacac cctgtccacg cccctggttc ttagttccag ccccactcat    3360
aggacactca tagctcagga gggctccgcc ttcaatccca cccgctaaag tacttggagc    3420
ggtctctccc tccctcatca gcccaccaaa ccaaacctag cctccaagag tgggaagaaa    3480
ttaaagcaag ataggctatt aagtgcagag ggagagaaaa tgcctccaac atgtgaggaa    3540
gtaatgagag aaatcataga attttaaggc catgatttaa ggccatcatg gccttaatct    3600
tccgcttcct cgctcactga ctcgctgcgc tcggtcgttc ggctgcggcg agcggtatca    3660
gctcactcaa aggcggtaat acggttatcc acagaatcag gggataacgc aggaaagaac    3720
atgtgagcaa aaggccagca aaaggccagg aaccgtaaaa aggccgcgtt gctggcgttt    3780
ttccataggc tccgcccccc tgacgagcat cacaaaaatc gacgctcaag tcagaggtgg    3840
cgaaacccga caggactata aagataccag gcgtttcccc ctggaagctc cctcgtgcgc    3900
tctcctgttc cgaccctgcc gcttaccgga tacctgtccg cctttctccc ttcgggaagc    3960
gtggcgcttt ctcatagctc acgctgtagg tatctcagtt cggtgtaggt cgttcgctcc    4020
aagctgggct gtgtgcacga accccccgtt cagcccgacc gctgcgcctt atccggtaac    4080
tatcgtcttg agtccaaccc ggtaagacac gacttatcgc cactggcagc agccactggt    4140
aacaggatta gcagagcgag gtatgtaggc ggtgctacag agttcttgaa gtggtggcct    4200
```

```
aactacggct acactagaag aacagtattt ggtatctgcg ctctgctgaa gccagttacc   4260
ttcggaaaaa gagttggtag ctcttgatcc ggcaaacaaa ccaccgctgg tagcggtggt   4320
ttttttgttt gcaagcagca gattacgcgc agaaaaaaag gatctcaaga agatcctttg   4380
atcttttcta cggggtctga cgctcagtgg aacgaaaact cacgttaagg gattttggtc   4440
atgagattat caaaaaggat cttcacctag atccttttaa attaaaaatg aagttttaaa   4500
tcaatctaaa gtatatatga gtaaacttgg tctgacagtt accaatgctt aatcagtgag   4560
gcacctatct cagcgatctg tctatttcgt tcatccatag ttgcctgact cggggggggg   4620
gggcgctgag gtctgcctcg tgaagaaggt gttgctgact cataccaggc ctgaatcgcc   4680
ccatcatcca gccagaaagt gagggagcca cggttgatga gctttgtt gtaggtggac    4740 cagttggtga ttttgaactt ttgctttgcc acggaacggt ctgcgttgtc gggaagatgc   4800
gtgatctgat ccttcaactc agcaaaagtt cgatttattc aacaaagccg ccgtcccgtc   4860
aagtcagcgt aatgctctgc cagtgttaca accaattaac caattctgat tagaaaaact   4920
catcgagcat caaatgaaac tgcaatttat tcatatcagg attatcaata ccatattttt   4980
gaaaaagccg tttctgtaat gaaggagaaa actcaccgag gcagttccat aggatggcaa   5040
gatcctggta tcggtctgcg attccgactc gtccaacatc aatacaacct attaatttcc   5100
cctcgtcaaa aataaggtta tcaagtgaga atcaccatg agtgacgact gaatccggtg    5160
agaatggcaa aagcttatgc atttctttcc agacttgttc aacaggccag ccattacgct   5220
cgtcatcaaa atcactcgca tcaaccaaac cgttattcat tcgtgattgc gcctgagcga   5280
gacgaaatac gcgatcgctg ttaaaaggac aattacaaac aggaatcgaa tgcaaccggc   5340
gcaggaacac tgccagcgca tcaacaatat tttcacctga atcaggatat tcttctaata   5400 cctgaatgc tgttttcccg gggatcgcag tggtgagtaa ccatgcatca tcaggagtac    5460
ggataaaatg cttgatggtc ggaagaggca taaattccgt cagccagttt agtctgacca   5520
tctcatctgt aacatcattg gcaacgctac ctttgccatg tttcagaaac aactctggcg   5580
catcgggctt cccatacaat cgatagattg tcgcacctga ttgcccgaca ttatcgcgag   5640
cccatttata cccatataaa tcagcatcca tgttggaatt taatcgcggc ctcgagcaag   5700
acgtttcccg ttgaatatgg ctcataacac cccttgtatt actgtttatg taagcagaca   5760
gttttattgt tcatgatgat atattttat cttgtgcaat gtaacatcag agattttgag    5820
acacaacgtg ctttccccc cccccccatt attgaagcat ttatcagggt tattgtctca    5880
tgagcggata catatttgaa tgtatttaga aaaataaaca aataggggtt ccgcgcacat   5940
ttccccgaaa agtgccacct gacgtctaag aaaccattat tatcatgaca ttaacctata   6000
aaaataggcg tatcacgagg ccctttcgtc                                    6030
```

<210> SEQ ID NO 33
<211> LENGTH: 5949
<212> TYPE: DNA
<213> ORGANISM: Artificial Sequence
<220> FEATURE:
<223> OTHER INFORMATION: protein nanoparticle sequence

<400> SEQUENCE: 33

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
```

```
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
gtaacttcca taagcttgca ttatgcccag tacatgacct tatgggaatt cctacttgg     660 cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg ggcggtaggc gtgtacggtg gaggtctat ataagcagag      900 ctcgtttagt gaaccgtcag atcgcctgga gacgccatcc acgctgtttt gacctccata    960
gaagacaccg ggaccgatcc agcctccatc ggctcgcatc tctccttcac gcgcccgccg    1020
ccctacctga ggccgccatc cacgccggtt gagtcgcgtt ctgccgcctc ccgcctgtgg    1080
tgcctcctga actgcgtccg ccgtctaggt aagtttaaag ctcaggtcga ccgggcct      1140 ttgtccggcg ctcccttgga gcctacctag actcagccgg ctctccacgc tttgcctgac    1200
cctgcttgct caactctagt aacggtgga gggcagtgta gtctgagcag tactcgttgc      1260
tgccgcgcgc gccaccagac ataatagctg acagactaac agactgttcc tttccatggg    1320
tcttttctgc agtcaccgtc gtcgacacgt gtgatcagat atcgcggccg ctctagacac    1380
catgcccatg gcagcctgc agccctggc caccctgtac ctgctgggca tgctggtggc       1440
tagcgtgctg gccatggagt tcctgaagag gagcttcgcc cctctgaccg agaagcagtg    1500
gcaggagatc gacaacaggg ccaggagat cttcaagacc cagctgtacg caggaagtt       1560 cgtggacgtg gagggcccct acggctggga gtacgccgcc caccccctgg gcgaggtgga    1620
ggtgctgagc gacgagaacg aggtggtgaa gtggggcctg aggaagagcc tgccctgat     1680 cgagctgagg gccaccttca ccctggacct gtgggagctg acaacctgg agaggggcaa      1740 gcccaacgtg gacctgagca gcctggagga gaccgtgagg aaggtggccg agttcgagga    1800
cgaggtgatc ttcagggct gcgagaagag cggcgtgaag ggcctgctga gcttcgagga      1860
gaggaagatc gagtgcggca gcaccccaa ggacctgctg gaggccatcg tgagggccct      1920
gagcatcttc agcaaggacg gcatcgaggg cccctacacc ctggtgatca acaccgacag    1980
gtggatcaac ttcctgaagg aggaggccgg ccactacccc ctggagaaga ggtggagga     2040 gtgcctgagg ggcggcaaga tcatcaccac ccccaggatc gaggacgccc tggtggtgag    2100
cgagaggggc ggcgacttca gctgatcct gggccaggac ctgagcatcg ctacgagga       2160 cagggagaag gacgccgtga ggctgttcat caccgagacc ttcaccttcc aggtggtgaa    2220
ccccgaggcc ctgatcctgc tgaagtccgg agtggagtgc gatttcagtc ctctgctgtc    2280
agggaccccc cctcaggtgt acaacttcaa gcggctggtc tttactaact gtaactacaa    2340
tctgaccaag ctgctgtcac tgttcagcgt gaatgacttt acatgctccc agatcagccc    2400
cgcagccatt gctagtaact gttactcctc tctgatcctg gactacttct catatccact    2460
gagtatgaag agcgacctga gcgtgagttc agccggcccc atcagccagt tcaactataa    2520
acagagcttc agcaatccta catgcctgat tctggctact gtgccacata atctgactac    2580
```

```
catcactaag cccctgaaat actcctatat taacaagtgc agccggttcc tgtccgacga    2640
tagaaccgaa gtgccacagc tggtcaacgc caatcagtac tctccctgtg tgagtatcgt    2700
cccttcaacc gtgtgggaag acggggatta ctatagaaaa cagctgagcc ccctggaggg    2760
aggaggatgg ctggtggcat ccggatctac agtcgccatg actgagcagc tgcagatggg    2820
gttcggaatc acagtgcagt acggcacaga cactaactct gtctgtccca agctgtgatg    2880
aggatcccat catcatcatc atcattagtc tggaagggcg aattgatcca gatctgctgt    2940
gccttctagt tgccagccat ctgttgtttg cccctccccc gtgccttcct tgaccctgga    3000
aggtgccact cccactgtcc tttcctaata aaatgaggaa attgcatcgc attgtctgag    3060
taggtgtcat tctattctgg ggggtggggt ggggcaggac agcaaggggg aggattggga    3120
agacaatagc aggcatgctg gggatgcggt gggctctatg ggtacccagg tgctgaagaa    3180
ttgacccggt tcctcctggg ccagaaagaa gcaggcacat cccttctct gtgacacacc    3240 ctgtccacgc ccctggttct tagttccagc cccactcata ggacactcat agctcaggag    3300
ggctccgcct tcaatcccac ccgctaaagt acttggagcg gtctctccct ccctcatcag    3360
cccaccaaac caaacctagc ctccaagagt gggaagaaat taaagcaaga taggctatta    3420
agtgcagagg gagagaaaat gcctccaaca tgtgaggaag taatgagaga aatcatagaa    3480
ttttaaggcc atgatttaag gccatcatgg ccttaatctt ccgcttcctc gctcactgac    3540
tcgctgcgct cggtcgttcg gctgcggcga gcggtatcag ctcactcaaa ggcggtaata    3600
cggttatcca cagaatcagg ggataacgca ggaaagaaca tgtgagcaaa aggccagcaa    3660
aaggccagga accgtaaaaa ggccgcgttg ctggcgtttt tccataggct ccgcccccct    3720
gacgagcatc acaaaaatcg acgctcaagt cagaggtggc gaaacccgac aggactataa    3780
agataccagg cgtttccccc tggaagctcc ctcgtgcgct ctcctgttcc gaccctgccg    3840
cttaccggat acctgtccgc ctttctccct tcgggaagcg tggcgctttc tcatagctca    3900
cgctgtaggt atctcagttc ggtgtaggtc gttcgctcca agctgggctg tgtgcacgaa    3960
ccccccgttc agcccgaccg ctgcgcctta tccggtaact atcgtcttga gtccaacccg    4020
gtaagacacg acttatcgcc actggcagca gccactggta acaggattag cagagcgagg    4080
tatgtaggcg gtgctacaga gttcttgaag tggtggccta actacggcta cactagaaga    4140
acagtatttg gtatctgcgc tctgctgaag ccagttacct tcggaaaaag agttggtagc    4200
tcttgatccg gcaaacaaac caccgctggt agcggtggtt tttttgtttg caagcagcag    4260
attacgcgca gaaaaaaagg atctcaagaa gatcctttga tcttttctac ggggtctgac    4320
gctcagtgga acgaaaactc acgttaaggg attttggtca tgagattatc aaaaaggatc    4380
ttcacctaga tccttttaaa ttaaaaatga agttttaaat caatctaaag tatatatgag    4440
taaacttggt ctgacagtta ccaatgctta atcagtgagg cacctatctc agcgatctgt    4500
ctatttcgtt catccatagt tgcctgactc ccccggggggg ggcgctgagg tctgcctcgt    4560
gaagaaggtg ttgctgactc ataccaggcc tgaatcgccc catcatccag ccagaaagtg    4620
agggagccac ggttgatgag agctttgttt taggtggacc agttggtgat tttgaacttt    4680
tgctttgcca cggaacggtc tgcgttgtcg ggaagatgcg tgatctgatc cttcaactca    4740
gcaaaagttc gatttattca acaaagccgc cgtcccgtca agtcagcgta atgctctgcc    4800
agtgttacaa ccaattaacc aattctgatt agaaaaactc atcgagcatc aaatgaaact    4860
gcaatttatt catatcagga ttatcaatac catatttttg aaaaagccgt ttctgtaatg    4920
```

```
aaggagaaaa ctcaccgagg cagttccata ggatggcaag atcctggtat cggtctgcga    4980
ttccgactcg tccaacatca atacaaccta ttaatttccc ctcgtcaaaa ataaggttat    5040
caagtgagaa atcaccatga gtgacgactg aatccggtga gaatggcaaa agcttatgca    5100
tttctttcca gacttgttca acaggccagc cattacgctc gtcatcaaaa tcactcgcat    5160
caaccaaacc gttattcatt cgtgattgcg cctgagcgag acgaaatacg cgatcgctgt    5220
taaaaggaca attacaaaca ggaatcgaat gcaaccggcg caggaacact gccagcgcat    5280
caacaatatt ttcacctgaa tcaggatatt cttctaatac ctggaatgct gttttcccgg    5340
ggatcgcagt ggtgagtaac catgcatcat caggagtacg gataaaatgc ttgatggtcg    5400
gaagaggcat aaattccgtc agccagttta gtctgaccat ctcatctgta acatcattgg    5460
caacgctacc tttgccatgt ttcagaaaca actctggcgc atcgggcttc ccatacaatc    5520
gatagattgt cgcacctgat tgcccgacat tatcgcgagc ccatttatac ccatataaat    5580
cagcatccat gttggaattt aatcgcggcc tcgagcaaga cgtttcccgt tgaatatggc    5640
tcataacacc ccttgtatta ctgtttatgt aagcagacag ttttattgtt catgatgata    5700
tatttttatc ttgtgcaatg taacatcaga gattttgaga cacaacgtgg ctttccccc    5760 cccccccatta ttgaagcatt tatcagggtt attgtctcat gagcggatac atatttgaat    5820
gtatttagaa aaataaacaa ataggggttc cgcgcacatt tccccgaaaa gtgccacctg    5880
acgtctaaga aaccattatt atcatgacat taacctataa aaataggcgt atcacgaggc    5940
cctttcgtc                                                           5949
```

<210> SEQ ID NO 34
<211> LENGTH: 265
<212> TYPE: PRT
<213> ORGANISM: Artificial Sequence
<220> FEATURE:
<223> OTHER INFORMATION: protein nanoparticle sequence

<400> SEQUENCE: 34

```
Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175
```

```
Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
            245                 250                 255

Pro Glu Ala Leu Ile Leu Leu Lys Phe
        260                 265

<210> SEQ ID NO 35
<211> LENGTH: 381
<212> TYPE: DNA
<213> ORGANISM: Homo Sapiens

<400> SEQUENCE: 35
caggtgcagc tggtgcagtc tggggctgag gtgaagaagc ctgggtcctc ggtgaaggtc      60
tcctgcaagg cttctggagg caccttcagc atctatgcta tcagctgggt gcgacaggcc     120
cctggacaag gcttgagtg gatgggaggg atcatcccta tctttggtac agcaaactac     180
gcacagaagt tccagggcag agtcacgatt accgcggaca aatccacgag cacagcctac     240
atggagctga gcagcctgag atctgaggac acggccgtgt attactgtgc gagagagggg     300
ggccaccagg gatattgtag tggtggtagc tgctacgact ttgactactg gggccaggga     360
accctggtca ccgtctcctc a                                              381

<210> SEQ ID NO 36
<211> LENGTH: 127
<212> TYPE: PRT
<213> ORGANISM: Homo Sapiens

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ile Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Glu Gly Gly His Gln Gly Tyr Cys Ser Gly Gly Ser Cys Tyr
        100                 105                 110

Asp Phe Asp Tyr Trp Gly Gln Gly Thr Leu Val Thr Val Ser Ser
    115                 120                 125

<210> SEQ ID NO 37
<211> LENGTH: 333
<212> TYPE: DNA
<213> ORGANISM: Homo Sapiens

<400> SEQUENCE: 37
```

```
gatgttgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccgggatcc ctgacaggtt cagtggcagt ggatcaggca cagattttac actgaaaatc   240
agcagagtgg aggctgagga tgttggggtt tattattgca tgcaagctct acaaactcct   300
gcgttcggcg agggaccaa gctggagatc aaa                                  333
```

<210> SEQ ID NO 38
<211> LENGTH: 111
<212> TYPE: PRT
<213> ORGANISM: Homo Sapiens

<400> SEQUENCE: 38

```
Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Pro Ala Phe Gly Gly Gly Thr Lys Leu Glu Ile Lys
            100                 105                 110
```

<210> SEQ ID NO 39
<211> LENGTH: 378
<212> TYPE: DNA
<213> ORGANISM: Homo Sapiens

<400> SEQUENCE: 39

```
cagctgcagc tgcaggagtc gggcccagga ctggtgaagc cttcggagac cctgtccctc    60
acctgcactg tctctggtgg ctccatcagc agtagtagtt actactgggg ctggatccgc   120
cagcccccag ggaaggggct ggagtggatt gggagtatct attatagtgg gagcacctac   180
tacaacccgt ccctcaagag tcgagtcacc atatccgtag acacgtccaa gaaccagttc   240
tccctgaagc tgagctctgt gaccgccgca gacacggctg tgtattactg tgcgagcctc   300
ttaaggcccc tgatttattg tagtggtggt agctgcaccg actactgggg ccagggaacc   360
ctggtcaccg tctcctca                                                  378
```

<210> SEQ ID NO 40
<211> LENGTH: 126
<212> TYPE: PRT
<213> ORGANISM: Homo Sapiens

<400> SEQUENCE: 40

```
Gln Leu Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Ser
            20                  25                  30
Ser Tyr Tyr Trp Gly Trp Ile Arg Gln Pro Pro Gly Lys Gly Leu Glu
```

```
                35                  40                  45
Trp Ile Gly Ser Ile Tyr Tyr Ser Gly Ser Thr Tyr Tyr Asn Pro Ser
         50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Ser Leu Leu Arg Pro Leu Ile Tyr Cys Ser Gly Gly Ser Cys
                100                 105                 110

Thr Asp Tyr Trp Gly Gln Gly Thr Leu Val Thr Val Ser Ser
            115                 120                 125

<210> SEQ ID NO 41
<211> LENGTH: 330
<212> TYPE: DNA
<213> ORGANISM: Homo Sapiens

<400> SEQUENCE: 41
cagtctgccc tgactcagcc tgcctccgtg tctgggtctc ctggacagtc gatcaccatc      60
tcctgcactg gaaccagcag tgacgttggt ggttataact atgtctcctg gtgccaacag     120
cacccaggca aagcccccaa actcatgatt tatgaggtca gtaatcggcc ctcaggggtt     180
tctaatcgct tctctggctc caagtctggc aacacggcct ccctgaccat ctctgggctc     240
caggctgagg acgaggctga ttattactgc agctcatata caagcaacat cactcttgtc     300
ttcggaactg ggaccaaggt caccgtccta                                       330

<210> SEQ ID NO 42
<211> LENGTH: 110
<212> TYPE: PRT
<213> ORGANISM: Homo Sapiens

<400> SEQUENCE: 42

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
                 20                  25                  30

Asn Tyr Val Ser Trp Cys Gln Gln His Pro Gly Lys Ala Pro Lys Leu
             35                  40                  45

Met Ile Tyr Glu Val Ser Asn Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Asn
                 85                  90                  95

Ile Thr Leu Val Phe Gly Thr Gly Thr Lys Val Thr Val Leu
                100                 105                 110

<210> SEQ ID NO 43
<211> LENGTH: 366
<212> TYPE: DNA
<213> ORGANISM: Homo Sapiens

<400> SEQUENCE: 43
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtagtac catatactac     180
```

```
gcagactctg tgaagggccg attcaccatc tccagggaca acgccaagaa ctcactgtat    240
ctgcaaatga acagcctgag agccgaggac acggccgtgt attactgtgc gagagtaggg    300
ttaggcagtg gctggtacga ctggttcgac ccctggggcc agggaaccct ggtcaccgtc    360
tcctca                                                               366
```

<210> SEQ ID NO 44
<211> LENGTH: 122
<212> TYPE: PRT
<213> ORGANISM: Homo Sapiens

<400> SEQUENCE: 44

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Gly Ser Gly Trp Tyr Asp Trp Phe Asp Pro Trp
            100                 105                 110

Gly Gln Gly Thr Leu Val Thr Val Ser Ser
        115                 120

<210> SEQ ID NO 45
<211> LENGTH: 334
<212> TYPE: DNA
<213> ORGANISM: Homo Sapiens

<400> SEQUENCE: 45

```
cagtctgccc tgactcagcc gccctcagtg tctggggccc cagggcagag ggtcaccatc     60
tcctgcactg ggagcagctc caacatcggg gcaagttatg atgtacactg gtaccagcac    120
cttccaggaa cagcccccaa actcctcatc tatggtaaca ccaatcggcc ctcaggggtc    180
cctgaccgat tctctggctc caagtctggc acctcagcct ccctggccat cactgggctc    240
caggctgagg atgaggctga ttattactgc cagtcctatg acagcagcct gagtggtgtg    300
gtattcagcg agggaccaa gctgaccgtc ctag                                  334
```

<210> SEQ ID NO 46
<211> LENGTH: 111
<212> TYPE: PRT
<213> ORGANISM: Homo Sapiens

<400> SEQUENCE: 46

Gln Ser Ala Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Ser
            20                  25                  30

Tyr Asp Val His Trp Tyr Gln His Leu Pro Gly Thr Ala Pro Lys Leu
        35                  40                  45

Leu Ile Tyr Gly Asn Thr Asn Arg Pro Ser Gly Val Pro Asp Arg Phe

```
                50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Val Val Phe Ser Gly Gly Thr Lys Leu Thr Val Leu
                100                 105                 110

<210> SEQ ID NO 47
<211> LENGTH: 366
<212> TYPE: DNA
<213> ORGANISM: Homo Sapiens

<400> SEQUENCE: 47
caggtgcagc tggtgcagtc tggggctgag gtgaagaagc ctgggtcctc ggtgaaggtc      60
tcctgcaagg cttctggagg caccttcagc acctatgctc tcagctgggt gcgacaggcc    120
cctggacaag gcttgagtg gatgggaggg atcatccctatctttggtac agcaaactac      180
```

```
cctggacaag gcttgagtg gatgggaggg atcatcccta tctttggtac agcaaactac    180
gcacagaagt tccagggcag agtcacgatt accgcggacg aatccacgag cacggcctac    240
atggagttga acagcctgag atctgaggac acggccgtgt attactgtgc gagaggaagc    300
cggagcagct cttccgctga atacttccag cactggggcc agggcaccct ggtcaccgtc    360
tcctca                                                              366

<210> SEQ ID NO 48
<211> LENGTH: 122
<212> TYPE: PRT
<213> ORGANISM: Homo Sapiens

<400> SEQUENCE: 48

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Thr Tyr
                 20                  25                  30

Ala Leu Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Asn Ser Leu Arg Ser Glu Asp Thr Ala Val Tyr Tyr Cys
                 85                  90                  95

Ala Arg Gly Ser Arg Ser Ser Ser Ala Glu Tyr Phe Gln His Trp
                100                 105                 110

Gly Gln Gly Thr Leu Val Thr Val Ser Ser
            115                 120

<210> SEQ ID NO 49
<211> LENGTH: 337
<212> TYPE: DNA
<213> ORGANISM: Homo Sapiens

<400> SEQUENCE: 49
cagtctgccc tgactcagcc tcgctcagtg tccgggtctc ctggacagtc agtcaccatc     60
tcctgcactg gaaccagcag tgatgttggt ggttataact atgtctcctg gtaccaacag    120
cacccaggca aagcccccaa actcatgatt tatgatgtca gtaagcggcc ctcaggggtc    180
```

```
cctgatcgct tctctggctc caagtctggc aacacggcct ccctgaccat ctctgggctc    240
caggctgagg atgaggctga ttattactgc tgctcatatg caggcagcta cactttagaa    300
gtggtattcg gcggagggac caagctgacc gtcctag                             337
```

<210> SEQ ID NO 50
<211> LENGTH: 112
<212> TYPE: PRT
<213> ORGANISM: Homo Sapiens

<400> SEQUENCE: 50

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Leu Glu Val Val Phe Gly Gly Gly Thr Lys Leu Thr Val Leu
            100                 105                 110
```

<210> SEQ ID NO 51
<211> LENGTH: 354
<212> TYPE: DNA
<213> ORGANISM: Macaca Mulatta

<400> SEQUENCE: 51

```
caggtgcagc tgcaggagtc gggcccagga ctggtgaagc cttcggagac cctgtctctc     60
acctgcgctg tttctggtgg ctccatcagc agcaactact ggtactggat ccgccagtcc    120
ccagtgaagg gctggagtg gattgggtat atctatggtg gtagtggggg caccgaatac    180
aacccctccc tcaagagtcg agtcaccatt tcaacagaca cgtccaagaa ccagtttttc    240
ctgaagctga gctctgtgac cgccgcggac accgccgtat attactgtgc gagatccttt    300
tatagctgga acggggaatc ctgggggccaa ggggtcgtcg tcaccgtctc ctca         354
```

<210> SEQ ID NO 52
<211> LENGTH: 118
<212> TYPE: PRT
<213> ORGANISM: Macaca Mulatta

<400> SEQUENCE: 52

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Ser Asn
            20                  25                  30

Tyr Trp Tyr Trp Ile Arg Gln Ser Pro Val Lys Gly Leu Glu Trp Ile
        35                  40                  45

Gly Tyr Ile Tyr Gly Gly Ser Gly Gly Thr Glu Tyr Asn Pro Ser Leu
    50                  55                  60

Lys Ser Arg Val Thr Ile Ser Thr Asp Thr Ser Lys Asn Gln Phe Phe
65                  70                  75                  80

Leu Lys Leu Ser Ser Val Thr Ala Ala Asp Thr Ala Val Tyr Tyr Cys
```

```
                   85                  90                  95

Ala Arg Ser Phe Tyr Ser Trp Asn Gly Glu Ser Trp Gly Gln Gly Val
            100                 105                 110

Val Val Thr Val Ser Ser
        115

<210> SEQ ID NO 53
<211> LENGTH: 321
<212> TYPE: DNA
<213> ORGANISM: Macaca Mulatta

<400> SEQUENCE: 53
gacattcaga tgtcccagac tccatcctcc ctgtctgcat ctgtaggaga cagagtcacc     60
atcacttgcc gggcaagtca gggcattaac gattatttaa attggtatca gcagaaaccg    120
gggaaagccc ctaagctcct gatctattat ggaaacagtt tggcaagtgg ggtcccatca    180
aggttcagtg gcagtggttc tgggacagat ttctctctca ccatcagcag cctgcagcct    240
gaagattttg caacttatta ctgtcaacag ggtgatagtt ccctctcac tttcggcgga    300 gggaccaaag tggatatcaa a                                             321

<210> SEQ ID NO 54
<211> LENGTH: 107
<212> TYPE: PRT
<213> ORGANISM: Macaca Mulatta

<400> SEQUENCE: 54

Asp Ile Gln Met Ser Gln Thr Pro Ser Ser Leu Ser Ala Ser Val Gly
1               5                   10                  15

Asp Arg Val Thr Ile Thr Cys Arg Ala Ser Gln Gly Ile Asn Asp Tyr
            20                  25                  30

Leu Asn Trp Tyr Gln Gln Lys Pro Gly Lys Ala Pro Lys Leu Leu Ile
        35                  40                  45

Tyr Tyr Gly Asn Ser Leu Ala Ser Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln Gln Gly Asp Ser Phe Pro Leu
                85                  90                  95

Thr Phe Gly Gly Gly Thr Lys Val Asp Ile Lys
            100                 105

<210> SEQ ID NO 55
<211> LENGTH: 363
<212> TYPE: DNA
<213> ORGANISM: Macaca Mulatta

<400> SEQUENCE: 55
gaggtgcagc tggtgcagtc tggggctgag gtgaagaagc tggggcctc agtgaaggtc      60 tcctgcaaag cttctggaca catttttcacc agttatgtta tcaactggct gcaagaggcc    120
cctggacaag ggtttgagtg gatgggagga atccaccctg gtaatggtgg cagagactac    180
gcacagaagt tccagggcag agtcacgatt accgcggaca tgtccacgag cacagtctac    240
atggagctga aagtctgagg atctgaggac atggccgtgt attactgtgc agcatccagt    300
ggtagttatg gtgttagctc attggatgtc tggggccggg gagttctggt caccgtctcc    360
tca                                                                 363
```

<210> SEQ ID NO 56
<211> LENGTH: 121
<212> TYPE: PRT
<213> ORGANISM: Macaca Mulatta

<400> SEQUENCE: 56

Glu Val Gln Leu Val Gln Ser Gly Ala Glu Val Lys Lys Pro Gly Ala
1               5                   10                  15

Ser Val Lys Val Ser Cys Lys Ala Ser Gly His Ile Phe Thr Ser Tyr
            20                  25                  30

Val Ile Asn Trp Leu Gln Glu Ala Pro Gly Gln Gly Phe Glu Trp Met
        35                  40                  45

Gly Gly Ile His Pro Gly Asn Gly Gly Arg Asp Tyr Ala Gln Lys Phe
    50                  55                  60

Gln Gly Arg Val Thr Ile Thr Ala Asp Met Ser Thr Ser Thr Val Tyr
65                  70                  75                  80

Met Glu Leu Arg Ser Leu Arg Ser Glu Asp Met Ala Val Tyr Tyr Cys
                85                  90                  95

Ala Ala Ser Ser Gly Ser Tyr Gly Val Ser Leu Asp Val Trp Gly
            100                 105                 110

Arg Gly Val Leu Val Thr Val Ser Ser
        115                 120

<210> SEQ ID NO 57
<211> LENGTH: 348
<212> TYPE: DNA
<213> ORGANISM: Macaca Mulatta

<400> SEQUENCE: 57
cagtctgccc tgactcagcc accctccctg tctgcatccc cgggagcatc ggccagactc      60
ccctgcaccc tgagcagtga cctcagtgtt ggtagtaaaa acatgtactg gtaccagcag     120
aagccaggga gcgctcccag gttattcctg tactactact ccgactcaga caagcagctg     180
ggacctgggg tccccaatcg agtctctggc tccaaggaga cctcaagtaa cacagcgttt     240
ttgctcatct ctgggctcca gcctgaggac gaggccgatt attactgtca ggtgtatgac     300
agtagtgcta attgggtatt cggcggaggg accggctga cagtacta                   348

<210> SEQ ID NO 58
<211> LENGTH: 116
<212> TYPE: PRT
<213> ORGANISM: Macaca Mulatta

<400> SEQUENCE: 58

Gln Ser Ala Leu Thr Gln Pro Pro Ser Leu Ser Ala Ser Pro Gly Ala
1               5                   10                  15

Ser Ala Arg Leu Pro Cys Thr Leu Ser Ser Asp Leu Ser Val Gly Ser
            20                  25                  30

Lys Asn Met Tyr Trp Tyr Gln Gln Lys Pro Gly Ser Ala Pro Arg Leu
        35                  40                  45

Phe Leu Tyr Tyr Tyr Ser Asp Ser Asp Lys Gln Leu Gly Pro Gly Val
    50                  55                  60

Pro Asn Arg Val Ser Gly Ser Lys Glu Thr Ser Ser Asn Thr Ala Phe
65                  70                  75                  80

Leu Leu Ile Ser Gly Leu Gln Pro Glu Asp Glu Ala Asp Tyr Tyr Cys
                85                  90                  95

Gln Val Tyr Asp Ser Ser Ala Asn Trp Val Phe Gly Gly Gly Thr Arg

```
<210> SEQ ID NO 59
<211> LENGTH: 8
<212> TYPE: PRT
<213> ORGANISM: Artificial Sequence
<220> FEATURE:
<223> OTHER INFORMATION: Antibody CDR

<400> SEQUENCE: 59

Gly Gly Ser Ile Ser Ser Asn Tyr
1               5

<210> SEQ ID NO 60
<211> LENGTH: 8
<212> TYPE: PRT
<213> ORGANISM: Artificial Sequence
<220> FEATURE:
<223> OTHER INFORMATION: Antibody CDR

<400> SEQUENCE: 60

Ile Tyr Gly Gly Ser Gly Ser Thr
1               5

<210> SEQ ID NO 61
<211> LENGTH: 14
<212> TYPE: PRT
<213> ORGANISM: Artificial Sequence
<220> FEATURE:
<223> OTHER INFORMATION: Antibody CDR

<400> SEQUENCE: 61

Ala Arg Leu Leu Pro Leu Gly Gly Gly Tyr Cys Phe Asp Tyr
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Antibody CDR

<400> SEQUENCE: 62

Gln Ser Leu Phe Asp Ser Asp Tyr Gly Asn Thr Tyr
1               5                   10

<210> SEQ ID NO 63
<211> LENGTH: 3
<212> TYPE: PRT
<213> ORGANISM: Artificial Sequence
<220> FEATURE:
<223> OTHER INFORMATION: Antibody CDR

<400> SEQUENCE: 63

Met Leu Ser
1

<210> SEQ ID NO 64
<211> LENGTH: 9
<212> TYPE: PRT
<213> ORGANISM: Artificial Sequence
<220> FEATURE:
<223> OTHER INFORMATION: Antibody CDR

<400> SEQUENCE: 64
```

Leu Thr Val Leu
        115

(preceding sequence continuation, positions 100, 105, 110, 115)

```
Met Gln Ser Val Glu Tyr Pro Phe Thr
1               5

<210> SEQ ID NO 65
<211> LENGTH: 8
<212> TYPE: PRT
<213> ORGANISM: Artificial Sequence
<220> FEATURE:
<223> OTHER INFORMATION: Antibody CDR

<400> SEQUENCE: 65

Gly Ser Ile Ser Asp Ser Tyr Arg
1               5

<210> SEQ ID NO 66
<211> LENGTH: 8
<212> TYPE: PRT
<213> ORGANISM: Artificial Sequence
<220> FEATURE:
<223> OTHER INFORMATION: Antibody CDR

<400> SEQUENCE: 66

Ile Phe Ala Thr Gly Thr Thr Thr
1               5

<210> SEQ ID NO 67
<211> LENGTH: 23
<212> TYPE: PRT
<213> ORGANISM: Artificial Sequence
<220> FEATURE:
<223> OTHER INFORMATION: Antibody CDR

<400> SEQUENCE: 67

Ala Arg Glu Pro Phe Lys Tyr Cys Ser Gly Gly Val Cys Tyr Ala His
1               5                   10                  15

Lys Asp Asn Ser Leu Asp Val
            20

<210> SEQ ID NO 68
<211> LENGTH: 6
<212> TYPE: PRT
<213> ORGANISM: Artificial Sequence
<220> FEATURE:
<223> OTHER INFORMATION: Antibody CDR

<400> SEQUENCE: 68

Gln Ser Val Ser Ser Asn
1               5

<210> SEQ ID NO 69
<211> LENGTH: 3
<212> TYPE: PRT
<213> ORGANISM: Artificial Sequence
<220> FEATURE:
<223> OTHER INFORMATION: Antibody CDR

<400> SEQUENCE: 69

Ser Ala Ser
1

<210> SEQ ID NO 70
<211> LENGTH: 8
<212> TYPE: PRT
<213> ORGANISM: Artificial Sequence
<220> FEATURE:
<223> OTHER INFORMATION: Antibody CDR
```

<400> SEQUENCE: 70

Tyr Gln His Ser Ser Gly Tyr Thr
1               5

<210> SEQ ID NO 71
<211> LENGTH: 8
<212> TYPE: PRT
<213> ORGANISM: Artificial Sequence
<220> FEATURE:
<223> OTHER INFORMATION: Antibody CDR

<400> SEQUENCE: 71

Gly Asp Ser Ile Ser Ser Asn Tyr
1               5

<210> SEQ ID NO 72
<211> LENGTH: 8
<212> TYPE: PRT
<213> ORGANISM: Artificial Sequence
<220> FEATURE:
<223> OTHER INFORMATION: Antibody CDR

<400> SEQUENCE: 72

Phe Ser Gly Ser Gly Gly Ser Thr
1               5

<210> SEQ ID NO 73
<211> LENGTH: 10
<212> TYPE: PRT
<213> ORGANISM: Artificial Sequence
<220> FEATURE:
<223> OTHER INFORMATION: Antibody CDR

<400> SEQUENCE: 73

Ala Lys Thr Tyr Ser Gly Thr Phe Asp Tyr
1               5                   10

<210> SEQ ID NO 74
<211> LENGTH: 6
<212> TYPE: PRT
<213> ORGANISM: Artificial Sequence
<220> FEATURE:
<223> OTHER INFORMATION: Antibody CDR

<400> SEQUENCE: 74

Gln Asp Ile Asn Asn Tyr
1               5

<210> SEQ ID NO 75
<211> LENGTH: 3
<212> TYPE: PRT
<213> ORGANISM: Artificial Sequence
<220> FEATURE:
<223> OTHER INFORMATION: Antibody CDR

<400> SEQUENCE: 75

Tyr Ala Ser
1

<210> SEQ ID NO 76
<211> LENGTH: 9
<212> TYPE: PRT
<213> ORGANISM: Artificial Sequence
<220> FEATURE:
<223> OTHER INFORMATION: Antibody CDR

```
<400> SEQUENCE: 76

Gln Gln Tyr Asn Asn Ser Pro Tyr Ser
1               5

<210> SEQ ID NO 77
<211> LENGTH: 8
<212> TYPE: PRT
<213> ORGANISM: Artificial Sequence
<220> FEATURE:
<223> OTHER INFORMATION: Antibody CDR

<400> SEQUENCE: 77

Gly Gly Thr Phe Ser Ile Tyr Ala
1               5

<210> SEQ ID NO 78
<211> LENGTH: 8
<212> TYPE: PRT
<213> ORGANISM: Artificial Sequence
<220> FEATURE:
<223> OTHER INFORMATION: Antibody CDR

<400> SEQUENCE: 78

Ile Ile Pro Ile Phe Gly Thr Ala
1               5

<210> SEQ ID NO 79
<211> LENGTH: 20
<212> TYPE: PRT
<213> ORGANISM: Artificial Sequence
<220> FEATURE:
<223> OTHER INFORMATION: Antibody CDR

<400> SEQUENCE: 79

Ala Arg Glu Gly Gly His Gln Gly Tyr Cys Ser Gly Gly Ser Cys Tyr
1               5                   10                  15

Asp Phe Asp Tyr
            20

<210> SEQ ID NO 80
<211> LENGTH: 11
<212> TYPE: PRT
<213> ORGANISM: Artificial Sequence
<220> FEATURE:
<223> OTHER INFORMATION: Antibody CDR

<400> SEQUENCE: 80

Gln Ser Leu Leu His Ser Asn Gly Tyr Asn Tyr
1               5                   10

<210> SEQ ID NO 81
<211> LENGTH: 3
<212> TYPE: PRT
<213> ORGANISM: Artificial Sequence
<220> FEATURE:
<223> OTHER INFORMATION: Antibody CDR

<400> SEQUENCE: 81

Leu Gly Ser
1

<210> SEQ ID NO 82
<211> LENGTH: 8
<212> TYPE: PRT
<213> ORGANISM: Artificial Sequence
<220> FEATURE:
```

<223> OTHER INFORMATION: Antibody CDR

<400> SEQUENCE: 82

Met Gln Ala Leu Gln Thr Pro Ala
1               5

<210> SEQ ID NO 83
<211> LENGTH: 10
<212> TYPE: PRT
<213> ORGANISM: Artificial Sequence
<220> FEATURE:
<223> OTHER INFORMATION: Antibody CDR

<400> SEQUENCE: 83

Gly Gly Ser Ile Ser Ser Ser Ser Tyr Tyr
1               5                   10

<210> SEQ ID NO 84
<211> LENGTH: 7
<212> TYPE: PRT
<213> ORGANISM: Artificial Sequence
<220> FEATURE:
<223> OTHER INFORMATION: Antibody CDR

<400> SEQUENCE: 84

Ile Tyr Tyr Ser Gly Ser Thr
1               5

<210> SEQ ID NO 85
<211> LENGTH: 18
<212> TYPE: PRT
<213> ORGANISM: Artificial Sequence
<220> FEATURE:
<223> OTHER INFORMATION: Antibody CDR

<400> SEQUENCE: 85

Ala Ser Leu Leu Arg Pro Leu Ile Tyr Cys Ser Gly Gly Ser Cys Thr
1               5                   10                  15
Asp Tyr

<210> SEQ ID NO 86
<211> LENGTH: 9
<212> TYPE: PRT
<213> ORGANISM: Artificial Sequence
<220> FEATURE:
<223> OTHER INFORMATION: Antibody CDR

<400> SEQUENCE: 86

Ser Ser Asp Val Gly Gly Tyr Asn Tyr
1               5

<210> SEQ ID NO 87
<211> LENGTH: 3
<212> TYPE: PRT
<213> ORGANISM: Artificial Sequence
<220> FEATURE:
<223> OTHER INFORMATION: Antibody CDR

<400> SEQUENCE: 87

Glu Val Ser
1

<210> SEQ ID NO 88
<211> LENGTH: 10
<212> TYPE: PRT
<213> ORGANISM: Artificial Sequence -continued

```
<220> FEATURE:
<223> OTHER INFORMATION: Antibody CDR

<400> SEQUENCE: 88

Ser Ser Tyr Thr Ser Asn Ile Thr Leu Val
1               5                   10

<210> SEQ ID NO 89
<211> LENGTH: 8
<212> TYPE: PRT
<213> ORGANISM: Artificial Sequence
<220> FEATURE:
<223> OTHER INFORMATION: Antibody CDR

<400> SEQUENCE: 89

Gly Phe Thr Phe Ser Asp Tyr Tyr
1               5

<210> SEQ ID NO 90
<211> LENGTH: 8
<212> TYPE: PRT
<213> ORGANISM: Artificial Sequence
<220> FEATURE:
<223> OTHER INFORMATION: Antibody CDR

<400> SEQUENCE: 90

Ile Ser Ser Ser Gly Ser Thr Ile
1               5

<210> SEQ ID NO 91
<211> LENGTH: 15
<212> TYPE: PRT
<213> ORGANISM: Artificial Sequence
<220> FEATURE:
<223> OTHER INFORMATION: Antibody CDR

<400> SEQUENCE: 91

Ala Arg Val Gly Leu Gly Ser Gly Trp Tyr Asp Trp Phe Asp Pro
1               5                   10                  15

<210> SEQ ID NO 92
<211> LENGTH: 9
<212> TYPE: PRT
<213> ORGANISM: Artificial Sequence
<220> FEATURE:
<223> OTHER INFORMATION: Antibody CDR

<400> SEQUENCE: 92

Ser Ser Asn Ile Gly Ala Ser Tyr Asp
1               5

<210> SEQ ID NO 93
<211> LENGTH: 3
<212> TYPE: PRT
<213> ORGANISM: Artificial Sequence
<220> FEATURE:
<223> OTHER INFORMATION: Antibody CDR

<400> SEQUENCE: 93

Gly Asn Thr
1

<210> SEQ ID NO 94
<211> LENGTH: 11
<212> TYPE: PRT
<213> ORGANISM: Artificial Sequence
<220> FEATURE:
```

<223> OTHER INFORMATION: Antibody CDR

<400> SEQUENCE: 94

Gln Ser Tyr Asp Ser Ser Leu Ser Gly Val Val
1               5                   10

<210> SEQ ID NO 95
<211> LENGTH: 8
<212> TYPE: PRT
<213> ORGANISM: Artificial Sequence
<220> FEATURE:
<223> OTHER INFORMATION: Antibody CDR

<400> SEQUENCE: 95

Gly Gly Thr Phe Ser Thr Tyr Ala
1               5

<210> SEQ ID NO 96
<211> LENGTH: 15
<212> TYPE: PRT
<213> ORGANISM: Artificial Sequence
<220> FEATURE:
<223> OTHER INFORMATION: Antibody CDR

<400> SEQUENCE: 96

Ala Arg Gly Ser Arg Ser Ser Ser Ala Glu Tyr Phe Gln His
1               5                   10                  15

<210> SEQ ID NO 97
<211> LENGTH: 3
<212> TYPE: PRT
<213> ORGANISM: Artificial Sequence
<220> FEATURE:
<223> OTHER INFORMATION: Antibody CDR

<400> SEQUENCE: 97

Asp Val Ser
1

<210> SEQ ID NO 98
<211> LENGTH: 11
<212> TYPE: PRT
<213> ORGANISM: Artificial Sequence
<220> FEATURE:
<223> OTHER INFORMATION: Antibody CDR

<400> SEQUENCE: 98

Ser Tyr Ala Gly Ser Tyr Thr Leu Glu Val Val
1               5                   10

<210> SEQ ID NO 99
<211> LENGTH: 8
<212> TYPE: PRT
<213> ORGANISM: Artificial Sequence
<220> FEATURE:
<223> OTHER INFORMATION: Antibody CDR

<400> SEQUENCE: 99

Ile Tyr Gly Gly Ser Gly Gly Thr
1               5

<210> SEQ ID NO 100
<211> LENGTH: 11
<212> TYPE: PRT
<213> ORGANISM: Artificial Sequence
<220> FEATURE:
<223> OTHER INFORMATION: Antibody CDR

```
<400> SEQUENCE: 100

Ala Arg Ser Phe Tyr Ser Trp Asn Gly Glu Ser
1               5                   10

<210> SEQ ID NO 101
<211> LENGTH: 6
<212> TYPE: PRT
<213> ORGANISM: Artificial Sequence
<220> FEATURE:
<223> OTHER INFORMATION: Antibody CDR

<400> SEQUENCE: 101

Gln Gly Ile Asn Asp Tyr
1               5

<210> SEQ ID NO 102
<211> LENGTH: 3
<212> TYPE: PRT
<213> ORGANISM: Artificial Sequence
<220> FEATURE:
<223> OTHER INFORMATION: Antibody CDR

<400> SEQUENCE: 102

Tyr Gly Asn
1

<210> SEQ ID NO 103
<211> LENGTH: 9
<212> TYPE: PRT
<213> ORGANISM: Artificial Sequence
<220> FEATURE:
<223> OTHER INFORMATION: Antibody CDR

<400> SEQUENCE: 103

Gln Gln Gly Asp Ser Phe Pro Leu Thr
1               5

<210> SEQ ID NO 104
<211> LENGTH: 8
<212> TYPE: PRT
<213> ORGANISM: Artificial Sequence
<220> FEATURE:
<223> OTHER INFORMATION: Antibody CDR

<400> SEQUENCE: 104

Gly His Ile Phe Thr Ser Tyr Val
1               5

<210> SEQ ID NO 105
<211> LENGTH: 8
<212> TYPE: PRT
<213> ORGANISM: Artificial Sequence
<220> FEATURE:
<223> OTHER INFORMATION: Antibody CDR

<400> SEQUENCE: 105

Ile His Pro Gly Asn Gly Gly Arg
1               5

<210> SEQ ID NO 106
<211> LENGTH: 14
<212> TYPE: PRT
<213> ORGANISM: Artificial Sequence
<220> FEATURE:
<223> OTHER INFORMATION: Antibody CDR
```

-continued

```
<400> SEQUENCE: 106

Ala Ala Ser Ser Gly Ser Tyr Gly Val Ser Ser Leu Asp Val
1               5                   10

<210> SEQ ID NO 107
<211> LENGTH: 9
<212> TYPE: PRT
<213> ORGANISM: Artificial Sequence
<220> FEATURE:
<223> OTHER INFORMATION: Antibody CDR

<400> SEQUENCE: 107

Ser Asp Leu Ser Val Gly Ser Lys Asn
1               5

<210> SEQ ID NO 108
<211> LENGTH: 7
<212> TYPE: PRT
<213> ORGANISM: Artificial Sequence
<220> FEATURE:
<223> OTHER INFORMATION: Antibody CDR

<400> SEQUENCE: 108

Tyr Tyr Ser Asp Ser Asp Lys
1               5

<210> SEQ ID NO 109
<211> LENGTH: 10
<212> TYPE: PRT
<213> ORGANISM: Artificial Sequence
<220> FEATURE:
<223> OTHER INFORMATION: Antibody CDR

<400> SEQUENCE: 109

Gln Val Tyr Asp Ser Ser Ala Asn Trp Val
1               5                   10

<210> SEQ ID NO 110
<211> LENGTH: 111
<212> TYPE: PRT
<213> ORGANISM: Artificial Sequence
<220> FEATURE:
<223> OTHER INFORMATION: Antibody variable region

<400> SEQUENCE: 110

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Ser Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ala Phe Gly Gly Gly Thr Lys Leu Glu Ile Lys
            100                 105                 110

<210> SEQ ID NO 111
<211> LENGTH: 111
<212> TYPE: PRT
```

<213> ORGANISM: Artificial Sequence
<220> FEATURE:
<223> OTHER INFORMATION: Antibody variable region

<400> SEQUENCE: 111

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Ala Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ala Phe Gly Gly Gly Thr Lys Leu Glu Ile Lys
            100                 105                 110
```

<210> SEQ ID NO 112
<211> LENGTH: 11
<212> TYPE: PRT
<213> ORGANISM: Artificial Sequence
<220> FEATURE:
<223> OTHER INFORMATION: Antibody CDR

<400> SEQUENCE: 112

```
Gln Ser Leu Leu His Ser Asn Ser Tyr Asn Tyr
1               5                   10
```

<210> SEQ ID NO 113
<211> LENGTH: 11
<212> TYPE: PRT
<213> ORGANISM: Artificial Sequence
<220> FEATURE:
<223> OTHER INFORMATION: Antibody CDR

<400> SEQUENCE: 113

```
Gln Ser Leu Leu His Ser Asn Ala Tyr Asn Tyr
1               5                   10
```

<210> SEQ ID NO 114
<211> LENGTH: 360
<212> TYPE: DNA
<213> ORGANISM: Mus Musculus

<400> SEQUENCE: 114

```
cattcccagg tgcagctgca gcagtctgga ggtgagctgg tgaagcctgg ggcttcagtg      60
aagctgtcct gcaagacttc tggcttcacc ttcagcagta gctatataag ttggttgaag    120
caaaagcctg gacagagtct tgagtggatt gcatggattt atgctggaac tggtggtact    180
gaatataatc agaagttcac aggcaaggcc caagtgactg tagacacatc ctccagcaca    240
gcctacatgc aattcagcag cctgacaact gaggactctg ccatctatta ctgtgcaaga    300
ggaggtagta gcttcgctat ggactactgg ggtcaaggaa cctcagtcac cgtctcctca    360
```

<210> SEQ ID NO 115
<211> LENGTH: 118
<212> TYPE: PRT
<213> ORGANISM: Mus Musculus

<400> SEQUENCE: 115

Gln Val Gln Leu Gln Gln Ser Gly Gly Glu Leu Val Lys Pro Gly Ala
1               5                   10                  15

Ser Val Lys Leu Ser Cys Lys Thr Ser Gly Phe Thr Phe Ser Ser Ser
            20                  25                  30

Tyr Ile Ser Trp Leu Lys Gln Lys Pro Gly Gln Ser Leu Glu Trp Ile
        35                  40                  45

Ala Trp Ile Tyr Ala Gly Thr Gly Gly Thr Tyr Asn Gln Lys Phe
    50                  55                  60

Thr Gly Lys Ala Gln Val Thr Val Asp Thr Ser Ser Thr Ala Tyr
65                  70                  75                  80

Met Gln Phe Ser Ser Leu Thr Glu Asp Ser Ala Ile Tyr Tyr Cys
                85                  90                  95

Ala Arg Gly Gly Ser Ser Phe Ala Met Asp Tyr Trp Gly Gln Gly Thr
                100                 105                 110

Ser Val Thr Val Ser Ser
        115

<210> SEQ ID NO 116
<211> LENGTH: 333
<212> TYPE: DNA
<213> ORGANISM: Mus Musculus

<400> SEQUENCE: 116
caacttgtgc tgacccaatc tccagcttct ttggctgtgt ctctagggca gagggccacc      60
atctcctgca gagccagcga aagtgttgat aattatggca ttagtttat gaactggttc     120
caacagaaac caggacagcc acccaaactc ctcatccata ctgcatccaa ccaaggatcc     180
ggggtccctg ccaggtttag tggcagtggg tctgggacag acttcagcct caacatccat     240
cctgtggagg acgatgatac tgcaatgtat ttctgtcagc aaagtgagga ggttcctctc     300
acgttcggtg ctgggaccaa gctggaaatc aaa                                  333

<210> SEQ ID NO 117
<211> LENGTH: 111
<212> TYPE: PRT
<213> ORGANISM: Mus Musculus

<400> SEQUENCE: 117

Gln Leu Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile His Thr Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Asp Asp Asp Thr Ala Met Tyr Phe Cys Gln Gln Ser Glu
                85                  90                  95

Glu Val Pro Leu Thr Phe Gly Ala Gly Thr Lys Leu Glu Leu Lys
                100                 105                 110

<210> SEQ ID NO 118
<211> LENGTH: 366
<212> TYPE: DNA

<213> ORGANISM: Mus Musculus

<400> SEQUENCE: 118

```
caggtccagc tgcagcagtc tgggcctgag ctggtgaggc ctggggtctc agtgaagatt      60
tcctgcaagg gttccggcta cacattcact gattatgcta tacactgggt gaagcagagt     120
catgcaaaga gtctagagtg gattggggtt tttagtactt actatggtaa tacaaactac     180
aaccagaagt ttaagggcag ggccacaatg actgtagaca atcctccag cacagcctat      240
atggaacttg ccagattgac atctgaggat tctgccatct attactgtgc aagaaagtcc     300
tactatgttg actacgttga tgctatggac tactggggtc aaggaaccctc agtcaccgtc    360
tcctca                                                                366
```

<210> SEQ ID NO 119
<211> LENGTH: 122
<212> TYPE: PRT
<213> ORGANISM: Mus Musculus

<400> SEQUENCE: 119

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Ile His Trp Val Lys Gln Ser His Ala Lys Ser Leu Glu Trp Ile
        35                  40                  45

Gly Val Phe Ser Thr Tyr Tyr Gly Asn Thr Asn Tyr Asn Gln Lys Phe
    50                  55                  60

Lys Gly Arg Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Lys Ser Tyr Tyr Val Asp Tyr Val Asp Ala Met Asp Tyr Trp
            100                 105                 110

Gly Gln Gly Thr Ser Val Thr Val Ser Ser
        115                 120

<210> SEQ ID NO 120
<211> LENGTH: 334
<212> TYPE: DNA
<213> ORGANISM: Mus Musculus

<400> SEQUENCE: 120

```
gacattgtgc tgacccaatc tccagcttct ttggctgtgt ctctagggca gagggccacc      60
atctcctgca gagccagcga aagtgttgat aattatggca ttagttttat gaactggttc     120
caacagaaac caggacagcc acccaaactc ctcatctctg ctacatccaa ccaaggatcc     180
ggggtccctg ccaggtttat tggcagtggg tctgggacag acttcagcct caacatccat     240
cctgtggagg aggatgatac tgcaatgtat ttctgtcagc aaagtaagga ggttcctcgg     300
acgttcggtg aggcaccaa gctggaaatc aaac                                  334
```

<210> SEQ ID NO 121
<211> LENGTH: 111
<212> TYPE: PRT
<213> ORGANISM: Mus Musculus

<400> SEQUENCE: 121

Asp Ile Val Leu Thr Gln Ser Pro Ala Ser Leu Ala Val Ser Leu Gly

```
              1               5                  10                 15
            Gln Arg Ala Thr Ile Ser Cys Arg Ala Ser Glu Ser Val Asp Asn Tyr
                            20                  25                 30

Gly Ile Ser Phe Met Asn Trp Phe Gln Gln Lys Pro Gly Gln Pro Pro
                            35                  40                 45

Lys Leu Leu Ile Ser Ala Thr Ser Asn Gln Gly Ser Gly Val Pro Ala
                    50                  55                 60

Arg Phe Ile Gly Ser Gly Ser Gly Thr Asp Phe Ser Leu Asn Ile His
             65                 70                  75                 80

Pro Val Glu Glu Asp Asp Thr Ala Met Tyr Phe Cys Gln Gln Ser Lys
                            85                  90                 95

Glu Val Pro Arg Thr Phe Gly Gly Gly Thr Lys Leu Glu Ile Lys
                            100                 105                110
```

<210> SEQ ID NO 122
<211> LENGTH: 350
<212> TYPE: DNA
<213> ORGANISM: Mus Musculus

<400> SEQUENCE: 122

```
gaggtgaagc tggtggagtc tgggggaggc ttagtgaagc ctggagggtc cctgaaactc     60
tcctgtgcag cctctggatt cactttcagt agctatgcca tgtcttgggt tcgccagact    120
ccggagaaga ggctggagtg ggtcgcaacc attagtagtg gtggtactta cacctactat    180
ccagacagtg tgaaggggcg attcaccatc tccagagaca atgccgagaa caccctgtac    240
ctgcaaatga gcagtctgag gtctgaggac acggccatgt attactgtgt aagagatggt    300
aattctatgg actactgggg tcaaggaacc tcagtcaccg tctcctcagc               350
```

<210> SEQ ID NO 123
<211> LENGTH: 116
<212> TYPE: PRT
<213> ORGANISM: Mus Musculus

<400> SEQUENCE: 123

```
            Glu Val Lys Leu Val Glu Ser Gly Gly Gly Leu Val Lys Pro Gly Gly
             1               5                  10                 15

Ser Leu Lys Leu Ser Cys Ala Ala Ser Gly Phe Thr Phe Ser Ser Tyr
                            20                  25                 30

Ala Met Ser Trp Val Arg Gln Thr Pro Glu Lys Arg Leu Glu Trp Val
                            35                  40                 45

Ala Thr Ile Ser Ser Gly Gly Thr Tyr Thr Tyr Tyr Pro Asp Ser Val
                    50                  55                 60

Lys Gly Arg Phe Thr Ile Ser Arg Asp Asn Ala Glu Asn Thr Leu Tyr
             65                 70                  75                 80

Leu Gln Met Ser Ser Leu Arg Ser Glu Asp Thr Ala Met Tyr Tyr Cys
                            85                  90                 95

Val Arg Asp Gly Asn Ser Met Asp Tyr Trp Gly Gln Gly Thr Ser Val
                            100                 105                110

Thr Val Ser Ser
                    115
```

<210> SEQ ID NO 124
<211> LENGTH: 321
<212> TYPE: DNA
<213> ORGANISM: Mus Musculus

<400> SEQUENCE: 124

```
gatatccaga tgacacagac tacatcctcc ctgtctgcct ctctgggaga cagagtcacc      60
atcatttgca gggcaagtca ggacattaac aattatttaa actggtatca acagaaacca     120
gatggaactg ttaaactcct gatctactac acatcaagat tacactcagg agtcccatca     180
aggttcagtg gcagtgggtc tggatcagat tattctctca ccattagcaa cctggaacaa     240
gaagatattg ccacttactt ttgccaacag gctaatacgc ttcctcccac gttcggtgct     300
gggaccaagc tggaactgag a                                                321
```

<210> SEQ ID NO 125
<211> LENGTH: 107
<212> TYPE: PRT
<213> ORGANISM: Mus Musculus

<400> SEQUENCE: 125

```
Asp Ile Gln Met Thr Gln Thr Thr Ser Ser Leu Ser Ala Ser Leu Gly
1               5                   10                  15

Asp Arg Val Thr Ile Ile Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Ser Asp Tyr Ser Leu Thr Ile Ser Asn Leu Glu Gln
65                  70                  75                  80

Glu Asp Ile Ala Thr Tyr Phe Cys Gln Gln Ala Asn Thr Leu Pro Pro
                85                  90                  95

Thr Phe Gly Ala Gly Thr Lys Leu Glu Leu Arg
            100                 105
```

<210> SEQ ID NO 126
<211> LENGTH: 374
<212> TYPE: DNA
<213> ORGANISM: Mus Musculus

<400> SEQUENCE: 126

```
cattccgagg tgaagctgga ggagtctggg ggaggcttag tgaagcctgg agggtccctg      60
aaactctcct gtgcagcctc tggattcact ttcagtaggt atgccatgtc ttgggttcgc     120
cagactccgg agaagaggct ggagtgggtc gcaaccatta taatggtgg tagttacagt      180 tactatccag acagtgtgaa gggtcgactc accatctcca gagacaatgc caagaacacc     240
ctgtacctgc aaatgagcag tctgaggtct gaggacacgg ccttgtatta ctgtgcaaga     300
cactatgatt acgacggata ttactatact atggacttct ggggtcaagg aacctcagtc     360
accgtctcct cagc                                                        374
```

<210> SEQ ID NO 127
<211> LENGTH: 122
<212> TYPE: PRT
<213> ORGANISM: Mus Musculus

<400> SEQUENCE: 127

```
Glu Val Lys Leu Glu Glu Ser Gly Gly Gly Leu Val Lys Pro Gly Gly
1               5                   10                  15

Ser Leu Lys Leu Ser Cys Ala Ala Ser Gly Phe Thr Phe Ser Arg Tyr
            20                  25                  30

Ala Met Ser Trp Val Arg Gln Thr Pro Glu Lys Arg Leu Glu Trp Val
```

```
                35                  40                  45
Ala Thr Ile Asn Asn Gly Gly Ser Tyr Ser Tyr Tyr Pro Asp Ser Val
    50                  55                  60
Lys Gly Arg Leu Thr Ile Ser Arg Asp Asn Ala Lys Asn Thr Leu Tyr
65                  70                  75                  80
Leu Gln Met Ser Ser Leu Arg Ser Glu Asp Thr Ala Leu Tyr Tyr Cys
                85                  90                  95
Ala Arg His Tyr Asp Tyr Asp Gly Tyr Tyr Tyr Thr Met Asp Phe Trp
            100                 105                 110
Gly Gln Gly Thr Ser Val Thr Val Ser Ser
            115                 120

<210> SEQ ID NO 128
<211> LENGTH: 338
<212> TYPE: DNA
<213> ORGANISM: Mus Musculus

<400> SEQUENCE: 128
gatgttttga tgacccaaat tccactctcc ctgcctgtca gtcttggaga tcaagcctcc      60
atttcttgca gatctagtca gagcattgta catagtaatg aaacaccta tttagaatgg     120 tacctgcaga accaggcca gtctccaaag cccctgatct acaaagtttc caaccgaatt     180
tctggggtcc cagacaggtt cagtggcagt ggatcaggga cagatttcac actcaagatc     240
agcagagtgg aggctgagga tctgggagtt tattactgct ttcaaggttc acatgttccg     300
tacacgttcg agggggggac caacctggaa ataaaacg                             338

<210> SEQ ID NO 129
<211> LENGTH: 113
<212> TYPE: PRT
<213> ORGANISM: Mus Musculus

<400> SEQUENCE: 129

Asp Val Leu Met Thr Gln Ile Pro Leu Ser Leu Pro Val Ser Leu Gly
1               5                  10                  15
Asp Gln Ala Ser Ile Ser Cys Arg Ser Ser Gln Ser Ile Val His Ser
            20                  25                  30
Asn Gly Asn Thr Tyr Leu Glu Trp Tyr Leu Gln Lys Pro Gly Gln Ser
            35                  40                  45
Pro Lys Pro Leu Ile Tyr Lys Val Ser Asn Arg Ile Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Tyr Thr Phe Gly Gly Gly Thr Asn Leu Glu Ile Lys
            100                 105                 110
Arg

<210> SEQ ID NO 130
<211> LENGTH: 8
<212> TYPE: PRT
<213> ORGANISM: Artificial Sequence
<220> FEATURE:
<223> OTHER INFORMATION: Antibody CDR

<400> SEQUENCE: 130

Gly Phe Thr Phe Ser Ser Ser Tyr
```

```
1               5

<210> SEQ ID NO 131
<211> LENGTH: 8
<212> TYPE: PRT
<213> ORGANISM: Artificial Sequence
<220> FEATURE:
<223> OTHER INFORMATION: Antibody CDR

<400> SEQUENCE: 131

Ile Tyr Ala Gly Thr Gly Gly Thr
1               5

<210> SEQ ID NO 132
<211> LENGTH: 11
<212> TYPE: PRT
<213> ORGANISM: Artificial Sequence
<220> FEATURE:
<223> OTHER INFORMATION: Antibody CDR

<400> SEQUENCE: 132

Ala Arg Gly Gly Ser Ser Phe Ala Met Asp Tyr
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Antibody CDR

<400> SEQUENCE: 133

Glu Ser Val Asp Asn Tyr Gly Ile Ser Phe
1               5                   10

<210> SEQ ID NO 134
<211> LENGTH: 3
<212> TYPE: PRT
<213> ORGANISM: Artificial Sequence
<220> FEATURE:
<223> OTHER INFORMATION: Antibody CDR

<400> SEQUENCE: 134

Thr Ala Ser
1

<210> SEQ ID NO 135
<211> LENGTH: 5
<212> TYPE: PRT
<213> ORGANISM: Artificial Sequence
<220> FEATURE:
<223> OTHER INFORMATION: Antibody CDR

<400> SEQUENCE: 135

Gln Gln Ser Glu Glu
1               5

<210> SEQ ID NO 136
<211> LENGTH: 8
<212> TYPE: PRT
<213> ORGANISM: Artificial Sequence
<220> FEATURE:
<223> OTHER INFORMATION: Antibody CDR

<400> SEQUENCE: 136

Gly Tyr Thr Phe Thr Asp Tyr Ala
1               5
```

<210> SEQ ID NO 137
<211> LENGTH: 8
<212> TYPE: PRT
<213> ORGANISM: Artificial Sequence
<220> FEATURE:
<223> OTHER INFORMATION: Antibody CDR

<400> SEQUENCE: 137

Phe Ser Thr Tyr Tyr Gly Asn Thr
1               5

<210> SEQ ID NO 138
<211> LENGTH: 15
<212> TYPE: PRT
<213> ORGANISM: Artificial Sequence
<220> FEATURE:
<223> OTHER INFORMATION: Antibody CDR

<400> SEQUENCE: 138

Ala Arg Lys Ser Tyr Tyr Val Asp Tyr Val Asp Ala Met Asp Tyr
1               5                   10                  15

<210> SEQ ID NO 139
<211> LENGTH: 10
<212> TYPE: PRT
<213> ORGANISM: Artificial Sequence
<220> FEATURE:
<223> OTHER INFORMATION: Antibody CDR

<400> SEQUENCE: 139

Glu Ser Val Asp Asn Tyr Gly Ile Ser Phe
1               5                   10

<210> SEQ ID NO 140
<211> LENGTH: 3
<212> TYPE: PRT
<213> ORGANISM: Artificial Sequence
<220> FEATURE:
<223> OTHER INFORMATION: Antibody CDR

<400> SEQUENCE: 140

Ala Thr Ser
1

<210> SEQ ID NO 141
<211> LENGTH: 9
<212> TYPE: PRT
<213> ORGANISM: Artificial Sequence
<220> FEATURE:
<223> OTHER INFORMATION: Antibody CDR

<400> SEQUENCE: 141

Gln Gln Ser Lys Glu Val Pro Arg Thr
1               5

<210> SEQ ID NO 142
<211> LENGTH: 8
<212> TYPE: PRT
<213> ORGANISM: Artificial Sequence
<220> FEATURE:
<223> OTHER INFORMATION: Antibody CDR

<400> SEQUENCE: 142

Gly Phe Thr Phe Ser Ser Tyr Ala
1               5

<210> SEQ ID NO 143
<211> LENGTH: 8
<212> TYPE: PRT
<213> ORGANISM: Artificial Sequence
<220> FEATURE:
<223> OTHER INFORMATION: Antibody CDR

<400> SEQUENCE: 143

Ile Ser Ser Gly Gly Thr Tyr Thr
1               5

<210> SEQ ID NO 144
<211> LENGTH: 9
<212> TYPE: PRT
<213> ORGANISM: Artificial Sequence
<220> FEATURE:
<223> OTHER INFORMATION: Antibody CDR

<400> SEQUENCE: 144

Val Arg Asp Gly Asn Ser Met Asp Tyr
1               5

<210> SEQ ID NO 145
<211> LENGTH: 3
<212> TYPE: PRT
<213> ORGANISM: Artificial Sequence
<220> FEATURE:
<223> OTHER INFORMATION: Antibody CDR

<400> SEQUENCE: 145

Tyr Thr Ser
1

<210> SEQ ID NO 146
<211> LENGTH: 9
<212> TYPE: PRT
<213> ORGANISM: Artificial Sequence
<220> FEATURE:
<223> OTHER INFORMATION: Antibody CDR

<400> SEQUENCE: 146

Gln Gln Ala Asn Thr Leu Pro Pro Thr
1               5

<210> SEQ ID NO 147
<211> LENGTH: 8
<212> TYPE: PRT
<213> ORGANISM: Artificial Sequence
<220> FEATURE:
<223> OTHER INFORMATION: Antibody CDR

<400> SEQUENCE: 147

Gly Phe Thr Phe Ser Arg Tyr Ala
1               5

<210> SEQ ID NO 148
<211> LENGTH: 8
<212> TYPE: PRT
<213> ORGANISM: Artificial Sequence
<220> FEATURE:
<223> OTHER INFORMATION: Antibody CDR

<400> SEQUENCE: 148

Ile Asn Asn Gly Gly Ser Tyr Ser
1               5

```
<210> SEQ ID NO 149
<211> LENGTH: 15
<212> TYPE: PRT
<213> ORGANISM: Artificial Sequence
<220> FEATURE:
<223> OTHER INFORMATION: Antibody CDR

<400> SEQUENCE: 149

Ala Arg His Tyr Asp Tyr Asp Gly Tyr Tyr Tyr Thr Met Asp Phe
1               5                   10                  15

<210> SEQ ID NO 150
<211> LENGTH: 11
<212> TYPE: PRT
<213> ORGANISM: Artificial Sequence
<220> FEATURE:
<223> OTHER INFORMATION: Antibody CDR

<400> SEQUENCE: 150

Gln Ser Ile Val His Ser Asn Gly Asn Thr Tyr
1               5                   10

<210> SEQ ID NO 151
<211> LENGTH: 3
<212> TYPE: PRT
<213> ORGANISM: Artificial Sequence
<220> FEATURE:
<223> OTHER INFORMATION: Antibody CDR

<400> SEQUENCE: 151

Lys Val Ser
1

<210> SEQ ID NO 152
<211> LENGTH: 9
<212> TYPE: PRT
<213> ORGANISM: Artificial Sequence
<220> FEATURE:
<223> OTHER INFORMATION: Antibody CDR

<400> SEQUENCE: 152

Phe Gln Gly Ser His Val Pro Tyr Thr
1               5

<210> SEQ ID NO 153
<211> LENGTH: 1404
<212> TYPE: DNA
<213> ORGANISM: Artificial Sequence
<220> FEATURE:
<223> OTHER INFORMATION: antibody heavy chain

<400> SEQUENCE: 153
atgggatggt catgtatcat ccttttttcta gtagcaactg caaccggtgt acattcccag     60
gtgcagctgc agcagtctgg aggtgagctg gtgaagcctg ggcttcagt gaagctgtcc      120 tgcaagactt ctggcttcac cttcagcagt agctatataa gttggttgaa gcaaaagcct     180
ggacagagtc ttgagtggat tgcatggatt tatgctggaa ctggtggtac tgaatataat     240
cagaagttca caggcaaggc ccaagtgact gtagacacat cctccagcac agcctacatg     300
caattcagca gcctgacaac tgaggactct gccatctatt actgtgcaag aggaggtagt     360
agcttcgcta tggactactg gggtcaagga acctcagtca ccgtctcctc agcgtcgacc     420 acgccccat cggtcttccc cctggcaccc tcctccaaga gcacctctgg ggcacagcg     480 gccctgggct gcctggtcaa ggactacttc cccgaaccg tgacggtgtc gtggaactca     540
```

```
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720
gacaaaactc acacatgccc accgtgccca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca gagcaggtg gcagcagggg   1320
aacgtcttct catgctccgt gatgcatgag gctctgcaca accactacac gcagaagagc   1380
ctctccctgt ctccgggtaa atga                                           1404
```

<210> SEQ ID NO 154
<211> LENGTH: 467
<212> TYPE: PRT
<213> ORGANISM: Artificial Sequence
<220> FEATURE:
<223> OTHER INFORMATION: Antibody heavy chain

<400> SEQUENCE: 154

Met Gly Trp Ser Cys Ile Ile Leu Phe Leu Val Ala Thr Ala Thr Gly
1               5                   10                  15

Val His Ser Gln Val Gln Leu Gln Gln Ser Gly Gly Glu Leu Val Lys
            20                  25                  30

Pro Gly Ala Ser Val Lys Leu Ser Cys Lys Thr Ser Gly Phe Thr Phe
        35                  40                  45

Ser Ser Ser Tyr Ile Ser Trp Leu Lys Gln Lys Pro Gly Gln Ser Leu
    50                  55                  60

Glu Trp Ile Ala Trp Ile Tyr Ala Gly Thr Gly Gly Thr Glu Tyr Asn
65                  70                  75                  80

Gln Lys Phe Thr Gly Lys Ala Gln Val Thr Val Asp Thr Ser Ser Ser
                85                  90                  95

Thr Ala Tyr Met Gln Phe Ser Ser Leu Thr Thr Glu Asp Ser Ala Ile
            100                 105                 110

Tyr Tyr Cys Ala Arg Gly Gly Ser Ser Phe Ala Met Asp Tyr Trp Gly
        115                 120                 125

Gln Gly Thr Ser Val Thr Val Ser Ser Ala Ser Thr Thr Pro Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

```
Pro Ser Ser Leu Gly Thr Gln Thr Tyr Ile Cys Asn Val Asn His
    210             215             220
Lys Pro Ser Asn Thr Lys Val Asp Lys Val Glu Pro Lys Ser Cys
225             230              235             240
Asp Lys Thr His Thr Cys Pro Pro Cys Pro Ala Pro Glu Leu Leu Gly
                245             250             255
Gly Pro Ser Val Phe Leu Phe Pro Pro Lys Pro Lys Asp Thr Leu Met
            260             265             270
Ile Ser Arg Thr Pro Glu Val Thr Cys Val Val Val Asp Val Ser His
        275             280             285
Glu Asp Pro Glu Val Lys Phe Asn Trp Tyr Val Asp Gly Val Glu Val
    290             295             300
His Asn Ala Lys Thr Lys Pro Arg Glu Glu Gln Tyr Asn Ser Thr Tyr
305             310             315             320
Arg Val Val Ser Val Leu Thr Val Leu His Gln Asp Trp Leu Asn Gly
                325             330             335
Lys Glu Tyr Lys Cys Lys Val Ser Asn Lys Ala Leu Pro Ala Pro Ile
            340             345             350
Glu Lys Thr Ile Ser Lys Ala Lys Gly Gln Pro Arg Glu Pro Gln Val
        355             360             365
Tyr Thr Leu Pro Pro Ser Arg Asp Glu Leu Thr Lys Asn Gln Val Ser
    370             375             380
Leu Thr Cys Leu Val Lys Gly Phe Tyr Pro Ser Asp Ile Ala Val Glu
385             390             395             400
Trp Glu Ser Asn Gly Gln Pro Glu Asn Asn Tyr Lys Thr Thr Pro Pro
                405             410             415
Val Leu Asp Ser Asp Gly Ser Phe Phe Leu Tyr Ser Lys Leu Thr Val
            420             425             430
Asp Lys Ser Arg Trp Gln Gln Gly Asn Val Phe Ser Cys Ser Val Met
        435             440             445
His Glu Ala Leu His Asn His Tyr Thr Gln Lys Ser Leu Ser Leu Ser
    450             455             460
Pro Gly Lys
465

<210> SEQ ID NO 155
<211> LENGTH: 5
<212> TYPE: PRT
<213> ORGANISM: Artificial Sequence
<220> FEATURE:
<223> OTHER INFORMATION: Peptide linker sequence

<400> SEQUENCE: 155

Gly Gly Gly Gly Ser
1               5
```